(12) United States Patent
Nakamura et al.

(10) Patent No.: US 10,154,992 B2
(45) Date of Patent: Dec. 18, 2018

(54) COMPOUNDS AND METHODS FOR TREATING HIV INFECTION

(71) Applicants: THE REGENTS OF THE UNIVERSITY OF CALIFORNIA, Oakland, CA (US); ADVANCED GENETIC SYSTEMS, INC., San Francisco, CA (US)

(72) Inventors: Robert Nakamura, San Francisco, CA (US); Mark Burlingame, Oakland, CA (US); Alan Frankel, Mill Valley, CA (US); Adam Renslo, Oakland, CA (US)

(73) Assignees: The Regents of the University of California, Oakland, CA (US); Advanced Genetic Systems, Inc., San Francisco, CA (US)

( * ) Notice: Subject to any disclaimer, the term of this patent is extended or adjusted under 35 U.S.C. 154(b) by 0 days.

(21) Appl. No.: 15/648,245

(22) Filed: Jul. 12, 2017

(65) Prior Publication Data
US 2018/0015077 A1    Jan. 18, 2018

Related U.S. Application Data

(60) Provisional application No. 62/361,262, filed on Jul. 12, 2016.

(51) Int. Cl.
| | | |
|---|---|---|
| *C07D 401/14* | (2006.01) |
| *A61K 31/5377* | (2006.01) |
| *A61K 31/444* | (2006.01) |
| *A61K 31/4545* | (2006.01) |
| *A61K 31/4365* | (2006.01) |
| *C07D 495/04* | (2006.01) |
| *A61K 45/06* | (2006.01) |
| *C07D 519/00* | (2006.01) |
| *A61K 31/496* | (2006.01) |
| *A61K 31/506* | (2006.01) |
| *C07D 495/14* | (2006.01) |

(52) U.S. Cl.
CPC ........ *A61K 31/4365* (2013.01); *A61K 31/444* (2013.01); *A61K 31/4545* (2013.01); *A61K 31/496* (2013.01); *A61K 31/506* (2013.01); *A61K 31/5377* (2013.01); *A61K 45/06* (2013.01); *C07D 495/04* (2013.01); *C07D 495/14* (2013.01); *C07D 519/00* (2013.01)

(58) Field of Classification Search
CPC .. C07D 285/24; C07D 401/14; C07D 413/14; C07D 495/14; C07D 495/04; A61K 31/5377; A61K 31/444; A61K 31/506; A61K 31/4545
USPC .................... 546/167, 114; 544/12, 105, 128
See application file for complete search history.

(56) References Cited

U.S. PATENT DOCUMENTS

| | | | |
|---|---|---|---|
| 6,232,320 B1 * | 5/2001 | Stewart | C07D 493/04 514/233.8 |
| 8,138,347 B2 * | 3/2012 | Knight | C07D 285/24 544/105 |
| 2006/0074102 A1 * | 4/2006 | Cusack | A61K 31/4743 514/301 |

FOREIGN PATENT DOCUMENTS

| | | |
|---|---|---|
| WO | 9962908 | * 12/1999 |
| WO | 2000075145 | * 12/2000 |
| WO | WO-2003/022856 A1 | 3/2003 |
| WO | WO-2005/110410 A2 | 11/2005 |
| WO | WO-2005/110410 A3 | 11/2005 |
| WO | WO-2010/054393 A1 | 5/2010 |

OTHER PUBLICATIONS

Zhu et al., Journal of Heterocyclic Chemistry (2008), 45(1), 91-96.*
Cusack et al., Bioorganic & Medicinal Chemistry Letters (2009),19(6), 1722-1725.*
Baba, M. et al. (Aug. 1988). "Mechanism of inhibitory effect of dextran sulfate and heparin on replication of human immunodeficiency virus in vitro," *PNAS USA* 85(16):6132-6136.
Battiste, J.L. et al. (Sep. 13, 1996). "Alpha helix-RNA major groove recognition in an HIV-1 rev peptide-RRE RNA complex," *Science* 273(5281):1547-1551.
Calnan, B.J. et al. (May 24, 1991). "Arginine-mediated RNA recognition: the arginine fork," *Science* 252(5009):1167-1171.
Chen, L. et al. (Mar. 8, 1994). "An RNA-binding peptide from bovine immunodeficiency virus Tat protein recognizes an unusual RNA structure," *Biochemistry* 33(9):2708-2715.
Chen, L. et al. (May 23, 1995). "A peptide interaction in the major groove of RNA resembles protein interactions in the minor groove of DNA," *PNAS USA* 92(11):5077-5081.
Dejong, E.S. et al. (Jul. 8, 2003). "Proflavine acts as a Rev inhibitor by targeting the high-affinity Rev binding site of the Rev responsive element of HIV-1," *Biochemistry* 42(26):8035-8046.
Feinberg, M.B. et al. (May 1, 1991). "The role of Tat in the human immunodeficiency virus life cycle indicates a primary effect on transcriptional elongation," *PNAS USA* 88(9):4045-4049.
Hope, T.J. et al. (Oct. 1990). "Steroid-receptor fusion of the human immunodeficiency virus type 1 Rev transactivator: mapping cryptic functions of the arginine-rich motif," *PNAS USA* 87(19):7787-7791.
Jayaraman, B. et al. (Dec. 8, 2014). "RNA-directed remodeling of the HIV-1 protein Rev orchestrates assembly of the Rev-Rev response element complex," *Elife* 3:e04120.
Kao, S-Y. et al. (Dec. 3-9, 1987). "Anti-termination of transcription within the long terminal repeat of HIV-1 by tat gene product," *Nature* 330(6147):489-493.
Kudo, N. et al. (Feb. 13, 2006). "A versatile method for Suzuki cross-coupling reactions of nitrogen heterocycles," *Angew Chem Int Ed Engl* 45(8):1282-1284.
Landt, S.G. et al. (2000). "Screening RNA-binding libraries using Tat-fusion system in mammalian cells," *Methods Enzymol* 318:350-363.

(Continued)

*Primary Examiner* — Niloofar Rahmani
(74) *Attorney, Agent, or Firm* — Zachary L. Terranova; Mintz, Levin, Cohn, Ferris, Glovsky and Popeo, P.C.

(57) ABSTRACT

Provided herein, inter alia, are methods and compounds for treating an HIV infection.

20 Claims, 12 Drawing Sheets

Specification includes a Sequence Listing.

(56) References Cited

OTHER PUBLICATIONS

Marciniak, R.A. et al. (Dec. 1991). "HIV-1 Tat protein promotes formation of more-processive elongation complexes," *EMBO J* 10(13):4189-4196.

Mosmann, T. et al. (Dec. 16, 1983). "Rapid colorimetric assay for cellular growth and survival: application to proliferation and cytotoxicity assays," *J Immunol Methods* 65(1-2):55-63.

Nakamura, R.L. et al. (2012). "A cell-based method for screening RNA-protein interactions: identification of constitutive transport element-interacting proteins," *PLoS One* 7(10):e48194.

Peled-Zehavi, H. et al. (Aug. 20010. "Recognition of RNA branch point sequences by the KH domain of splicing factor 1 (mammalian branch point binding protein) in a splicing factor complex," *Mol Cell Biol* 21(15):5232-5241.

Reed, L.J. et al. (May 1938). "A Simple Method of Estimating Fifty Per Cent Endpoints," *The American Journal of Hygiene* 27(3):493-497.

Rosen, C.A. et al. (Jul. 1985). "The location of *cis*-acting regulatory sequences in the human T cell lymphotropic virus type III (HTLV-III/LAV) long terminal repeat," *Cell* 41(3):813-823.

Roy, S. et al. (Aug. 1990). "A bulge structure in HIV-1 TAR RNA is required for Tat binding and Tat-mediated trans-activation," *Genes Dev* 4(8):1365-1373.

Selby, M.J. et al. (Aug. 24, 1990). "*Trans*-activation by HIV-1 Tat via a heterologous RNA binding protein," *Cell* 62(4):769-776.

Smith, C.A. et al. (Nov. 2000). "An RNA-Binding Chameleon," *Molecular Cell* 6:1067-1076.

Southgate, C. et al. (Jun. 14, 1990). "Activation of transcription by HIV-1 Tat protein tethered to nascent RNA through another protein," *Nature* 345(6276):640-642.

Tan, R. et al. (Dec. 6, 1994). "Costabilization of peptide and RNA structure in an HIV Rev peptide-RRE complex," Biochemistry 33(48):14579-14585.

Tan, R. et al. (Apr. 14, 1998). "A novel glutamine-RNA interaction identified by screening libraries in mammalian cells," *PNAS USA* 95(8):4247-4252.

Ye, X. et al. (Dec. 1996). "Deep penetration of an alpha-helix into a widened RNA major groove in the HIV-1 rev peptide-RNA aptamer complex," *Nat Struct Biol* 3(12):1026-1033.

Shuck-Lee, D. et al. (Sep. 2008, e-published Jul. 14, 2008). "Heterocyclic compounds that inhibit Rev-RRE function and human immunodeficiency virus type 1 replication," *Antimicrob Agents Chemother* 52(9):3169-3179.

\* cited by examiner

1a ($R^1$ = H; $R^2$ = Me)
1b ($R^1$ = H; $R^2$ = $CH_2OMe$)
1c ($R^1$ = Et; $R^2$ = Me)

1d ($R^1$ = H; $R^2$ = Me; $R^3$ = OH)
1e ($R^1$ = H; $R^2$ = Me; $R^3$ = Me)

1f  2a

COMPOUNDS AND METHODS FOR TREATING HIV INFECTION

CROSS-REFERENCES TO RELATED APPLICATIONS

This application claims the benefit of U.S. Provisional Application No. 62/361,262, filed Jul. 12, 2016, which is incorporated herein by reference in entirety and for all purposes

STATEMENT AS TO RIGHTS TO INVENTIONS MADE UNDER FEDERALLY SPONSORED RESEARCH AND DEVELOPMENT

This invention was made with government support under grant nos. R41 AI076087, R43 AI075143, R41 CA103407 and GM056531, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 12, 2017, is named 48536-548001US_ST25.txt and is 1,468 bytes in size.

BACKGROUND OF THE INVENTION

Viral regulatory complexes perform critical functions and are important targets for therapeutic intervention. In HIV, the Tat and Rev proteins form regulatory complexes with multiple viral and cellular factors to direct transcription and export of the viral RNA.

Rev is a 116 amino acid RNA binding protein that is expressed early in the life cycle of the virus. Rev binds the Rev Response Element (RRE), a highly structured 270 nt RNA element encoded within the env gene. Current models suggest that six Rev molecules bind the RNA in order to properly position two of the nuclear export sequences on Rev for binding to a dimer of the Crm1-RanGTP export complex. This complex is then exported through the nuclear pore and the complex disassembles allowing for translation of the late HIV proteins and packaging of the viral genome. Identifying compounds which may provide interference with any of these interactions thus preventing the formation of a competent export complex is a challenge. Provided herein are solutions to these and other problems in the art.

BRIEF SUMMARY OF THE INVENTION

In an aspect is provided a compound having the formula:

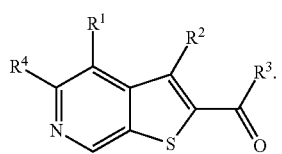

(I)

$R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)$ $NR^{1A}R^{1B}$, $-OR^{1D}$, $-NR^{1A}SO_2R^{1D}$, $-NR^{1A}C(O)R^{1C}$, $-NR^{1A}C(O)O\ R^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, $-NR^{2A}R^{2B}$, $-C(O)R^{2C}$, $-C(O)-OR^{2C}$, $-C(O)$ $NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)$ $NR^{3A}R^{3B}$, $-OR^{3D}$, $-NR^{3A}SO_2R^{3D}$, $-NR^{3A}C(O)R^{3C}$, $-NR^{3A}C(O)O\ R^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)$ $NR^{4A}R^{4B}$, $-OR^{4D}$, $-NR^{4A}SO_2R^{4D}$, $-NR^{4A}C(O)R^{4C}$, $-NR^{4A}C(O)O\ R^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, and $R^{4D}$ is independently hydrogen, $-CX_3$, $-CN$, $-NH_2$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl. Each X, $X^1$, $X^2$, $X^3$, and $X^4$ is independently $-F$, $-Cl$, $-Br$, or $-I$. n1, n3, and n4 are independently an integer from 0 to 4. m1, m3, m4, v1, v3, and v4 are independently an integer from 1 to 2.

In an aspect is provided a pharmaceutical composition including a compound described herein.

In an aspect is provided a method of inhibiting the level of Rev protein activity, the method including contacting the Rev protein with a compound described herein.

In an aspect is provided a method of inhibiting HIV virion formation in an HIV infected cell, the method including contacting the HIV infected cell with a compound described herein.

In an aspect is provided a method of inhibiting HIV viral shedding from an HIV infected cell, the method including contacting the HIV infected cell with a compound described herein.

In an aspect is provided a method of inhibiting HIV proliferation, the method including contacting HIV with a compound described herein.

In an aspect is provided a method of treating HIV infection, the method including administering to a subject in need thereof an effective amount of a compound described herein.

BRIEF DESCRIPTION OF THE DRAWINGS

FIG. 8A corresponds to analog 2b, FIG. 8B corresponds to analog 4e, and FIG. 8C corresponds to analog 4h.

FIG. 10 corresponds to analog 4e with HIV-1 isolate NL4-3 in Jurkat cells and with HIV-1 isolate NL4-3 deleted for Vpu in Jurkat cells. The IC50 value for isolate NL4-3 was determined to be 5 nM and the IC50 value for isolate NL4-3 deleted for Vpu was determined to be 150 nM.

FIG. 15A) 0.2 ng of siTat or siGFP control were transfected to the Rev-RRE reporter cell line. After 48 hours, luciferase assays were performed as previously described. This procedure effectively knocked down reporter activity while the mock transfected and siGFP control had only a modest effect on reporter output. Using this method we were able to identify two RRE IIB-Rev cell lines with z' values of 0.69 and 0.75 that were used for the small molecule library screen. FIG. 15B) We also tested the cell lines using the 3,6 diaminoacridine as a control compound that inhibits expression of the reporter.

DETAILED DESCRIPTION

I. Definitions

Figure 1:
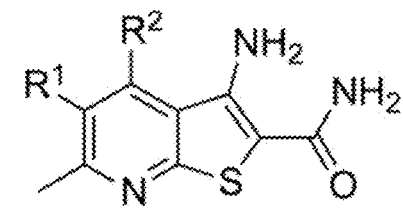
FIG. 1. Structures of hits 1a, 1b, 1c, and 1f identified in the primary screen. Commercially available analogs 1d and 1e are congeners of compounds 1a lacking the carboxamide function and were found to be inactive in the reporter assay. Compound 2a is a regioisomer of hit 1f and the heterocyclic scaffold upon which additional synthetic analogs were based.
Figure 1:
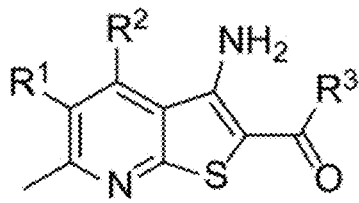
Figure 1:
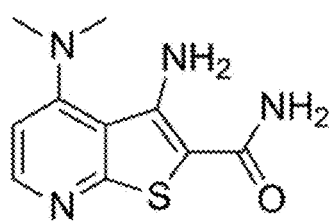
Figure 1:
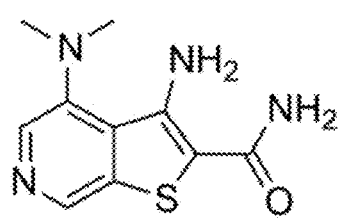

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, or Si) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuranyl, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "  " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

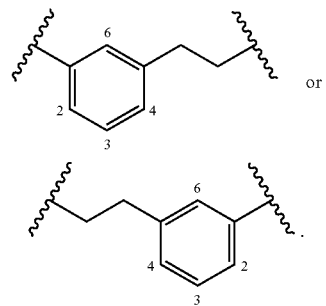

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —Cl$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cyclalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O) NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —NR'NR''R''', —ONR'R'', —NR'C(O)NR''NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R'', —NR'C(O)R'', —NR'C(O)—OR'', —NR'OR'', in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R'', R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C''R''R''')$_d$—, where s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered), and (B) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2F$, —$OCH_2I$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (ii) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2F$, —$OCH_2I$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2F$, —$OCH_2I$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An amino acid residue in a protein "corresponds" to a given residue when it occupies the same essential structural position within the protein as the given residue. Instead of a primary sequence alignment, a three dimensional structural alignment can also be used, e.g., where the structure of the selected protein is aligned for maximum correspondence with the human protein and the overall structures compared.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "REV" and "Rev" and "HIV Rev" and "regulator of expression of virion proteins" refer to a protein (including homologs, isoforms, and functional fragments thereof) that regulates the expression of human immunodeficiency virus (HIV) proteins. The term includes any recombinant or naturally-occurring form of Rev or variants thereof that maintain Rev activity (e.g. within at least 30%, 40%, 50%, 60%, 70%, 80%, 90%, 95%, or 100% activity compared to wildtype Rev). In embodiments, the Rev protein has the amino acid sequence set forth in or corresponding to GI: 12831140. In embodiments, Rev corresponds to the sequence below. In embodiments, Rev corresponds to sequences 60%, 70%, 80%, 90%, 95%, 96%, 97%, 98%, 99%, or 100% identical to the sequence below. In embodiments, Rev corresponds to a sequence that differs from the sequence below by one or more (e.g., 1, 2,3, 4,5, 6, 7, 8, 9, 10, 11, 12, 13, 14, 15, 16, 17, 18, 19, or 20) amino acid mutations. In embodiments, Rev corresponds to a fragment of the sequence below (e.g., a truncated protein):

```
                                            (SEQ ID NO: 1)
MAGRSGDSDEELIRTVRLIKLLYQSNPPPNPEGTRQARRNRRRRWRERQR
QIHSISERILSTYLGRSAEPVPLQLPPLERLTLDCNEDCGTSGTQGVGSP
QILVESPTVLESGTKE
```

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be an autoimmune disease. The disease may be an inflammatory disease. The disease may be an infectious disease (e.g., HIV infection).

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." The full therapeutic effect does not necessarily occur by administration of one dose, and may occur only after administration of a series of doses. Thus, a therapeutically effective amount may be administered in one or more administrations. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease means that the disease (e.g. inflammatory disease, autoimmune disease, or infectious disease) is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components.

II. Compounds

In as aspect is provided a compound having the formula:

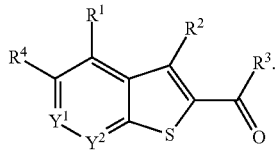

(I)

$R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ and $R^{4A1}$ may optionally be joined to form a substituted or unsubstituted cycloalkyl, substituted or unsubstituted heterocycloalkyl, substituted or unsubstituted aryl, or substituted or unsubstituted heteroaryl.

$R^{4A1}$ and $R^{4B1}$ are independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, and $R^{4D}$ is independently hydrogen, —$CX_3$, —CN, —$NH_2$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl.

Each X, $X^1$, $X^2$, $X^3$, and $X^4$ is independently —F, —Cl, —Br, or —I. The symbols n1, n2, n3, and n4 are independently an integer from 0 to 4. The symbols m1, m2, m3, m4, v1, v2, v3, and v4 are independently an integer from 1 to 2.

The symbol $Y^1$ is $CR^{4A1}$ or N. The symbol $Y^2$ is $CR^{4B1}$ or N. In embodiments, $Y^1$ is $CR^{4A1}$. In embodiments, $Y^1$ is CH. In embodiments, $Y^1$ is N. In embodiments, $Y^2$ is $CR^{4B1}$. In embodiments, $Y^2$ is CH. In embodiments, $Y^2$ is N. In embodiments, $Y^1$ is $CR^{4A1}$ and $Y^2$ is N. In embodiments, $Y^1$ is CH and $Y^2$ is N. In embodiments, $Y^1$ is N and $Y^2$ is $CR^{4B1}$. In embodiments, $Y^1$ is N and $Y^2$ is CH.

In embodiments, the compound has the formula:

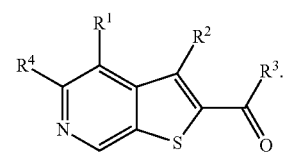

(IIA)

$R^1$, $R^2$, $R^3$, and $R^4$ are as described herein (including in embodiments).

In embodiments, the compound has the formula:

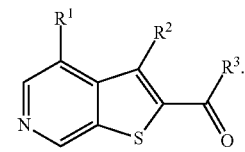

(IIB)

$R^1$, $R^2$, and $R^3$ are as described herein (including in embodiments).

In embodiments, the compound has the formula:

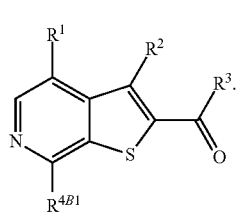
(IIC)

$R^1$, $R^2$, $R^3$, and $R^{4B1}$ are as described herein (including in embodiments).

In embodiments, the compound has the formula:

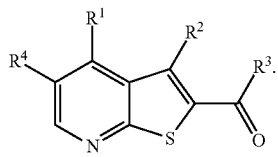
(IID)

$R^1$, $R^2$, $R^3$, and $R^4$ are as described herein (including in embodiments).

In embodiments, the compound has the formula:

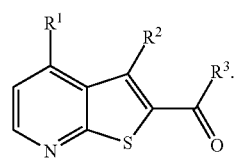
(IIE)

$R^1$, $R^2$, and $R^3$ are as described herein (including in embodiments).

In embodiments, the compound has the formula:

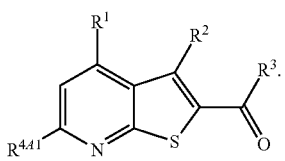
(IIF)

$R^1$, $R^2$, $R^3$, and $R^{4A1}$ are as described herein (including in embodiments).

In embodiments, the compound has the formula:

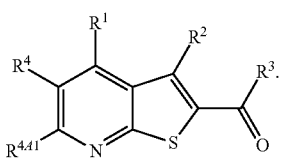
(IIG)

$R^1$, $R^2$, $R^3$, $R^4$, and $R^{4A1}$ are as described herein (including in embodiments).

In embodiments, the compound has the formula:

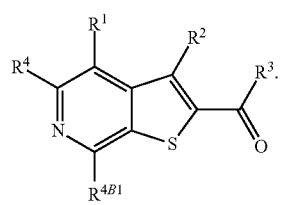
(IIH)

$R^1$, $R^2$, $R^3$, $R^4$, and $R^{4B1}$ are as described herein (including in embodiments).

In embodiments, the compound has the formula:

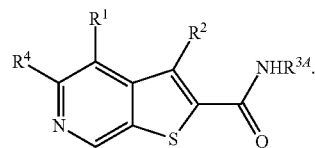
(IIIA)

$R^1$, $R^2$, $R^{3A}$, and $R^4$ are as described herein (including in embodiments).

In embodiments, the compound has the formula:

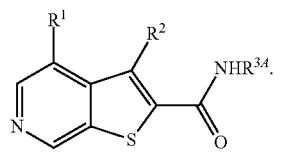
(IIIB)

$R^1$, $R^2$, and $R^{3A}$ are as described herein (including in embodiments).

In embodiments, the compound has the formula:

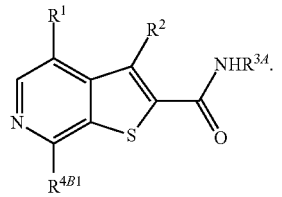
(IIIC)

$R^1$, $R^2$, $R^{3A}$, and $R^{4B1}$ are as described herein (including in embodiments).

In embodiments, the compound has the formula:

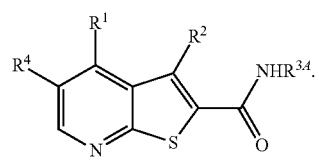
(IIID)

$R^1$, $R^2$, $R^{3A}$, and $R^4$ are as described herein (including in embodiments).

In embodiments, the compound has the formula:

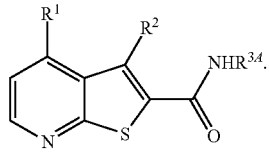
(IIIE)

$R^1$, $R^2$, and $R^{3A}$ are as described herein (including in embodiments).

In embodiments, the compound has the formula:

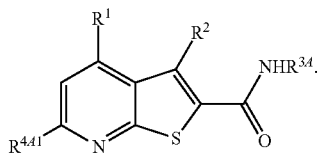
(IIIF)

$R^1$, $R^2$, $R^{3A}$, and $R^{4A1}$ are as described herein (including in embodiments).

In embodiments, the compound has the formula:

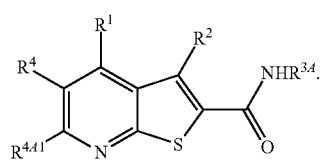
(IIIG)

$R^1$, $R^2$, $R^{3A}$, $R^4$, and $R^{4A1}$ are as described herein (including in embodiments).

In embodiments, the compound has the formula:

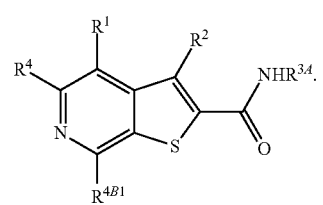
(IIIH)

$R^1$, $R^2$, $R^{3A}$, $R^4$, and $R^{4B1}$ are as described herein (including in embodiments).

In embodiments, the compound has the formula:

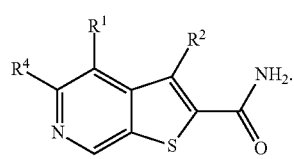
(IVA)

$R^1$, $R^2$, and $R^4$ are as described herein (including in embodiments).

In embodiments, the compound has the formula:

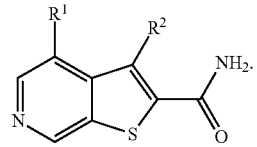
(IVB)

$R^1$, and $R^2$ are as described herein (including in embodiments).

In embodiments, the compound has the formula:

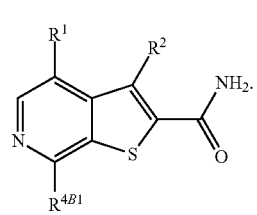
(IVC)

$R^1$, $R^2$, and $R^{4B1}$ are as described herein (including in embodiments).

In embodiments, the compound has the formula:

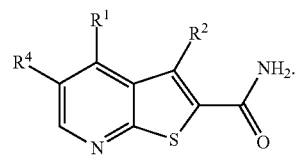
(IVD)

$R^1$, $R^2$, and $R^4$ are as described herein (including in embodiments).

In embodiments, the compound has the formula:

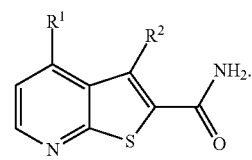
(IVE)

$R^1$ and $R^2$ are as described herein (including in embodiments).

In embodiments, the compound has the formula:

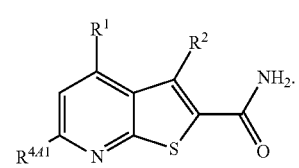
(IVF)

R¹, R², and R⁴ᴬ¹ are as described herein (including in embodiments).

In embodiments, the compound has the formula:

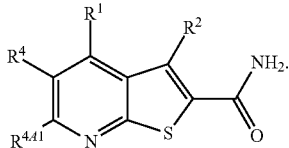
(IVG)

R¹, R², R⁴, and R⁴ᴬ¹ are as described herein (including in embodiments).

In embodiments, the compound has the formula:

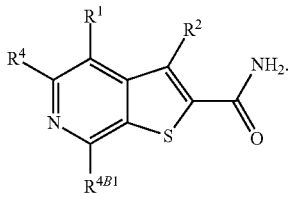
(IVH)

R¹, R², R⁴, and R⁴ᴮ¹ are as described herein (including in embodiments).

In embodiments, the compound has the formula:

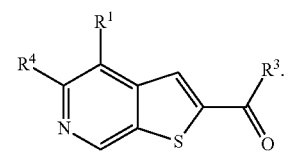
(VA)

R¹, R³, and R⁴ are as described herein (including in embodiments).

In embodiments, the compound has the formula:

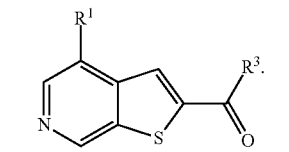
(VB)

R¹ and R³ are as described herein (including in embodiments).

In embodiments, the compound has the formula:

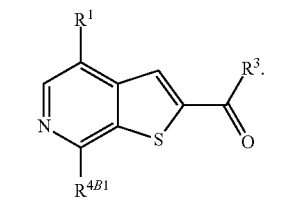
(VC)

R¹, R³, and R⁴ᴮ¹ are as described herein (including in embodiments).

In embodiments, the compound has the formula:

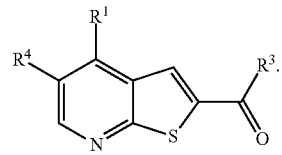
(VD)

R¹, R³, and R⁴ are as described herein (including in embodiments).

In embodiments, the compound has the formula:

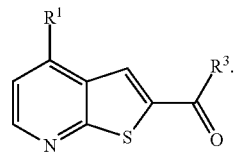
(VE)

R¹ and R³ are as described herein (including in embodiments).

In embodiments, the compound has the formula:

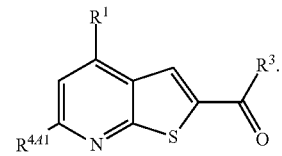
(VF)

R¹, R³, and R⁴ᴬ¹ are as described herein (including in embodiments).

In embodiments, the compound has the formula:

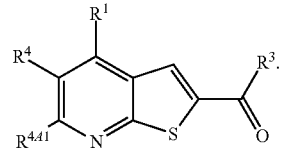
(VG)

R¹, R³, R⁴, and R⁴ᴬ¹ are as described herein (including in embodiments).

In embodiments, the compound has the formula:

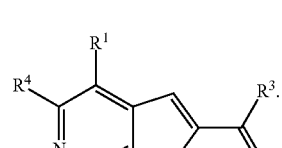
(VH)

R¹, R³, R⁴, and R⁴ᴮ¹ are as described herein (including in embodiments).

In embodiments, R¹ is independently hydrogen, halogen, —CX¹₃, —CN, —OH, —NH₂, —COOH, —CONH₂, —NO₂, —SH, —OCX¹₃, —OCHX¹₂, —CHX¹₂, —CH₂X¹, substituted or unsubstituted C₁-C₈ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^1$ is independently halogen, —$CX^1_3$, —CN, unsubstituted $C_1$-$C_4$ alkyl, or unsubstituted 2 to 4 membered heteroalkyl. In embodiments, $R^1$ is substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^1$ is independently unsubstituted methyl, unsubstituted ethyl, unsubstituted isopropyl, or unsubstituted tert-butyl. In embodiments, $R^1$ is independently unsubstituted 4-methyl, unsubstituted 4-ethyl, unsubstituted 4-isopropyl, or unsubstituted 4-tert-butyl. In embodiments, $R^1$ is independently unsubstituted 4-methyl. In embodiments, $R^1$ is independently unsubstituted 4-ethyl. In embodiments, $R^1$ is independently unsubstituted 4-isopropyl. In embodiments, $R^1$ is independently unsubstituted 4-tert-butyl. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted n-propyl. In embodiments, $R^1$ is independently unsubstituted isopropyl. In embodiments, $R^1$ is independently unsubstituted butyl. In embodiments, $R^1$ is independently unsubstituted n-butyl. In embodiments, $R^1$ is independently unsubstituted isobutyl. In embodiments, $R^1$ is independently unsubstituted tert-butyl. In embodiments, $R^1$ is independently unsubstituted pentyl. In embodiments, $R^1$ is independently unsubstituted hexyl. In embodiments, $R^1$ is independently unsubstituted heptyl. In embodiments, $R^1$ is independently unsubstituted octyl. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently unsubstituted methoxy. In embodiments, $R^1$ is independently unsubstituted ethoxy. In embodiments, $R^1$ is independently halogen. In embodiments, $R^1$ is independently —$CF_3$. In embodiments, $R^1$ is independently —$CCl_3$. In embodiments, z1 is 2 and $R^1$ is independently unsubstituted 4-isopropyl and unsubstituted 3-methyl.

In embodiments, $R^1$ is independently hydrogen. In embodiments, $R^1$ is independently halogen. In embodiments, $R^1$ is independently —$CX^1_3$. In embodiments, $R^1$ is independently —$CHX^1_2$. In embodiments, $R^1$ is independently —$CH_2X^1$. In embodiments, $R^1$ is independently —$OCX^1_3$. In embodiments, $R^1$ is independently —$OCH_2X^1$. In embodiments, $R^1$ is independently —$OCHX^1_2$. In embodiments, $R^1$ is independently —CN. In embodiments, $R^1$ is independently —$SO_{n1}R^{1D}$. In embodiments, $R^1$ is independently —$SO_{v1}NR^{1A}R^{1B}$. In embodiments, $R^1$ is independently —NHC(O)$NR^{1A}R^{1B}$. In embodiments, $R^1$ is independently —$N(O)_m$. In embodiments, $R^1$ is independently —$NR^{1A}R^{1B}$. In embodiments, $R^1$ is independently —C(O)$R^{1C}$. In embodiments, $R^1$ is independently —C(O)—$OR^{1C}$. In embodiments, $R^1$ is independently —C(O)$NR^{1A}R^{1B}$. In embodiments, $R^1$ is independently —$OR^{1D}$. In embodiments, $R^1$ is independently —$NR^{1A}SO_2R^{1D}$. In embodiments, $R^1$ is independently —$NR^{1A}C(O)R^{1C}$. In embodiments, $R^1$ is independently —$NR^{1A}C(O)OR^{1C}$. In embodiments, $R^1$ is independently —$NR^{1A}OR^{1C}$. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$NO_2$. In embodiments, $R^1$ is independently —SH.

In embodiments, $R^1$ is independently —$NR^{1A}R^{1B}$, wherein $R^{1A}$ and $R^{1B}$ are independently unsubstituted methyl. In embodiments, $R^1$ is independently —$NR^{1A}R^{1B}$, wherein $R^{1A}$ and $R^{1B}$ are independently substituted or unsubstituted $C_1$-$C_4$ alkyl. In embodiments, $R^1$ is not —$OR^{1D}$. In embodiments, $R^1$ is not —$SR^{1D}$. In embodiments, $R^1$ is not halogen. In embodiments, $R^1$ is not —$NHR^{1B}$, wherein $R^{1B}$ is a substituted or unsubstituted phenyl.

In embodiments, $R^1$ is independently substituted or unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently, substituted or unsubstituted heterocycloalkyl. In embodiments, $R^1$ is independently substituted or unsubstituted aryl. In embodiments, $R^1$ is independently substituted or unsubstituted heteroaryl.

In embodiments, $R^1$ is independently substituted alkyl. In embodiments, $R^1$ is independently substituted heteroalkyl. In embodiments, $R^1$ is independently substituted cycloalkyl. In embodiments, $R^1$ is independently, substituted heterocycloalkyl. In embodiments, $R^1$ is independently substituted aryl. In embodiments, $R^1$ is independently substituted heteroaryl. In embodiments, $R^1$ is independently unsubstituted alkyl. In embodiments, $R^1$ is independently unsubstituted heteroalkyl. In embodiments, $R^1$ is independently unsubstituted cycloalkyl. In embodiments, $R^1$ is independently, unsubstituted heterocycloalkyl. In embodiments, $R^1$ is independently unsubstituted aryl. In embodiments, $R^1$ is independently unsubstituted heteroaryl.

In embodiments, $R^1$ is independently substituted or unsubstituted $C_1$-$C_8$ alkyl. In embodiments, $R^1$ is independently substituted or unsubstituted 2 to 8 membered heteroalkyl. In embodiments, $R^1$ is independently substituted or unsubstituted $C_3$-$C_8$ cycloalkyl. In embodiments, $R^1$ is independently, substituted or unsubstituted 3 to 8 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, $R^1$ is independently substituted $C_1$-$C_8$ alkyl. In embodiments, $R^1$ is independently substituted 2 to 8 membered heteroalkyl. In embodiments, $R^1$ is independently substituted $C_3$-$C_8$ cycloalkyl. In embodiments, $R^1$ is independently, substituted 3 to 8 membered heterocycloalkyl. In embodiments, $R^1$ is independently substituted $C_6$-$C_{10}$ aryl. In embodiments, $R^1$ is independently substituted 5 to 10 membered heteroaryl. In embodiments, $R^1$ is independently unsubstituted $C_1$-$C_8$ alkyl. In embodiments, $R^1$ is independently unsubstituted 2 to 8 membered heteroalkyl. In embodiments, $R^1$ is independently unsubstituted $C_3$-$C_8$ cycloalkyl. In embodiments, $R^1$ is independently, unsubstituted 3 to 8 membered heterocycloalkyl. In embodiments, $R^1$ is independently unsubstituted $C_6$-$C_{10}$ aryl. In embodiments, $R^1$ is independently unsubstituted 5 to 10 membered heteroaryl.

In embodiments, $R^1$ is independently substituted or unsubstituted $C_1$-$C_4$ alkyl. In embodiments, $R^1$ is independently substituted or unsubstituted 2 to 4 membered heteroalkyl. In embodiments, $R^1$ is independently substituted or unsubstituted $C_3$-$C_6$ cycloalkyl. In embodiments, $R^1$ is independently, substituted or unsubstituted 3 to 6 membered heterocycloalkyl. In embodiments, $R^1$ is independently substituted or unsubstituted phenyl. In embodiments, $R^1$ is independently substituted or unsubstituted 5 to 6 membered heteroaryl.

In embodiments, $R^1$ is independently substituted $C_1$-$C_4$ alkyl. In embodiments, $R^1$ is independently substituted 2 to 4 membered heteroalkyl. In embodiments, $R^1$ is independently substituted $C_3$-$C_6$ cycloalkyl. In embodiments, $R^1$ is independently, substituted 3 to 6 membered heterocycloalkyl. In embodiments, $R^1$ is independently substituted phenyl. In embodiments, $R^1$ is independently substituted 5 to 6 membered heteroaryl. In embodiments, $R^1$ is independently unsubstituted $C_1$-$C_4$ alkyl. In embodiments, $R^1$ is independently unsubstituted 2 to 4 membered heteroalkyl. In embodiments, $R^1$ is independently unsubstituted $C_3$-$C_6$ cycloalkyl. In embodiments, $R^1$ is independently unsubstituted 3 to 6 membered heterocycloalkyl. In embodiments, $R^1$ is independently unsubstituted phenyl. In embodiments, $R^1$ is independently unsubstituted 5 to 6 membered heteroaryl.

In embodiments, $R^{1A}$ is independently hydrogen. In embodiments, $R^{1A}$ is independently —$CX^{1A}_3$. In embodiments, $R^{1A}$ is independently —$CHX^{1A}_2$. In embodiments, $R^{1A}$ is independently —$CH_2X^{1A}$. In embodiments, $R^{1A}$ is independently —CN. In embodiments, $R^{1A}$ is independently —COOH. In embodiments, $R^{1A}$ is independently —$CONH_2$. In embodiments, $R^{1A}$ is independently substituted or unsubstituted alkyl. In embodiments, $R^{1A}$ is independently substituted or unsubstituted heteroalkyl. In embodiments, $R^{1A}$ is independently substituted or unsubstituted cycloalkyl. In embodiments, $R^{1A}$ is independently, substituted or unsubstituted heterocycloalkyl. In embodiments, $R^{1A}$ is independently substituted or unsubstituted aryl. In embodiments, $R^{1A}$ is independently substituted or unsubstituted heteroaryl.

In embodiments, $R^{1A}$ is independently substituted alkyl. In embodiments, $R^{1A}$ is independently substituted heteroalkyl. In embodiments, $R^{1A}$ is independently substituted cycloalkyl. In embodiments, $R^{1A}$ is independently, substituted heterocycloalkyl. In embodiments, $R^{1A}$ is independently substituted aryl. In embodiments, $R^{1A}$ is independently substituted heteroaryl. In embodiments, $R^{1A}$ is independently unsubstituted alkyl. In embodiments, $R^{1A}$ is independently unsubstituted heteroalkyl. In embodiments, $R^{1A}$ is independently unsubstituted cycloalkyl. In embodiments, $R^{1A}$ is independently, unsubstituted heterocycloalkyl. In embodiments, $R^{1A}$ is independently unsubstituted aryl. In embodiments, $R^{1A}$ is independently unsubstituted heteroaryl.

In embodiments, $R^{1A}$ is independently substituted or unsubstituted $C_1$-$C_8$ alkyl. In embodiments, $R^{1A}$ is independently substituted or unsubstituted 2 to 8 membered heteroalkyl. In embodiments, $R^{1A}$ is independently substituted or unsubstituted $C_3$-$C_8$ cycloalkyl. In embodiments, $R^{1A}$ is independently, substituted or unsubstituted 3 to 8 membered heterocycloalkyl. In embodiments, $R^{1A}$ is independently substituted or unsubstituted $C_6$-$C_{10}$ aryl. In embodiments, $R^{1A}$ is independently substituted or unsubstituted 5 to 10 membered heteroaryl.

In embodiments, $R^{1A}$ is independently substituted $C_1$-$C_8$ alkyl. In embodiments, $R^{1A}$ is independently substituted 2 to 8 membered heteroalkyl. In embodiments, $R^{1A}$ is independently substituted $C_3$-$C_8$ cycloalkyl. In embodiments, $R^{1A}$ is independently, substituted 3 to 8 membered heterocycloalkyl. In embodiments, $R^{1A}$ is independently substituted $C_6$-$C_{10}$ aryl. In embodiments, $R^{1A}$ is independently substituted 5 to 10 membered heteroaryl. In embodiments, $R^{1A}$ is independently unsubstituted $C_1$-$C_8$ alkyl. In embodiments, $R^{1A}$ is independently unsubstituted 2 to 8 membered heteroalkyl. In embodiments, $R^{1A}$ is independently unsubstituted $C_3$-$C_8$ cycloalkyl. In embodiments, $R^{1A}$ is independently, unsubstituted 3 to 8 membered heterocycloalkyl. In embodiments, $R^{1A}$ is independently unsubstituted $C_6$-$C_{10}$ aryl. In embodiments, $R^{1A}$ is independently unsubstituted 5 to 10 membered heteroaryl.

In embodiments, $R^{1A}$ is independently substituted or unsubstituted $C_1$-$C_4$ alkyl. In embodiments, $R^{1A}$ is independently substituted or unsubstituted $C_1$-$C_2$ alkyl. In embodiments, $R^{1A}$ is independently substituted or unsubstituted 2 to 4 membered heteroalkyl. In embodiments, $R^{1A}$ is independently substituted or unsubstituted $C_3$-$C_6$ cycloalkyl. In embodiments, $R^{1A}$ is independently, substituted or unsubstituted 3 to 6 membered heterocycloalkyl. In embodiments, $R^{1A}$ is independently substituted or unsubstituted phenyl. In embodiments, $R^{1A}$ is independently substituted or unsubstituted 5 to 6 membered heteroaryl. In embodiments, $R^{1A}$ is independently substituted $C_1$-$C_4$ alkyl. In embodiments, $R^{1A}$ is independently substituted 2 to 4 membered heteroalkyl. In embodiments, $R^{1A}$ is independently substituted $C_3$-$C_6$ cycloalkyl. In embodiments, $R^{1A}$ is independently, substituted 3 to 6 membered heterocycloalkyl. In embodiments, $R^{1A}$ is independently substituted phenyl. In embodiments, $R^{1A}$ is independently substituted 5 to 6 membered heteroaryl. In embodiments, $R^{1A}$ is independently unsubstituted $C_1$-$C_4$ alkyl. In embodiments, $R^{1A}$ is independently unsubstituted 2 to 4 membered heteroalkyl. In embodiments, $R^{1A}$ is independently unsubstituted $C_3$-$C_6$ cycloalkyl. In embodiments, $R^{1A}$ is independently unsubstituted 3 to 6 membered heterocycloalkyl. In embodiments, $R^{1A}$ is independently unsubstituted phenyl. In embodiments, $R^{1A}$ is independently unsubstituted 5 to 6 membered heteroaryl.

In embodiments, $R^{1A}$ is independently unsubstituted methyl. In embodiments, $R^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl.

In embodiments, $R^{1B}$ is independently hydrogen. In embodiments, $R^{1B}$ is independently —$CX^{1B}_3$. In embodiments, $R^{1B}$ is independently —$CHX^{1B}_2$. In embodiments, $R^{1B}$ is independently —$CH_2X^{1B}$. In embodiments, $R^{1B}$ is independently —CN. In embodiments, $R^{1B}$ is independently —COOH. In embodiments, $R^{1B}$ is independently —$CONH_2$. In embodiments, $R^{1B}$ is independently substituted or unsubstituted alkyl. In embodiments, $R^{1B}$ is independently substituted or unsubstituted heteroalkyl. In embodiments, $R^{1B}$ is independently substituted or unsubstituted cycloalkyl. In embodiments, $R^{1B}$ is independently, substituted or unsubstituted heterocycloalkyl. In embodiments, $R^{1B}$ is independently substituted or unsubstituted aryl. In embodiments, $R^{1B}$ is independently substituted or unsubstituted heteroaryl.

In embodiments, $R^{1B}$ is independently substituted alkyl. In embodiments, $R^{1B}$ is independently substituted heteroalkyl. In embodiments, $R^{1B}$ is independently substituted cycloalkyl. In embodiments, $R^{1B}$ is independently, substituted heterocycloalkyl. In embodiments, $R^{1B}$ is independently substituted aryl. In embodiments, $R^{1B}$ is independently substituted heteroaryl. In embodiments, $R^{1B}$ is independently unsubstituted alkyl. In embodiments, $R^{1B}$ is independently unsubstituted heteroalkyl. In embodiments, $R^{1B}$ is independently unsubstituted cycloalkyl. In embodiments, $R^{1B}$ is independently, unsubstituted heterocycloalkyl. In embodiments, $R^{1B}$ is independently unsubstituted aryl. In embodiments, $R^{1B}$ is independently unsubstituted heteroaryl.

In embodiments, $R^{1B}$ is independently substituted or unsubstituted $C_1$-$C_8$ alkyl. In embodiments, $R^{1B}$ is independently substituted or unsubstituted 2 to 8 membered heteroalkyl. In embodiments, $R^{1B}$ is independently substituted or unsubstituted $C_3$-$C_8$ cycloalkyl. In embodiments, $R^{1B}$ is independently, substituted or unsubstituted 3 to 8 membered heterocycloalkyl. In embodiments, $R^{1B}$ is independently substituted or unsubstituted $C_6$-$C_{10}$ aryl. In embodiments, $R^{1B}$ is independently substituted or unsubstituted 5 to 10 membered heteroaryl. In embodiments, $R^{1B}$ is independently substituted $C_1$-$C_8$ alkyl. In embodiments, $R^{1B}$ is independently substituted 2 to 8 membered heteroalkyl. In embodiments, $R^{1B}$ is independently substituted $C_3$-$C_8$ cycloalkyl. In embodiments, $R^{1B}$ is independently, substituted 3 to 8 membered heterocycloalkyl. In embodiments, $R^{1B}$ is independently substituted $C_6$-$C_{10}$ aryl. In embodiments, $R^{1B}$ is independently substituted 5 to 10 membered heteroaryl. In embodiments, $R^{1B}$ is independently unsubstituted $C_1$-$C_8$ alkyl. In embodiments, $R^{1B}$ is independently unsubstituted 2 to 8 membered heteroalkyl. In embodiments, $R^{1B}$ is independently unsubstituted $C_3$-$C_8$ cycloalkyl. In embodiments, $R^{1B}$ is independently, unsubstituted 3 to 8 membered heterocycloalkyl. In embodiments, $R^{1B}$ is independently unsubstituted $C_6$-$C_{10}$ aryl. In embodiments, $R^{1B}$ is independently unsubstituted 5 to 10 membered heteroaryl.

In embodiments, $R^{1B}$ is independently substituted or unsubstituted $C_1$-$C_4$ alkyl. In embodiments, $R^{1B}$ is independently substituted or unsubstituted $C_1$-$C_2$ alkyl. In embodiments, $R^{1B}$ is independently substituted or unsubstituted 2 to 4 membered heteroalkyl. In embodiments, $R^{1B}$ is independently substituted or unsubstituted $C_3$-$C_6$ cycloalkyl. In embodiments, $R^{1B}$ is independently, substituted or unsubstituted 3 to 6 membered heterocycloalkyl. In embodiments, $R^{1B}$ is independently substituted or unsubstituted phenyl. In embodiments, $R^{1B}$ is independently substituted or unsubstituted 5 to 6 membered heteroaryl.

In embodiments, $R^{1B}$ is independently substituted $C_1$-$C_4$ alkyl. In embodiments, $R^{1B}$ is independently substituted 2 to 4 membered heteroalkyl. In embodiments, $R^{1B}$ is independently substituted $C_3$-$C_6$ cycloalkyl. In embodiments, $R^{1B}$ is independently, substituted 3 to 6 membered heterocycloalkyl. In embodiments, $R^{1B}$ is independently substituted phenyl. In embodiments, $R^{1B}$ is independently substituted 5 to 6 membered heteroaryl. In embodiments, $R^{1B}$ is independently unsubstituted $C_1$-$C_4$ alkyl. In embodiments, $R^{1B}$ is independently unsubstituted 2 to 4 membered heteroalkyl. In embodiments, $R^{1B}$ is independently unsubstituted $C_3$-$C_6$ cycloalkyl. In embodiments, $R^{1B}$ is independently unsubstituted 3 to 6 membered heterocycloalkyl. In embodiments, $R^{1B}$ is independently unsubstituted phenyl. In embodiments, $R^{1B}$ is independently unsubstituted 5 to 6 membered heteroaryl.

In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl.

In embodiments, $R^{1A}$ and $R^{1B}$ substituents bonded to the same nitrogen atom may be joined to form a substituted or unsubstituted heterocycloalkyl. In embodiments, $R^{1A}$ and $R^{1B}$ substituents bonded to the same nitrogen atom may be joined to form a substituted or unsubstituted heteroaryl. In embodiments, $R^{1A}$ and $R^{1B}$ substituents bonded to the same nitrogen atom may be joined to form a substituted heterocycloalkyl. In embodiments, $R^{1A}$ and $R^{1B}$ substituents bonded to the same nitrogen atom may be joined to form a substituted heteroaryl. In embodiments, $R^{1A}$ and $R^{1B}$ substituents bonded to the same nitrogen atom may be joined to form an unsubstituted heterocycloalkyl. In embodiments, $R^{1A}$ and $R^{1B}$ substituents bonded to the same nitrogen atom may be joined to form an unsubstituted heteroaryl. In embodiments, $R^{1A}$ and $R^{1B}$ substituents bonded to the same nitrogen atom may be joined to form a substituted or unsubstituted 3 to 8 membered heterocycloalkyl. In embodiments, $R^{1A}$ and $R^{1B}$ substituents bonded to the same nitrogen atom may be joined to form a substituted or unsubstituted 5 to 10 membered heteroaryl. In embodiments, $R^{1A}$ and $R^{1B}$ substituents bonded to the same nitrogen atom may be joined to form a substituted 3 to 8 membered heterocycloalkyl. In embodiments, $R^{1A}$ and $R^{1B}$ substituents bonded to the same nitrogen atom may be joined to form a substituted 5 to 10 membered heteroaryl. In embodiments, $R^{1A}$ and $R^{1B}$ substituents bonded to the same nitrogen atom may be joined to form an unsubstituted 3 to 8 membered heterocycloalkyl. In embodiments, $R^{1A}$ and $R^{1B}$ substituents bonded to the same nitrogen atom may be joined to form an unsubstituted 5 to 10 membered heteroaryl. In embodiments, $R^{1A}$ and $R^{1B}$ substituents bonded to the same nitrogen atom may be joined to form a substituted or unsubstituted 3 to 6 membered heterocycloalkyl. In embodiments, $R^{1A}$ and $R^{1B}$ substituents bonded to the same nitrogen atom may be joined to form a substituted or unsubstituted 5 to 6 membered heteroaryl. In embodiments, $R^{1A}$ and $R^{1B}$ substituents bonded to the same nitrogen atom may be joined to form a substituted 3 to 6 membered heterocycloalkyl. In embodiments, $R^{1A}$ and $R^{1B}$ substituents bonded to the same nitrogen atom may be joined to form a substituted 5 to 6 membered heteroaryl. In embodiments, $R^{1A}$ and $R^{1B}$ substituents bonded to the same nitrogen atom may be joined to form an unsubstituted 3 to 6 membered heterocycloalkyl. In embodiments, $R^{1A}$ and $R^{1B}$ substituents bonded to the same nitrogen atom may be joined to form an unsubstituted 5 to 6 membered heteroaryl.

In embodiments, $R^{1C}$ is independently hydrogen. In embodiments, $R^{1C}$ is independently —$CX^{1C}_3$. In embodiments, $R^{1C}$ is independently —$CHX^{1C}_2$. In embodiments, $R^{1C}$ is independently —$CH_2X^{1C}$. In embodiments, $R^{1C}$ is independently —CN. In embodiments, $R^{1C}$ is independently —COOH. In embodiments, $R^{1C}$ is independently —$CONH_2$. In embodiments, $R^{1C}$ is independently substituted or unsubstituted alkyl. In embodiments, $R^{1C}$ is independently substituted or unsubstituted heteroalkyl. In embodiments, $R^{1C}$ is independently substituted or unsubstituted cycloalkyl. In embodiments, $R^{1C}$ is independently, substituted or unsubstituted heterocycloalkyl. In embodiments, $R^{1C}$ is independently substituted or unsubstituted aryl. In embodiments, $R^{1C}$ is independently substituted or unsubstituted heteroaryl.

In embodiments, $R^{1C}$ is independently substituted alkyl. In embodiments, $R^{1C}$ is independently substituted heteroalkyl. In embodiments, $R^{1C}$ is independently substituted cycloalkyl. In embodiments, $R^{1C}$ is independently, substituted heterocycloalkyl. In embodiments, $R^{1C}$ is independently substituted aryl. In embodiments, $R^{1C}$ is independently substituted heteroaryl. In embodiments, $R^{1C}$ is independently unsubstituted alkyl. In embodiments, $R^{1C}$ is independently unsubstituted heteroalkyl. In embodiments, $R^{1C}$ is independently unsubstituted cycloalkyl. In embodiments, $R^{1C}$ is independently, unsubstituted heterocycloalkyl. In embodiments, $R^{1C}$ is independently unsubstituted aryl. In embodiments, $R^{1C}$ is independently unsubstituted heteroaryl.

In embodiments, $R^{1C}$ is independently substituted or unsubstituted $C_1$-$C_8$ alkyl. In embodiments, $R^{1C}$ is independently substituted or unsubstituted 2 to 8 membered heteroalkyl. In embodiments, $R^{1C}$ is independently substituted or unsubstituted $C_3$-$C_8$ cycloalkyl. In embodiments, $R^{1C}$ is independently, substituted or unsubstituted 3 to 8 membered heterocycloalkyl. In embodiments, $R^{1C}$ is independently substituted or unsubstituted $C_6$-$C_{10}$ aryl. In embodiments, $R^{1C}$ is independently substituted or unsubstituted 5 to 10 membered heteroaryl.

In embodiments, $R^{1C}$ is independently substituted $C_1$-$C_8$ alkyl. In embodiments, $R^{1C}$ is independently substituted 2 to 8 membered heteroalkyl. In embodiments, $R^{1C}$ is independently substituted $C_3$-$C_8$ cycloalkyl. In embodiments, $R^{1C}$ is independently, substituted 3 to 8 membered heterocycloalkyl. In embodiments, $R^{1C}$ is independently substituted $C_6$-$C_{10}$ aryl. In embodiments, $R^{1C}$ is independently substituted 5 to 10 membered heteroaryl. In embodiments, $R^{1C}$ is independently unsubstituted $C_1$-$C_8$ alkyl. In embodiments, $R^{1C}$ is independently unsubstituted 2 to 8 membered heteroalkyl. In embodiments, $R^{1C}$ is independently unsubstituted $C_3$-$C_8$ cycloalkyl. In embodiments, $R^{1C}$ is independently, unsubstituted 3 to 8 membered heterocycloalkyl. In embodiments, $R^{1C}$ is independently unsubstituted $C_6$-$C_{10}$ aryl. In embodiments, $R^{1C}$ is independently unsubstituted 5 to 10 membered heteroaryl.

In embodiments, $R^{1C}$ is independently substituted or unsubstituted $C_1$-$C_4$ alkyl. In embodiments, $R^{1C}$ is independently substituted or unsubstituted 2 to 4 membered heteroalkyl. In embodiments, $R^{1C}$ is independently substituted or unsubstituted $C_3$-$C_6$ cycloalkyl. In embodiments, $R^{1C}$ is independently, substituted or unsubstituted 3 to 6 membered heterocycloalkyl. In embodiments, $R^{1C}$ is independently substituted or unsubstituted phenyl. In embodiments, $R^{1C}$ is independently substituted or unsubstituted 5 to 6 membered heteroaryl.

In embodiments, $R^{1C}$ is independently substituted $C_1$-$C_4$ alkyl. In embodiments, $R^{1C}$ is independently substituted 2 to 4 membered heteroalkyl. In embodiments, $R^{1C}$ is independently substituted $C_3$-$C_6$ cycloalkyl. In embodiments, $R^{1C}$ is independently, substituted 3 to 6 membered heterocycloalkyl. In embodiments, $R^{1C}$ is independently substituted phenyl. In embodiments, $R^{1C}$ is independently substituted 5 to 6 membered heteroaryl. In embodiments, $R^{1C}$ is independently unsubstituted $C_1$-$C_4$ alkyl. In embodiments, $R^{1C}$ is independently unsubstituted 2 to 4 membered heteroalkyl. In embodiments, $R^{1C}$ is independently unsubstituted $C_3$-$C_6$ cycloalkyl. In embodiments, $R^{1C}$ is independently unsubstituted 3 to 6 membered heterocycloalkyl. In embodiments, $R^{1C}$ is independently unsubstituted phenyl. In embodiments, $R^{1C}$ is independently unsubstituted 5 to 6 membered heteroaryl. In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl.

In embodiments, $R^{1D}$ is independently hydrogen. In embodiments, $R^{1D}$ is independently $-CX^{1D}_3$. In embodiments, $R^{1D}$ is independently $-CHX^{1D}_2$. In embodiments, $R^{1D}$ is independently $-CH_2X^{1D}$. In embodiments, $R^{1D}$ is independently $-CN$. In embodiments, $R^{1D}$ is independently $-COOH$. In embodiments, $R^{1D}$ is independently $-CONH_2$. In embodiments, $R^{1D}$ is independently substituted or unsubstituted alkyl. In embodiments, $R^{1D}$ is independently substituted or unsubstituted heteroalkyl. In embodiments, $R^{1D}$ is independently substituted or unsubstituted cycloalkyl. In embodiments, $R^{1D}$ is independently, substituted or unsubstituted heterocycloalkyl. In embodiments, $R^{1D}$ is independently substituted or unsubstituted aryl. In embodiments, $R^{1D}$ is independently substituted or unsubstituted heteroaryl.

In embodiments, $R^{1D}$ is independently substituted alkyl. In embodiments, $R^{1D}$ is independently substituted heteroalkyl. In embodiments, $R^{1D}$ is independently substituted cycloalkyl. In embodiments, $R^{1D}$ is independently, substituted heterocycloalkyl. In embodiments, $R^{1D}$ is independently substituted aryl. In embodiments, $R^{1D}$ is independently substituted heteroaryl. In embodiments, $R^{1D}$ is independently unsubstituted alkyl. In embodiments, $R^{1D}$ is independently unsubstituted heteroalkyl. In embodiments, $R^{1D}$ is independently unsubstituted cycloalkyl. In embodiments, $R^{1D}$ is independently, unsubstituted heterocycloalkyl. In embodiments, $R^{1D}$ is independently unsubstituted aryl. In embodiments, $R^{1D}$ is independently unsubstituted heteroaryl.

In embodiments, $R^{1D}$ is independently substituted or unsubstituted $C_1$-$C_8$ alkyl. In embodiments, $R^{1D}$ is independently substituted or unsubstituted 2 to 8 membered heteroalkyl. In embodiments, $R^{1D}$ is independently substituted or unsubstituted $C_3$-$C_8$ cycloalkyl. In embodiments, $R^{1D}$ is independently, substituted or unsubstituted 3 to 8 membered heterocycloalkyl. In embodiments, $R^{1D}$ is independently substituted or unsubstituted $C_6$-$C_{10}$ aryl. In embodiments, $R^{1D}$ is independently substituted or unsubstituted 5 to 10 membered heteroaryl.

In embodiments, $R^{1D}$ is independently substituted $C_1$-$C_8$ alkyl. In embodiments, $R^{1D}$ is independently substituted 2 to 8 membered heteroalkyl. In embodiments, $R^{1D}$ is independently substituted $C_3$-$C_8$ cycloalkyl. In embodiments, $R^{1D}$ is independently, substituted 3 to 8 membered heterocycloalkyl. In embodiments, $R^{1D}$ is independently substituted $C_6$-$C_{10}$ aryl. In embodiments, $R^{1D}$ is independently substituted 5 to 10 membered heteroaryl. In embodiments, $R^{1D}$ is independently unsubstituted $C_1$-$C_8$ alkyl. In embodiments, $R^{1D}$ is independently unsubstituted 2 to 8 membered heteroalkyl. In embodiments, $R^{1D}$ is independently unsubstituted $C_3$-$C_8$ cycloalkyl. In embodiments, $R^{1D}$ is independently, unsubstituted 3 to 8 membered heterocycloalkyl. In embodiments, $R^{1D}$ is independently unsubstituted $C_6$-$C_{10}$ aryl. In embodiments, $R^{1D}$ is independently unsubstituted 5 to 10 membered heteroaryl.

In embodiments, $R^{1D}$ is independently substituted or unsubstituted $C_1$-$C_4$ alkyl. In embodiments, $R^{1D}$ is independently substituted or unsubstituted 2 to 4 membered heteroalkyl. In embodiments, $R^{1D}$ is independently substituted or unsubstituted $C_3$-$C_6$ cycloalkyl. In embodiments, $R^{1D}$ is independently, substituted or unsubstituted 3 to 6 membered heterocycloalkyl. In embodiments, $R^{1D}$ is independently substituted or unsubstituted phenyl. In embodiments, $R^{1D}$ is independently substituted or unsubstituted 5 to 6 membered heteroaryl.

In embodiments, $R^{1D}$ is independently substituted $C_1$-$C_4$ alkyl. In embodiments, $R^{1D}$ is independently substituted 2 to 4 membered heteroalkyl. In embodiments, $R^{1D}$ is independently substituted $C_3$-$C_6$ cycloalkyl. In embodiments, $R^{1D}$ is independently, substituted 3 to 6 membered heterocycloalkyl. In embodiments, $R^{1D}$ is independently substituted phenyl. In embodiments, $R^{1D}$ is independently substituted 5 to 6 membered heteroaryl. In embodiments, $R^{1D}$ is independently unsubstituted $C_1$-$C_4$ alkyl. In embodiments, $R^{1D}$ is independently unsubstituted 2 to 4 membered heteroalkyl. In embodiments, $R^{1D}$ is independently unsubstituted $C_3$-$C_6$ cycloalkyl. In embodiments, $R^{1D}$ is independently unsubstituted 3 to 6 membered heterocycloalkyl. In embodiments, $R^{1D}$ is independently unsubstituted phenyl. In embodiments, $R^{1D}$ is independently unsubstituted 5 to 6 membered heteroaryl. In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl.

In embodiments, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl. In embodiments, $R^1$ is independently halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^1_3$, $-OCHX^1_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In embodiments, $R^1$ is independently halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^1_3$, $-OCHX^1_2$, $R^{20}$-substituted or unsubstituted $C_1$-$C_8$ alkyl, $R^{20}$-substituted or unsubstituted 2 to 8 membered heteroalkyl, $R^{20}$-substituted or unsubstituted $C_3$-$C_8$ cycloalkyl, $R^{20}$-substituted or unsubstituted 3 to 6 membered heterocycloalkyl, $R^{20}$-substituted or unsubstituted phenyl, or $R^{20}$-substituted or unsubstituted 5 to 6 membered heteroaryl. $X^1$ is $-F$, $-Cl$, $-Br$, or $-I$.

In embodiments, $R^1$ is independently hydrogen. In embodiments, $R^1$ is independently substituted or unsubstituted methyl. In embodiments, $R^1$ is independently substituted or unsubstituted ethyl. In embodiments, $R^1$ is independently an unsubstituted methyl. In embodiments, $R^1$ is independently an unsubstituted ethyl. In embodiments, $R^1$ is independently a $R^{20}$-substituted methyl. In embodiments, $R^1$ is $R^{20}$-substituted ethyl. In embodiments, $R^1$ is substituted or unsubstituted cycloalkyl, substituted or unsubstituted heterocycloalkyl, substituted or unsubstituted aryl, or substituted or unsubstituted heteroaryl. In embodiments, $R^1$ is $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In embodiments, $R^1$ is a substituted phenyl. In embodiments, $R^1$ is a substituted pyridinyl. In embodiments, $R^1$ is a substituted pyridyl. In embodiments, $R^1$ is a substituted pyrazinyl. In embodiments, $R^1$ is a substituted pyrimidinyl. In embodiments, $R^1$ is a substituted pyridazinyl. In embodiments, $R^1$ is a substituted pyrrolyl. In embodiments, $R^1$ is a substituted furanyl. In embodiments, $R^1$ is a substituted thienyl. In embodiments, $R^1$ is a substituted imidazolyl. In embodiments, $R^1$ is a substituted pyrazolyl. In embodiments, $R^1$ is a substituted oxazolyl. In embodiments, $R^1$ is a substituted isoxazolyl. In embodiments, $R^1$ is a substituted thiazolyl. In embodiments, $R^1$ is a substituted isothiazolyl. In embodiments, $R^1$ is a substituted triazolyl. In embodiments, $R^1$ is a substituted oxadiazolyl. In embodiments, $R^1$ is a substituted piperazinyl. In embodiments, $R^1$ is a substituted piperidinyl. In embodiments, $R^1$ is a substituted pyrrolidinyl. In embodiments, $R^1$ is a substituted azetidinyl. In embodiments, $R^1$ is a substituted aziridinyl. In embodiments, $R^1$ is a substituted morpholinyl. In embodiments, $R^1$ is a substituted dioxanyl. In embodiments, R is a substituted tetrahydropyranyl. In embodiments, $R^1$ is a substituted tetrahydrofuranyl. In embodiments, $R^1$ is a substituted oxetanyl. In embodiments, $R^1$ is a substituted oxiranyl. In embodiments, $R^1$ is a substituted triazinyl. In embodiments, $R^1$ is a substituted quinolinyl. In embodiments, $R^1$ is a substituted isoquinolinyl. In embodiments, $R^1$ is a substituted quinazolinyl. In embodiments, $R^1$ is a substituted quinoxalinyl. In embodiments, $R^1$ is a substituted thiadiazolyl. In embodiments, $R^1$ is a substituted tetrazolyl. In embodiments, $R^1$ is a substituted indolyl. In embodiments, $R^1$ is a substituted indazolyl. In embodiments, $R^1$ is a substituted benzimidazolyl. In embodiments, $R^1$ is a substituted azaindolyl. In embodiments, $R^1$ is a substituted purinyl. In embodiments, $R^1$ is a substituted benzofuranyl. In embodiments, $R^1$ is a substituted benzothienyl.

In embodiments, $R^1$ is a $R^{20}$-substituted phenyl. In embodiments, $R^1$ is a $R^{20}$-substituted pyridinyl. In embodiments, $R^1$ is a $R^{20}$-substituted pyridyl. In embodiments, $R^1$ is a $R^{20}$-substituted pyrazinyl. In embodiments, $R^1$ is a $R^{20}$-substituted pyrimidinyl. In embodiments, $R^1$ is a $R^{20}$-substituted pyridazinyl. In embodiments, $R^1$ is a $R^{20}$-substituted pyrrolyl. In embodiments, $R^1$ is a $R^{20}$-substituted furanyl. In embodiments, $R^1$ is a $R^{20}$-substituted thienyl. In embodiments, $R^1$ is a $R^{20}$-substituted imidazolyl. In embodiments, $R^1$ is a $R^{20}$-substituted pyrazolyl. In embodiments, $R^1$ is a $R^{20}$-substituted oxazolyl. In embodiments, $R^1$ is a $R^{20}$-substituted isoxazolyl. In embodiments, $R^1$ is a $R^{20}$-substituted thiazolyl. In embodiments, $R^1$ is a $R^{20}$-substituted isothiazolyl. In embodiments, $R^1$ is a $R^{20}$-substituted triazolyl. In embodiments, $R^1$ is a $R^{20}$-substituted oxadiazolyl. In embodiments, $R^1$ is a $R^{20}$-substituted piperazinyl. In embodiments, $R^1$ is a $R^{20}$-substituted piperidinyl. In embodiments, $R^1$ is a $R^{20}$-substituted pyrrolidinyl. In embodiments, $R^1$ is a $R^{20}$-substituted azetidinyl. In embodiments, $R^1$ is a $R^{20}$-substituted aziridinyl. In embodiments, $R^1$ is a $R^{20}$-substituted morpholinyl. In embodiments, $R^1$ is a $R^{20}$-substituted dioxanyl. In embodiments, $R^1$ is a $R^{20}$-substituted tetrahydropyranyl. In embodiments, $R^1$ is a $R^{20}$-substituted tetrahydrofuranyl. In embodiments, $R^1$ is a $R^{20}$-substituted oxetanyl. In embodiments, $R^1$ is a $R^{20}$-substituted oxiranyl. In embodiments, $R^1$ is a $R^{20}$-substituted triazinyl. In embodiments, $R^1$ is a $R^{20}$-substituted quinolinyl. In embodiments, $R^1$ is a $R^{20}$-substituted isoquinolinyl. In embodiments, $R^1$ is a $R^{20}$-substituted quinazolinyl. In embodiments, $R^1$ is a $R^{20}$-substituted quinoxalinyl. In embodiments, $R^1$ is a $R^{20}$-substituted thiadiazolyl. In embodiments, $R^1$ is a $R^{20}$-substituted tetrazolyl. In embodiments, $R^1$ is a $R^{20}$-substituted indolyl. In embodiments, $R^1$ is a $R^{20}$-substituted indazolyl. In embodiments, $R^1$ is a $R^{20}$-substituted benzimidazolyl. In embodiments, $R^1$ is a $R^{20}$-substituted azaindolyl. In embodiments, $R^1$ is a $R^{20}$-substituted purinyl. In embodiments, $R^1$ is a $R^{20}$-substituted benzofuranyl. In embodiments, $R^1$ is a $R^{20}$-substituted benzothienyl.

In embodiments, $R^1$ is an unsubstituted phenyl. In embodiments, $R^1$ is an unsubstituted pyridinyl. In embodiments, $R^1$ is an unsubstituted pyridyl. In embodiments, R is an unsubstituted pyrazinyl. In embodiments, $R^1$ is an unsubstituted pyrimidinyl. In embodiments, $R^1$ is an unsubstituted pyridazinyl. In embodiments, $R^1$ is an unsubstituted pyrrolyl. In embodiments, $R^1$ is an unsubstituted furanyl. In embodiments, $R^1$ is an unsubstituted thienyl. In embodiments, $R^1$ is an unsubstituted imidazolyl. In embodiments, $R^1$ is an unsubstituted pyrazolyl. In embodiments, $R^1$ is an unsubstituted oxazolyl. In embodiments, R¹ is an unsubstituted isoxazolyl. In embodiments, R¹ is an unsubstituted thiazolyl. In embodiments, R¹ is an unsubstituted isothiazolyl. In embodiments, R¹ is an unsubstituted triazolyl. In embodiments, R¹ is an unsubstituted oxadiazolyl. In embodiments, R¹ is an unsubstituted piperazinyl. In embodiments, R¹ is an unsubstituted piperidinyl. In embodiments, R¹ is an unsubstituted pyrrolidinyl. In embodiments, R¹ is an unsubstituted azetidinyl. In embodiments, R¹ is an unsubstituted aziridinyl. In embodiments, R¹ is an unsubstituted morpholinyl. In embodiments, R¹ is an unsubstituted dioxanyl. In embodiments, R¹ is an unsubstituted tetrahydropyranyl. In embodiments, R¹ is an unsubstituted tetrahydrofuranyl. In embodiments, R¹ is an unsubstituted oxetanyl. In embodiments, R¹ is an unsubstituted oxiranyl. In embodiments, R¹ is an unsubstituted triazinyl. In embodiments, R¹ is an unsubstituted quinolinyl. In embodiments, R¹ is an unsubstituted isoquinolinyl. In embodiments, R¹ is an unsubstituted quinazolinyl. In embodiments, R¹ is an unsubstituted quinoxalinyl. In embodiments, R¹ is an unsubstituted thiadiazolyl. In embodiments, R¹ is an unsubstituted tetrazolyl. In embodiments, R¹ is an unsubstituted indolyl. In embodiments, R¹ is an unsubstituted indazolyl. In embodiments, R¹ is an unsubstituted benzimidazolyl. In embodiments, R¹ is an unsubstituted azaindolyl. In embodiments, R¹ is an unsubstituted purinyl. In embodiments, R¹ is an unsubstituted benzofuranyl. In embodiments, R¹ is an unsubstituted benzothienyl.

$R^{20}$ is independently oxo, halogen, —$CX^{203}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{20}_3$, —$OCHX^{20}_2$, —$OR^{21}$, —$NHR^{21}$, —$COOR^{21}$, —$CONHR^{21}$, —$SR^{21}$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In embodiments, $R^{20}$ is independently oxo, halogen, —$CX^{203}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{20}_3$, —$OCHX^{20}_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In embodiments, $R^{20}$ is independently oxo, halogen, —$CX^{203}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHC(O)NH_2$, —$NHSO_2H$, —NHC(O)H, —NHC(O)OH, —NHOH, —$OCX^{20}_3$, —$OCHX^{20}_2$, $R^{21}$-substituted or unsubstituted $C_1$-$C_8$ alkyl, $R^{21}$-substituted or unsubstituted 2 to 8 membered heteroalkyl, $R^{21}$-substituted or unsubstituted $C_3$-$C_8$ cycloalkyl, $R^{21}$-substituted or unsubstituted 3 to 6 membered heterocycloalkyl, $R^{21}$-substituted or unsubstituted phenyl, or $R^{21}$-substituted or unsubstituted 5 to 6 membered heteroaryl. $X^{20}$ is —F, —Cl, —Br, or —I. In embodiments, $R^{20}$ is independently substituted or unsubstituted $C_1$-$C_8$ alkoxy, substituted or unsubstituted $C_3$-$C_5$ cycloalkoxy, substituted or unsubstituted 3 to 6 membered heterocycloalkoxy, substituted or unsubstituted phenoxy, or substituted or unsubstituted 5 to 6 membered heteroaryloxy. In embodiments, $R^{20}$ is not —$NH_2$ or C(O)H.

In embodiments, two adjacent $R^{20}$ substituents may optionally be joined to form a $R^{21}$-substituted or unsubstituted cycloalkyl (e.g., $C_3$-$C_8$, $C_3$-$C_6$, or $C_5$-$C_6$), $R^{21}$-substituted or unsubstituted heterocycloalkyl (e.g., 3 to 8 membered, 3 to 6 membered, or 5 to 6 membered), $R^{21}$-substituted or unsubstituted aryl (e.g., $C_6$-$C_{10}$, $C_{10}$, or phenyl), or $R^{21}$-substituted or unsubstituted heteroaryl (e.g., 5 to 10 membered, 5 to 9 membered, or 5 to 6 membered). In embodiments, two adjacent $R^{20}$ substituents may optionally be joined to form a $R^{21}$-substituted or unsubstituted $C_3$-$C_8$ cycloalkyl, $R^{21}$-substituted or unsubstituted 3 to 6 membered heterocycloalkyl, $R^{21}$-substituted or unsubstituted phenyl, or $R^{21}$-substituted or unsubstituted 5 to 6 membered heteroaryl.

In embodiments, $R^{20}$ is —$OCF_3$. In embodiments, $R^{20}$ is —$OCX^{203}$. In embodiments, $R^{20}$ is $R^{21}$-substituted 2 to 4 membered heteroalkyl. In embodiments, $R^{20}$ is unsubstituted 2 to 4 membered heteroalkyl. In embodiments, $R^{20}$ is —$OCH_3$. In embodiments, $R^{20}$ is unsubstituted 2 to 4 membered heteroalkyl. In embodiments, $R^{20}$ is halogen. In embodiments, $R^{20}$ is —F. In embodiments, $R^{20}$ is —Cl. In embodiments, $R^{20}$ is —Br. In embodiments, $R^{20}$ is —I. In embodiments, $R^{20}$ is —CN. In embodiments, $R^{20}$ is —OPh. In embodiments, $R^{20}$ is —$NH_2$. In embodiments, $R^{20}$ is —$N(CH_3)_2$. In embodiments, $R^{20}$ is —$N(CH_2CH_3)_2$. In embodiments, two $R^{20}$ attached to the same atom are joined to form an unsubstituted 1,3-dioxolane. In embodiments, two $R^{20}$ attached to the same atom are joined to form an $R^{21}$-substituted 1,3-dioxolane. In embodiments, two $R^{20}$ attached to the same atom are joined to form an unsubstituted 1,3-dioxolanyl. In embodiments, two $R^{20}$ attached to the same atom are joined to form an $R^{21}$-substituted 1,3-dioxolanyl. In embodiments, two $R^{20}$ attached to the same atom are joined to form an unsubstituted 5 to 6 membered heterocycloalkyl. In embodiments, two $R^{20}$ attached to the same atom are joined to form an $R^{21}$-substituted 5 to 6 membered heterocycloalkyl. In embodiments, $R^{20}$ is —C(O)$NH_2$. In embodiments, $R^{20}$ is —C(O)N(CH_3)_2. In embodiments, $R^{20}$ is —C(O)N(CH_2CH_3)_2. In embodiments, $R^{20}$ is —C(O)H. In embodiments, $R^{20}$ is —C(O)$CH_3$. In embodiments, $R^{20}$ is —C(O)$CH_2CH_3$. In embodiments, $R^{20}$ is $R^{21}$-substituted 5 to 6 membered heteroaryl. In embodiments, $R^{20}$ is unsubstituted 5 to 6 membered heteroaryl. In embodiments, $R^{20}$ is $R^{21}$-substituted pyridyl. In embodiments, $R^{20}$ is unsubstituted pyridyl. In embodiments, $R^{20}$ is $R^{21}$-substituted $C_1$-$C_4$ alkyl. In embodiments, $R^{20}$ is $R^{21}$-substituted 2 to 4 membered heteroalkyl. In embodiments, $R^{20}$ is $R^{21}$-substituted phenyl. In embodiments, $R^{20}$ is $R^{21}$-substituted $C_6$-$C_{10}$ aryl. In embodiments, $R^{20}$ is unsubstituted phenyl. In embodiments, $R^{20}$ is unsubstituted $C_6$-$C_{10}$ aryl. In embodiments, $R^{20}$ is $R^{21}$-substituted methyl. In embodiments, $R^{20}$ is —C(O)$R^{21}$. In embodiments, $R^{20}$ is —C(O)$R^{21}$, wherein $R^{21}$ is a $C_1$-$C_4$ unsubstituted alkyl. In embodiments, $R^{20}$ is —C(O)$R^{21}$, wherein $R^{21}$ is an unsubstituted methyl. In embodiments, $R^{20}$ is —C(O)$R^{21}$, wherein $R^{21}$ is an unsubstituted ethyl.

In embodiments, $R^{20}$ is

In embodiments, R²⁰ is
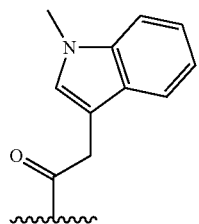
In embodiments, R²⁰ is
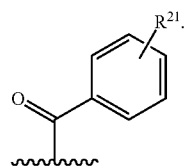
In embodiments, R²⁰ is
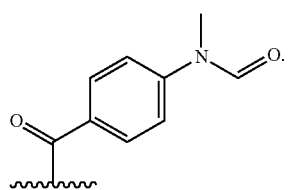 [SMILES: *C(=O)c1ccc(N(C)C=O)cc1]
In embodiments, R²⁰ is
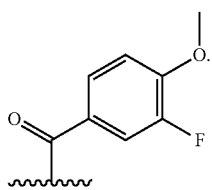 [SMILES: *C(=O)c1ccc(OC)c(F)c1]
In embodiments, R²⁰ is
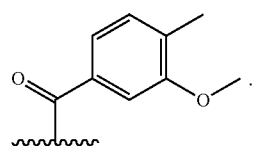 [SMILES: *C(=O)c1ccc(C)c(OC)c1]
In embodiments, R²⁰ is
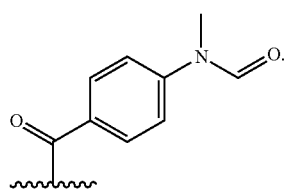 [SMILES: *C(=O)c1ccc(N(C)C=O)cc1]
In embodiments, R²⁰ is
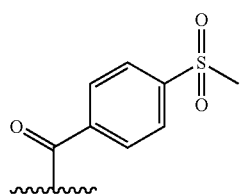
In embodiments, R²⁰ is
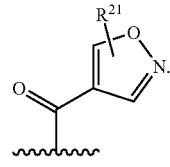
In embodiments, R²⁰ is
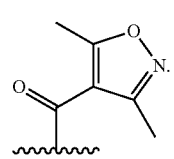 [SMILES: *C(=O)c1c(C)noc1C]
In embodiments, R²⁰ is
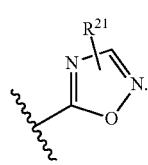
In embodiments, R²⁰ is
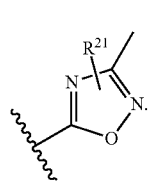
In embodiments, R²⁰ is
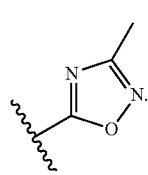 [SMILES: *c1nc(C)no1]

In embodiments, $R^{20}$ is $$\underset{\xi}{O} \underset{}{\overset{H}{\underset{N}{\parallel}}}$$

In embodiments, $R^{20}$ is unsubstituted oxadiazolyl. In embodiments, $R^{20}$ is unsubstituted 1,2,4-oxadiazolyl. In embodiments, $R^{20}$ is $R^{21}$-substituted oxadiazolyl. In embodiments, $R^{20}$ is $R^{21}$-substituted 1,2,4-oxadiazolyl.

In embodiments, $R^{20}$ is a $R^{21}$-substituted phenyl. In embodiments, $R^{20}$ is a $R^{21}$-substituted pyridinyl. In embodiments, $R^{20}$ is a $R^{21}$-substituted pyrazinyl. In embodiments, $R^{20}$ is a $R^{21}$-substituted pyrimidinyl. In embodiments, $R^{20}$ is a $R^{21}$-substituted pyridazinyl. In embodiments, $R^{20}$ is a $R^{21}$-substituted pyrrolyl. In embodiments, $R^{20}$ is a $R^{21}$-substituted furanyl. In embodiments, $R^{20}$ is a $R^{21}$-substituted thienyl. In embodiments, $R^{20}$ is a $R^{21}$-substituted imidazolyl. In embodiments, $R^{20}$ is a $R^{21}$-substituted pyrazolyl. In embodiments, $R^{20}$ is a $R^{21}$-substituted oxazolyl. In embodiments, $R^{20}$ is a $R^{21}$-substituted isoxazolyl. In embodiments, $R^{20}$ is a $R^{21}$-substituted thiazolyl. In embodiments, $R^{20}$ is a $R^{21}$-substituted isothiazolyl. In embodiments, $R^{20}$ is a $R^{21}$-substituted triazolyl. In embodiments, $R^{20}$ is a $R^{21}$-substituted oxadiazolyl. In embodiments, $R^{20}$ is a $R^{21}$-substituted piperazinyl. In embodiments, $R^{20}$ is a $R^{21}$-substituted piperidinyl. In embodiments, $R^{20}$ is a $R^{21}$-substituted pyrrolidinyl. In embodiments, $R^{20}$ is a $R^{21}$-substituted azetidinyl. In embodiments, $R^{20}$ is a $R^{21}$-substituted aziridinyl. In embodiments, $R^{20}$ is a $R^{21}$-substituted morpholinyl. In embodiments, $R^{20}$ is a $R^{21}$-substituted dioxanyl. In embodiments, $R^{20}$ is a $R^{21}$-substituted tetrahydropyranyl. In embodiments, $R^{20}$ is a $R^{21}$-substituted tetrahydrofuranyl. In embodiments, $R^{20}$ is a $R^{21}$-substituted oxetanyl. In embodiments, $R^{20}$ is a $R^{21}$-substituted oxiranyl. In embodiments, $R^{20}$ is a $R^{21}$-substituted triazinyl. In embodiments, $R^{20}$ is a $R^{21}$-substituted quinolinyl. In embodiments, $R^{20}$ is a $R^{21}$-substituted isoquinolinyl. In embodiments, $R^{20}$ is a $R^{21}$-substituted quinazolinyl. In embodiments, $R^{20}$ is a $R^{21}$-substituted quinoxalinyl. In embodiments, $R^{20}$ is a $R^{21}$-substituted thiadiazolyl. In embodiments, $R^{20}$ is a $R^{21}$-substituted tetrazolyl. In embodiments, $R^{20}$ is a $R^{21}$-substituted indolyl. In embodiments, $R^{20}$ is a $R^{21}$-substituted indazolyl. In embodiments, $R^{20}$ is a $R^{21}$-substituted benzimidazolyl. In embodiments, $R^{20}$ is a $R^{21}$-substituted azaindolyl. In embodiments, $R^{20}$ is a $R^{21}$-substituted purinyl. In embodiments, $R^{20}$ is a $R^{21}$-substituted benzofuranyl. In embodiments, $R^{20}$ is a $R^{21}$-substituted benzothienyl.

In embodiments, $R^{20}$ is an unsubstituted phenyl. In embodiments, $R^{20}$ is an unsubstituted pyridinyl. In embodiments, $R^{20}$ is an unsubstituted pyrazinyl. In embodiments, $R^{20}$ is an unsubstituted pyrimidinyl. In embodiments, $R^{20}$ is an unsubstituted pyridazinyl. In embodiments, $R^{20}$ is an unsubstituted pyrrolyl. In embodiments, $R^{20}$ is an unsubstituted furanyl. In embodiments, $R^{20}$ is an unsubstituted thienyl. In embodiments, $R^{20}$ is an unsubstituted imidazolyl. In embodiments, $R^{20}$ is an unsubstituted pyrazolyl. In embodiments, $R^{20}$ is an unsubstituted oxazolyl. In embodiments, $R^{20}$ is an unsubstituted isoxazolyl. In embodiments, $R^{20}$ is an unsubstituted thiazolyl. In embodiments, $R^{20}$ is an unsubstituted isothiazolyl. In embodiments, $R^{20}$ is an unsubstituted triazolyl. In embodiments, $R^{20}$ is an unsubstituted oxadiazolyl. In embodiments, $R^{20}$ is an unsubstituted piperazinyl. In embodiments, $R^{20}$ is an unsubstituted piperidinyl. In embodiments, $R^{20}$ is an unsubstituted pyrrolidinyl. In embodiments, $R^{20}$ is an unsubstituted azetidinyl. In embodiments, $R^{20}$ is an unsubstituted aziridinyl. In embodiments, $R^{20}$ is an unsubstituted morpholinyl. In embodiments, $R^{20}$ is an unsubstituted dioxanyl. In embodiments, $R^{20}$ is an unsubstituted tetrahydropyranyl. In embodiments, $R^{20}$ is an unsubstituted tetrahydrofuranyl. In embodiments, $R^{20}$ is an unsubstituted oxetanyl. In embodiments, $R^{20}$ is an unsubstituted oxiranyl. In embodiments, $R^{20}$ is an unsubstituted triazinyl. In embodiments, $R^{20}$ is an unsubstituted quinolinyl. In embodiments, $R^{20}$ is an unsubstituted isoquinolinyl. In embodiments, $R^{20}$ is an unsubstituted quinazolinyl. In embodiments, $R^{20}$ is an unsubstituted quinoxalinyl. In embodiments, $R^{20}$ is an unsubstituted thiadiazolyl. In embodiments, $R^{20}$ is an unsubstituted tetrazolyl. In embodiments, $R^{20}$ is an unsubstituted indolyl. In embodiments, $R^{20}$ is an unsubstituted indazolyl. In embodiments, $R^{20}$ is an unsubstituted benzimidazolyl. In embodiments, $R^{20}$ is an unsubstituted azaindolyl. In embodiments, $R^{20}$ is an unsubstituted purinyl. In embodiments, $R^{20}$ is an unsubstituted benzofuranyl. In embodiments, $R^{20}$ is an unsubstituted benzothienyl.

In embodiments, $R^{20}$ is a substituted phenyl. In embodiments, $R^{20}$ is a substituted pyridinyl. In embodiments, $R^{20}$ is a substituted pyrazinyl. In embodiments, $R^{20}$ is a substituted pyrimidinyl. In embodiments, $R^{20}$ is a substituted pyridazinyl. In embodiments, $R^{20}$ is a substituted pyrrolyl. In embodiments, $R^{20}$ is a substituted furanyl. In embodiments, $R^{20}$ is a substituted thienyl. In embodiments, $R^{20}$ is a substituted imidazolyl. In embodiments, $R^{20}$ is a substituted pyrazolyl. In embodiments, $R^{20}$ is a substituted oxazolyl. In embodiments, $R^{20}$ is a substituted isoxazolyl. In embodiments, $R^{20}$ is a substituted thiazolyl. In embodiments, $R^{20}$ is a substituted isothiazolyl. In embodiments, $R^{20}$ is a substituted triazolyl. In embodiments, $R^{20}$ is a substituted oxadiazolyl. In embodiments, $R^{20}$ is a substituted piperazinyl. In embodiments, $R^{20}$ is a substituted piperidinyl. In embodiments, $R^{20}$ is a substituted pyrrolidinyl. In embodiments, $R^{20}$ is a substituted azetidinyl. In embodiments, $R^{20}$ is a substituted aziridinyl. In embodiments, $R^{20}$ is a substituted morpholinyl. In embodiments, $R^{20}$ is a substituted dioxanyl. In embodiments, $R^{20}$ is a substituted tetrahydropyranyl. In embodiments, $R^{20}$ is a substituted tetrahydrofuranyl. In embodiments, $R^{20}$ is a substituted oxetanyl. In embodiments, $R^{20}$ is a substituted oxiranyl. In embodiments, $R^{20}$ is a substituted triazinyl. In embodiments, $R^{20}$ is a substituted quinolinyl. In embodiments, $R^{20}$ is a substituted isoquinolinyl. In embodiments, $R^{20}$ is a substituted quinazolinyl. In embodiments, $R^{20}$ is a substituted quinoxalinyl. In embodiments, $R^{20}$ is a substituted thiadiazolyl. In embodiments, $R^{20}$ is a substituted tetrazolyl. In embodiments, $R^{20}$ is a substituted indolyl. In embodiments, $R^{20}$ is a substituted indazolyl. In embodiments, $R^{20}$ is a substituted benzimidazolyl. In embodiments, $R^{20}$ is a substituted azaindolyl. In embodiments, $R^{20}$ is a substituted purinyl. In embodiments, $R^{20}$ is a substituted benzofuranyl. In embodiments, $R^{20}$ is a substituted benzothienyl. In embodiments, two adjacent $R^{20}$ are joined to form an $R^{21}$-substituted tetrahydropyranyl. In embodiments, two adjacent $R^{20}$ are joined to form an unsubstituted tetrahydropyranyl. In embodiments, two adjacent $R^{20}$ are joined to form an $R^{21}$-substituted dihydrodioxinyl. In embodiments, two adjacent $R^{20}$ are joined to form an unsubstituted dihydrodioxinyl. In embodiments, two adjacent $R^{20}$ are joined to form an $R^{21}$-substituted dioxolanyl. In embodiments, two adjacent $R^{20}$ are joined to form an unsubstituted dioxolanyl. In embodiments, two adjacent $R^{20}$ are joined to form an $R^{21}$-substituted dioxolyl. In embodiments, two adjacent $R^{20}$ are joined to form an unsubstituted dioxolyl.

$R^{21}$ is independently oxo, halogen, —$CX^{21}{}_3$, —CN, —OH, —$NH_2$, —COOH, —$CONH_2$, —$NO_2$, —SH, —$SO_3H$, —$SO_4H$, —$SO_2NH_2$, —$OR^{22}$, —$NHR^{22}$, —$N(CH_3)R^{22}$, —$COOR^{22}$, —$CONHR^{22}$, —$SR^{22}$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21}{}_3$, —$OCHX^{21}{}_2$, $R^{22}$-substituted or unsubstituted alkyl, $R^{22}$-substituted or unsubstituted heteroalkyl, $R^{22}$-substituted or unsubstituted cycloalkyl, $R^2{}_2$-substituted or unsubstituted heterocycloalkyl, $R^{22}$-substituted or unsubstituted aryl, or $R^2{}_2$-substituted or unsubstituted heteroaryl. In embodiments, $R^{21}$ is independently oxo, halogen, —$CX^{21}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21}{}_3$, —$OCHX^{21}{}_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl. In embodiments, $R^{21}$ is independently oxo, halogen, —$CX^{21}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21}{}_3$, —$OCHX^{21}{}_2$, $R^{22}$-substituted or unsubstituted $C_1$-$C_8$ alkyl, $R^{22}$-substituted or unsubstituted 2 to 8 membered heteroalkyl, $R^{22}$-substituted or unsubstituted $C_3$-$C_8$ cycloalkyl, $R^{22}$-substituted or unsubstituted 3 to 6 membered heterocycloalkyl, $R^{22}$-substituted or unsubstituted phenyl, or $R^{22}$-substituted or unsubstituted 5 to 6 membered heteroaryl. $X^{21}$ is —F, —Cl, —Br, or —I.

In embodiments, $R^{21}$ is halogen. In embodiments, $R^{21}$ is —F. In embodiments, $R^{21}$ is —Cl. In embodiments, $R^{21}$ is —Br. In embodiments, $R^{21}$ is —I. In embodiments, $R^{21}$ is an unsubstituted methyl. In embodiments, $R^{21}$ is an unsubstituted ethyl. In embodiments, $R^{21}$ is an unsubstituted isopropyl. In embodiments, $R^{21}$ is an unsubstituted $C_3$ alkyl. In embodiments, $R^{21}$ is unsubstituted $C_1$-$C_4$ alkyl. In embodiments, $R^{21}$ is $R^{22}$-substituted $C_1$-$C_4$ alkyl. In embodiments, $R^{21}$ is oxo. In embodiments, $R^{21}$ is $R^{22}$-substituted indolyl. In embodiments, $R^{21}$ is $R^{22}$-substituted 5 to 9 membered heteroaryl. In embodiments, $R^{21}$ is $R^{22}$-substituted phenyl. In embodiments, $R^{21}$ is $R^{22}$-substituted $C_6$-$C_{10}$ aryl. In embodiments, $R^{21}$ is unsubstituted 2 to 4 membered heteroalkyl. In embodiments, $R^{21}$ is —$OCH_3$. embodiments, $R^{21}$ is

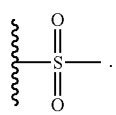

In embodiments, $R^{21}$ is

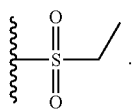

In embodiments, $R^{21}$ is

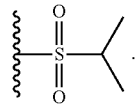

In embodiments, $R^{21}$ is

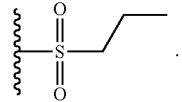

In embodiments, $R^{1A}$ is independently hydrogen, —$CX^{1A}{}_3$, —CN, —COOH, —$CONH_2$, —$CHX^{1A}{}_2$, —$CH_2X^{1A}$, $R^{20A}$-substituted or unsubstituted alkyl, $R^{20A}$-substituted or unsubstituted heteroalkyl, $R^{20A}$-substituted or unsubstituted cycloalkyl, $R^{20A}$-substituted or unsubstituted heterocycloalkyl, $R^{20A}$-substituted or unsubstituted aryl, or $R^{20A}$-substituted or unsubstituted heteroaryl. In embodiments, $R^{1A}$ is independently hydrogen, —$CX^{1A}{}_3$, —CN, —COOH, —$CONH_2$, —$CHX^{1A}{}_2$, —$CH_2X^{1A}$, $R^{20A}$-substituted or unsubstituted $C_1$-$C_8$ alkyl, $R^{20A}$-substituted or unsubstituted 2 to 8 membered heteroalkyl, $R^{20A}$-substituted or unsubstituted $C_3$-$C_8$ cycloalkyl, $R^{20A}$-substituted or unsubstituted 3 to 6 membered heterocycloalkyl, $R^{20A}$-substituted or unsubstituted phenyl, or $R^{20A}$-substituted or unsubstituted 5 to 6 membered heteroaryl. $X^{1A}$ is —F, —Cl, —Br, or —I. In embodiments, $R^{1A}$ is independently hydrogen. In embodiments, $R^{1A}$ is independently substituted or unsubstituted methyl. In embodiments, $R^{1A}$ is independently substituted or unsubstituted ethyl.

In embodiments, $R^{1A}$ is unsubstituted methyl. In embodiments, $R^{1A}$ is unsubstituted ethyl. In embodiments, $R^{1A}$ is unsubstituted $C_1$-$C_4$ alkyl. In embodiments, $R^{1A}$ is $R^{20A}$-substituted methyl. In embodiments, $R^{1A}$ is $R^{20A}$-substituted $C_1$-$C_4$ alkyl. $R^{20A}$ is $R^{21A}$-substituted thienyl. In embodiments, $R^{20A}$ is unsubstituted thienyl.

In embodiments, $R^{1A}$ and $R^{1B}$ substituents bonded to the same nitrogen atom may optionally be joined to form a $R^{20A}$-substituted or unsubstituted heterocycloalkyl or $R^{20A}$-substituted or unsubstituted heteroaryl. In embodiments, $R^{1A}$ and $R^{1B}$ substituents bonded to the same nitrogen atom may optionally be joined to form a $R^{20A}$-substituted or unsubstituted 3 to 6 membered heterocycloalkyl or $R^{20A}$-substituted or unsubstituted 5 to 6 membered heteroaryl.

$R^{20A}$ is independently oxo, halogen, —$CX^{20A}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20A}{}_3$, —$OCHX^{20A}{}_2$, $R^{21A}$-substituted or unsubstituted alkyl, $R^{21A}$-substituted or unsubstituted heteroalkyl, $R^{21A}$-substituted or unsubstituted cycloalkyl, $R^{21A}$-substituted or unsubstituted heterocycloalkyl, $R^{21A}$-substituted or unsubstituted aryl, or $R^{21A}$-substituted or unsubstituted heteroaryl. In embodiments, $R^{20A}$ is independently oxo, halogen, —$CX^{20A}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20A}{}_3$, —$OCHX^{20A}{}_2$, $R^{21A}$-substituted or unsubstituted $C_1$-$C_8$ alkyl, $R^{21A}$-substituted or unsubstituted 2 to 8 membered heteroalkyl, $R^{21A}$-substituted or unsubstituted $C_3$-$C_8$ cycloalkyl, $R^{21A}$-substituted or unsubstituted 3 to 6 membered heterocycloalkyl, $R^{21A}$-substituted or unsubstituted phenyl, or $R^{21A}$-substituted or unsubstituted 5 to 6 membered heteroaryl. $X^{20A}$ is —F, —Cl, —Br, or —I.

$R^{21A}$ is independently oxo, halogen, —$CX^{21A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21A}_3$, —$OCHX^{21A}_2$, $R^{22A}$-substituted or unsubstituted alkyl, $R^{22A}$-substituted or unsubstituted heteroalkyl, $R^{22A}$-substituted or unsubstituted cycloalkyl, $R^{22A}$-substituted or unsubstituted heterocycloalkyl, $R^{22A}$-substituted or unsubstituted aryl, or $R^{22A}$-substituted or unsubstituted heteroaryl. In embodiments, $R^{21A}$ is independently oxo, halogen, —$CX^{21A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21A}_3$, —$OCHX^{21A}_2$, $R^{22A}$-substituted or unsubstituted $C_1$-$C_8$ alkyl, $R^{22A}$-substituted or unsubstituted 2 to 8 membered heteroalkyl, $R^{22A}$-substituted or unsubstituted $C_3$-$C_8$ cycloalkyl, $R^{22A}$-substituted or unsubstituted 3 to 6 membered heterocycloalkyl, $R^{22A}$-substituted or unsubstituted phenyl, or $R^{22A}$-substituted or unsubstituted 5 to 6 membered heteroaryl. $X^{21A}$ is —F, —Cl, —Br, or —I.

In embodiments, $R^{1B}$ is independently hydrogen, —$CX^{1B}_3$, —CN, —COOH, —$CONH_2$, —$CHX^{1B}_2$, —$CH_2X^{1B}$, $R^{20B}$-substituted or unsubstituted alkyl, $R^{20B}$-substituted or unsubstituted heteroalkyl, $R^{20B}$-substituted or unsubstituted cycloalkyl, $R^{20B}$-substituted or unsubstituted heterocycloalkyl, $R^{20B}$-substituted or unsubstituted aryl, or R20B-substituted or unsubstituted heteroaryl. In embodiments, $R^{1B}$ is independently hydrogen, —$CX^{1B}_3$, —CN, —COOH, —$CONH_2$, $CHX^{1B}_2$, —$CH_2X^{1B}$, $R^{20B}$-substituted or unsubstituted $C_1$-$C_8$ alkyl, $R^{20B}$-substituted or unsubstituted 2 to 8 membered heteroalkyl, $R^{20B}$-substituted or unsubstituted $C_3$-$C_8$ cycloalkyl, $R^{20B}$-substituted or unsubstituted 3 to 6 membered heterocycloalkyl, $R^{20B}$-substituted or unsubstituted phenyl, or $R^{20B}$-substituted or unsubstituted 5 to 6 membered heteroaryl. $X^{1B}$ is —F, —Cl, —Br, or —I. In embodiments, $R^{1B}$ is independently hydrogen. In embodiments, $R^{1B}$ is independently methyl. In embodiments, $R^{1B}$ is independently ethyl.

In embodiments, $R^{1B}$ is unsubstituted methyl. In embodiments, $R^{1B}$ is unsubstituted ethyl. In embodiments, $R^{1B}$ is unsubstituted $C_1$-$C_4$ alkyl. In embodiments, $R^{1B}$ is $R^{20B}$-substituted methyl. In embodiments, $R^{1B}$ is $R^{20B}$-substituted $C_1$-$C_4$ alkyl. In embodiments, $R^{20B}$ is $R^{21B}$-substituted thienyl. In embodiments, $R^{20B}$ is unsubstituted thienyl.

In embodiments, $R^{1A}$ and $R^{1B}$ substituents bonded to the same nitrogen atom may optionally be joined to form a $R^{20B}$-substituted or unsubstituted heterocycloalkyl or $R^{20B}$-substituted or unsubstituted heteroaryl. In embodiments, $R^{1A}$ and $R^{1B}$ substituents bonded to the same nitrogen atom may optionally be joined to form a $R^{20B}$-substituted or unsubstituted 3 to 6 membered heterocycloalkyl or $R^{20B}$-substituted or unsubstituted 5 to 6 membered heteroaryl.

$R^{20B}$ is independently oxo, halogen, —$CX^{20B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20B}_3$, —$OCHX^{20B}_2$, $R^{21B}$-substituted or unsubstituted alkyl, $R^{21B}$-substituted or unsubstituted heteroalkyl, $R^{21B}$-substituted or unsubstituted cycloalkyl, $R^{21B}$-substituted or unsubstituted heterocycloalkyl, $R^{21B}$-substituted or unsubstituted aryl, or $R^{21B}$-substituted or unsubstituted heteroaryl. In embodiments, $R^{20B}$ is independently oxo, halogen, —$CX^{20B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20B}_3$, —$OCHX^{20B}_2$, $R^{21B}$-substituted or unsubstituted $C_1$-$C_8$ alkyl, $R^{21B}$-substituted or unsubstituted 2 to 8 membered heteroalkyl, $R^{21B}$-substituted or unsubstituted $C_3$-$C_8$ cycloalkyl, $R^{21B}$-substituted or unsubstituted 3 to 6 membered heterocycloalkyl, $R^{21B}$-substituted or unsubstituted phenyl, or $R^{21B}$-substituted or unsubstituted 5 to 6 membered heteroaryl. $X^{20B}$ is —F, —Cl, —Br, or —I.

$R^{21B}$ is independently oxo, halogen, —$CX^{21B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21B}_3$, —$OCHX^{21B}_2$, $R^{22B}$-substituted or unsubstituted alkyl, $R^{22B}$-substituted or unsubstituted heteroalkyl, $R^{22B}$-substituted or unsubstituted cycloalkyl, $R^{22B}$-substituted or unsubstituted heterocycloalkyl, $R^{22B}$-substituted or unsubstituted aryl, or $R^{22B}$-substituted or unsubstituted heteroaryl. In embodiments, $R^{21B}$ is independently oxo, halogen, —$CX^{21B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21B}_3$, —$OCHX^{21B}_2$, $R^{22B}$-substituted or unsubstituted $C_1$-$C_8$ alkyl, $R^{22B}$-substituted or unsubstituted 2 to 8 membered heteroalkyl, $R^{22B}$-substituted or unsubstituted $C_3$-$C_8$ cycloalkyl, $R^{22B}$-substituted or unsubstituted 3 to 6 membered heterocycloalkyl, $R^{22B}$-substituted or unsubstituted phenyl, or $R^{22B}$-substituted or unsubstituted 5 to 6 membered heteroaryl. $X^{21B}$ is —F, —Cl, —Br, or —I.

In embodiments, $R^{1C}$ is independently hydrogen, —$CX^{1C}_3$, —CN, —COOH, —$CONH_2$, —$CHX^{1C}_2$, —$CH_2X^{1C}$, $R^{20C}$-substituted or unsubstituted alkyl, $R^{20C}$-substituted or unsubstituted heteroalkyl, $R^{20C}$-substituted or unsubstituted cycloalkyl, $R^{20C}$-substituted or unsubstituted heterocycloalkyl, $R^{20C}$-substituted or unsubstituted aryl, or $R^{20C}$-substituted or unsubstituted heteroaryl. In embodiments, $R^{1C}$ is independently hydrogen, —$CX^{1C}_3$, —CN, —COOH, —$CONH_2$, —$CHX^{1C}_2$, —$CH_2X^{1C}$, $R^{20C}$-substituted or unsubstituted $C_1$-$C_8$ alkyl, $R^{20C}$-substituted or unsubstituted 2 to 8 membered heteroalkyl, $R^{20C}$-substituted or unsubstituted $C_3$-$C_8$ cycloalkyl, $R^{20C}$-substituted or unsubstituted 3 to 6 membered heterocycloalkyl, $R^{20C}$-substituted or unsubstituted phenyl, or $R^{20C}$-substituted or unsubstituted 5 to 6 membered heteroaryl. $X^{1C}$ is —F, —Cl, —Br, or —I. In embodiments, $R^{1C}$ is independently hydrogen. In embodiments, $R^{1C}$ is independently methyl. In embodiments, $R^{1C}$ is independently ethyl.

In embodiments, $R^{1C}$ is unsubstituted methyl. In embodiments, $R^{1C}$ is unsubstituted ethyl. In embodiments, $R^{1C}$ is unsubstituted $C_1$-$C_4$ alkyl.

$R^{20C}$ is independently oxo, halogen, —$CX^{20C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20C}_3$, —$OCHX^{20C}_2$, $R^{21C}$-substituted or unsubstituted alkyl, $R^{21C}$-substituted or unsubstituted heteroalkyl, $R^{21C}$-substituted or unsubstituted cycloalkyl, $R^{21C}$-substituted or unsubstituted heterocycloalkyl, $R^{21C}$-substituted or unsubstituted aryl, or $R^{21C}$-substituted or unsubstituted heteroaryl. In embodiments, $R^{20C}$ is independently oxo, halogen, —$CX^{20C}_3$, —CN, —OH, —$NH_2$, —COOH, —$CONH_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20C}_3$, —OCHX$^{20C}_2$, R$^{21C}$-substituted or unsubstituted C$_1$-C$_8$ alkyl, R$^{21C}$-substituted or unsubstituted 2 to 8 membered heteroalkyl, R$^{21C}$-substituted or unsubstituted C$_3$-C$_8$ cycloalkyl, R$^{21C}$-substituted or unsubstituted 3 to 6 membered heterocycloalkyl, R$^{21C}$-substituted or unsubstituted phenyl, or R$^{21C}$-substituted or unsubstituted 5 to 6 membered heteroaryl. X$^{20C}$ is —F, —Cl, —Br, or —I.

R$^{21C}$ is independently oxo, halogen, —CX$^{21C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21C}_3$, —OCHX$^{21C}_2$, R$^{22C}$-substituted or unsubstituted alkyl, R$^{22C}$-substituted or unsubstituted heteroalkyl, R$^{22C}$-substituted or unsubstituted cycloalkyl, R$^{22C}$-substituted or unsubstituted heterocycloalkyl, R$^{22C}$-substituted or unsubstituted aryl, or R$^{22C}$-substituted or unsubstituted heteroaryl. In embodiments, R$^{21C}$ is independently oxo, halogen, —CX$^{21C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21C}_3$, —OCHX$^{21C}_2$, R$^{22C}$-substituted or unsubstituted C$_1$-C$_8$ alkyl, R$^{22C}$-substituted or unsubstituted 2 to 8 membered heteroalkyl, R$^{22C}$-substituted or unsubstituted C$_3$-C$_8$ cycloalkyl, R$^{22C}$-substituted or unsubstituted 3 to 6 membered heterocycloalkyl, R$^{22C}$-substituted or unsubstituted phenyl, or R$^{22C}$-substituted or unsubstituted 5 to 6 membered heteroaryl. X$^{21C}$ is —F, —Cl, —Br, or —I.

In embodiments, R$^{1D}$ is independently hydrogen, —CX$^{1D}_3$, —CN, —COOH, —CONH$_2$, —CHX$^{1D}_2$, —CH$_2$X$^{1D}$, R$^{20D}$-substituted or unsubstituted alkyl, R$^{20D}$-substituted or unsubstituted heteroalkyl, R$^{20D}$-substituted or unsubstituted cycloalkyl, R$^{20D}$-substituted or unsubstituted heterocycloalkyl, R$^{20D}$-substituted or unsubstituted aryl, or R$^{20D}$-substituted or unsubstituted heteroaryl. In embodiments, R$^{1D}$ is independently hydrogen, —CX$^{1D}_3$, —CN, —COOH, —CONH$_2$, —CHX$^{1D}_2$, —CH$_2$X$^{1D}$, R$^{20D}$-substituted or unsubstituted C$_1$-C$_8$ alkyl, R$^{20D}$-substituted or unsubstituted 2 to 8 membered heteroalkyl, R$^{20D}$-substituted or unsubstituted C$_3$-C$_8$ cycloalkyl, R$^{20D}$-substituted or unsubstituted 3 to 6 membered heterocycloalkyl, R$^{20D}$-substituted or unsubstituted phenyl, or R$^{20D}$-substituted or unsubstituted 5 to 6 membered heteroaryl. X$^{1D}$ is —F, —Cl, —Br, or —I. In embodiments, R$^{1D}$ is independently hydrogen. In embodiments, R$^{1D}$ is independently methyl. In embodiments, R$^{1D}$ is independently ethyl. In embodiments, R$^{1D}$ is unsubstituted methyl. In embodiments, R$^{1D}$ is unsubstituted ethyl. In embodiments, R$^{1D}$ is unsubstituted C$_1$-C$_4$ alkyl. In embodiments, R$^{1D}$ is unsubstituted phenyl.

R$^{20D}$ is independently oxo, halogen, —CX$^{20D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20D}_3$, —OCHX$^{20D}_2$, R$^{21D}$-substituted or unsubstituted alkyl, R$^{21D}$-substituted or unsubstituted heteroalkyl, R$^{21D}$-substituted or unsubstituted cycloalkyl, R$^{21D}$-substituted or unsubstituted heterocycloalkyl, R$^{21D}$-substituted or unsubstituted aryl, or R$^{21D}$-substituted or unsubstituted heteroaryl. In embodiments, R$^{20D}$ is independently oxo, halogen, —CX$^{20D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20D}_3$, —OCHX$^{20D}_2$, R$^{21D}$-substituted or unsubstituted C$_1$-C$_8$ alkyl, R$^{21D}$-substituted or unsubstituted 2 to 8 membered heteroalkyl, R$^{21D}$-substituted or unsubstituted C$_3$-C$_8$ cycloalkyl, R$^{21D}$-substituted or unsubstituted 3 to 6 membered heterocycloalkyl, R$^{21D}$-substituted or unsubstituted phenyl, or R$^{21D}$-substituted or unsubstituted 5 to 6 membered heteroaryl. X$^{20D}$ is —F, —Cl, —Br, or —I.

R$^{21D}$ is independently oxo, halogen, —CX$^{21D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21D}_3$, —OCHX$^{21D}_2$, R$^{22D}$-substituted or unsubstituted alkyl, R$^{22D}$-substituted or unsubstituted heteroalkyl, R$^{22D}$-substituted or unsubstituted cycloalkyl, R$^{22D}$-substituted or unsubstituted heterocycloalkyl, R$^{22D}$-substituted or unsubstituted aryl, or R$^{22D}$-substituted or unsubstituted heteroaryl. In embodiments, R$^{21D}$ is independently oxo, halogen, —CX$^{21D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21D}_3$, —OCHX$^{21D}_2$, R$^{22D}$-substituted or unsubstituted C$_1$-C$_8$ alkyl, R$^{22D}$-substituted or unsubstituted 2 to 8 membered heteroalkyl, R$^{22D}$-substituted or unsubstituted C$_3$-C$_8$ cycloalkyl, R$^{22D}$-substituted or unsubstituted 3 to 6 membered heterocycloalkyl, R$^{22D}$-substituted or unsubstituted phenyl, or R$^{22D}$-substituted or unsubstituted 5 to 6 membered heteroaryl. X$^{21D}$ is —F, —Cl, —Br, or —I.

R$^{22}$, R$^{22A}$, R$^{22B}$, R$^{22C}$, and R$^{22D}$ are independently hydrogen, oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{22}$, R$^{22A}$, R$^{22B}$, R$^{22C}$, and R$^{22D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{22}$, R$^{22A}$, R$^{22B}$, R$^{22C}$, and R$^{22D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl.

In embodiments, R$^{22}$ is unsubstituted methyl. In embodiments, R$^{22}$ is unsubstituted ethyl. In embodiments, R$^{22}$ is unsubstituted C$_1$-C$_4$ alkyl. In embodiments, R$^{22}$ is halogen. In embodiments, R$^{22}$ is —F. In embodiments, R$^{22}$ is —Cl. In embodiments, R$^{22}$ is —Br. In embodiments, R$^{22}$ is —I. In embodiments, R$^{22}$ is —N(CH$_3$)(C(O)H). In embodiments, R$^{22}$ is unsubstituted 2 to 4 membered heteroalkyl. In embodiments, R$^{22}$ is —OCH$_3$. In embodiments, R$^{22}$ is

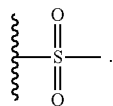

In embodiments, $R^{22}$ is

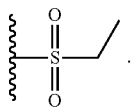 [SMILES: *S(=O)(=O)CC]

In embodiments, $R^{22}$ is

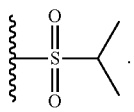 [SMILES: *S(=O)(=O)C(C)C]

In embodiments, $R^{22}$ is

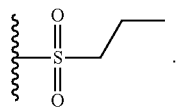 [SMILES: *S(=O)(=O)CCC]

In embodiments, $R^1$ is independently halogen. In embodiments, $R^1$ is independently hydrogen. In embodiments, z1 is 2 and $R^1$ is independently hydrogen or halogen. In embodiments, z1 is 2 and one $R^1$ is independently hydrogen and one $R^1$ is halogen. In embodiments, $R^1$ is independently methyl. In embodiments, $R^1$ is independently $C_1$-$C_4$ alkyl. In embodiments, z1 is 2 and one $R^1$ is independently halogen and one $R^1$ is unsubstituted $C_1$-$C_4$ alkyl. In embodiments, z1 is 2 and one $R^1$ is independently halogen and one $R^1$ is unsubstituted $C_1$-$C_3$ alkyl. In embodiments, z1 is 2 and one $R^1$ is independently halogen and one $R^1$ is unsubstituted $C_1$-$C_2$ alkyl. In embodiments, $R^1$ is independently halogen or unsubstituted $C_1$-$C_3$ alkyl. In embodiments, z1 is 2 and one $R^1$ is independently halogen and one $R^1$ is methyl.

In embodiments, $R^1$ is independently substituted or unsubstituted methyl. In embodiments, $R^1$ is independently substituted or unsubstituted $C_1$-$C_4$ alkyl. In embodiments, $R^1$ is independently halogen or substituted or unsubstituted $C_1$-$C_4$ alkyl. In embodiments, $R^1$ is independently halogen or substituted or unsubstituted $C_1$-$C_3$ alkyl. In embodiments, $R^1$ is independently halogen or substituted or unsubstituted $C_1$-$C_2$ alkyl. In embodiments, $R^1$ is independently halogen or substituted or unsubstituted methyl. In embodiments, $R^1$ is independently substituted methyl.

In embodiments, $R^1$ is unsubstituted heterocycloalkyl. In embodiments, $R^1$ is unsubstituted piperidinyl. In embodiments, $R^1$ is —$NR^{1A}R^{1B}$. In embodiments, $R^1$ is —F. In embodiments, $R^1$ is —Cl. In embodiments, $R^1$ is —Br. In embodiments, $R^1$ is —I. In embodiments, $R^1$ is unsubstituted 2,3-dihydrobenzofuranyl. In embodiments, $R^1$ is unsubstituted napthtyl. In embodiments, $R^1$ is unsubstituted pyrrolidinyl. In embodiments, $R^1$ is unsubstituted 5 to 6 membered heterocycloalkyl. In embodiments, $R^1$ is unsubstituted quinolinyl. In embodiments, $R^1$ is unsubstituted piperazinyl. In embodiments, $R^1$ is —$C(O)R^{1C}$. In embodiments, $R^1$ is unsubstituted benzo[d][1,3]dioxole. In embodiments, $R^1$ is unsubstituted 4,5,6,7-tetrahydrothieno[3,2-b]pyridine. In embodiments, $R^1$ is unsubstituted 1,2,3,4-tetrahydroisoquinoline. In embodiments, $R^1$ is unsubstituted morpholinyl. In embodiments, $R^1$ is $R^{20}$-substituted heterocycloalkyl. In embodiments, $R^1$ is $R^{20}$-substituted piperidinyl. In embodiments, $R^1$ is $R^{20}$-substituted 2,3-dihydrobenzofuranyl. In embodiments, $R^1$ is $R^{20}$-substituted napthtyl. In embodiments, $R^1$ is $R^{20}$-substituted pyrrolidinyl. In embodiments, $R^1$ is $R^{20}$-substituted 5 to 6 membered heterocycloalkyl. In embodiments, $R^1$ is $R^{20}$-substituted quinolinyl. In embodiments, $R^1$ is $R^{20}$-substituted piperazinyl. In embodiments, $R^1$ is $R^{20}$-substituted benzo[d][1,3]dioxolyl. In embodiments, $R^1$ is $R^{20}$-substituted 4,5,6,7-tetrahydrothieno[3,2-b]pyridinyl. In embodiments, $R^1$ is $R^{20}$-substituted 1,2,3,4-tetrahydroisoquinolinyl. In embodiments, $R^1$ is $R^{20}$-substituted morpholinyl. In embodiments, $R^1$ is unsubstituted morpholinyl. In embodiments, $R^1$ is $R^{20}$-substituted benzofuranyl. In embodiments, $R^1$ is unsubstituted benzofuranyl. In embodiments, $R^1$ is $R^{20}$-substituted pyrimidinyl. In embodiments, $R^1$ is unsubstituted pyrimidinyl. In embodiments, $R^1$ is $R^{20}$-substituted 2,3-dihydrobenzo[b][1,4]dioxinyl. In embodiments, $R^1$ is unsubstituted 2,3-dihydrobenzo[b][1,4]dioxinyl. In embodiments, $R^1$ is $R^{20}$-substituted 1,4,6,7-tetrahydro-5l2-pyrazolo[4,3-c]pyridinyl. In embodiments, $R^1$ is unsubstituted 1,4,6,7-tetrahydro-5l2-pyrazolo[4,3-c]pyridinyl. In embodiments, $R^1$ is $R^{20}$-substituted pyridyl. In embodiments, $R^1$ is unsubstituted pyridyl. In embodiments, $R^1$ is $R^{20}$-substituted indolyl. In embodiments, $R^1$ is unsubstituted indolyl. In embodiments, $R^1$ is unsubstituted phenyl. In embodiments, $R^1$ is unsubstituted $C_6$-$C_{10}$ aryl. In embodiments, $R^1$ is $R^{20}$-substituted phenyl. In embodiments, $R^1$ is $R^{20}$-substituted $C_6$-$C_{10}$ aryl.

In embodiments, the compound has the formula:

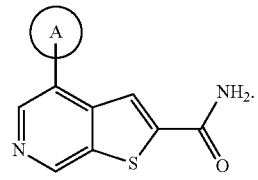

Ring A is a substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered). In embodiments, Ring A is a substituted cycloalkyl (e.g., $C_3$-$C_8$, $C_3$-$C_6$, or $C_5$-$C_6$), substituted heterocycloalkyl (e.g., 3 to 8 membered, 3 to 6 membered, or 5 to 6 membered), substituted aryl (e.g., $C_6$-$C_{10}$, $C_{10}$, or phenyl), or substituted heteroaryl (e.g., 5 to 10 membered, 5 to 9 membered, or 5 to 6 membered). In embodiments, Ring A is an unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, the compound has the formula:

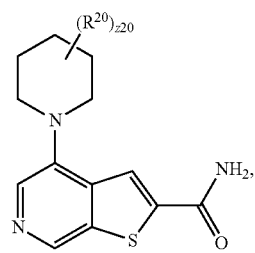

(VI)

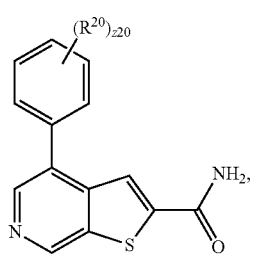

(VII)

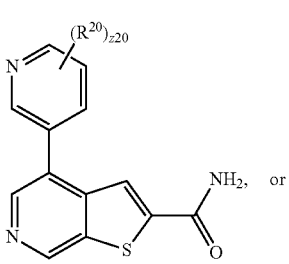

(VIII)

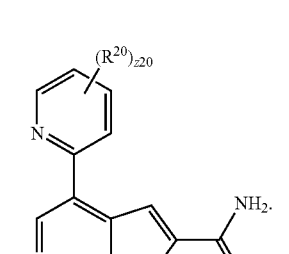

(IX)

$R^{20}$ is as described herein (including in embodiments). The symbol z20 is an integer from 0 to 10. In embodiments, z20 is an integer from 0 to 5. z20 is an integer from 0 to 2.

In embodiments, the compound has the formula:

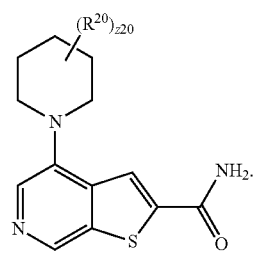

(VI)

In embodiments, the compound has the formula:

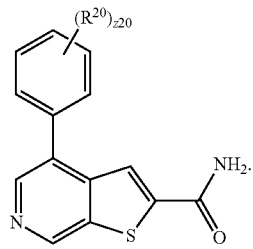

(VII)

In embodiments, the compound has the formula:

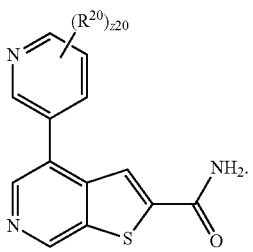

(VIII)

In embodiments, the compound has the formula:

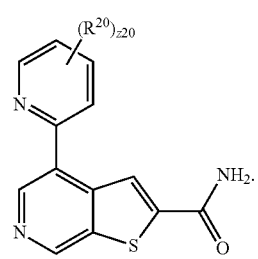

(IX)

$R^{20}$ and z20 are as described herein (including in embodiments).

In embodiments, the compound has the formula:

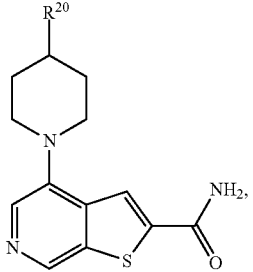

(VIA)

-continued

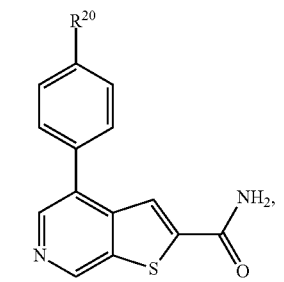

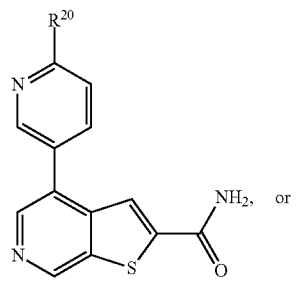

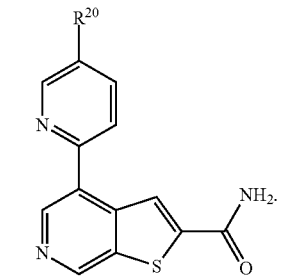

$R^{20}$ is as described herein (including in embodiments).

In embodiments, the compound has the formula:

(VIA)

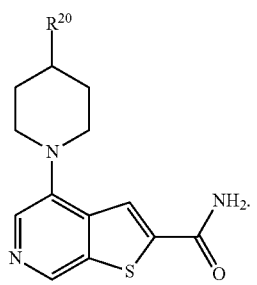

In embodiments, the compound has the formula:

(VIIA)

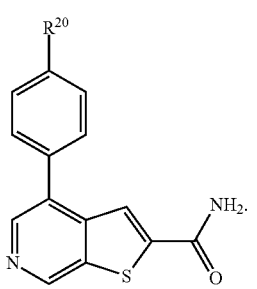

In embodiments, the compound has the formula:

(VIIIA)

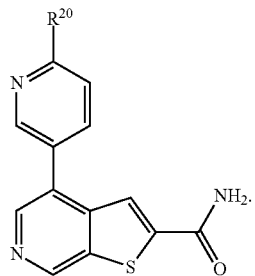

In embodiments, the compound has the formula:

(IXA)

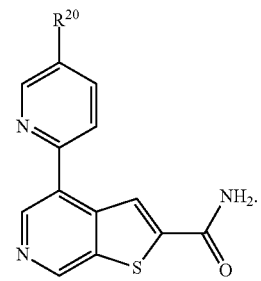

$R^{20}$ is as described herein (including in embodiments).

In embodiments, the compound has the formula:

(VIB)

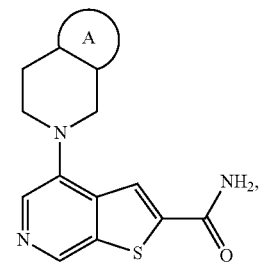

(VIIB)

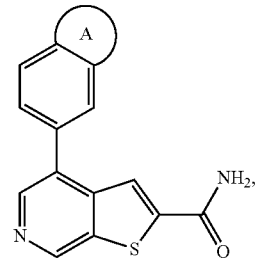

-continued (VIIIB)

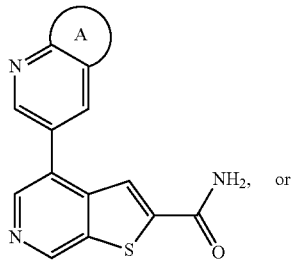

, or

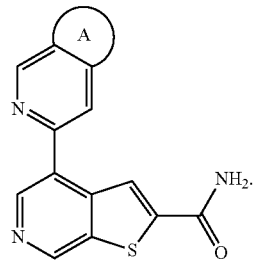

In embodiments, the compound has the formula:

(VIB)

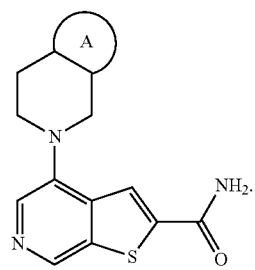

In embodiments, the compound has the formula:

(VIIB)

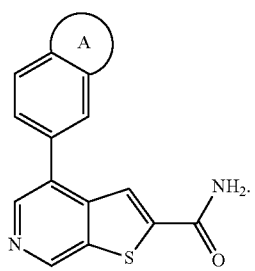

In embodiments, the compound has the formula:

(VIIIB)

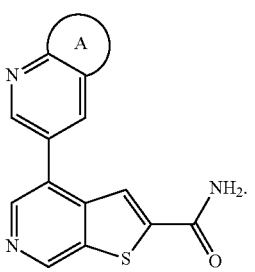

In embodiments, the compound has the formula:

(IXB)

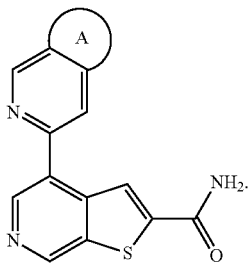

Ring A is a substituted or unsubstituted cycloalkyl (e.g., $C_3$-$C_8$, $C_3$-$C_6$, or $C_5$-$C_6$), substituted or unsubstituted heterocycloalkyl (e.g., 3 to 8 membered, 3 to 6 membered, or 5 to 6 membered), substituted or unsubstituted aryl (e.g., $C_6$-$C_{10}$, $C_{10}$, or phenyl), or substituted or unsubstituted heteroaryl (e.g., 5 to 10 membered, 5 to 9 membered, or 5 to 6 membered). In embodiments, Ring A is a substituted cycloalkyl (e.g., $C_3$-$C_8$, $C_3$-$C_6$, or $C_5$-$C_6$), substituted heterocycloalkyl (e.g., 3 to 8 membered, 3 to 6 membered, or 5 to 6 membered), substituted aryl (e.g., $C_6$-$C_{10}$, $C_{10}$, or phenyl), or substituted heteroaryl (e.g., 5 to 10 membered, 5 to 9 membered, or 5 to 6 membered). In embodiments, Ring A is an unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, Ring A is a $R^{21}$-substituted cycloalkyl (e.g., $C_3$-$C_8$, $C_3$-$C_6$, or $C_5$-$C_6$), $R^{21}$-substituted heterocycloalkyl (e.g., 3 to 8 membered, 3 to 6 membered, or 5 to 6 membered), $R^{21}$-substituted aryl (e.g., $C_6$-$C_{10}$, $C_{10}$, or phenyl), or $R^{21}$-substituted heteroaryl (e.g., 5 to 10 membered, 5 to 9 membered, or 5 to 6 membered).

In embodiments, Ring A is a substituted or unsubstituted phenyl, substituted or unsubstituted pyridinyl, substituted or unsubstituted pyrazinyl, substituted or unsubstituted pyrimidinyl, substituted or unsubstituted pyridazinyl, substituted or unsubstituted pyrrolyl, substituted or unsubstituted furanyl, substituted or unsubstituted thienyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted oxadiazolyl, substituted or unsubstituted piperazinyl, substituted or unsubstituted piperidinyl, substituted or unsubstituted pyrrolidinyl, substituted or unsubstituted azetidinyl, substituted or unsubstituted aziridinyl, substituted or unsubstituted morpholinyl, substituted or unsubstituted dioxanyl, substituted or unsubstituted dioxolyl, substituted or unsubstituted tetrahydropyranyl, substituted or unsubstituted dihydrodioxinyl, substituted or unsubstituted tetrahydrofuranyl, substituted or unsubstituted oxetanyl, or substituted or unsubstituted oxiranyl. In embodiments, Ring A is a substituted or unsubstituted phenyl. In embodiments, Ring A is a substituted or unsubstituted tetrahydrofuranyl. In embodiments, Ring A is a substituted or unsubstituted 1,3-dioxolanyl.

In embodiments, Ring A is a substituted phenyl, substituted pyridinyl, substituted pyrazinyl, substituted pyrimidinyl, substituted pyridazinyl, substituted pyrrolyl, substituted furanyl, substituted thienyl, substituted imidazolyl, substituted pyrazolyl, substituted oxazolyl, substituted isoxazolyl, substituted thiazolyl, substituted isothiazolyl, substituted triazolyl, substituted oxadiazolyl, substituted piperazinyl, substituted piperidinyl, substituted pyrrolidinyl, substituted azetidinyl, substituted aziridinyl, substituted morpholinyl, substituted dioxanyl, substituted dioxolyl, substituted tetrahydropyranyl, substituted dihydrodioxinyl, substituted tetrahydrofuranyl, substituted oxetanyl, or substituted oxiranyl.

In embodiments, Ring A is an unsubstituted phenyl, unsubstituted pyridinyl, unsubstituted pyrazinyl, unsubstituted pyrimidinyl, unsubstituted pyridazinyl, unsubstituted pyrrolyl, unsubstituted furanyl, unsubstituted thienyl, unsubstituted imidazolyl, unsubstituted pyrazolyl, unsubstituted oxazolyl, unsubstituted isoxazolyl, unsubstituted thiazolyl, unsubstituted isothiazolyl, unsubstituted triazolyl, unsubstituted oxadiazolyl, unsubstituted piperazinyl, unsubstituted piperidinyl, unsubstituted pyrrolidinyl, unsubstituted azetidinyl, unsubstituted aziridinyl, unsubstituted morpholinyl, unsubstituted dioxanyl, unsubstituted dioxolyl, unsubstituted tetrahydropyranyl, unsubstituted dihydrodioxinyl, unsubstituted tetrahydrofuranyl, unsubstituted oxetanyl, or unsubstituted oxiranyl.

In embodiments, Ring A is a $R^{21}$-substituted phenyl, $R^{21}$-substituted pyridinyl, $R^{21}$-substituted pyrazinyl, $R^{21}$-substituted pyrimidinyl, $R^{21}$-substituted pyridazinyl, $R^{21}$-substituted pyrrolyl, $R^{21}$-substituted furanyl, $R^{21}$-substituted thienyl, $R^{21}$-substituted imidazolyl, $R^{21}$-substituted pyrazolyl, $R^{21}$-substituted oxazolyl, $R^{21}$-substituted isoxazolyl, $R^{21}$-substituted thiazolyl, $R^{21}$-substituted isothiazolyl, $R^{21}$-substituted triazolyl, $R^{21}$-substituted oxadiazolyl, $R^{21}$-substituted piperazinyl, $R^{21}$-substituted piperidinyl, $R^{21}$-substituted pyrrolidinyl, $R^{21}$-substituted azetidinyl, $R^{21}$-substituted aziridinyl, $R^{21}$-substituted morpholinyl, $R^{21}$-substituted dioxanyl, $R^{21}$-substituted dioxolyl, $R^{21}$-substituted tetrahydropyranyl, $R^{21}$-substituted dihydrodioxinyl, $R^{21}$-substituted tetrahydrofuranyl, $R^{21}$-substituted oxetanyl, or $R^{21}$-substituted oxiranyl.

In embodiments, Ring A is a substituted or unsubstituted phenyl, substituted or unsubstituted pyridinyl, substituted or unsubstituted pyrrolyl, substituted or unsubstituted furanyl, substituted or unsubstituted thienyl, substituted or unsubstituted piperidinyl, substituted or unsubstituted pyrrolidinyl, substituted or unsubstituted azetidinyl, substituted or unsubstituted aziridinyl, substituted or unsubstituted tetrahydropyranyl, substituted or unsubstituted tetrahydrofuranyl, substituted or unsubstituted oxetanyl, or substituted or unsubstituted oxiranyl. In embodiments, Ring A is a substituted or unsubstituted pyrrolyl, substituted or unsubstituted furanyl, substituted or unsubstituted thienyl, substituted or unsubstituted pyrrolidinyl, or substituted or unsubstituted tetrahydrofuranyl. In embodiments, Ring A is a substituted or unsubstituted 1,4-dioxanyl. In embodiments, Ring A is an unsubstituted 1,4-dioxanyl. In embodiments, Ring A is a substituted or unsubstituted 1,3-dioxolyl. In embodiments, Ring A is an unsubstituted 1,3-dioxolyl. In embodiments, Ring A is a substituted or unsubstituted 1,3-dioxanyl. In embodiments, Ring A is an unsubstituted 1,3-dioxanyl. In embodiments, Ring A is a substituted or unsubstituted 2,3-dihydro-1,4-dioxinyl. In embodiments, Ring A is an unsubstituted 2,3-dihydro-1,4-dioxinyl.

In embodiments, $R^2$ is hydrogen, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is independently hydrogen, halogen, $-CX^2_3$, $-CN$, $-OH$, $-NH_2$, $-COOH$, $-CONH_2$, $-NO_2$, $-SH$, $-OCX^2_3$, $-OCHX^2_2$, $-CHX^2_2$, $-CH_2X^2$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^2$ is independently halogen, $-CX^2_3$, $-CN$, unsubstituted $C_1$-$C_4$ alkyl, or unsubstituted 2 to 4 membered heteroalkyl. In embodiments, $R^2$ is independently unsubstituted methyl, unsubstituted ethyl, unsubstituted isopropyl, or unsubstituted tert-butyl. In embodiments, $R^2$ is independently halogen, $-CX^2_3$, $-CN$, unsubstituted methyl, unsubstituted ethyl, unsubstituted methoxy, or unsubstituted ethoxy. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted n-propyl. In embodiments, $R^2$ is independently unsubstituted isopropyl. In embodiments, $R^2$ is independently unsubstituted butyl. In embodiments, $R^2$ is independently unsubstituted n-butyl. In embodiments, $R^2$ is independently unsubstituted isobutyl. In embodiments, $R^2$ is independently unsubstituted tert-butyl. In embodiments, $R^2$ is independently unsubstituted pentyl. In embodiments, $R^2$ is independently unsubstituted hexyl. In embodiments, $R^2$ is independently unsubstituted heptyl. In embodiments, $R^2$ is independently unsubstituted octyl. In embodiments, $R^2$ is independently $-F$. In embodiments, $R^2$ is independently $-Cl$. In embodiments, $R^2$ is independently $-Br$. In embodiments, $R^2$ is independently $-I$. In embodiments, $R^2$ is independently unsubstituted methoxy. In embodiments, $R^2$ is independently unsubstituted ethoxy. In embodiments, $R^2$ is independently halogen, $-CF_3$. In embodiments, $R^2$ is independently $-CCl3$.

In embodiments, $R^2$ is independently hydrogen. In embodiments, $R^2$ is independently halogen. In embodiments, $R^2$ is independently $-CX^2_3$. In embodiments, $R^2$ is independently $-CHX^{22}$. In embodiments, $R^2$ is independently $-CH_2X^2$. In embodiments, $R^2$ is independently $-OCX^2_3$. In embodiments, $R^2$ is independently $-OCH_2X^2$. In embodiments, $R^2$ is independently $-OCHX^{22}$. In embodiments, $R^2$ is independently $-CN$. In embodiments, $R^2$ is independently $-SO_{n2}R^{2D}$. In embodiments, $R^2$ is independently $-SO_{v2}NR^{2A}R^{2B}$. In embodiments, $R^2$ is independently $-NHC(O)NR^{2A}R^{2B}$. In embodiments, $R^2$ is independently $-N(O)_{m2}$. In embodiments, $R^2$ is independently $-NR^{2A}R^{2B}$. In embodiments, $R^2$ is independently $-C(O)R^{2C}$. In embodiments, $R^2$ is independently $-C(O)-OR^{2C}$. In embodiments, $R^2$ is independently $-C(O)NR^{2A}R^{2B}$. In embodiments, $R^2$ is independently $-OR^{2D}$. In embodiments, $R^2$ is independently $-NR^{2A}SO_2R^{2D}$. In embodiments, $R^2$ is independently $-NR^{2A}C(O)R^{2C}$. In embodiments, $R^2$ is independently $-NR^{2A}C(O)OR^{2C}$. In embodiments, $R^2$ is independently $-NR^{2A}OR^{2C}$. In embodiments, $R^2$ is independently $-OH$. In embodiments, $R^2$ is independently $-NH_2$. In embodiments, $R^2$ is independently $-COOH$. In embodiments, $R^2$ is independently $-CONH_2$. In embodiments, $R^2$ is independently $-NO_2$. In embodiments, $R^2$ is independently $-SH$.

In embodiments, $R^2$ is independently substituted or unsubstituted alkyl. In embodiments, $R^2$ is independently substituted or unsubstituted heteroalkyl. In embodiments, $R^2$ is independently substituted or unsubstituted cycloalkyl. In embodiments, $R^2$ is independently, substituted or unsubstituted heterocycloalkyl. In embodiments, $R^2$ is independently substituted or unsubstituted aryl. In embodiments, $R^2$ is independently substituted or unsubstituted heteroaryl.

In embodiments, $R^2$ is independently substituted alkyl. In embodiments, $R^2$ is independently substituted heteroalkyl. In embodiments, $R^2$ is independently substituted cycloalkyl. In embodiments, $R^2$ is independently, substituted heterocycloalkyl. In embodiments, $R^2$ is independently substituted aryl. In embodiments, $R^2$ is independently substituted heteroaryl. In embodiments, $R^2$ is independently unsubstituted alkyl. In embodiments, $R^2$ is independently unsubstituted heteroalkyl. In embodiments, $R^2$ is independently unsubstituted cycloalkyl. In embodiments, $R^2$ is independently, unsubstituted heterocycloalkyl. In embodiments, $R^2$ is independently unsubstituted aryl. In embodiments, $R^2$ is independently unsubstituted heteroaryl.

In embodiments, $R^2$ is independently substituted or unsubstituted $C_1$-$C_8$ alkyl. In embodiments, $R^2$ is independently substituted or unsubstituted 2 to 8 membered heteroalkyl. In embodiments, $R^2$ is independently substituted or unsubstituted $C_3$-$C_8$ cycloalkyl. In embodiments, $R^2$ is independently, substituted or unsubstituted 3 to 8 membered heterocycloalkyl. In embodiments, $R^2$ is independently substituted or unsubstituted $C_6$-$C_{10}$ aryl. In embodiments, $R^2$ is independently substituted or unsubstituted 5 to 10 membered heteroaryl.

In embodiments, $R^2$ is independently substituted $C_1$-$C_8$ alkyl. In embodiments, $R^2$ is independently substituted 2 to 8 membered heteroalkyl. In embodiments, $R^2$ is independently substituted $C_3$-$C_8$ cycloalkyl. In embodiments, $R^2$ is independently, substituted 3 to 8 membered heterocycloalkyl. In embodiments, $R^2$ is independently substituted $C_6$-$C_{10}$ aryl. In embodiments, $R^2$ is independently substituted 5 to 10 membered heteroaryl. In embodiments, $R^2$ is independently unsubstituted $C_1$-$C_8$ alkyl. In embodiments, $R^2$ is independently unsubstituted 2 to 8 membered heteroalkyl. In embodiments, $R^2$ is independently unsubstituted $C_3$-$C_8$ cycloalkyl. In embodiments, $R^2$ is independently, unsubstituted 3 to 8 membered heterocycloalkyl. In embodiments, $R^2$ is independently unsubstituted $C_6$-$C_{10}$ aryl. In embodiments, $R^2$ is independently unsubstituted 5 to 10 membered heteroaryl.

In embodiments, $R^2$ is independently substituted or unsubstituted $C_1$-$C_4$ alkyl. In embodiments, $R^2$ is independently substituted or unsubstituted 2 to 4 membered heteroalkyl. In embodiments, $R^2$ is independently substituted or unsubstituted $C_3$-$C_6$ cycloalkyl. In embodiments, $R^2$ is independently, substituted or unsubstituted 3 to 6 membered heterocycloalkyl. In embodiments, $R^2$ is independently substituted or unsubstituted phenyl. In embodiments, $R^2$ is independently substituted or unsubstituted 5 to 6 membered heteroaryl. In embodiments, $R^2$ is independently substituted $C_1$-$C_4$ alkyl. In embodiments, $R^2$ is independently substituted 2 to 4 membered heteroalkyl. In embodiments, $R^2$ is independently substituted $C_3$-$C_6$ cycloalkyl. In embodiments, $R^2$ is independently, substituted 3 to 6 membered heterocycloalkyl. In embodiments, $R^2$ is independently substituted phenyl. In embodiments, $R^2$ is independently substituted 5 to 6 membered heteroaryl. In embodiments, $R^2$ is independently unsubstituted $C_1$-$C_4$ alkyl. In embodiments, $R^2$ is independently unsubstituted 2 to 4 membered heteroalkyl. In embodiments, $R^2$ is independently unsubstituted $C_3$-$C_6$ cycloalkyl. In embodiments, $R^2$ is independently unsubstituted 3 to 6 membered heterocycloalkyl. In embodiments, $R^2$ is independently unsubstituted phenyl. In embodiments, $R^2$ is independently unsubstituted 5 to 6 membered heteroaryl.

In embodiments, $R^{2A}$ is independently hydrogen. In embodiments, $R^{2A}$ is independently —$CX^{2A}{}_3$. In embodiments, $R^{2A}$ is independently —$CHX^{2A}{}_2$. In embodiments, $R^{2A}$ is independently —$CH_2X^{2A}$. In embodiments, $R^{2A}$ is independently —CN. In embodiments, $R^{2A}$ is independently —COOH. In embodiments, $R^{2A}$ is independently —$CONH_2$. In embodiments, $R^{2A}$ is independently substituted or unsubstituted alkyl. In embodiments, $R^{2A}$ is independently substituted or unsubstituted heteroalkyl. In embodiments, $R^{2A}$ is independently substituted or unsubstituted cycloalkyl. In embodiments, $R^{2A}$ is independently, substituted or unsubstituted heterocycloalkyl. In embodiments, $R^{2A}$ is independently substituted or unsubstituted aryl. In embodiments, $R^{2A}$ is independently substituted or unsubstituted heteroaryl.

In embodiments, $R^{2A}$ is independently substituted alkyl. In embodiments, $R^{2A}$ is independently substituted heteroalkyl. In embodiments, $R^{2A}$ is independently substituted cycloalkyl. In embodiments, $R^{2A}$ is independently, substituted heterocycloalkyl. In embodiments, $R^{2A}$ is independently substituted aryl. In embodiments, $R^{2A}$ is independently substituted heteroaryl. In embodiments, $R^{2A}$ is independently unsubstituted alkyl. In embodiments, $R^{2A}$ is independently unsubstituted heteroalkyl. In embodiments, $R^{2A}$ is independently unsubstituted cycloalkyl. In embodiments, $R^{2A}$ is independently, unsubstituted heterocycloalkyl. In embodiments, $R^{2A}$ is independently unsubstituted aryl. In embodiments, $R^{2A}$ is independently unsubstituted heteroaryl.

In embodiments, $R^{2A}$ is independently substituted or unsubstituted $C_1$-$C_8$ alkyl. In embodiments, $R^{2A}$ is independently substituted or unsubstituted 2 to 8 membered heteroalkyl. In embodiments, $R^{2A}$ is independently substituted or unsubstituted $C_3$-$C_8$ cycloalkyl. In embodiments, $R^{2A}$ is independently, substituted or unsubstituted 3 to 8 membered heterocycloalkyl. In embodiments, $R^{2A}$ is independently substituted or unsubstituted $C_6$-$C_{10}$ aryl. In embodiments, $R^{2A}$ is independently substituted or unsubstituted 5 to 10 membered heteroaryl.

In embodiments, $R^{2A}$ is independently substituted $C_1$-$C_8$ alkyl. In embodiments, $R^{2A}$ is independently substituted 2 to 8 membered heteroalkyl. In embodiments, $R^{2A}$ is independently substituted $C_3$-$C_8$ cycloalkyl. In embodiments, $R^{2A}$ is independently, substituted 3 to 8 membered heterocycloalkyl. In embodiments, $R^{2A}$ is independently substituted $C_6$-$C_{10}$ aryl. In embodiments, $R^{2A}$ is independently substituted 5 to 10 membered heteroaryl. In embodiments, $R^{2A}$ is independently unsubstituted $C_1$-$C_8$ alkyl. In embodiments, $R^{2A}$ is independently unsubstituted 2 to 8 membered heteroalkyl. In embodiments, $R^{2A}$ is independently unsubstituted $C_3$-$C_8$ cycloalkyl. In embodiments, $R^{2A}$ is independently, unsubstituted 3 to 8 membered heterocycloalkyl. In embodiments, $R^{2A}$ is independently unsubstituted $C_6$-$C_{10}$ aryl. In embodiments, $R^{2A}$ is independently unsubstituted 5 to 10 membered heteroaryl.

In embodiments, $R^{2A}$ is independently substituted or unsubstituted $C_1$-$C_4$ alkyl. In embodiments, $R^{2A}$ is independently substituted or unsubstituted 2 to 4 membered heteroalkyl. In embodiments, $R^{2A}$ is independently substituted or unsubstituted $C_3$-$C_6$ cycloalkyl. In embodiments, $R^{2A}$ is independently, substituted or unsubstituted 3 to 6 membered heterocycloalkyl. In embodiments, $R^{2A}$ is independently substituted or unsubstituted phenyl. In embodiments, $R^{2A}$ is independently substituted or unsubstituted 5 to 6 membered heteroaryl.

In embodiments, $R^{2A}$ is independently substituted $C_1$-$C_4$ alkyl. In embodiments, $R^{2A}$ is independently substituted 2 to 4 membered heteroalkyl. In embodiments, $R^{2A}$ is independently substituted $C_3$-$C_6$ cycloalkyl. In embodiments, $R^{2A}$ is independently, substituted 3 to 6 membered heterocycloalkyl. In embodiments, $R^{2A}$ is independently substituted phenyl. In embodiments, $R^{2A}$ is independently substituted 5 to 6 membered heteroaryl. In embodiments, $R^{2A}$ is independently unsubstituted $C_1$-$C_4$ alkyl. In embodiments, $R^{2A}$ is independently unsubstituted 2 to 4 membered heteroalkyl. In embodiments, $R^{2A}$ is independently unsubstituted $C_3$-$C_6$ cycloalkyl. In embodiments, $R^{2A}$ is independently unsubstituted 3 to 6 membered heterocycloalkyl. In embodiments, $R^{2A}$ is independently unsubstituted phenyl. In embodiments, $R^{2A}$ is independently unsubstituted 5 to 6 membered heteroaryl. In embodiments, $R^{2A}$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently unsubstituted isopropyl. In embodiments, $R^{2A}$ is independently unsubstituted tert-butyl.

In embodiments, $R^{2B}$ is independently hydrogen. In embodiments, $R^{2B}$ is independently —$CX^{2B}_3$. In embodiments, $R^{2B}$ is independently —$CHX^{2B}_2$. In embodiments, $R^{2B}$ is independently —$CH_2X^{2B}$. In embodiments, $R^{2B}$ is independently —CN. In embodiments, $R^{2B}$ is independently —COOH. In embodiments, $R^{2B}$ is independently —$CONH_2$.

In embodiments, $R^{2B}$ is independently substituted or unsubstituted alkyl. In embodiments, $R^{2B}$ is independently substituted or unsubstituted heteroalkyl. In embodiments, $R^{2B}$ is independently substituted or unsubstituted cycloalkyl. In embodiments, $R^{2B}$ is independently, substituted or unsubstituted heterocycloalkyl. In embodiments, $R^{2B}$ is independently substituted or unsubstituted aryl. In embodiments, $R^{2B}$ is independently substituted or unsubstituted heteroaryl.

In embodiments, $R^{2B}$ is independently substituted alkyl. In embodiments, $R^{2B}$ is independently substituted heteroalkyl. In embodiments, $R^{2B}$ is independently substituted cycloalkyl. In embodiments, $R^{2B}$ is independently, substituted heterocycloalkyl. In embodiments, $R^{2B}$ is independently substituted aryl. In embodiments, $R^{2B}$ is independently substituted heteroaryl. In embodiments, $R^{2B}$ is independently unsubstituted alkyl. In embodiments, $R^{2B}$ is independently unsubstituted heteroalkyl. In embodiments, $R^{2B}$ is independently unsubstituted cycloalkyl. In embodiments, $R^{2B}$ is independently, unsubstituted heterocycloalkyl. In embodiments, $R^{2B}$ is independently unsubstituted aryl. In embodiments, $R^{2B}$ is independently unsubstituted heteroaryl.

In embodiments, $R^{2B}$ is independently substituted or unsubstituted $C_1$-$C_8$ alkyl. In embodiments, $R^{2B}$ is independently substituted or unsubstituted 2 to 8 membered heteroalkyl. In embodiments, $R^{2B}$ is independently substituted or unsubstituted $C_3$-$C_8$ cycloalkyl. In embodiments, $R^{2B}$ is independently, substituted or unsubstituted 3 to 8 membered heterocycloalkyl. In embodiments, $R^{2B}$ is independently substituted or unsubstituted $C_6$-$C_{10}$ aryl. In embodiments, $R^{2B}$ is independently substituted or unsubstituted 5 to 10 membered heteroaryl.

In embodiments, $R^{2B}$ is independently substituted $C_1$-$C_8$ alkyl. In embodiments, $R^{2B}$ is independently substituted 2 to 8 membered heteroalkyl. In embodiments, $R^{2B}$ is independently substituted $C_3$-$C_8$ cycloalkyl. In embodiments, $R^{2B}$ is independently, substituted 3 to 8 membered heterocycloalkyl. In embodiments, $R^{2B}$ is independently substituted $C_6$-$C_{10}$ aryl. In embodiments, $R^{2B}$ is independently substituted 5 to 10 membered heteroaryl. In embodiments, $R^{2B}$ is independently unsubstituted $C_1$-$C_8$ alkyl. In embodiments, $R^{2B}$ is independently unsubstituted 2 to 8 membered heteroalkyl. In embodiments, $R^{2B}$ is independently unsubstituted $C_3$-$C_8$ cycloalkyl. In embodiments, $R^{2B}$ is independently, unsubstituted 3 to 8 membered heterocycloalkyl. In embodiments, $R^{2B}$ is independently unsubstituted $C_6$-$C_{10}$ aryl. In embodiments, $R^{2B}$ is independently unsubstituted 5 to 10 membered heteroaryl.

In embodiments, $R^{2B}$ is independently substituted or unsubstituted $C_1$-$C_4$ alkyl. In embodiments, $R^{2B}$ is independently substituted or unsubstituted 2 to 4 membered heteroalkyl. In embodiments, $R^{2B}$ is independently substituted or unsubstituted $C_3$-$C_6$ cycloalkyl. In embodiments, $R^{2B}$ is independently, substituted or unsubstituted 3 to 6 membered heterocycloalkyl. In embodiments, $R^{2B}$ is independently substituted or unsubstituted phenyl. In embodiments, $R^{2B}$ is independently substituted or unsubstituted 5 to 6 membered heteroaryl.

In embodiments, $R^{2B}$ is independently substituted $C_1$-$C_4$ alkyl. In embodiments, $R^{2B}$ is independently substituted 2 to 4 membered heteroalkyl. In embodiments, $R^{2B}$ is independently substituted $C_3$-$C_6$ cycloalkyl. In embodiments, $R^{2B}$ is independently, substituted 3 to 6 membered heterocycloalkyl. In embodiments, $R^{2B}$ is independently substituted phenyl. In embodiments, $R^{2B}$ is independently substituted 5 to 6 membered heteroaryl. In embodiments, $R^{2B}$ is independently unsubstituted $C_1$-$C_4$ alkyl. In embodiments, $R^{2B}$ is independently unsubstituted 2 to 4 membered heteroalkyl. In embodiments, $R^{2B}$ is independently unsubstituted $C_3$-$C_6$ cycloalkyl. In embodiments, $R^{2B}$ is independently unsubstituted 3 to 6 membered heterocycloalkyl. In embodiments, $R^{2B}$ is independently unsubstituted phenyl. In embodiments, $R^{2B}$ is independently unsubstituted 5 to 6 membered heteroaryl. In embodiments, $R^{2B}$ is independently unsubstituted methyl. In embodiments, $R^{2B}$ is independently unsubstituted ethyl. In embodiments, $R^{2B}$ is independently unsubstituted propyl. In embodiments, $R^{2B}$ is independently unsubstituted isopropyl. In embodiments, $R^{2B}$ is independently unsubstituted tert-butyl.

In embodiments, $R^{2A}$ and $R^{2B}$ substituents bonded to the same nitrogen atom may be joined to form a substituted or unsubstituted heterocycloalkyl. In embodiments, $R^{2A}$ and $R^{2B}$ substituents bonded to the same nitrogen atom may be joined to form a substituted or unsubstituted heteroaryl. In embodiments, $R^{2A}$ and $R^{2B}$ substituents bonded to the same nitrogen atom may be joined to form a substituted heterocycloalkyl. In embodiments, $R^{2A}$ and $R^{2B}$ substituents bonded to the same nitrogen atom may be joined to form a substituted heteroaryl. In embodiments, $R^{2A}$ and $R^{2B}$ substituents bonded to the same nitrogen atom may be joined to form an unsubstituted heterocycloalkyl. In embodiments, $R^{2A}$ and $R^{2B}$ substituents bonded to the same nitrogen atom may be joined to form an unsubstituted heteroaryl.

In embodiments, $R^{2A}$ and $R^{2B}$ substituents bonded to the same nitrogen atom may be joined to form a substituted or unsubstituted 3 to 8 membered heterocycloalkyl. In embodiments, $R^{2A}$ and $R^{2B}$ substituents bonded to the same nitrogen atom may be joined to form a substituted or unsubstituted 5 to 10 membered heteroaryl. In embodiments, $R^{2A}$ and $R^{2B}$ substituents bonded to the same nitrogen atom may be joined to form a substituted 3 to 8 membered heterocycloalkyl. In embodiments, $R^{2A}$ and $R^{2B}$ substituents bonded to the same nitrogen atom may be joined to form a substituted 5 to 10 membered heteroaryl. In embodiments, $R^{2A}$ and $R^{2B}$ substituents bonded to the same nitrogen atom may be joined to form an unsubstituted 3 to 8 membered heterocycloalkyl. In embodiments, $R^{2A}$ and $R^{2B}$ substituents bonded to the same nitrogen atom may be joined to form an unsubstituted 5 to 10 membered heteroaryl. In embodiments, $R^{2A}$ and $R^{2B}$ substituents bonded to the same nitrogen atom may be joined to form a substituted or unsubstituted 3 to 6 membered heterocycloalkyl. In embodiments, $R^{2A}$ and $R^{2B}$ substituents bonded to the same nitrogen atom may be joined to form a substituted or unsubstituted 5 to 6 membered heteroaryl. In embodiments, $R^{2A}$ and $R^{2B}$ substituents bonded to the same nitrogen atom may be joined to form a substituted 3 to 6 membered heterocycloalkyl. In embodiments, $R^{2A}$ and $R^{2B}$ substituents bonded to the same nitrogen atom may be joined to form a substituted 5 to 6 membered heteroaryl. In embodiments, $R^{2A}$ and $R^{2B}$ substituents bonded to the same nitrogen atom may be joined to form an unsubstituted 3 to 6 membered heterocycloalkyl. In embodiments, $R^{2A}$ and $R^{2B}$ substituents bonded to the same nitrogen atom may be joined to form an unsubstituted 5 to 6 membered heteroaryl.

In embodiments, $R^{2C}$ is independently hydrogen. In embodiments, $R^{2C}$ is independently $-CX^{2C}_3$. In embodiments, $R^{2C}$ is independently $-CHX^{2C}_2$. In embodiments, $R^{2C}$ is independently $-CH_2X^{2C}$. In embodiments, $R^{2C}$ is independently $-CN$. In embodiments, $R^{2C}$ is independently $-COOH$. In embodiments, $R^{2C}$ is independently $-CONH_2$. In embodiments, $R^{2C}$ is independently substituted or unsubstituted alkyl. In embodiments, $R^{2C}$ is independently substituted or unsubstituted heteroalkyl. In embodiments, $R^{2C}$ is independently substituted or unsubstituted cycloalkyl. In embodiments, $R^{2C}$ is independently, substituted or unsubstituted heterocycloalkyl. In embodiments, $R^{2C}$ is independently substituted or unsubstituted aryl. In embodiments, $R^{2C}$ is independently substituted or unsubstituted heteroaryl.

In embodiments, $R^{2C}$ is independently substituted alkyl. In embodiments, $R^{2C}$ is independently substituted heteroalkyl. In embodiments, $R^{2C}$ is independently substituted cycloalkyl. In embodiments, $R^{2C}$ is independently, substituted heterocycloalkyl. In embodiments, $R^{2C}$ is independently substituted aryl. In embodiments, $R^{2C}$ is independently substituted heteroaryl. In embodiments, $R^{2C}$ is independently unsubstituted alkyl. In embodiments, $R^{2C}$ is independently unsubstituted heteroalkyl. In embodiments, $R^{2C}$ is independently unsubstituted cycloalkyl. In embodiments, $R^{2C}$ is independently, unsubstituted heterocycloalkyl. In embodiments, $R^{2C}$ is independently unsubstituted aryl. In embodiments, $R^{2C}$ is independently unsubstituted heteroaryl.

In embodiments, $R^{2C}$ is independently substituted or unsubstituted $C_1$-$C_8$ alkyl. In embodiments, $R^{2C}$ is independently substituted or unsubstituted 2 to 8 membered heteroalkyl. In embodiments, $R^{2C}$ is independently substituted or unsubstituted $C_3$-$C_8$ cycloalkyl. In embodiments, $R^{2C}$ is independently, substituted or unsubstituted 3 to 8 membered heterocycloalkyl. In embodiments, $R^{2C}$ is independently substituted or unsubstituted $C_6$-$C_{10}$ aryl. In embodiments, $R^{2C}$ is independently substituted or unsubstituted 5 to 10 membered heteroaryl.

In embodiments, $R^{2C}$ is independently substituted $C_1$-$C_8$ alkyl. In embodiments, $R^{2C}$ is independently substituted 2 to 8 membered heteroalkyl. In embodiments, $R^{2C}$ is independently substituted $C_3$-$C_8$ cycloalkyl. In embodiments, $R^{2C}$ is independently, substituted 3 to 8 membered heterocycloalkyl. In embodiments, $R^{2C}$ is independently substituted $C_6$-$C_{10}$ aryl. In embodiments, $R^{2C}$ is independently substituted 5 to 10 membered heteroaryl. In embodiments, $R^{2C}$ is independently unsubstituted $C_1$-$C_8$ alkyl. In embodiments, $R^{2C}$ is independently unsubstituted 2 to 8 membered heteroalkyl. In embodiments, $R^{2C}$ is independently unsubstituted $C_3$-$C_8$ cycloalkyl. In embodiments, $R^{2C}$ is independently, unsubstituted 3 to 8 membered heterocycloalkyl. In embodiments, $R^{2C}$ is independently unsubstituted $C_6$-$C_{10}$ aryl. In embodiments, $R^{2C}$ is independently unsubstituted 5 to 10 membered heteroaryl.

In embodiments, $R^{2C}$ is independently substituted or unsubstituted $C_1$-$C_4$ alkyl. In embodiments, $R^{2C}$ is independently substituted or unsubstituted 2 to 4 membered heteroalkyl. In embodiments, $R^{2C}$ is independently substituted or unsubstituted $C_3$-$C_6$ cycloalkyl. In embodiments, $R^{2C}$ is independently, substituted or unsubstituted 3 to 6 membered heterocycloalkyl. In embodiments, $R^{2C}$ is independently substituted or unsubstituted phenyl. In embodiments, $R^{2C}$ is independently substituted or unsubstituted 5 to 6 membered heteroaryl.

In embodiments, $R^{2C}$ is independently substituted $C_1$-$C_4$ alkyl. In embodiments, $R^{2C}$ is independently substituted 2 to 4 membered heteroalkyl. In embodiments, $R^{2C}$ is independently substituted $C_3$-$C_6$ cycloalkyl. In embodiments, $R^{2C}$ is independently, substituted 3 to 6 membered heterocycloalkyl. In embodiments, $R^{2C}$ is independently substituted phenyl. In embodiments, $R^{2C}$ is independently substituted 5 to 6 membered heteroaryl. In embodiments, $R^{2C}$ is independently unsubstituted $C_1$-$C_4$ alkyl. In embodiments, $R^{2C}$ is independently unsubstituted 2 to 4 membered heteroalkyl. In embodiments, $R^{2C}$ is independently unsubstituted $C_3$-$C_6$ cycloalkyl. In embodiments, $R^{2C}$ is independently unsubstituted 3 to 6 membered heterocycloalkyl. In embodiments, $R^{2C}$ is independently unsubstituted phenyl. In embodiments, $R^{2C}$ is independently unsubstituted 5 to 6 membered heteroaryl. In embodiments, $R^{2C}$ is independently unsubstituted methyl. In embodiments, $R^{2C}$ is independently unsubstituted ethyl. In embodiments, $R^{2C}$ is independently unsubstituted propyl. In embodiments, $R^{2C}$ is independently unsubstituted isopropyl. In embodiments, $R^{2C}$ is independently unsubstituted tert-butyl.

In embodiments, $R^{2D}$ is independently hydrogen. In embodiments, $R^{2D}$ is independently $-CX^{2D}_3$. In embodiments, $R^{2D}$ is independently $-CHX^{2D}_2$. In embodiments, $R^{2D}$ is independently $-CH_2X^{2D}$. In embodiments, $R^{2D}$ is independently $-CN$. In embodiments, $R^{2D}$ is independently $-COOH$. In embodiments, $R^{2D}$ is independently $-CONH_2$. In embodiments, $R^{2D}$ is independently substituted or unsubstituted alkyl. In embodiments, $R^{2D}$ is independently substituted or unsubstituted heteroalkyl. In embodiments, $R^{2D}$ is independently substituted or unsubstituted cycloalkyl. In embodiments, $R^{2D}$ is independently, substituted or unsubstituted heterocycloalkyl. In embodiments, $R^{2D}$ is independently substituted or unsubstituted aryl. In embodiments, $R^{2D}$ is independently substituted or unsubstituted heteroaryl.

In embodiments, $R^{2D}$ is independently substituted alkyl. In embodiments, $R^{2D}$ is independently substituted heteroalkyl. In embodiments, $R^{2D}$ is independently substituted cycloalkyl. In embodiments, $R^{2D}$ is independently, substituted heterocycloalkyl. In embodiments, $R^{2D}$ is independently substituted aryl. In embodiments, $R^{2D}$ is independently substituted heteroaryl. In embodiments, $R^{2D}$ is independently unsubstituted alkyl. In embodiments, $R^{2D}$ is independently unsubstituted heteroalkyl. In embodiments, $R^{2D}$ is independently unsubstituted cycloalkyl. In embodiments, $R^{2D}$ is independently, unsubstituted heterocycloalkyl.

In embodiments, $R^{2D}$ is independently unsubstituted aryl. In embodiments, $R^{2D}$ is independently unsubstituted heteroaryl.

In embodiments, $R^{2D}$ is independently substituted or unsubstituted $C_1$-$C_8$ alkyl. In embodiments, $R^{2D}$ is independently substituted or unsubstituted 2 to 8 membered heteroalkyl. In embodiments, $R^{2D}$ is independently substituted or unsubstituted $C_3$-$C_8$ cycloalkyl. In embodiments, $R^{2D}$ is independently, substituted or unsubstituted 3 to 8 membered heterocycloalkyl. In embodiments, $R^{2D}$ is independently substituted or unsubstituted $C_6$-$C_{10}$ aryl. In embodiments, $R^{2D}$ is independently substituted or unsubstituted 5 to 10 membered heteroaryl.

In embodiments, $R^{2D}$ is independently substituted $C_1$-$C_8$ alkyl. In embodiments, $R^{2D}$ is independently substituted 2 to 8 membered heteroalkyl. In embodiments, $R^{2D}$ is independently substituted $C_3$-$C_8$ cycloalkyl. In embodiments, $R^{2D}$ is independently, substituted 3 to 8 membered heterocycloalkyl. In embodiments, $R^{2D}$ is independently substituted $C_6$-$C_{10}$ aryl. In embodiments, $R^{2D}$ is independently substituted 5 to 10 membered heteroaryl. In embodiments, $R^{2D}$ is independently unsubstituted $C_1$-$C_8$ alkyl. In embodiments, $R^{2D}$ is independently unsubstituted 2 to 8 membered heteroalkyl. In embodiments, $R^{2D}$ is independently unsubstituted $C_3$-$C_8$ cycloalkyl. In embodiments, $R^{2D}$ is independently, unsubstituted 3 to 8 membered heterocycloalkyl. In embodiments, $R^{2D}$ is independently unsubstituted $C_6$-$C_{10}$ aryl. In embodiments, $R^{2D}$ is independently unsubstituted 5 to 10 membered heteroaryl.

In embodiments, $R^{2D}$ is independently substituted or unsubstituted $C_1$-$C_4$ alkyl. In embodiments, $R^{2D}$ is independently substituted or unsubstituted 2 to 4 membered heteroalkyl. In embodiments, $R^{2D}$ is independently substituted or unsubstituted $C_3$-$C_6$ cycloalkyl. In embodiments, $R^{2D}$ is independently, substituted or unsubstituted 3 to 6 membered heterocycloalkyl. In embodiments, $R^{2D}$ is independently substituted or unsubstituted phenyl. In embodiments, $R^{2D}$ is independently substituted or unsubstituted 5 to 6 membered heteroaryl.

In embodiments, $R^{2D}$ is independently substituted $C_1$-$C_4$ alkyl. In embodiments, $R^{2D}$ is independently substituted 2 to 4 membered heteroalkyl. In embodiments, $R^{2D}$ is independently substituted $C_3$-$C_6$ cycloalkyl. In embodiments, $R^{2D}$ is independently, substituted 3 to 6 membered heterocycloalkyl. In embodiments, $R^{2D}$ is independently substituted phenyl. In embodiments, $R^{2D}$ is independently substituted 5 to 6 membered heteroaryl. In embodiments, $R^{2D}$ is independently unsubstituted $C_1$-$C_4$ alkyl. In embodiments, $R^{2D}$ is independently unsubstituted 2 to 4 membered heteroalkyl. In embodiments, $R^{2D}$ is independently unsubstituted $C_3$-$C_6$ cycloalkyl. In embodiments, $R^{2D}$ is independently unsubstituted 3 to 6 membered heterocycloalkyl. In embodiments, $R^{2D}$ is independently unsubstituted phenyl. In embodiments, $R^{2D}$ is independently unsubstituted 5 to 6 membered heteroaryl. In embodiments, $R^{2D}$ is independently unsubstituted methyl. In embodiments, $R^{2D}$ is independently unsubstituted ethyl. In embodiments, $R^{2D}$ is independently unsubstituted propyl. In embodiments, $R^{2D}$ is independently unsubstituted isopropyl. In embodiments, $R^{2D}$ is independently unsubstituted tert-butyl.

In embodiments, $R^2$ is independently halogen, $—CX^2_3$, $—CHX^{22}$, $—CH_2X^2$, $—OCX^2_3$, $—OCH_2X^2$, $—OCHX^{22}$, $—CN$, $—SOn_2R^{2D}$, $—SO_{v2}NR^{2A}R^{2B}$, $—NHC(O)NR^{2A}R^{2B}$, $—N(O)_{m2}$, $—NR^{2A}R^{2B}$, $—C(O)R^2$, $—C(O)OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, R23-substituted or unsubstituted alkyl, $R^2_3$-substituted or unsubstituted heteroalkyl, $R^2_3$-substituted or unsubstituted cycloalkyl, $R^2_3$-substituted or unsubstituted heterocycloalkyl, $R^2_3$-substituted or unsubstituted aryl, or $R^2_3$-substituted or unsubstituted heteroaryl. In embodiments, $R^2$ is independently halogen, $—CX^2_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^2_3$, $—OCHX^{22}$, $R^2_3$-substituted or unsubstituted alkyl, $R^2_3$-substituted or unsubstituted heteroalkyl, $R^2_3$-substituted or unsubstituted cycloalkyl, $R^2_3$-substituted or unsubstituted heterocycloalkyl, $R^2_3$-substituted or unsubstituted aryl, or $R^2_3$-substituted or unsubstituted heteroaryl. In embodiments, $R^2$ is independently halogen, $—CX^2_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^2_3$, $—OCHX^{22}$, $R^2_3$-substituted or unsubstituted $C_1$-$C_8$ alkyl, $R^2_3$-substituted or unsubstituted 2 to 8 membered heteroalkyl, $R^2_3$-substituted or unsubstituted $C_3$-$C_8$ cycloalkyl, $R^2_3$-substituted or unsubstituted 3 to 6 membered heterocycloalkyl, $R^2_3$-substituted or unsubstituted phenyl, or $R^2_3$-substituted or unsubstituted 5 to 6 membered heteroaryl. $X^2$ is $—F$, $—Cl$, $—Br$, or $—I$. In embodiments, $R^2$ is independently hydrogen. In embodiments, $R^2$ is independently methyl. In embodiments, $R^2$ is independently ethyl.

$R^{23}$ is independently oxo, halogen, $—CX^{23}_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^{23}_3$, $—OCHX^{23}_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. In embodiments, $R^{23}$ is independently oxo, halogen, $—CX^{23}_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^{23}_3$, $—OCHX^{23}_2$, $R^{24}$-substituted or unsubstituted $C_1$-$C_8$ alkyl, $R^{24}$-substituted or unsubstituted 2 to 8 membered heteroalkyl, $R^{24}$-substituted or unsubstituted $C_3$-$C_8$ cycloalkyl, $R^{24}$-substituted or unsubstituted 3 to 6 membered heterocycloalkyl, $R^{24}$-substituted or unsubstituted phenyl, or $R^{24}$-substituted or unsubstituted 5 to 6 membered heteroaryl. $X^{23}$ is $—F$, $—Cl$, $—Br$, or $—I$.

$R^{24}$ is independently oxo, halogen, $—CX^{24}_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^{24}_3$, $—OCHX^{24}_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. In embodiments, $R^{24}$ is independently oxo, halogen, $—CX^{24}_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^{24}_3$, $—OCHX^{24}_2$, $R^{25}$-substituted or unsubstituted $C_1$-$C_8$ alkyl, $R^{25}$-substituted or unsubstituted 2 to 8 membered heteroalkyl, $R^{25}$-substituted or unsubstituted $C_3$-$C_8$ cycloalkyl, $R^{25}$-substituted or unsubstituted 3 to 6 membered heterocycloalkyl, $R^{25}$-substituted or unsubstituted phenyl, or $R^{25}$-substituted or unsubstituted 5 to 6 membered heteroaryl. $X^{24}$ is —F, —Cl, —Br, or —I.

In embodiments, $R^{2A}$ is independently hydrogen, —$CX^{2A}_3$, —CN, —COOH, —$CONH_2$, —$CHX^{2A}_2$, —$CH_2X^{2A}$, $R^{23A}$-substituted or unsubstituted alkyl, $R^{23A}$-substituted or unsubstituted heteroalkyl, $R^{23A}$-substituted or unsubstituted cycloalkyl, $R^{23A}$-substituted or unsubstituted heterocycloalkyl, $R^{23A}$-substituted or unsubstituted aryl, or $R^{23A}$-substituted or unsubstituted heteroaryl. In embodiments, $R^{2A}$ is independently hydrogen, —$CX^{2A}_3$, —CN, —COOH, —$CONH_2$, —$CHX^{2A}_2$, —$CH_2X^{2A}$, $R^{23A}$-substituted or unsubstituted $C_1$-$C_8$ alkyl, $R^{23A}$-substituted or unsubstituted 2 to 8 membered heteroalkyl, $R^{23A}$-substituted or unsubstituted $C_3$-$C_8$ cycloalkyl, $R^{23A}$-substituted or unsubstituted 3 to 6 membered heterocycloalkyl, $R^{23A}$-substituted or unsubstituted phenyl, or $R^{23A}$-substituted or unsubstituted 5 to 6 membered heteroaryl. $X^{2A}$ is —F, —Cl, —Br, or —I. In embodiments, $R^{2A}$ is independently hydrogen. In embodiments, $R^{2A}$ is independently methyl. In embodiments, $R^{2A}$ is independently ethyl.

In embodiments, $R^{2A}$ and $R^{2B}$ substituents bonded to the same nitrogen atom may optionally be joined to form a $R^{23A}$-substituted or unsubstituted heterocycloalkyl or $R^{23A}$-substituted or unsubstituted heteroaryl. In embodiments, $R^{2A}$ and $R^{2B}$ substituents bonded to the same nitrogen atom may optionally be joined to form a $R^{23A}$-substituted or unsubstituted 3 to 6 membered heterocycloalkyl or $R^{23A}$-substituted or unsubstituted 5 to 6 membered heteroaryl.

$R^{23A}$ is independently oxo, halogen, —$CX^{23A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{23A}_3$, —$OCHX^{23A}_2$, $R^{24A}$-substituted or unsubstituted alkyl, $R^{24A}$-substituted or unsubstituted heteroalkyl, $R^{24A}$-substituted or unsubstituted cycloalkyl, $R^{24A}$-substituted or unsubstituted heterocycloalkyl, $R^{24A}$-substituted or unsubstituted aryl, or $R^{24A}$-substituted or unsubstituted heteroaryl. In embodiments, $R^{23A}$ is independently oxo, halogen, —$CX^{23A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{23A}_3$, —$OCHX^{23A}2$, $R^{24A}$-substituted or unsubstituted $C_1$-$C_8$ alkyl, $R^{24A}$-substituted or unsubstituted 2 to 8 membered heteroalkyl, $R^{24A}$-substituted or unsubstituted $C_3$-$C_8$ cycloalkyl, $R^{24A}$-substituted or unsubstituted 3 to 6 membered heterocycloalkyl, $R^{24A}$-substituted or unsubstituted phenyl, or $R^{24A}$-substituted or unsubstituted 5 to 6 membered heteroaryl. $X^{23A}$ is —F, —Cl, —Br, or —I.

$R^{24A}$ is independently oxo, halogen, —$CX^{24A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{24A}_3$, —$OCHX^{24A}_2$, $R^{25A}$-substituted or unsubstituted alkyl, $R^{25A}$-substituted or unsubstituted heteroalkyl, $R^{25A}$-substituted or unsubstituted cycloalkyl, $R^{25A}$-substituted or unsubstituted heterocycloalkyl, $R^{25A}$-substituted or unsubstituted aryl, or $R^{25A}$-substituted or unsubstituted heteroaryl. In embodiments, $R^{24A}$ is independently oxo, halogen, —$CX^{24A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{24A}_3$, —$OCHX^{24A}_2$, $R^{25A}$-substituted or unsubstituted $C_1$-$C_8$ alkyl, $R^{25A}$-substituted or unsubstituted 2 to 8 membered heteroalkyl, $R^{25A}$-substituted or unsubstituted $C_3$-$C_8$ cycloalkyl, $R^{25A}$-substituted or unsubstituted 3 to 6 membered heterocycloalkyl, $R^{25A}$-substituted or unsubstituted phenyl, or $R^{25A}$-substituted or unsubstituted 5 to 6 membered heteroaryl. $X^{24A}$ is —F, —Cl, —Br, or —I.

In embodiments, $R^{2B}$ is independently hydrogen, —$CX^{2B}_3$, —CN, —COOH, —$CONH_2$, —$CHX^{2B}_2$, —$CH_2X^{2B}$, $R^{23B}$-substituted or unsubstituted alkyl, $R^{23B}$-substituted or unsubstituted heteroalkyl, $R^{23B}$-substituted or unsubstituted cycloalkyl, $R^{23B}$-substituted or unsubstituted heterocycloalkyl, $R^{23B}$-substituted or unsubstituted aryl, or $R^{23B}$-substituted or unsubstituted heteroaryl. In embodiments, $R^{2B}$ is independently hydrogen, —$CX^{2B}_3$, —CN, —COOH, —$CONH_2$, —$CHX^{2B}_2$, —$CH_2X^{2B}$, $R^{23B}$-substituted or unsubstituted $C_1$-$C_8$ alkyl, $R^{23B}$-substituted or unsubstituted 2 to 8 membered heteroalkyl, $R^{23B}$-substituted or unsubstituted $C_3$-$C_8$ cycloalkyl, $R^{23B}$-substituted or unsubstituted 3 to 6 membered heterocycloalkyl, $R^{23B}$-substituted or unsubstituted phenyl, or $R^{23B}$-substituted or unsubstituted 5 to 6 membered heteroaryl. $X^{2B}$ is —F, —Cl, —Br, or —I. In embodiments, $R^{2B}$ is independently hydrogen. In embodiments, $R^{2B}$ is independently methyl. In embodiments, $R^{2B}$ is independently ethyl.

In embodiments, $R^{2A}$ and $R^{2B}$ substituents bonded to the same nitrogen atom may optionally be joined to form a $R^{23B}$-substituted or unsubstituted heterocycloalkyl or $R^{23B}$-substituted or unsubstituted heteroaryl. In embodiments, $R^{2A}$ and $R^{2B}$ substituents bonded to the same nitrogen atom may optionally be joined to form a $R^{23B}$-substituted or unsubstituted 3 to 6 membered heterocycloalkyl or $R^{23B}$-substituted or unsubstituted 5 to 6 membered heteroaryl.

$R^{23B}$ is independently oxo, halogen, —$CX^{23B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{23B}_3$, —$OCHX^{23B}_2$, $R^{24B}$-substituted or unsubstituted alkyl, $R^{24B}$-substituted or unsubstituted heteroalkyl, $R^{24B}$-substituted or unsubstituted cycloalkyl, $R^{24B}$-substituted or unsubstituted heterocycloalkyl, $R^{24B}$-substituted or unsubstituted aryl, or $R^{24B}$-substituted or unsubstituted heteroaryl. In embodiments, $R^{23B}$ is independently oxo, halogen, —$CX^{23B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{23B}_3$, —$OCHX^{23B}_2$, $R^{24B}$-substituted or unsubstituted $C_1$-$C_8$ alkyl, $R^{24B}$-substituted or unsubstituted 2 to 8 membered heteroalkyl, $R^{24B}$-substituted or unsubstituted $C_3$-$C_8$ cycloalkyl, $R^{24B}$-substituted or unsubstituted 3 to 6 membered heterocycloalkyl, $R^{24B}$-substituted or unsubstituted phenyl, or $R^{24B}$-substituted or unsubstituted 5 to 6 membered heteroaryl. $X^{23B}$ is —F, —Cl, —Br, or —I.

$R^{24B}$ is independently oxo, halogen, —$CX^{24B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{24B}_3$, —$OCHX^{24B}_2$, $R^{25B}$-substituted or unsubstituted alkyl, $R^{25B}$-substituted or unsubstituted heteroalkyl, $R^{25B}$-substituted or unsubstituted cycloalkyl, $R^{25B}$-substituted or unsubstituted heterocycloalkyl, $R^{25B}$-substituted or unsubstituted aryl, or $R^{25B}$-substituted or unsubstituted heteroaryl. In embodiments, $R^{24B}$ is independently oxo, halogen, —$CX^{24B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —OCX$^{24B}_3$, —OCHX$^{24B}_2$, R$^{25B}$-substituted or unsubstituted C$_1$-C$_8$ alkyl, R$^{25B}$-substituted or unsubstituted 2 to 8 membered heteroalkyl, R$^{25B}$-substituted or unsubstituted C$_3$-C$_8$ cycloalkyl, R$^{25B}$-substituted or unsubstituted 3 to 6 membered heterocycloalkyl, R$^{25B}$-substituted or unsubstituted phenyl, or R$^{25B}$-substituted or unsubstituted 5 to 6 membered heteroaryl. X$^{24B}$ is —F, —Cl, —Br, or —I.

In embodiments, R$^{2C}$ is independently hydrogen, —CX$^{2C}_3$, —CN, —COOH, —CONH$_2$, —CHX$^{2C}_2$, —CH$_2$X$^{2C}$, R$^{23C}$-substituted or unsubstituted alkyl, R$^{23C}$-substituted or unsubstituted heteroalkyl, R$^{23C}$-substituted or unsubstituted cycloalkyl, R$^{23C}$-substituted or unsubstituted heterocycloalkyl, R$^{23C}$-substituted or unsubstituted aryl, or R$^{23C}$-substituted or unsubstituted heteroaryl. In embodiments, R$^{2C}$ is independently hydrogen, —CX$^{2C}_3$, —CN, —COOH, —CONH$_2$, —CHX$^{2C}_2$, —CH$_2$X$^{2C}$, R$^{23C}$-substituted or unsubstituted C$_1$-C$_8$ alkyl, R$^{23C}$-substituted or unsubstituted 2 to 8 membered heteroalkyl, R$^{23C}$-substituted or unsubstituted C$_3$-C$_8$ cycloalkyl, R$^{23C}$-substituted or unsubstituted 3 to 6 membered heterocycloalkyl, R$^{23C}$-substituted or unsubstituted phenyl, or R$^{23C}$-substituted or unsubstituted 5 to 6 membered heteroaryl. X$^{2C}$ is —F, —Cl, —Br, or —I. In embodiments, R$^{2C}$ is independently hydrogen. In embodiments, R$^{2C}$ is independently methyl. In embodiments, R$^{2C}$ is independently ethyl.

R$^{23C}$ is independently oxo, halogen, —CX$^{23C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23C}_3$, —OCHX$^{23C}_2$, R$^{24C}$-substituted or unsubstituted alkyl, R$^{24C}$-substituted or unsubstituted heteroalkyl, R$^{24C}$-substituted or unsubstituted cycloalkyl, R$^{24C}$-substituted or unsubstituted heterocycloalkyl, R$^{24C}$-substituted or unsubstituted aryl, or R$^{24C}$-substituted or unsubstituted heteroaryl. In embodiments, R$^{23C}$ is independently oxo, halogen, —CX$^{23C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23C}_3$, —OCHX$^{23C}_2$, R$^{24C}$-substituted or unsubstituted C$_1$-C$_8$ alkyl, R$^{24C}$-substituted or unsubstituted 2 to 8 membered heteroalkyl, R$^{24C}$-substituted or unsubstituted C$_3$-C$_8$ cycloalkyl, R$^{24C}$-substituted or unsubstituted 3 to 6 membered heterocycloalkyl, R$^{24C}$-substituted or unsubstituted phenyl, or R$^{24C}$-substituted or unsubstituted 5 to 6 membered heteroaryl. X$^{23C}$ is —F, —Cl, —Br, or —I.

R$^{24C}$ is independently oxo, halogen, —CX$^{24C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{24C}_3$, —OCHX$^{24C}_2$, R$^{25C}$-substituted or unsubstituted alkyl, R$^{25C}$-substituted or unsubstituted heteroalkyl, R$^{25C}$-substituted or unsubstituted cycloalkyl, R$^{25C}$-substituted or unsubstituted heterocycloalkyl, R$^{25C}$-substituted or unsubstituted aryl, or R$^{25C}$-substituted or unsubstituted heteroaryl. In embodiments, R$^{24C}$ is independently oxo, halogen, —CX$^{24C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —OCX$^{24C}_3$, —OCHX$^{24C}_2$, R$^{25C}$-substituted or unsubstituted C$_1$-C$_8$ alkyl, R$^{25C}$-substituted or unsubstituted 2 to 8 membered heteroalkyl, R$^{25C}$-substituted or unsubstituted C$_3$-C$_8$ cycloalkyl, R$^{25C}$-substituted or unsubstituted 3 to 6 membered heterocycloalkyl, R$^{25C}$-substituted or unsubstituted phenyl, or R$^{25C}$-substituted or unsubstituted 5 to 6 membered heteroaryl. X$^{24C}$ is —F, —Cl, —Br, or —I.

In embodiments, R$^{2D}$ is independently hydrogen, —CX$^{2D}_3$, —CN, —COOH, —CONH$_2$, —CHX$^{2D}_2$, —CH$_2$X$^{2D}$, R$^{23D}$-substituted or unsubstituted alkyl, R$^{23D}$-substituted or unsubstituted heteroalkyl, R$^{23D}$-substituted or unsubstituted cycloalkyl, R$^{23D}$-substituted or unsubstituted heterocycloalkyl, R$^{23D}$-substituted or unsubstituted aryl, or R$^{23D}$-substituted or unsubstituted heteroaryl. In embodiments, R$^{2D}$ is independently hydrogen, —CX$^{2D}_3$, —CN, —COOH, —CONH$_2$, —CHX$^{2D}_2$, —CH$_2$X$^{2}$D, R$^{23D}$-substituted or unsubstituted C$_1$-C$_8$ alkyl, R$^{23D}$-substituted or unsubstituted 2 to 8 membered heteroalkyl, R$^{23D}$-substituted or unsubstituted C$_3$-C$_8$ cycloalkyl, R$^{23D}$-substituted or unsubstituted 3 to 6 membered heterocycloalkyl, R$^{23D}$-substituted or unsubstituted phenyl, or R$^{23D}$-substituted or unsubstituted 5 to 6 membered heteroaryl. X$^{2D}$ is —F, —Cl, —Br, or —I. In embodiments, R$^{2D}$ is independently hydrogen. In embodiments, R$^{2D}$ is independently methyl. In embodiments, R$^{2D}$ is independently ethyl.

R$^{23D}$ is independently oxo, halogen, —CX$^{23D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23D}_3$, —OCHX$^{23D}_2$, R$^{24D}$-substituted or unsubstituted alkyl, R$^{24D}$-substituted or unsubstituted heteroalkyl, R$^{24D}$-substituted or unsubstituted cycloalkyl, R$^{24D}$-substituted or unsubstituted heterocycloalkyl, R$^{24D}$-substituted or unsubstituted aryl, or R$^{24D}$-substituted or unsubstituted heteroaryl. In embodiments, R$^{23D}$ is independently oxo, halogen, —CX$^{23D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23D}_3$, —OCHX$^{23D}_2$, R$^{24D}$-substituted or unsubstituted C$_1$-C$_8$ alkyl, R$^{24D}$-substituted or unsubstituted 2 to 8 membered heteroalkyl, R$^{24D}$-substituted or unsubstituted C$_3$-C$_8$ cycloalkyl, R$^{24D}$-substituted or unsubstituted 3 to 6 membered heterocycloalkyl, R$^{24D}$-substituted or unsubstituted phenyl, or R$^{24D}$-substituted or unsubstituted 5 to 6 membered heteroaryl. X$^{23D}$ is —F, —Cl, —Br, or —I.

R$^{24D}$ is independently oxo, halogen, —CX$^{24D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{24D}_3$, —OCHX$^{24D}_2$, R$^{25D}$-substituted or unsubstituted alkyl, R$^{25D}$-substituted or unsubstituted heteroalkyl, R$^{25D}$-substituted or unsubstituted cycloalkyl, R$^{25D}$-substituted or unsubstituted heterocycloalkyl, R$^{25D}$-substituted or unsubstituted aryl, or R$^{25D}$-substituted or unsubstituted heteroaryl. In embodiments, R$^{24D}$ is independently oxo, halogen, —CX$^{24D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{24D}_3$, —OCHX$^{24D}_2$, R$^{25D}$-substituted or unsubstituted C$_1$-C$_8$ alkyl, R$^{25D}$-substituted or unsubstituted 2 to 8 membered heteroalkyl, R$^{25D}$-substituted or unsubstituted C$_3$-C$_8$ cycloalkyl, R$^{25D}$-substituted or unsubstituted 3 to 6 membered heterocycloalkyl, R$^{25D}$-substituted or unsubstituted phenyl, or R$^{25D}$-substituted or unsubstituted 5 to 6 membered heteroaryl. X$^{24D}$ is —F, —Cl, —Br, or —I.

R$^{25}$, R$^{25A}$, R$^{25B}$, R$^{25C}$, and R$^{25D}$ are independently hydrogen, oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{25}$, $R^{25A}$, $R^{25B}$, $R^{25C}$, and $R^{25D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{25}$, $R^{25A}$, $R^{25B}$, $R^{25C}$, and $R^{25D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl.

In embodiments, $R^2$ is independently halogen. In embodiments, $R^2$ is independently hydrogen. In embodiments, $R^2$ is independently hydrogen or halogen. In embodiments, $R^2$ is independently methyl. In embodiments, $R^2$ is independently C$_1$-C$_4$ alkyl. In embodiments, $R^2$ is independently halogen or C$_1$-C$_4$ alkyl. In embodiments, $R^2$ is independently halogen or C$_1$-C$_3$ alkyl. In embodiments, $R^2$ is independently halogen or C$_1$-C$_2$ alkyl. In embodiments, $R^2$ is independently halogen or methyl. In embodiments, $R^2$ is independently substituted or unsubstituted methyl. In embodiments, $R^2$ is independently substituted or unsubstituted C$_1$-C$_4$ alkyl. In embodiments, $R^2$ is independently halogen or substituted or unsubstituted C$_1$-C$_4$ alkyl. In embodiments, $R^2$ is independently halogen or substituted or unsubstituted C$_1$-C$_3$ alkyl. In embodiments, $R^2$ is independently halogen or substituted or unsubstituted C$_1$-C$_2$ alkyl. In embodiments, $R^2$ is independently halogen or substituted or unsubstituted methyl. In embodiments, $R^2$ is independently substituted methyl. In embodiments, $R^2$ is independently substituted C$_1$-C$_4$ alkyl. In embodiments, $R^2$ is independently halogen or substituted C$_1$-C$_4$ alkyl. In embodiments, $R^2$ is independently halogen or substituted C$_1$-C$_3$ alkyl. In embodiments, $R^2$ is independently halogen or substituted C$_1$-C$_2$ alkyl. In embodiments, $R^2$ is independently halogen or substituted methyl. In embodiments, $R^2$ is independently unsubstituted methyl. In embodiments, $R^2$ is independently unsubstituted C$_1$-C$_4$ alkyl. In embodiments, $R^2$ is independently halogen or unsubstituted C$_1$-C$_4$ alkyl. In embodiments, $R^2$ is independently halogen or unsubstituted C$_1$-C$_3$ alkyl. In embodiments, $R^2$ is independently halogen or unsubstituted C$_1$-C$_2$ alkyl. In embodiments, $R^2$ is independently halogen or unsubstituted methyl.

In embodiments, $R^2$ is independently C$_1$-C$_4$ alkyl. In embodiments, $R^2$ is independently C$_1$-C$_3$ alkyl. In embodiments, $R^2$ is independently C$_1$-C$_2$ alkyl. In embodiments, $R^2$ is independently methyl. In embodiments, $R^2$ is independently ispropyl. In embodiments, $R^2$ is independently substituted or unsubstituted methyl or substituted or unsubstituted isopropyl.

In embodiments, $R^2$ is independently substituted or unsubstituted C$_1$-C$_4$ alkyl. In embodiments, $R^2$ is independently substituted or unsubstituted C$_1$-C$_3$ alkyl. In embodiments, $R^2$ is independently substituted or unsubstituted C$_1$-C$_2$ alkyl. In embodiments, $R^2$ is independently substituted or unsubstituted methyl. In embodiments, $R^2$ is independently substituted or unsubstituted ispropyl. In embodiments, $R^2$ is independently an unsubstituted C$_1$-C$_4$ alkyl. In embodiments, $R^2$ is independently an unsubstituted C$_1$-C$_3$ alkyl. In embodiments, $R^2$ is independently an unsubstituted C$_1$-C$_2$ alkyl. In embodiments, $R^2$ is independently an unsubstituted methyl. In embodiments, $R^2$ is independently an unsubstituted ispropyl. In embodiments, $R^2$ is independently a substituted C$_1$-C$_4$ alkyl. In embodiments, $R^2$ is independently a substituted C$_1$-C$_3$ alkyl. In embodiments, $R^2$ is independently a substituted C$_1$-C$_2$ alkyl. In embodiments, $R^2$ is independently a substituted methyl. In embodiments, $R^2$ is independently a substituted ispropyl.

In embodiments, $R^3$ is independently hydrogen, halogen, —CX$^3_3$, —CN, —OH, —NH$_2$, —COOH, —CONH$_2$, —NO$_2$, —SH, —OCX$^3_3$, —OCHX$^3_2$, —CHX$^3_2$, —CH$_2$X$^3$, substituted or unsubstituted C$_1$-C$_8$ alkyl, or substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^3$ is independently halogen, —CX$^3_3$, —CN, unsubstituted C$_1$-C$_4$ alkyl, or unsubstituted 2 to 4 membered heteroalkyl.

In embodiments, $R^3$ is independently unsubstituted methyl, unsubstituted ethyl, unsubstituted isopropyl, or unsubstituted tert-butyl. In embodiments, $R^3$ is independently halogen, —CX$^3_3$, —CN, unsubstituted methyl, unsubstituted ethyl, unsubstituted methoxy, or unsubstituted ethoxy. In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted n-propyl. In embodiments, $R^3$ is independently unsubstituted isopropyl. In embodiments, $R^3$ is independently unsubstituted butyl. In embodiments, $R^3$ is independently unsubstituted n-butyl. In embodiments, $R^3$ is independently unsubstituted isobutyl. In embodiments, $R^3$ is independently unsubstituted tert-butyl. In embodiments, $R^3$ is independently unsubstituted pentyl. In embodiments, $R^3$ is independently unsubstituted hexyl. In embodiments, $R^3$ is independently unsubstituted heptyl. In embodiments, $R^3$ is independently unsubstituted octyl. In embodiments, $R^3$ is independently —F. In embodiments, $R^3$ is independently —Cl. In embodiments, $R^3$ is independently —Br. In embodiments, $R^3$ is independently —I. In embodiments, $R^3$ is independently unsubstituted methoxy. In embodiments, $R^3$ is independently unsubstituted ethoxy. In embodiments, $R^3$ is independently halogen, —CF$_3$. In embodiments, $R^3$ is independently —CCl3.

In embodiments, $R^3$ is independently hydrogen. In embodiments, $R^3$ is independently halogen. In embodiments, $R^3$ is independently —CX$^3_3$. In embodiments, $R^3$ is independently —CHX$^3_2$. In embodiments, $R^3$ is independently —CH$_2$X$^3$. In embodiments, $R^3$ is independently —OCX$^3_3$. In embodiments, $R^3$ is independently —OCH$_2$X$^3$. In embodiments, $R^3$ is independently —OCHX$^3_2$. In embodiments, $R^3$ is independently —CN. In embodiments, $R^3$ is independently —SO$_{n3}$R$^{3D}$. In embodiments, $R^3$ is independently —SO$_{v3}$NR$^{3A}$R$^{3B}$. In embodiments, $R^3$ is independently —NHC(O)NR$^{3A}$R$^{3B}$. In embodiments, $R^3$ is independently —N(O)$_{m3}$. In embodiments, $R^3$ is independently —NR$^{3A}$R$^{3B}$. In embodiments, $R^3$ is independently —C(O)R$^{3C}$. In embodiments, $R^3$ is independently —C(O)—OR$^{3C}$. In embodiments, $R^3$ is independently —C(O)NR$^{3A}$R$^{3B}$. In embodiments, $R^3$ is independently —OR$^{3D}$. In embodiments, R$^3$ is independently —NR$^{3A}$SO$_2$R$^{3D}$. In embodiments, R$^3$ is independently —NR$^{3A}$C(O)R$^{3C}$. In embodiments, R$^3$ is independently —NR$^{3A}$C(O)OR$^{3C}$ In embodiments, R$^3$ is independently —NR$^{3A}$OR$^{3C}$. In embodiments, R$^3$ is independently —OH. In embodiments, R$^3$ is independently —NH$_2$. In embodiments, R$^3$ is independently —COOH. In embodiments, R$^3$ is independently —CONH$_2$. In embodiments, R$^3$ is independently —NO$_2$. In embodiments, R$^3$ is independently —SH.

In embodiments, R$^3$ is independently substituted or unsubstituted alkyl. In embodiments, R$^3$ is independently substituted or unsubstituted heteroalkyl. In embodiments, R$^3$ is independently substituted or unsubstituted cycloalkyl. In embodiments, R$^3$ is independently, substituted or unsubstituted heterocycloalkyl. In embodiments, R$^3$ is independently substituted or unsubstituted aryl. In embodiments, R$^3$ is independently substituted or unsubstituted heteroaryl.

In embodiments, R$^3$ is independently substituted alkyl. In embodiments, R$^3$ is independently substituted heteroalkyl. In embodiments, R$^3$ is independently substituted cycloalkyl. In embodiments, R$^3$ is independently, substituted heterocycloalkyl. In embodiments, R$^3$ is independently substituted aryl. In embodiments, R$^3$ is independently substituted heteroaryl. In embodiments, R$^3$ is independently unsubstituted alkyl. In embodiments, R$^3$ is independently unsubstituted heteroalkyl. In embodiments, R$^3$ is independently unsubstituted cycloalkyl. In embodiments, R$^3$ is independently unsubstituted heterocycloalkyl. In embodiments, R$^3$ is independently unsubstituted aryl. In embodiments, R$^3$ is independently unsubstituted heteroaryl.

In embodiments, R$^3$ is independently substituted or unsubstituted C$_1$-C$_8$ alkyl. In embodiments, R$^3$ is independently substituted or unsubstituted 2 to 8 membered heteroalkyl. In embodiments, R$^3$ is independently substituted or unsubstituted C$_3$-C$_8$ cycloalkyl. In embodiments, R$^3$ is independently, substituted or unsubstituted 3 to 8 membered heterocycloalkyl. In embodiments, R$^3$ is independently substituted or unsubstituted C$_6$-C$_{10}$ aryl. In embodiments, R$^3$ is independently substituted or unsubstituted 5 to 10 membered heteroaryl.

In embodiments, R$^3$ is independently substituted C$_1$-C$_8$ alkyl. In embodiments, R$^3$ is independently substituted 2 to 8 membered heteroalkyl. In embodiments, R$^3$ is independently substituted C$_3$-C$_8$ cycloalkyl. In embodiments, R$^3$ is independently, substituted 3 to 8 membered heterocycloalkyl. In embodiments, R$^3$ is independently substituted C$_6$-C$_{10}$ aryl. In embodiments, R$^3$ is independently substituted 5 to 10 membered heteroaryl. In embodiments, R$^3$ is independently unsubstituted C$_1$-C$_8$ alkyl. In embodiments, R$^3$ is independently unsubstituted 2 to 8 membered heteroalkyl. In embodiments, R$^3$ is independently unsubstituted C$_3$-C$_8$ cycloalkyl. In embodiments, R$^3$ is independently, unsubstituted 3 to 8 membered heterocycloalkyl. In embodiments, R$^3$ is independently unsubstituted C$_6$-C$_{10}$ aryl. In embodiments, R$^3$ is independently unsubstituted 5 to 10 membered heteroaryl. In embodiments, R$^3$ is independently substituted or unsubstituted C$_1$-C$_4$ alkyl. In embodiments, R$^3$ is independently substituted or unsubstituted 2 to 4 membered heteroalkyl. In embodiments, R$^3$ is independently substituted or unsubstituted C$_3$-C$_6$ cycloalkyl. In embodiments, R$^3$ is independently, substituted or unsubstituted 3 to 6 membered heterocycloalkyl. In embodiments, R$^3$ is independently substituted or unsubstituted phenyl. In embodiments, R$^3$ is independently substituted or unsubstituted 5 to 6 membered heteroaryl.

In embodiments, R$^3$ is independently substituted C$_1$-C$_4$ alkyl. In embodiments, R$^3$ is independently substituted 2 to 4 membered heteroalkyl. In embodiments, R$^3$ is independently substituted C$_3$-C$_6$ cycloalkyl. In embodiments, R$^3$ is independently, substituted 3 to 6 membered heterocycloalkyl. In embodiments, R$^3$ is independently substituted phenyl. In embodiments, R$^3$ is independently substituted 5 to 6 membered heteroaryl. In embodiments, R$^3$ is independently unsubstituted C$_1$-C$_4$ alkyl. In embodiments, R$^3$ is independently unsubstituted 2 to 4 membered heteroalkyl. In embodiments, R$^3$ is independently unsubstituted C$_3$-C$_6$ cycloalkyl. In embodiments, R$^3$ is independently unsubstituted 3 to 6 membered heterocycloalkyl. In embodiments, R$^3$ is independently unsubstituted phenyl. In embodiments, R$^3$ is independently unsubstituted 5 to 6 membered heteroaryl.

In embodiments, R$^{3A}$ is independently hydrogen. In embodiments, R$^{3A}$ is independently —CX$^{3A}$$_3$. In embodiments, R$^{3A}$ is independently —CHX$^{3A}$$_2$. In embodiments, R$^{3A}$ is independently —CH$_2$X$^{3A}$. In embodiments, R$^{3A}$ is independently —CN. In embodiments, R$^{3A}$ is independently —COOH. In embodiments, R$^{3A}$ is independently —CONH$_2$. In embodiments, R$^{3A}$ is independently substituted or unsubstituted alkyl. In embodiments, R$^{3A}$ is independently substituted or unsubstituted heteroalkyl. In embodiments, R$^{3A}$ is independently substituted or unsubstituted cycloalkyl. In embodiments, R$^{3A}$ is independently, substituted or unsubstituted heterocycloalkyl. In embodiments, R$^{3A}$ is independently substituted or unsubstituted aryl. In embodiments, R$^{3A}$ is independently substituted or unsubstituted heteroaryl.

In embodiments, R$^{3A}$ is independently substituted alkyl. In embodiments, R$^{3A}$ is independently substituted heteroalkyl. In embodiments, R$^{3A}$ is independently substituted cycloalkyl. In embodiments, R$^{3A}$ is independently, substituted heterocycloalkyl. In embodiments, R$^{3A}$ is independently substituted aryl. In embodiments, R$^{3A}$ is independently substituted heteroaryl. In embodiments, R$^{3A}$ is independently unsubstituted alkyl. In embodiments, R$^{3A}$ is independently unsubstituted heteroalkyl. In embodiments, R$^{3A}$ is independently unsubstituted cycloalkyl. In embodiments, R$^{3A}$ is independently, unsubstituted heterocycloalkyl. In embodiments, R$^{3A}$ is independently unsubstituted aryl. In embodiments, R$^{3A}$ is independently unsubstituted heteroaryl.

In embodiments, R$^{3A}$ is independently substituted or unsubstituted C$_1$-C$_8$ alkyl. In embodiments, R$^{3A}$ is independently substituted or unsubstituted 2 to 8 membered heteroalkyl. In embodiments, R$^{3A}$ is independently substituted or unsubstituted C$_3$-C$_8$ cycloalkyl. In embodiments, R$^{3A}$ is independently, substituted or unsubstituted 3 to 8 membered heterocycloalkyl. In embodiments, R$^{3A}$ is independently substituted or unsubstituted C$_6$-C$_{10}$ aryl. In embodiments, R$^{3A}$ is independently substituted or unsubstituted 5 to 10 membered heteroaryl.

In embodiments, R$^{3A}$ is independently substituted C$_1$-C$_8$ alkyl. In embodiments, R$^{3A}$ is independently substituted 2 to 8 membered heteroalkyl. In embodiments, R$^{3A}$ is independently substituted C$_3$-C$_8$ cycloalkyl. In embodiments, R$^{3A}$ is independently, substituted 3 to 8 membered heterocycloalkyl. In embodiments, R$^{3A}$ is independently substituted C$_6$-C$_{10}$ aryl. In embodiments, R$^{3A}$ is independently substituted 5 to 10 membered heteroaryl. In embodiments, R$^{3A}$ is independently unsubstituted C$_1$-C$_8$ alkyl. In embodiments, R$^{3A}$ is independently unsubstituted 2 to 8 membered heteroalkyl. In embodiments, R$^{3A}$ is independently unsubstituted C$_3$-C$_8$ cycloalkyl. In embodiments, R$^{3A}$ is independently, unsubstituted 3 to 8 membered heterocycloalkyl. In embodiments, $R^{3A}$ is independently unsubstituted $C_6$-$C_{10}$ aryl. In embodiments, $R^{3A}$ is independently unsubstituted 5 to 10 membered heteroaryl.

In embodiments, $R^{3A}$ is independently substituted or unsubstituted $C_1$-$C_4$ alkyl. In embodiments, $R^{3A}$ is independently substituted or unsubstituted 2 to 4 membered heteroalkyl. In embodiments, $R^{3A}$ is independently substituted or unsubstituted $C_3$-$C_6$ cycloalkyl. In embodiments, $R^{3A}$ is independently, substituted or unsubstituted 3 to 6 membered heterocycloalkyl. In embodiments, $R^{3A}$ is independently substituted or unsubstituted phenyl. In embodiments, $R^{3A}$ is independently substituted or unsubstituted 5 to 6 membered heteroaryl.

In embodiments, $R^{3A}$ is independently substituted $C_1$-$C_4$ alkyl. In embodiments, $R^{3A}$ is independently substituted 2 to 4 membered heteroalkyl. In embodiments, $R^{3A}$ is independently substituted $C_3$-$C_6$ cycloalkyl. In embodiments, $R^{3A}$ is independently, substituted 3 to 6 membered heterocycloalkyl. In embodiments, $R^{3A}$ is independently substituted phenyl. In embodiments, $R^{3A}$ is independently substituted 5 to 6 membered heteroaryl. In embodiments, $R^{3A}$ is independently $C_1$-$C_4$ alkyl. In embodiments, $R^{3A}$ is independently unsubstituted 2 to 4 membered heteroalkyl. In embodiments, $R^{3A}$ is independently unsubstituted $C_3$-$C_6$ cycloalkyl. In embodiments, $R^{3A}$ is independently unsubstituted 3 to 6 membered heterocycloalkyl. In embodiments, $R^{3A}$ is independently unsubstituted phenyl. In embodiments, $R^{3A}$ is independently unsubstituted 5 to 6 membered heteroaryl. In embodiments, $R^{3A}$ is independently unsubstituted methyl. In embodiments, $R^{3A}$ is independently unsubstituted ethyl. In embodiments, $R^{3A}$ is independently unsubstituted propyl. In embodiments, $R^{3A}$ is independently unsubstituted isopropyl. In embodiments, $R^{3A}$ is independently unsubstituted tert-butyl.

In embodiments, $R^{3B}$ is independently hydrogen. In embodiments, $R^{3B}$ is independently $-CX^{3B}{}_3$. In embodiments, $R^{3B}$ is independently $-CHX^{3B}{}_2$. In embodiments, $R^{3B}$ is independently $-CH_2X^{3B}$. In embodiments, $R^{3B}$ is independently $-CN$. In embodiments, $R^{3B}$ is independently $-COOH$. In embodiments, $R^{3B}$ is independently $-CONH_2$. In embodiments, $R^{3B}$ is independently substituted or unsubstituted alkyl. In embodiments, $R^{3B}$ is independently substituted or unsubstituted heteroalkyl. In embodiments, $R^{3B}$ is independently substituted or unsubstituted cycloalkyl. In embodiments, $R^{3B}$ is independently, substituted or unsubstituted heterocycloalkyl. In embodiments, $R^{3B}$ is independently substituted or unsubstituted aryl. In embodiments, $R^{3B}$ is independently substituted or unsubstituted heteroaryl.

In embodiments, $R^{3B}$ is independently substituted alkyl. In embodiments, $R^{3B}$ is independently substituted heteroalkyl. In embodiments, $R^{3B}$ is independently substituted cycloalkyl. In embodiments, $R^{3B}$ is independently, substituted heterocycloalkyl. In embodiments, $R^{3B}$ is independently substituted aryl. In embodiments, $R^{3B}$ is independently substituted heteroaryl. In embodiments, $R^{3B}$ is independently unsubstituted alkyl. In embodiments, $R^{3B}$ is independently unsubstituted heteroalkyl. In embodiments, $R^{3B}$ is independently unsubstituted cycloalkyl. In embodiments, $R^{3B}$ is independently, unsubstituted heterocycloalkyl. In embodiments, $R^{3B}$ is independently unsubstituted aryl. In embodiments, $R^{3B}$ is independently unsubstituted heteroaryl.

In embodiments, $R^{3B}$ is independently substituted or unsubstituted $C_1$-$C_8$ alkyl. In embodiments, $R^{3B}$ is independently substituted or unsubstituted 2 to 8 membered heteroalkyl. In embodiments, $R^{3B}$ is independently substituted or unsubstituted $C_3$-$C_8$ cycloalkyl. In embodiments, $R^{3B}$ is independently, substituted or unsubstituted 3 to 8 membered heterocycloalkyl. In embodiments, $R^{3B}$ is independently substituted or unsubstituted $C_6$-$C_{10}$ aryl. In embodiments, $R^{3B}$ is independently substituted or unsubstituted 5 to 10 membered heteroaryl. In embodiments, $R^{3B}$ is independently substituted $C_1$-$C_8$ alkyl. In embodiments, $R^{3B}$ is independently substituted 2 to 8 membered heteroalkyl. In embodiments, $R^{3B}$ is independently substituted $C_3$-$C_8$ cycloalkyl. In embodiments, $R^{3B}$ is independently, substituted 3 to 8 membered heterocycloalkyl. In embodiments, $R^{3B}$ is independently substituted $C_6$-$C_{10}$ aryl. In embodiments, $R^{3B}$ is independently substituted 5 to 10 membered heteroaryl.

In embodiments, $R^{3B}$ is independently unsubstituted $C_1$-$C_8$ alkyl. In embodiments, $R^{3B}$ is independently unsubstituted 2 to 8 membered heteroalkyl. In embodiments, $R^{3B}$ is independently unsubstituted $C_3$-$C_8$ cycloalkyl. In embodiments, $R^{3B}$ is independently, unsubstituted 3 to 8 membered heterocycloalkyl. In embodiments, $R^{3B}$ is independently unsubstituted $C_6$-$C_{10}$ aryl. In embodiments, $R^{3B}$ is independently unsubstituted 5 to 10 membered heteroaryl. In embodiments, $R^{3B}$ is independently substituted or unsubstituted $C_1$-$C_4$ alkyl. In embodiments, $R^{3B}$ is independently substituted or unsubstituted 2 to 4 membered heteroalkyl. In embodiments, $R^{3B}$ is independently substituted or unsubstituted $C_3$-$C_6$ cycloalkyl. In embodiments, $R^{3B}$ is independently, substituted or unsubstituted 3 to 6 membered heterocycloalkyl. In embodiments, $R^{3B}$ is independently substituted or unsubstituted phenyl. In embodiments, $R^{3B}$ is independently substituted or unsubstituted 5 to 6 membered heteroaryl.

In embodiments, $R^{3B}$ is independently substituted $C_1$-$C_4$ alkyl. In embodiments, $R^{3B}$ is independently substituted 2 to 4 membered heteroalkyl. In embodiments, $R^{3B}$ is independently substituted $C_3$-$C_6$ cycloalkyl. In embodiments, $R^{3B}$ is independently, substituted 3 to 6 membered heterocycloalkyl. In embodiments, $R^{3B}$ is independently substituted phenyl. In embodiments, $R^{3B}$ is independently substituted 5 to 6 membered heteroaryl. In embodiments, $R^{3B}$ is independently unsubstituted $C_1$-$C_4$ alkyl. In embodiments, $R^{3B}$ is independently unsubstituted 2 to 4 membered heteroalkyl. In embodiments, $R^{3B}$ is independently unsubstituted $C_3$-$C_6$ cycloalkyl. In embodiments, $R^{3B}$ is independently unsubstituted 3 to 6 membered heterocycloalkyl. In embodiments, $R^{3B}$ is independently unsubstituted phenyl. In embodiments, $R^{3B}$ is independently unsubstituted 5 to 6 membered heteroaryl. In embodiments, $R^{3B}$ is independently unsubstituted methyl. In embodiments, $R^{3B}$ is independently unsubstituted ethyl. In embodiments, $R^{3B}$ is independently unsubstituted propyl. In embodiments, $R^{3B}$ is independently unsubstituted isopropyl. In embodiments, $R^{3B}$ is independently unsubstituted tert-butyl.

In embodiments, $R^{3A}$ and $R^{3B}$ substituents bonded to the same nitrogen atom may be joined to form a substituted or unsubstituted heterocycloalkyl. In embodiments, $R^{3A}$ and $R^{3B}$ substituents bonded to the same nitrogen atom may be joined to form a substituted or unsubstituted heteroaryl. In embodiments, $R^{3A}$ and $R^{3B}$ substituents bonded to the same nitrogen atom may be joined to form a substituted heterocycloalkyl. In embodiments, $R^{3A}$ and $R^{3B}$ substituents bonded to the same nitrogen atom may be joined to form a substituted heteroaryl. In embodiments, $R^{3A}$ and $R^{3B}$ substituents bonded to the same nitrogen atom may be joined to form an unsubstituted heterocycloalkyl. In embodiments, $R^{3A}$ and $R^{3B}$ substituents bonded to the same nitrogen atom may be joined to form an unsubstituted heteroaryl.

In embodiments, $R^{3A}$ and $R^{3B}$ substituents bonded to the same nitrogen atom may be joined to form a substituted or unsubstituted 3 to 8 membered heterocycloalkyl. In embodiments, $R^{3A}$ and $R^{3B}$ substituents bonded to the same nitrogen atom may be joined to form a substituted or unsubstituted 5 to 10 membered heteroaryl. In embodiments, $R^{3A}$ and $R^{3B}$ substituents bonded to the same nitrogen atom may be joined to form a substituted 3 to 8 membered heterocycloalkyl. In embodiments, $R^{3A}$ and $R^{3B}$ substituents bonded to the same nitrogen atom may be joined to form a substituted 5 to 10 membered heteroaryl. In embodiments, $R^{3A}$ and $R^{3B}$ substituents bonded to the same nitrogen atom may be joined to form an unsubstituted 3 to 8 membered heterocycloalkyl. In embodiments, $R^{3A}$ and $R^{3B}$ substituents bonded to the same nitrogen atom may be joined to form an unsubstituted 5 to 10 membered heteroaryl. In embodiments, $R^{3A}$ and $R^{3B}$ substituents bonded to the same nitrogen atom may be joined to form a substituted or unsubstituted 3 to 6 membered heterocycloalkyl. In embodiments, $R^{3A}$ and $R^{3B}$ substituents bonded to the same nitrogen atom may be joined to form a substituted or unsubstituted 5 to 6 membered heteroaryl. In embodiments, $R^{3A}$ and $R^{3B}$ substituents bonded to the same nitrogen atom may be joined to form a substituted 3 to 6 membered heterocycloalkyl. In embodiments, $R^{3A}$ and $R^{3B}$ substituents bonded to the same nitrogen atom may be joined to form a substituted 5 to 6 membered heteroaryl. In embodiments, $R^{3A}$ and $R^{3B}$ substituents bonded to the same nitrogen atom may be joined to form an unsubstituted 3 to 6 membered heterocycloalkyl. In embodiments, $R^{3A}$ and $R^{3B}$ substituents bonded to the same nitrogen atom may be joined to form an unsubstituted 5 to 6 membered heteroaryl.

In embodiments, $R^{3C}$ is independently hydrogen. In embodiments, $R^{3C}$ is independently —$CX^{3C}_3$. In embodiments, $R^{3C}$ is independently —$CHX^{3C}_2$. In embodiments, $R^{3C}$ is independently —$CH_2X^{3C}$. In embodiments, $R^{3C}$ is independently —CN. In embodiments, $R^{3C}$ is independently —COOH. In embodiments, $R^{3C}$ is independently —$CONH_2$. In embodiments, $R^{3C}$ is independently substituted or unsubstituted alkyl. In embodiments, $R^{3C}$ is independently substituted or unsubstituted heteroalkyl. In embodiments, $R^{3C}$ is independently substituted or unsubstituted cycloalkyl. In embodiments, $R^{3C}$ is independently, substituted or unsubstituted heterocycloalkyl. In embodiments, $R^{3C}$ is independently substituted or unsubstituted aryl. In embodiments, $R^{3C}$ is independently substituted or unsubstituted heteroaryl.

In embodiments, $R^{3C}$ is independently substituted alkyl. In embodiments, $R^{3C}$ is independently substituted heteroalkyl. In embodiments, $R^{3C}$ is independently substituted cycloalkyl. In embodiments, $R^{3C}$ is independently, substituted heterocycloalkyl. In embodiments, $R^{3C}$ is independently substituted aryl. In embodiments, $R^{3C}$ is independently substituted heteroaryl. In embodiments, $R^{3C}$ is independently unsubstituted alkyl. In embodiments, $R^{3C}$ is independently unsubstituted heteroalkyl. In embodiments, $R^{3C}$ is independently unsubstituted cycloalkyl. In embodiments, $R^{3C}$ is independently, unsubstituted heterocycloalkyl. In embodiments, $R^{3C}$ is independently unsubstituted aryl. In embodiments, $R^{3C}$ is independently unsubstituted heteroaryl.

In embodiments, $R^{3C}$ is independently substituted or unsubstituted $C_1$-$C_8$ alkyl. In embodiments, $R^{3C}$ is independently substituted or unsubstituted 2 to 8 membered heteroalkyl. In embodiments, $R^{3C}$ is independently substituted or unsubstituted $C_3$-$C_8$ cycloalkyl. In embodiments, $R^{3C}$ is independently, substituted or unsubstituted 3 to 8 membered heterocycloalkyl. In embodiments, $R^{3C}$ is independently substituted or unsubstituted $C_6$-$C_{10}$ aryl. In embodiments, $R^{3C}$ is independently substituted or unsubstituted 5 to 10 membered heteroaryl.

In embodiments, $R^{3C}$ is independently substituted $C_1$-$C_8$ alkyl. In embodiments, $R^{3C}$ is independently substituted 2 to 8 membered heteroalkyl. In embodiments, $R^{3C}$ is independently substituted $C_3$-$C_8$ cycloalkyl. In embodiments, $R^{3C}$ is independently, substituted 3 to 8 membered heterocycloalkyl. In embodiments, $R^{3C}$ is independently substituted $C_6$-$C_{10}$ aryl. In embodiments, $R^{3C}$ is independently substituted 5 to 10 membered heteroaryl. In embodiments, $R^{3C}$ is independently unsubstituted $C_1$-$C_8$ alkyl. In embodiments, $R^{3C}$ is independently unsubstituted 2 to 8 membered heteroalkyl. In embodiments, $R^{3C}$ is independently unsubstituted $C_3$-$C_8$ cycloalkyl. In embodiments, $R^{3C}$ is independently, unsubstituted 3 to 8 membered heterocycloalkyl. In embodiments, $R^{3C}$ is independently unsubstituted $C_6$-$C_{10}$ aryl. In embodiments, $R^{3C}$ is independently unsubstituted 5 to 10 membered heteroaryl.

In embodiments, $R^{3C}$ is independently substituted or unsubstituted $C_1$-$C_4$ alkyl. In embodiments, $R^{3C}$ is independently substituted or unsubstituted 2 to 4 membered heteroalkyl. In embodiments, $R^{3C}$ is independently substituted or unsubstituted $C_3$-$C_6$ cycloalkyl. In embodiments, $R^{3C}$ is independently, substituted or unsubstituted 3 to 6 membered heterocycloalkyl. In embodiments, $R^{3C}$ is independently substituted or unsubstituted phenyl. In embodiments, $R^{3C}$ is independently substituted or unsubstituted 5 to 6 membered heteroaryl.

In embodiments, $R^{3C}$ is independently substituted $C_1$-$C_4$ alkyl. In embodiments, $R^{3C}$ is independently substituted 2 to 4 membered heteroalkyl. In embodiments, $R^{3C}$ is independently substituted $C_3$-$C_6$ cycloalkyl. In embodiments, $R^{3C}$ is independently, substituted 3 to 6 membered heterocycloalkyl. In embodiments, $R^{3C}$ is independently substituted phenyl. In embodiments, $R^{3C}$ is independently substituted 5 to 6 membered heteroaryl. In embodiments, $R^{3C}$ is independently unsubstituted $C_1$-$C_4$ alkyl. In embodiments, $R^{3C}$ is independently unsubstituted 2 to 4 membered heteroalkyl. In embodiments, $R^{3C}$ is independently unsubstituted $C_3$-$C_6$ cycloalkyl. In embodiments, $R^{3C}$ is independently unsubstituted 3 to 6 membered heterocycloalkyl. In embodiments, $R^{3C}$ is independently unsubstituted phenyl. In embodiments, $R^{3C}$ is independently unsubstituted 5 to 6 membered heteroaryl. In embodiments, $R^{3C}$ is independently unsubstituted methyl. In embodiments, $R^{3C}$ is independently unsubstituted ethyl. In embodiments, $R^{3C}$ is independently unsubstituted propyl. In embodiments, $R^{3C}$ is independently unsubstituted isopropyl. In embodiments, $R^{3C}$ is independently unsubstituted tert-butyl.

In embodiments, $R^{3D}$ is independently hydrogen. In embodiments, $R^{3D}$ is independently —$CX^{3D}_3$. In embodiments, $R^{3D}$ is independently —$CHX^{3D}_2$. In embodiments, $R^{3D}$ is independently —$CH_2X^{3D}$. In embodiments, $R^{3D}$ is independently —CN. In embodiments, $R^{3D}$ is independently —COOH. In embodiments, $R^{3D}$ is independently —$CONH_2$. In embodiments, $R^{3D}$ is independently substituted or unsubstituted alkyl. In embodiments, $R^{3D}$ is independently substituted or unsubstituted heteroalkyl. In embodiments, $R^{3D}$ is independently substituted or unsubstituted cycloalkyl. In embodiments, $R^{3D}$ is independently, substituted or unsubstituted heterocycloalkyl. In embodiments, $R^{3D}$ is independently substituted or unsubstituted aryl. In embodiments, $R^{3D}$ is independently substituted or unsubstituted heteroaryl.

In embodiments, $R^{3D}$ is independently substituted alkyl. In embodiments, $R^{3D}$ is independently substituted heteroalkyl. In embodiments, $R^{3D}$ is independently substituted cycloalkyl. In embodiments, $R^{3D}$ is independently, substituted heterocycloalkyl. In embodiments, $R^{3D}$ is independently substituted aryl. In embodiments, $R^{3D}$ is independently substituted heteroaryl. In embodiments, $R^{3D}$ is independently unsubstituted alkyl. In embodiments, $R^{3D}$ is independently unsubstituted heteroalkyl. In embodiments, $R^{3D}$ is independently unsubstituted cycloalkyl. In embodiments, $R^{3D}$ is independently, unsubstituted heterocycloalkyl. In embodiments, $R^{3D}$ is independently unsubstituted aryl. In embodiments, $R^{3D}$ is independently unsubstituted heteroaryl.

In embodiments, $R^{3D}$ is independently substituted or unsubstituted $C_1$-$C_8$ alkyl. In embodiments, $R^{3D}$ is independently substituted or unsubstituted 2 to 8 membered heteroalkyl. In embodiments, $R^{3D}$ is independently substituted or unsubstituted $C_3$-$C_8$ cycloalkyl. In embodiments, $R^{3D}$ is independently, substituted or unsubstituted 3 to 8 membered heterocycloalkyl. In embodiments, $R^{3D}$ is independently substituted or unsubstituted $C_6$-$C_{10}$ aryl. In embodiments, $R^{3D}$ is independently substituted or unsubstituted 5 to 10 membered heteroaryl.

In embodiments, $R^{3D}$ is independently substituted $C_1$-$C_8$ alkyl. In embodiments, $R^{3D}$ is independently substituted 2 to 8 membered heteroalkyl. In embodiments, $R^{3D}$ is independently substituted $C_3$-$C_8$ cycloalkyl. In embodiments, $R^{3D}$ is independently, substituted 3 to 8 membered heterocycloalkyl. In embodiments, $R^{3D}$ is independently substituted $C_6$-$C_{10}$ aryl. In embodiments, $R^{3D}$ is independently substituted 5 to 10 membered heteroaryl. In embodiments, $R^{3D}$ is independently unsubstituted $C_1$-$C_8$ alkyl. In embodiments, $R^{3D}$ is independently unsubstituted 2 to 8 membered heteroalkyl. In embodiments, $R^{3D}$ is independently unsubstituted $C_3$-$C_8$ cycloalkyl. In embodiments, $R^{3D}$ is independently, unsubstituted 3 to 8 membered heterocycloalkyl. In embodiments, $R^{3D}$ is independently unsubstituted $C_6$-$C_{10}$ aryl. In embodiments, $R^{3D}$ is independently unsubstituted 5 to 10 membered heteroaryl.

In embodiments, $R^{3D}$ is independently substituted or unsubstituted $C_1$-$C_4$ alkyl. In embodiments, $R^{3D}$ is independently substituted or unsubstituted 2 to 4 membered heteroalkyl. In embodiments, $R^{3D}$ is independently substituted or unsubstituted $C_3$-$C_6$ cycloalkyl. In embodiments, $R^{3D}$ is independently, substituted or unsubstituted 3 to 6 membered heterocycloalkyl. In embodiments, $R^{3D}$ is independently substituted or unsubstituted phenyl. In embodiments, $R^{3D}$ is independently substituted or unsubstituted 5 to 6 membered heteroaryl.

In embodiments, $R^{3D}$ is independently substituted $C_1$-$C_4$ alkyl. In embodiments, $R^{3D}$ is independently substituted 2 to 4 membered heteroalkyl. In embodiments, $R^{3D}$ is independently substituted $C_3$-$C_6$ cycloalkyl. In embodiments, $R^{3D}$ is independently, substituted 3 to 6 membered heterocycloalkyl. In embodiments, $R^{3D}$ is independently substituted phenyl. In embodiments, $R^{3D}$ is independently substituted 5 to 6 membered heteroaryl. In embodiments, $R^{3D}$ is independently unsubstituted $C_1$-$C_4$ alkyl. In embodiments, $R^{3D}$ is independently unsubstituted 2 to 4 membered heteroalkyl. In embodiments, $R^{3D}$ is independently unsubstituted $C_3$-$C_6$ cycloalkyl. In embodiments, $R^{3D}$ is independently unsubstituted 3 to 6 membered heterocycloalkyl. In embodiments, $R^{3D}$ is independently unsubstituted phenyl. In embodiments, $R^{3D}$ is independently unsubstituted 5 to 6 membered heteroaryl. In embodiments, $R^{3D}$ is independently unsubstituted methyl. In embodiments, $R^{3D}$ is independently ethyl. In embodiments, $R^{3D}$ is independently unsubstituted propyl. In embodiments, $R^{3D}$ is independently unsubstituted isopropyl. In embodiments, $R^{3D}$ is independently unsubstituted tert-butyl.

In embodiments, $R^3$ is independently halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl. In embodiments, $R^3$ is independently halogen, $-CX^3_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^3_3$, $-OCHX^3_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

In embodiments, $R^3$ is independently halogen, $-CX^3_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^3_3$, $-OCHX^3_2$, $R^{26}$-substituted or unsubstituted $C_1$-$C_8$ alkyl, $R^{26}$-substituted or unsubstituted 2 to 8 membered heteroalkyl, $R^{26}$-substituted or unsubstituted $C_3$-$C_8$ cycloalkyl, $R^{26}$-substituted or unsubstituted 3 to 6 membered heterocycloalkyl, $R^{26}$-substituted or unsubstituted phenyl, or $R^{26}$-substituted or unsubstituted 5 to 6 membered heteroaryl. $X^3$ is $-F$, $-Cl$, $-Br$, or $-I$. In embodiments, $R^3$ is independently hydrogen.

$R^{26}$ is independently oxo, halogen, $-CX^{26}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{26}_3$, $-OCHX^{26}_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

In embodiments, $R^{26}$ is independently oxo, halogen, $-CX^{263}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{263}$, $-OCHX^{262}$, $R^{27}$-substituted or unsubstituted $C_1$-$C_8$ alkyl, $R^{27}$-substituted or unsubstituted 2 to 8 membered heteroalkyl, $R^{27}$-substituted or unsubstituted $C_3$-$C_8$ cycloalkyl, $R^{27}$-substituted or unsubstituted 3 to 6 membered heterocycloalkyl, $R^{27}$-substituted or unsubstituted phenyl, or $R^{27}$-substituted or unsubstituted 5 to 6 membered heteroaryl. $X^{26}$ is $-F$, $-Cl$, $-Br$, or $-I$.

$R^{27}$ is independently oxo, halogen, $-CX^{27}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{27}_3$, $-OCHX^{272}$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl. In embodiments, $R^{27}$ is independently oxo, halogen, $-CX^{27}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{27}_3$, $-OCHX^{27}_2$, $R^{28}$-substituted or unsubstituted $C_1$-$C_8$ alkyl, $R^{28}$-substituted or unsubstituted 2 to 8 membered heteroalkyl, $R^{28}$-substituted or unsubstituted $C_3$-$C_8$ cycloalkyl, $R^{28}$-substituted or unsubstituted 3 to 6 membered heterocycloalkyl, $R^{28}$-substituted or unsubstituted phenyl, or $R^{28}$-substituted or unsubstituted 5 to 6 membered heteroaryl. $X^{27}$ is $-F$, $-Cl$, $-Br$, or $-I$.

In embodiments, $R^{3A}$ is independently hydrogen, $-CX^{3A}_3$, $-CN$, $-COOH$, $-CONH_2$, $-CHX^{3A}_2$, $-CH_2X^{3A}$, $R^{26A}$-substituted or unsubstituted alkyl, $R^{26A}$-substituted or unsubstituted heteroalkyl, $R^{26A}$-substituted or unsubstituted cycloalkyl, $R^{26A}$-substituted or unsubstituted heterocycloalkyl, $R^{26A}$-substituted or unsubstituted aryl, or $R^{26A}$-substituted or unsubstituted heteroaryl. In embodiments, $R^{3A}$ is independently hydrogen, $-CX^{3A}_3$, $-CN$, $-COOH$, $-CONH_2$, $-CHX^{3A}_2$, $-CH_2X^{3A}$, $R^{26A}$-substituted or unsubstituted $C_1$-$C_8$ alkyl, $R^{26A}$-substituted or unsubstituted 2 to 8 membered heteroalkyl, $R^{26A}$-substituted or unsubstituted $C_3$-$C_8$ cycloalkyl, $R^{26A}$-substituted or unsubstituted 3 to 6 membered heterocycloalkyl, $R^{26A}$-substituted or unsubstituted phenyl, or $R^{26A}$-substituted or unsubstituted 5 to 6 membered heteroaryl. $X^{3A}$ is independently $-F$, $-Cl$, $-Br$, or $-I$.

In embodiments, $R^{3A}$ is independently hydrogen. In embodiments, $R^{3A}$ is independently methyl. In embodiments, $R^{3A}$ is independently ethyl. In embodiments, $R^{3A}$ is hydrogen, $-CX^{3A}_3$, $-CHX^{3A}_2$, $-CH_2X^{3A}$, $-C(O)OH$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3A}$ is hydrogen, $-CX^{3A}_3$, $-CHX^{3A}_2$, $-CH_2X^{3A}$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3A}$ and $R^{3B}$ substituents bonded to the same nitrogen atom may optionally be joined to form a $R^{26A}$-substituted or unsubstituted heterocycloalkyl or $R^{26A}$-substituted or unsubstituted heteroaryl. In embodiments, $R^{3A}$ and $R^{3B}$ substituents bonded to the same nitrogen atom may optionally be joined to form a $R^{26A}$-substituted or unsubstituted 3 to 6 membered heterocycloalkyl or $R^{26A}$-substituted or unsubstituted 5 to 6 membered heteroaryl.

$R^{26A}$ is independently oxo, halogen, $-CX^{26A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{26A}_3$, $-OCHX^{26A}_2$, $R^{27A}$-substituted or unsubstituted alkyl, $R^{27A}$-substituted or unsubstituted heteroalkyl, $R^{27A}$-substituted or unsubstituted cycloalkyl, $R^{27A}$-substituted or unsubstituted heterocycloalkyl, $R^{27A}$-substituted or unsubstituted aryl, or $R^{27A}$-substituted or unsubstituted heteroaryl. In embodiments, $R^{26A}$ is independently oxo, halogen, $-CX^{26A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{26A}_3$, $-OCHX^{26A}_2$, $R^{27A}$-substituted or unsubstituted $C_1$-$C_8$ alkyl, $R^{27A}$-substituted or unsubstituted 2 to 8 membered heteroalkyl, $R^{27A}$-substituted or unsubstituted $C_3$-$C_8$ cycloalkyl, $R^{27A}$-substituted or unsubstituted 3 to 6 membered heterocycloalkyl, $R^{27A}$-substituted or unsubstituted phenyl, or $R^{27A}$-substituted or unsubstituted 5 to 6 membered heteroaryl. $X^{26A}$ is $-F$, $-Cl$, $-Br$, or $-I$.

$R^{27A}$ is independently oxo, halogen, $-CX^{27A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{27A}_3$, $-OCHX^{27A}_2$, $R^{28A}$-substituted or unsubstituted alkyl, $R^{28A}$-substituted or unsubstituted heteroalkyl, $R^{28A}$-substituted or unsubstituted cycloalkyl, $R^{28A}$-substituted or unsubstituted heterocycloalkyl, $R^{28A}$-substituted or unsubstituted aryl, or $R^{28A}$-substituted or unsubstituted heteroaryl. In embodiments, $R^{27A}$ is independently oxo, halogen, $-CX^{27A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{27A}_3$, $-OCHX^{27A}_2$, $R^{28A}$-substituted or unsubstituted $C_1$-$C_8$ alkyl, $R^{28A}$-substituted or unsubstituted 2 to 8 membered heteroalkyl, $R^{28A}$-substituted or unsubstituted $C_3$-$C_8$ cycloalkyl, $R^{28A}$-substituted or unsubstituted 3 to 6 membered heterocycloalkyl, $R^{28A}$-substituted or unsubstituted phenyl, or $R^{28A}$-substituted or unsubstituted 5 to 6 membered heteroaryl. $X^{27A}$ is $-F$, $-Cl$, $-Br$, or $-I$.

In embodiments, $R^{3B}$ is independently hydrogen, $-CX^{3B}_3$, $-CN$, $-COOH$, $-CONH_2$, $-CHX^{3B}_2$, $-CH_2X^{3B}$, $R^{26B}$-substituted or unsubstituted alkyl, $R^{26B}$-substituted or unsubstituted heteroalkyl, $R^{26B}$-substituted or unsubstituted cycloalkyl, $R^{26B}$-substituted or unsubstituted heterocycloalkyl, $R^{26B}$-substituted or unsubstituted aryl, or $R^{26B}$-substituted or unsubstituted heteroaryl. In embodiments, $R^{3B}$ is independently hydrogen, $-CX^{3B}_3$, $-CN$, $-COOH$, $-CONH_2$, $-CHX^{3B}_2$, $-CH_2X^{3B}$, $R^{26B}$-substituted or unsubstituted $C_1$-$C_8$ alkyl, $R^{26B}$-substituted or unsubstituted 2 to 8 membered heteroalkyl, $R^{26B}$-substituted or unsubstituted $C_3$-$C_8$ cycloalkyl, $R^{26B}$-substituted or unsubstituted 3 to 6 membered heterocycloalkyl, $R^{26B}$-substituted or unsubstituted phenyl, or $R^{26B}$-substituted or unsubstituted 5 to 6 membered heteroaryl. $X^{3B}$ is $-F$, $-Cl$, $-Br$, or $-I$. In embodiments, $R^{3B}$ is independently hydrogen. In embodiments, $R^{3B}$ is independently methyl. In embodiments, $R^{3B}$ is independently ethyl.

In embodiments, $R^{3A}$ and $R^{3B}$ substituents bonded to the same nitrogen atom may optionally be joined to form a $R^{26B}$-substituted or unsubstituted heterocycloalkyl or $R^{26B}$-substituted or unsubstituted heteroaryl. In embodiments, $R^{3A}$ and $R^{3B}$ substituents bonded to the same nitrogen atom may optionally be joined to form a $R^{26B}$-substituted or unsubstituted 3 to 6 membered heterocycloalkyl or $R^{26B}$-substituted or unsubstituted 5 to 6 membered heteroaryl.

$R^{26B}$ is independently oxo, halogen, $-CX^{26B}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{26B}_3$, $-OCHX^{26B}_2$, $R^{27B}$-substituted or unsubstituted alkyl, $R^{27B}$-substituted or unsubstituted heteroalkyl, $R^{27B}$-substituted or unsubstituted cycloalkyl, $R^{27B}$-substituted or unsubstituted heterocycloalkyl, $R^{27B}$-substituted or unsubstituted aryl, or $R^{27B}$-substituted or unsubstituted heteroaryl. In embodiments, $R^{26B}$ is independently oxo, halogen, $-CX^{26B}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, —NHC(O)NHNH$_2$, —NHC(O)NH$_2$, —NHSO$_2$H, —NHC(O)H, —NHC(O)OH, —NHOH, —OCX$^{26B}_3$, —OCHX$^{26B}_2$, R$^{27B}$-substituted or unsubstituted C$_1$-C$_8$ alkyl, R$^{27B}$-substituted or unsubstituted 2 to 8 membered heteroalkyl, R$^{27B}$-substituted or unsubstituted C$_3$-C$_8$ cycloalkyl, R$^{27B}$-substituted or unsubstituted 3 to 6 membered heterocycloalkyl, R$^{27B}$-substituted or unsubstituted phenyl, or R$^{27B}$-substituted or unsubstituted 5 to 6 membered heteroaryl. X$^{26B}$ is —F, —Cl, —Br, or —I.

R$^{27B}$ is independently oxo, halogen, —CX$^{27B}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{27B}_3$, —OCHX$^{27B}_2$, R$^{28B}$-substituted or unsubstituted alkyl, R$^{28B}$-substituted or unsubstituted heteroalkyl, R$^{28B}$-substituted or unsubstituted cycloalkyl, R$^{28B}$-substituted or unsubstituted heterocycloalkyl, R$^{28B}$-substituted or unsubstituted aryl, or R$^{28B}$-substituted or unsubstituted heteroaryl. In embodiments, R$^{27B}$ is independently oxo, halogen, —CX$^{27B}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{27B}_3$, —OCHX$^{27B}_2$, R$^{28B}$-substituted or unsubstituted C$_1$-C$_8$ alkyl, R$^{28B}$-substituted or unsubstituted 2 to 8 membered heteroalkyl, R$^{28B}$-substituted or unsubstituted C$_3$-C$_8$ cycloalkyl, R$^{28B}$-substituted or unsubstituted 3 to 6 membered heterocycloalkyl, R$^{28B}$-substituted or unsubstituted phenyl, or R$^{28B}$-substituted or unsubstituted 5 to 6 membered heteroaryl. X$^{27B}$ is —F, —Cl, —Br, or —I.

In embodiments, R$^{3C}$ is independently hydrogen, —CX$^{3C}_3$, —CN, —COOH, —CONH$_2$, —CHX$^{3C}_2$, —CH$_2$X$^{3C}$, R$^{26C}$-substituted or unsubstituted alkyl, R$^{26C}$-substituted or unsubstituted heteroalkyl, R$^{26C}$-substituted or unsubstituted cycloalkyl, R$^{26C}$-substituted or unsubstituted heterocycloalkyl, R$^{26C}$-substituted or unsubstituted aryl, or R$^{26C}$-substituted or unsubstituted heteroaryl. In embodiments, R$^{3C}$ is independently hydrogen, —CX$^{3C}_3$, —CN, —COOH, —CONH$_2$, —CHX$^{3C}_2$, —CH$_2$X$^{3C}$, R$^{26C}$-substituted or unsubstituted C$_1$-C$_8$ alkyl, R$^{26C}$-substituted or unsubstituted 2 to 8 membered heteroalkyl, R$^{26C}$-substituted or unsubstituted C$_3$-C$_8$ cycloalkyl, R$^{26C}$-substituted or unsubstituted 3 to 6 membered heterocycloalkyl, R$^{26C}$-substituted or unsubstituted phenyl, or R$^{26C}$-substituted or unsubstituted 5 to 6 membered heteroaryl. X$^{3C}$ is —F, —Cl, —Br, or —I. In embodiments, R$^{3C}$ is independently hydrogen. In embodiments, R$^{3C}$ is independently methyl. In embodiments, R$^{3C}$ is independently ethyl.

R$^{26C}$ is independently oxo, halogen, —CX$^{26C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{26C}_3$, —OCHX$^{26C}_2$, R$^{27C}$-substituted or unsubstituted alkyl, R$^{27C}$-substituted or unsubstituted heteroalkyl, R$^{27C}$-substituted or unsubstituted cycloalkyl, R$^{27C}$-substituted or unsubstituted heterocycloalkyl, R$^{27C}$-substituted or unsubstituted aryl, or R$^{27C}$-substituted or unsubstituted heteroaryl. In embodiments, R$^{26C}$ is independently oxo, halogen, —CX$^{26C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{26C}_3$, —OCHX$^{26C}_2$, R$^{27C}$-substituted or unsubstituted C$_1$-C$_8$ alkyl, R$^{27C}$-substituted or unsubstituted 2 to 8 membered heteroalkyl, R$^{27C}$-substituted or unsubstituted C$_3$-C$_8$ cycloalkyl, R$^{27C}$-substituted or unsubstituted 3 to 6 membered heterocycloalkyl, R$^{27C}$-substituted or unsubstituted phenyl, or R$^{27C}$-substituted or unsubstituted 5 to 6 membered heteroaryl. X$^{26C}$ is —F, —Cl, —Br, or —I.

R$^{27C}$ is independently oxo, halogen, —CX$^{27C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{27C}_3$, —OCHX$^{27C}_2$, R$^{28C}$-substituted or unsubstituted alkyl, R$^{28C}$-substituted or unsubstituted heteroalkyl, R$^{28C}$-substituted or unsubstituted cycloalkyl, R$^{28C}$-substituted or unsubstituted heterocycloalkyl, R$^{28C}$-substituted or unsubstituted aryl, or R$^{28C}$-substituted or unsubstituted heteroaryl. In embodiments, R$^{27C}$ is independently oxo, halogen, —CX$^{27C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{27C}_3$, —OCHX$^{27C}_2$, R$^{28C}$-substituted or unsubstituted C$_1$-C$_8$ alkyl, R$^{28C}$-substituted or unsubstituted 2 to 8 membered heteroalkyl, R$^{28C}$-substituted or unsubstituted C$_3$-C$_8$ cycloalkyl, R$^{28C}$-substituted or unsubstituted 3 to 6 membered heterocycloalkyl, R$^{28C}$-substituted or unsubstituted phenyl, or R$^{28C}$-substituted or unsubstituted 5 to 6 membered heteroaryl. X$^{27C}$ is —F, —Cl, —Br, or —I.

In embodiments, R$^{3D}$ is independently hydrogen, —CX$^{3D}_3$, —CN, —COOH, —CONH$_2$, —CHX$^{3D}_2$, —CH$_2$X$^{3D}$, R$^{26D}$-substituted or unsubstituted alkyl, R$^{26D}$-substituted or unsubstituted heteroalkyl, R$^{26D}$-substituted or unsubstituted cycloalkyl, R$^{26D}$-substituted or unsubstituted heterocycloalkyl, R$^{26D}$-substituted or unsubstituted aryl, or R$^{26D}$-substituted or unsubstituted heteroaryl. In embodiments, R$^{3D}$ is independently hydrogen, —CX$^{3D}_3$, —CN, —COOH, —CONH$_2$, —CHX$^{3D}_2$, —CH$_2$X$^{3D}$, R$^{26D}$-substituted or unsubstituted C$_1$-C$_8$ alkyl, R$^{26D}$-substituted or unsubstituted 2 to 8 membered heteroalkyl, R$^{26D}$-substituted or unsubstituted C$_3$-C$_8$ cycloalkyl, R$^{26D}$-substituted or unsubstituted 3 to 6 membered heterocycloalkyl, R$^{26D}$-substituted or unsubstituted phenyl, or R$^{26D}$-substituted or unsubstituted 5 to 6 membered heteroaryl. X$^{3D}$ is —F, —Cl, —Br, or —I. In embodiments, R$^{3D}$ is independently hydrogen. In embodiments, R$^{3D}$ is independently methyl. In embodiments, R$^{3D}$ is independently ethyl.

R$^{26D}$ is independently oxo, halogen, —CX$^{26D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{26D}_3$, —OCHX$^{26D}_2$, R$^{27D}$-substituted or unsubstituted alkyl, R$^{27D}$-substituted or unsubstituted heteroalkyl, R$^{27D}$-substituted or unsubstituted cycloalkyl, R$^{27D}$-substituted or unsubstituted heterocycloalkyl, R$^{27D}$-substituted or unsubstituted aryl, or R$^{27D}$-substituted or unsubstituted heteroaryl. In embodiments, R$^{26D}$ is independently oxo, halogen, —CX$^{26D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{26D}_3$, —OCHX$^{26D}_2$, R$^{27D}$-substituted or unsubstituted C$_1$-C$_8$ alkyl, R$^{27D}$-substituted or unsubstituted 2 to 8 membered heteroalkyl, R$^{27D}$-substituted or unsubstituted C$_3$-C$_8$ cycloalkyl, R$^{27D}$-substituted or unsubstituted 3 to 6 membered heterocycloalkyl, R$^{27D}$-substituted or unsubstituted phenyl, or R$^{27D}$-substituted or unsubstituted 5 to 6 membered heteroaryl. X$^{26D}$ is —F, —Cl, —Br, or —I.

$R^{27D}$ is independently oxo, halogen, —$CX^{27D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{27D}_3$, —$OCHX^{27D}_2$, $R^{28D}$-substituted or unsubstituted alkyl, $R^{28D}$-substituted or unsubstituted heteroalkyl, $R^{28D}$-substituted or unsubstituted cycloalkyl, $R^{28D}$-substituted or unsubstituted heterocycloalkyl, $R^{28D}$-substituted or unsubstituted aryl, or $R^{28D}$-substituted or unsubstituted heteroaryl. In embodiments, $R^{27D}$ is independently oxo, halogen, —$CX^{27D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{27D}_3$, —$OCHX^{27D}_2$, $R^{28D}$-substituted or unsubstituted $C_1$-$C_8$ alkyl, $R^{28D}$-substituted or unsubstituted 2 to 8 membered heteroalkyl, $R^{28D}$-substituted or unsubstituted $C_3$-$C_8$ cycloalkyl, $R^{28D}$-substituted or unsubstituted 3 to 6 membered heterocycloalkyl, $R^{28D}$-substituted or unsubstituted phenyl, or $R^{28D}$-substituted or unsubstituted 5 to 6 membered heteroaryl. $X^{27D}$ is —F, —Cl, —Br, or —I.

$R^{28}$, $R^{28A}$, $R^{28B}$, $R^{28C}$, and $R^{28D}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{28}$, $R^{28A}$, $R^{28B}$, $R^{28C}$, and $R^{28D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{28}$, $R^{28A}$, $R^{28B}$, $R^{28C}$, and $R^{28D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $R^3$ is independently halogen. In embodiments, $R^3$ is independently hydrogen. In embodiments, $R^3$ is independently hydrogen or halogen. In embodiments, $R^3$ is independently methyl. In embodiments, $R^3$ is independently $C_1$-$C_4$ alkyl. In embodiments, $R^3$ is independently halogen or $C_1$-$C_4$ alkyl. In embodiments, $R^3$ is independently halogen or $C_1$-$C_3$ alkyl. In embodiments, $R^3$ is independently halogen or $C_1$-$C_2$ alkyl. In embodiments, $R^3$ is independently halogen or methyl. In embodiments, $R^3$ is independently substituted or unsubstituted methyl. In embodiments, $R^3$ is independently substituted or unsubstituted $C_1$-$C_4$ alkyl. In embodiments, $R^3$ is independently halogen or substituted or unsubstituted $C_1$-$C_4$ alkyl. In embodiments, $R^3$ is independently halogen or substituted or unsubstituted $C_1$-$C_3$ alkyl. In embodiments, $R^3$ is independently halogen or substituted or unsubstituted $C_1$-$C_2$ alkyl. In embodiments, $R^3$ is independently halogen or substituted or unsubstituted methyl. In embodiments, $R^3$ is independently substituted methyl. In embodiments, $R^3$ is independently substituted $C_1$-$C_4$ alkyl. In embodiments, $R^3$ is independently halogen or substituted $C_1$-$C_4$ alkyl. In embodiments, $R^3$ is independently halogen or substituted $C_1$-$C_3$ alkyl. In embodiments, $R^3$ is independently halogen or substituted $C_1$-$C_2$ alkyl. In embodiments, $R^3$ is independently halogen or substituted methyl. In embodiments, $R^3$ is independently unsubstituted methyl. In embodiments, $R^3$ is independently unsubstituted $C_1$-$C_4$ alkyl. In embodiments, $R^3$ is independently halogen or unsubstituted $C_1$-$C_4$ alkyl. In embodiments, $R^3$ is independently halogen or unsubstituted $C_1$-$C_3$ alkyl. In embodiments, $R^3$ is independently halogen or unsubstituted $C_1$-$C_2$ alkyl. In embodiments, $R^3$ is independently halogen or unsubstituted methyl.

In embodiments, $R^3$ is independently $C_1$-$C_4$ alkyl. In embodiments, $R^3$ is independently $C_1$-$C_3$ alkyl. In embodiments, $R^3$ is independently $C_1$-$C_2$ alkyl. In embodiments, $R^3$ is independently methyl. In embodiments, $R^3$ is independently ispropyl. In embodiments, $R^3$ is independently substituted or unsubstituted methyl or substituted or unsubstituted isopropyl.

In embodiments, $R^4$ is independently hydrogen, halogen, —$CX^4_3$, —CN, —OH, —$NH_2$, —COOH, —$CONH_2$, —$NO_2$, —SH, —$OCX^4_3$, —$OCHX^4_2$, —$CHX^4_2$, —$CH_2X^4$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl; $R^4$ and $R^{4A1}$ may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^4$ is independently hydrogen, halogen, —$CX^4_3$, —CN, unsubstituted $C_1$-$C_4$ alkyl, or unsubstituted 2 to 4 membered heteroalkyl. In embodiments, $R^4$ is independently unsubstituted methyl, unsubstituted ethyl, unsubstituted isopropyl, or unsubstituted tert-butyl. In embodiments, $R^4$ is independently halogen, —$CX^4_3$, —CN, unsubstituted methyl, unsubstituted ethyl, unsubstituted methoxy, or unsubstituted ethoxy. In embodiments, $R^4$ is independently unsubstituted methyl. In embodiments, $R^4$ is independently unsubstituted ethyl. In embodiments, $R^4$ is independently unsubstituted propyl. In embodiments, $R^4$ is independently unsubstituted n-propyl. In embodiments, $R^4$ is independently unsubstituted isopropyl. In embodiments, $R^4$ is independently unsubstituted butyl. In embodiments, $R^4$ is independently unsubstituted n-butyl. In embodiments, $R^4$ is independently unsubstituted isobutyl. In embodiments, $R^4$ is independently unsubstituted tert-butyl. In embodiments, $R^4$ is independently unsubstituted pentyl. In embodiments, $R^4$ is independently unsubstituted hexyl. In embodiments, $R^4$ is independently unsubstituted heptyl. In embodiments, $R^4$ is independently unsubstituted octyl. In embodiments, $R^4$ is independently —F. In embodiments, $R^4$ is independently —Cl. In embodiments, $R^4$ is independently —Br. In embodiments, $R^4$ is independently —I. In embodiments, $R^4$ is independently unsubstituted methoxy. In embodiments, $R^4$ is independently unsubstituted ethoxy. In embodiments, $R^4$ is independently halogen, —$CF_3$. In embodiments, $R^4$ is independently —CCl3.

In embodiments, $R^4$ is independently hydrogen. In embodiments, $R^4$ is independently halogen. In embodiments, $R^4$ is independently —$CX^4_3$. In embodiments, $R^4$ is independently —$CHX^4_2$. In embodiments, $R^4$ is independently —$CH_2X^4$. In embodiments, $R^4$ is independently —$OCX^4_3$. In embodiments, $R^4$ is independently —OCH$_2$X$^4$. In embodiments, R$^4$ is independently —OCHX$^4_2$. In embodiments, R$^4$ is independently —CN. In embodiments, R$^4$ is independently —SO$_{n4}$R$^{4D}$. In embodiments, R$^4$ is independently —SO$_{v4}$NR$^{4A}$R$^{4B}$. In embodiments, R$^4$ is independently —NHC(O)NR$^{4A}$R$^{4B}$. In embodiments, R$^4$ is independently —N(O)$_{m4}$. In embodiments, R$^4$ is independently —NR$^{4A}$R$^{4B}$. In embodiments, R$^4$ is independently —C(O)R$^{4C}$. In embodiments, R$^4$ is independently —C(O)—OR$^{4C}$. In embodiments, R$^4$ is independently —C(O)NR$^{4A}$R$^{4B}$. In embodiments, R$^4$ is independently —OR$^{4D}$. In embodiments, R$^4$ is independently —NR$^{4A}$SO$_2$R$^{4D}$. In embodiments, R$^4$ is independently —NR$^{4A}$C(O)R$^{4C}$. In embodiments, R$^4$ is independently —NR$^{4A}$C(O)OR$^{4C}$ In embodiments, R$^4$ is independently —NR$^{4A}$OR$^{4C}$. In embodiments, R$^4$ is independently —OH. In embodiments, R$^4$ is independently —NH$_2$. In embodiments, R$^4$ is independently —COOH. In embodiments, R$^4$ is independently —CONH$_2$. In embodiments, R$^4$ is independently —NO$_2$. In embodiments, R$^4$ is independently —SH.

In embodiments, R$^4$ is independently substituted or unsubstituted alkyl. In embodiments, R$^4$ is independently substituted or unsubstituted heteroalkyl. In embodiments, R$^4$ is independently substituted or unsubstituted cycloalkyl. In embodiments, R$^4$ is independently, substituted or unsubstituted heterocycloalkyl. In embodiments, R$^4$ is independently substituted or unsubstituted aryl. In embodiments, R$^4$ is independently substituted or unsubstituted heteroaryl.

In embodiments, R$^4$ is independently substituted alkyl. In embodiments, R$^4$ is independently substituted heteroalkyl. In embodiments, R$^4$ is independently substituted cycloalkyl. In embodiments, R$^4$ is independently, substituted heterocycloalkyl. In embodiments, R$^4$ is independently substituted aryl. In embodiments, R$^4$ is independently substituted heteroaryl. In embodiments, R$^4$ is independently unsubstituted alkyl. In embodiments, R$^4$ is independently unsubstituted heteroalkyl. In embodiments, R$^4$ is independently unsubstituted cycloalkyl. In embodiments, R$^4$ is independently, unsubstituted heterocycloalkyl. In embodiments, R$^4$ is independently unsubstituted aryl. In embodiments, R$^4$ is independently unsubstituted heteroaryl.

In embodiments, R$^4$ is independently substituted or unsubstituted C$_1$-C$_8$ alkyl. In embodiments, R$^4$ is independently substituted or unsubstituted 2 to 8 membered heteroalkyl. In embodiments, R$^4$ is independently substituted or unsubstituted C$_3$-C$_8$ cycloalkyl. In embodiments, R$^4$ is independently, substituted or unsubstituted 3 to 8 membered heterocycloalkyl. In embodiments, R$^4$ is independently substituted or unsubstituted C$_6$-C$_{10}$ aryl. In embodiments, R$^4$ is independently substituted or unsubstituted 5 to 10 membered heteroaryl.

In embodiments, R$^4$ is independently substituted C$_1$-C$_8$ alkyl. In embodiments, R$^4$ is independently substituted 2 to 8 membered heteroalkyl. In embodiments, R$^4$ is independently substituted C$_3$-C$_8$ cycloalkyl. In embodiments, R$^4$ is independently, substituted 3 to 8 membered heterocycloalkyl. In embodiments, R$^4$ is independently substituted C$_6$-C$_{10}$ aryl. In embodiments, R$^4$ is independently substituted 5 to 10 membered heteroaryl. In embodiments, R$^4$ is independently unsubstituted C$_1$-C$_8$ alkyl. In embodiments, R$^4$ is independently unsubstituted 2 to 8 membered heteroalkyl. In embodiments, R$^4$ is independently unsubstituted C$_3$-C$_8$ cycloalkyl. In embodiments, R$^4$ is independently, unsubstituted 3 to 8 membered heterocycloalkyl. In embodiments, R$^4$ is independently unsubstituted C$_6$-C$_{10}$ aryl. In embodiments, R$^4$ is independently unsubstituted 5 to 10 membered heteroaryl.

In embodiments, R$^4$ is independently substituted or unsubstituted C$_1$-C$_4$ alkyl. In embodiments, R$^4$ is independently substituted or unsubstituted 2 to 4 membered heteroalkyl. In embodiments, R$^4$ is independently substituted or unsubstituted C$_3$-C$_6$ cycloalkyl. In embodiments, R$^4$ is independently, substituted or unsubstituted 3 to 6 membered heterocycloalkyl. In embodiments, R$^4$ is independently substituted or unsubstituted phenyl. In embodiments, R$^4$ is independently substituted or unsubstituted 5 to 6 membered heteroaryl.

In embodiments, R$^4$ is independently substituted C$_1$-C$_4$ alkyl. In embodiments, R$^4$ is independently substituted 2 to 4 membered heteroalkyl. In embodiments, R$^4$ is independently substituted C$_3$-C$_6$ cycloalkyl. In embodiments, R$^4$ is independently, substituted 3 to 6 membered heterocycloalkyl. In embodiments, R$^4$ is independently substituted phenyl. In embodiments, R$^4$ is independently substituted 5 to 6 membered heteroaryl. In embodiments, R$^4$ is independently unsubstituted C$_1$-C$_4$ alkyl. In embodiments, R$^4$ is independently unsubstituted 2 to 4 membered heteroalkyl. In embodiments, R$^4$ is independently unsubstituted C$_3$-C$_6$ cycloalkyl. In embodiments, R$^4$ is independently unsubstituted 3 to 6 membered heterocycloalkyl. In embodiments, R$^4$ is independently unsubstituted phenyl. In embodiments, R$^4$ is independently unsubstituted 5 to 6 membered heteroaryl.

In embodiments, R$^{4A1}$ is independently hydrogen, halogen, —CX$^4_3$, —CN, —OH, —NH$_2$, —COOH, —CONH$_2$, —NO$_2$, —SH, —OCX$^4_3$, —OCHX$^4_2$, —CHX$^4_2$, —CH$_2$X$^4$, substituted or unsubstituted C$_1$-C$_8$ alkyl, or substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, R$^{4A1}$ is independently hydrogen, halogen, —CX$^4_3$, —CN, unsubstituted C$_1$-C$_4$ alkyl, or unsubstituted 2 to 4 membered heteroalkyl. In embodiments, R$^{4A1}$ is independently unsubstituted methyl, unsubstituted ethyl, unsubstituted isopropyl, or unsubstituted tert-butyl. In embodiments, R$^{4A1}$ is independently halogen, —CX$^4_3$, —CN, unsubstituted methyl, unsubstituted ethyl, unsubstituted methoxy, or unsubstituted ethoxy. In embodiments, R$^{4A1}$ is independently unsubstituted methyl. In embodiments, R$^{4A1}$ is independently unsubstituted ethyl. In embodiments, R$^{4A1}$ is independently unsubstituted propyl. In embodiments, R$^{4A1}$ is independently unsubstituted n-propyl. In embodiments, R$^{4A1}$ is independently unsubstituted isopropyl. In embodiments, R$^{4A1}$ is independently unsubstituted butyl. In embodiments, R$^{4A1}$ is independently unsubstituted n-butyl. In embodiments, R$^{4A1}$ is independently unsubstituted isobutyl. In embodiments, R$^{4A1}$ is independently unsubstituted tert-butyl. In embodiments, R$^{4A1}$ is independently unsubstituted pentyl. In embodiments, R$^{4A1}$ is independently unsubstituted hexyl. In embodiments, R$^{4A1}$ is independently unsubstituted heptyl. In embodiments, R$^{4A1}$ is independently unsubstituted octyl. In embodiments, R$^{4A1}$ is independently —F. In embodiments, R$^{4A1}$ is independently —Cl. In embodiments, R$^{4A1}$ is independently —Br. In embodiments, R$^{4A1}$ is independently —I. In embodiments, R$^{4A1}$ is independently unsubstituted methoxy. In embodiments, R$^{4A1}$ is independently unsubstituted ethoxy. In embodiments, R$^{4A1}$ is independently halogen, —CF$_3$. In embodiments, R$^{4A1}$ is independently —CCl3.

In embodiments, R$^{4A1}$ is independently hydrogen. In embodiments, R$^{4A1}$ is independently halogen. In embodiments, R$^{4A1}$ is independently —CX$^4_3$. In embodiments, $R^{4A1}$ is independently —$CHX^4_2$. In embodiments, $R^{4A1}$ is independently —$CH_2X^4$. In embodiments, $R^{4A1}$ is independently —$OCX^4_3$. In embodiments, $R^{4A1}$ is independently —$OCH_2X^4$. In embodiments, $R^{4A1}$ is independently —$OCHX^4_2$. In embodiments, $R^{4A1}$ is independently —CN. In embodiments, $R^{4A1}$ is independently —$SO_{n4}R^{4D}$. In embodiments, $R^{4A1}$ is independently —$SO_{v4}NR^{4A}R^{4B}$. In embodiments, $R^{4A1}$ is independently —$NHC(O)NR^{4A}R^{4B}$ In embodiments, $R^{4A1}$ is independently —$N(O)_{m4}$. In embodiments, $R^{4A1}$ is independently —$NR^{4A}R^{4B}$. In embodiments, $R^{4A1}$ is independently —$C(O)R^{4C}$. In embodiments, $R^{4A1}$ is independently —C(O)—$OR^{4C}$. In embodiments, $R^{4A1}$ is independently —$C(O)NR^{4A}R^{4B}$. In embodiments, $R^{4A1}$ is independently —$OR^{4D}$. In embodiments, $R^{4A1}$ is independently —$NR^{4A}SO_2R^{4D}$. In embodiments, $R^{4A1}$ is independently —$NR^{4A}C(O)R^{4C}$. In embodiments, $R^{4A1}$ is independently —$NR^{4A}C(O)OR^{4C}$. In embodiments, $R^{4A1}$ is independently —$NR^{4A}OR^{4C}$. In embodiments, $R^{4A1}$ is independently —OH. In embodiments, $R^{4A1}$ is independently —$NH_2$. In embodiments, $R^{4A1}$ is independently —COOH. In embodiments, $R^{4A1}$ is independently —$CONH_2$. In embodiments, $R^{4A1}$ is independently —$NO_2$. In embodiments, $R^{4A1}$ is independently —SH.

In embodiments, $R^{4A1}$ is independently substituted or unsubstituted alkyl. In embodiments, $R^{4A1}$ is independently substituted or unsubstituted heteroalkyl. In embodiments, $R^{4A1}$ is independently substituted or unsubstituted cycloalkyl. In embodiments, $R^{4A1}$ is independently, substituted or unsubstituted heterocycloalkyl. In embodiments, $R^{4A1}$ is independently substituted or unsubstituted aryl. In embodiments, $R^{4A1}$ is independently substituted or unsubstituted heteroaryl.

In embodiments, $R^{4A1}$ is independently substituted alkyl. In embodiments, $R^{4A1}$ is independently substituted heteroalkyl. In embodiments, $R^{4A1}$ is independently substituted cycloalkyl. In embodiments, $R^{4A1}$ is independently, substituted heterocycloalkyl. In embodiments, $R^{4A1}$ is independently substituted aryl. In embodiments, $R^{4A1}$ is independently substituted heteroaryl. In embodiments, $R^{4A1}$ is independently unsubstituted alkyl. In embodiments, $R^{4A1}$ is independently unsubstituted heteroalkyl. In embodiments, $R^{4A1}$ is independently unsubstituted cycloalkyl. In embodiments, $R^{4A1}$ is independently, unsubstituted heterocycloalkyl. In embodiments, $R^{4A1}$ is independently unsubstituted aryl. In embodiments, $R^{4A1}$ is independently unsubstituted heteroaryl.

In embodiments, $R^{4A1}$ is independently substituted or unsubstituted $C_1$-$C_8$ alkyl. In embodiments, $R^{4A1}$ is independently substituted or unsubstituted 2 to 8 membered heteroalkyl. In embodiments, $R^{4A1}$ is independently substituted or unsubstituted $C_3$-$C_8$ cycloalkyl. In embodiments, $R^{4A1}$ is independently, substituted or unsubstituted 3 to 8 membered heterocycloalkyl. In embodiments, $R^{4A1}$ is independently substituted or unsubstituted $C_6$-$C_{10}$ aryl. In embodiments, $R^{4A1}$ is independently substituted or unsubstituted 5 to 10 membered heteroaryl.

In embodiments, $R^{4A1}$ is independently substituted $C_1$-$C_8$ alkyl. In embodiments, $R^{4A1}$ is independently substituted 2 to 8 membered heteroalkyl. In embodiments, $R^{4A1}$ is independently substituted $C_3$-$C_8$ cycloalkyl. In embodiments, $R^{4A1}$ is independently, substituted 3 to 8 membered heterocycloalkyl. In embodiments, $R^{4A1}$ is independently substituted $C_6$-$C_{10}$ aryl. In embodiments, $R^{4A1}$ is independently substituted 5 to 10 membered heteroaryl. In embodiments, $R^{4A1}$ is independently unsubstituted $C_1$-$C_8$ alkyl. In embodiments, $R^{4A1}$ is independently unsubstituted 2 to 8 membered heteroalkyl. In embodiments, $R^{4A1}$ is independently unsubstituted $C_3$-$C_8$ cycloalkyl. In embodiments, $R^{4A1}$ is independently, unsubstituted 3 to 8 membered heterocycloalkyl. In embodiments, $R^{4A1}$ is independently unsubstituted $C_6$-$C_{10}$ aryl. In embodiments, $R^{4A1}$ is independently unsubstituted 5 to 10 membered heteroaryl.

In embodiments, $R^{4A1}$ is independently substituted or unsubstituted $C_1$-$C_4$ alkyl. In embodiments, $R^{4A1}$ is independently substituted or unsubstituted 2 to 4 membered heteroalkyl. In embodiments, $R^{4A1}$ is independently substituted or unsubstituted $C_3$-$C_6$ cycloalkyl. In embodiments, $R^{4A1}$ is independently, substituted or unsubstituted 3 to 6 membered heterocycloalkyl. In embodiments, $R^{4A1}$ is independently substituted or unsubstituted phenyl. In embodiments, $R^{4A1}$ is independently substituted or unsubstituted 5 to 6 membered heteroaryl.

In embodiments, $R^{4A1}$ is independently substituted $C_1$-$C_4$ alkyl. In embodiments, $R^{4A1}$ is independently substituted 2 to 4 membered heteroalkyl. In embodiments, $R^{4A1}$ is independently substituted $C_3$-$C_6$ cycloalkyl. In embodiments, $R^{4A1}$ is independently, substituted 3 to 6 membered heterocycloalkyl. In embodiments, $R^{4A1}$ is independently substituted phenyl. In embodiments, $R^{4A1}$ is independently substituted 5 to 6 membered heteroaryl. In embodiments, $R^{4A1}$ is independently unsubstituted $C_1$-$C_4$ alkyl. In embodiments, $R^{4A1}$ is independently unsubstituted 2 to 4 membered heteroalkyl. In embodiments, $R^{4A1}$ is independently unsubstituted $C_3$-$C_6$ cycloalkyl. In embodiments, $R^{4A1}$ is independently unsubstituted 3 to 6 membered heterocycloalkyl. In embodiments, $R^{4A1}$ is independently unsubstituted phenyl. In embodiments, $R^{4A1}$ is independently unsubstituted 5 to 6 membered heteroaryl.

In embodiments, $R^{4B1}$ is independently hydrogen, halogen, —$CX^4_3$, —CN, —OH, —$NH_2$, —COOH, —$CONH_2$, —$NO_2$, —SH, —$OCX^4_3$, —$OCHX^4_2$, —$CHX^4_2$, —$CH_2X^4$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^{4B1}$ is independently hydrogen, halogen, —$CX^4_3$, —CN, unsubstituted $C_1$-$C_4$ alkyl, or unsubstituted 2 to 4 membered heteroalkyl. In embodiments, $R^{4B1}$ is independently unsubstituted methyl, unsubstituted ethyl, unsubstituted isopropyl, or unsubstituted tert-butyl. In embodiments, $R^{4B1}$ is independently halogen, —$CX^4_3$, —CN, unsubstituted methyl, unsubstituted ethyl, unsubstituted methoxy, or unsubstituted ethoxy. In embodiments, $R^{4B1}$ is independently unsubstituted methyl. In embodiments, $R^{4B1}$ is independently unsubstituted ethyl. In embodiments, $R^{4B1}$ is independently unsubstituted propyl. In embodiments, $R^{4B1}$ is independently unsubstituted n-propyl. In embodiments, $R^{4B1}$ is independently unsubstituted isopropyl. In embodiments, $R^{4B1}$ is independently unsubstituted butyl. In embodiments, $R^{4B1}$ is independently unsubstituted n-butyl. In embodiments, $R^{4B1}$ is independently unsubstituted isobutyl. In embodiments, $R^{4B1}$ is independently unsubstituted tert-butyl. In embodiments, $R^{4B1}$ is independently unsubstituted pentyl. In embodiments, $R^{4B1}$ is independently unsubstituted hexyl. In embodiments, $R^{4B1}$ is independently unsubstituted heptyl. In embodiments, $R^{4B1}$ is independently unsubstituted octyl. In embodiments, $R^{4B1}$ is independently —F. In embodiments, $R^{4B1}$ is independently —Cl. In embodiments, $R^{4B1}$ is independently —Br. In embodiments, $R^{4B1}$ is independently —I. In embodiments, $R^{4B1}$ is independently unsubstituted methoxy. In embodiments, $R^{4B1}$ is independently unsubstituted ethoxy. In embodiments, $R^{4B1}$ is independently halogen, —$CF_3$. In embodiments, $R^{4B1}$ is independently —$CCl_3$.

In embodiments, $R^{4B1}$ is independently hydrogen. In embodiments, $R^{4B1}$ is independently halogen. In embodiments, $R^{4B1}$ is independently —$CX^4{}_3$. In embodiments, $R^{4B1}$ is independently —$CHX^4{}_2$. In embodiments, $R^{4B1}$ is independently —$CH_2X^4$. In embodiments, $R^{4B1}$ is independently —$OCX^4{}_3$. In embodiments, $R^{4B1}$ is independently —$OCH_2X^4$. In embodiments, $R^{4B1}$ is independently —$OCHX^4{}_2$. In embodiments, $R^{4B1}$ is independently —CN. In embodiments, $R^{4B1}$ is independently —$SO_{n4}R^{4D}$. In embodiments, $R^{4B1}$ is independently —$SO_{v4}NR^{4A}R^{4B}$. In embodiments, $R^{4B1}$ is independently —$NHC(O)NR^{4A}R^{4B}$. In embodiments, $R^{4B1}$ is independently —$N(O)_{m4}$. In embodiments, $R^{4B1}$ is independently —$NR^{4A}R^{4B}$. In embodiments, $R^{4B1}$ is independently —$C(O)R^{4C}$. In embodiments, $R^{4B1}$ is independently —$C(O)$—$OR^{4C}$. In embodiments, $R^{4B1}$ is independently —$C(O)NR^{4A}R^{4B}$. In embodiments, $R^{4B1}$ is independently —$OR^{4D}$. In embodiments, $R^{4B1}$ is independently —$NR^{4A}SO_2R^{4D}$. In embodiments, $R^{4B1}$ is independently —$NR^{4A}C(O)R^{4C}$. In embodiments, $R^{4B1}$ is independently —$NR^{4A}C(O)OR^{4C}$. In embodiments, $R^{4B1}$ is independently —$NR^{4A}OR^{4C}$. In embodiments, $R^{4B1}$ is independently —OH. In embodiments, $R^{4B1}$ is independently —$NH_2$. In embodiments, $R^{4B1}$ is independently —COOH. In embodiments, $R^{4B1}$ is independently —$CONH_2$. In embodiments, $R^{4B1}$ is independently —$NO_2$. In embodiments, $R^{4B1}$ is independently —SH.

In embodiments, $R^{4B1}$ is independently substituted or unsubstituted alkyl. In embodiments, $R^{4B1}$ is independently substituted or unsubstituted heteroalkyl. In embodiments, $R^{4B1}$ is independently substituted or unsubstituted cycloalkyl. In embodiments, $R^{4B1}$ is independently, substituted or unsubstituted heterocycloalkyl. In embodiments, $R^{4B1}$ is independently substituted or unsubstituted aryl. In embodiments, $R^{4B1}$ is independently substituted or unsubstituted heteroaryl.

In embodiments, $R^{4B1}$ is independently substituted alkyl. In embodiments, $R^{4B1}$ is independently substituted heteroalkyl. In embodiments, $R^{4B1}$ is independently substituted cycloalkyl. In embodiments, $R^{4B1}$ is independently, substituted heterocycloalkyl. In embodiments, $R^{4B1}$ is independently substituted aryl. In embodiments, $R^{4B1}$ is independently substituted heteroaryl. In embodiments, $R^{4B1}$ is independently unsubstituted alkyl. In embodiments, $R^{4B1}$ is independently unsubstituted heteroalkyl. In embodiments, $R^{4B1}$ is independently unsubstituted cycloalkyl. In embodiments, $R^{4B1}$ is independently, unsubstituted heterocycloalkyl. In embodiments, $R^{4B1}$ is independently unsubstituted aryl. In embodiments, $R^{4B1}$ is independently unsubstituted heteroaryl.

In embodiments, $R^{4B1}$ is independently substituted or unsubstituted $C_1$-$C_8$ alkyl. In embodiments, $R^{4B1}$ is independently substituted or unsubstituted 2 to 8 membered heteroalkyl. In embodiments, $R^{4B1}$ is independently substituted or unsubstituted $C_3$-$C_8$ cycloalkyl. In embodiments, $R^{4B1}$ is independently, substituted or unsubstituted 3 to 8 membered heterocycloalkyl. In embodiments, $R^{4B1}$ is independently substituted or unsubstituted $C_6$-$C_{10}$ aryl. In embodiments, $R^{4B1}$ is independently substituted or unsubstituted 5 to 10 membered heteroaryl.

In embodiments, $R^{4B1}$ is independently substituted $C_1$-$C_8$ alkyl. In embodiments, $R^{4B1}$ is independently substituted 2 to 8 membered heteroalkyl. In embodiments, $R^{4B1}$ is independently substituted $C_3$-$C_8$ cycloalkyl. In embodiments, $R^{4B1}$ is independently, substituted 3 to 8 membered heterocycloalkyl. In embodiments, $R^{4B1}$ is independently substituted $C_6$-$C_{10}$ aryl. In embodiments, $R^{4B1}$ is independently substituted 5 to 10 membered heteroaryl. In embodiments, $R^{4B1}$ is independently unsubstituted $C_1$-$C_8$ alkyl. In embodiments, $R^{4B1}$ is independently unsubstituted 2 to 8 membered heteroalkyl. In embodiments, $R^{4B1}$ is independently unsubstituted $C_3$-$C_8$ cycloalkyl. In embodiments, $R^{4B1}$ is independently, unsubstituted 3 to 8 membered heterocycloalkyl. In embodiments, $R^{4B1}$ is independently unsubstituted $C_6$-$C_{10}$ aryl. In embodiments, $R^{4B1}$ is independently unsubstituted 5 to 10 membered heteroaryl.

In embodiments, $R^{4B1}$ is independently substituted or unsubstituted $C_1$-$C_4$ alkyl. In embodiments, $R^{4B1}$ is independently substituted or unsubstituted 2 to 4 membered heteroalkyl. In embodiments, $R^{4B1}$ is independently substituted or unsubstituted $C_3$-$C_6$ cycloalkyl. In embodiments, $R^{4B1}$ is independently, substituted or unsubstituted 3 to 6 membered heterocycloalkyl. In embodiments, $R^{4B1}$ is independently substituted or unsubstituted phenyl. In embodiments, $R^{4B1}$ is independently substituted or unsubstituted 5 to 6 membered heteroaryl.

In embodiments, $R^{4B1}$ is independently substituted $C_1$-$C_4$ alkyl. In embodiments, $R^{4B1}$ is independently substituted 2 to 4 membered heteroalkyl. In embodiments, $R^{4B1}$ is independently substituted $C_3$-$C_6$ cycloalkyl. In embodiments, $R^{4B1}$ is independently, substituted 3 to 6 membered heterocycloalkyl. In embodiments, $R^{4B1}$ is independently substituted phenyl. In embodiments, $R^{4B1}$ is independently substituted 5 to 6 membered heteroaryl. In embodiments, $R^{4B1}$ is independently unsubstituted $C_1$-$C_4$ alkyl. In embodiments, $R^{4B1}$ is independently unsubstituted 2 to 4 membered heteroalkyl. In embodiments, $R^{4B1}$ is independently unsubstituted $C_3$-$C_6$ cycloalkyl. In embodiments, $R^{4B1}$ is independently unsubstituted 3 to 6 membered heterocycloalkyl. In embodiments, $R^{4B1}$ is independently unsubstituted phenyl. In embodiments, $R^{4B1}$ is independently unsubstituted 5 to 6 membered heteroaryl.

In embodiments, $R^4$ and $R^{4A1}$ may optionally be joined to form a substituted or unsubstituted cycloalkyl, substituted or unsubstituted heterocycloalkyl, substituted or unsubstituted aryl, or substituted or unsubstituted heteroaryl.

In embodiments, $R^4$ and $R^{4A1}$ may optionally be joined to form a substituted or unsubstituted cycloalkyl. In embodiments, $R^4$ and $R^{4A1}$ may optionally be joined to form a substituted or unsubstituted heterocycloalkyl. In embodiments, $R^4$ and $R^{4A1}$ may optionally be joined to form a substituted or unsubstituted aryl. In embodiments, $R^4$ and $R^{4A1}$ may optionally be joined to form a substituted or unsubstituted heteroaryl. In embodiments, $R^4$ and $R^{4A1}$ may optionally be joined to form a substituted cycloalkyl. In embodiments, $R^4$ and $R^{4A1}$ may optionally be joined to form a substituted heterocycloalkyl. In embodiments, $R^4$ and $R^{4A1}$ may optionally be joined to form a substituted aryl. In embodiments, $R^4$ and $R^{4A1}$ may optionally be joined to form a substituted heteroaryl. In embodiments, $R^4$ and $R^{4A1}$ may optionally be joined to form an unsubstituted cycloalkyl. In embodiments, $R^4$ and $R^{4A1}$ may optionally be joined to form an unsubstituted heterocycloalkyl. In embodiments, $R^4$ and $R^{4A1}$ may optionally be joined to form an unsubstituted aryl. In embodiments, $R^4$ and $R^{4A1}$ may optionally be joined to form an unsubstituted heteroaryl.

In embodiments, $R^4$ and $R^{4A1}$ may optionally be joined to form a substituted or unsubstituted $C_3$-$C_8$ cycloalkyl. In embodiments, $R^4$ and $R^{4A1}$ may optionally be joined to form a substituted or unsubstituted 3 to 8 membered heterocycloalkyl. In embodiments, $R^4$ and $R^{4A1}$ may optionally be joined to form a substituted or unsubstituted $C_6$-$C_{10}$ aryl. In embodiments, $R^4$ and $R^{4A1}$ may optionally be joined to form a substituted or unsubstituted 5 to 10 membered heteroaryl. In embodiments, $R^4$ and $R^{4A1}$ may optionally be joined to form a substituted $C_3$-$C_8$ cycloalkyl. In embodiments, $R^4$ and $R^{4A1}$ may optionally be joined to form a substituted 3 to 8 membered heterocycloalkyl. In embodiments, $R^4$ and $R^{4A1}$ may optionally be joined to form a substituted $C_6$-$C_{10}$ aryl. In embodiments, $R^4$ and $R^{4A1}$ may optionally be joined to form a substituted 5 to 10 membered heteroaryl. In embodiments, $R^4$ and $R^{4A1}$ may optionally be joined to form an unsubstituted $C_3$-$C_8$ cycloalkyl. In embodiments, $R^4$ and $R^{4A1}$ may optionally be joined to form an unsubstituted 3 to 8 membered heterocycloalkyl. In embodiments, $R^4$ and $R^{4A1}$ may optionally be joined to form an unsubstituted $C_6$-$C_{10}$ aryl. In embodiments, $R^4$ and $R^{4A1}$ may optionally be joined to form an unsubstituted 5 to 10 membered heteroaryl.

In embodiments, $R^4$ and $R^{4A1}$ may optionally be joined to form a substituted or unsubstituted $C_3$-$C_6$ cycloalkyl. In embodiments, $R^4$ and $R^{4A1}$ may optionally be joined to form a substituted or unsubstituted 3 to 6 membered heterocycloalkyl. In embodiments, $R^4$ and $R^{4A1}$ may optionally be joined to form a substituted or unsubstituted phenyl. In embodiments, $R^4$ and $R^{4A1}$ may optionally be joined to form a substituted or unsubstituted 5 to 6 membered heteroaryl. In embodiments, $R^4$ and $R^{4A1}$ may optionally be joined to form a substituted $C_3$-$C_6$ cycloalkyl. In embodiments, $R^4$ and $R^{4A1}$ may optionally be joined to form a substituted 3 to 6 membered heterocycloalkyl. In embodiments, $R^4$ and $R^{4A1}$ may optionally be joined to form a substituted phenyl. In embodiments, $R^4$ and $R^{4A1}$ may optionally be joined to form a substituted 5 to 6 membered heteroaryl.

In embodiments, $R^4$ and $R^{4A1}$ may optionally be joined to form an unsubstituted $C_3$-$C_6$ cycloalkyl. In embodiments, $R^4$ and $R^{4A1}$ may optionally be joined to form an unsubstituted 3 to 6 membered heterocycloalkyl. In embodiments, $R^4$ and $R^{4A1}$ may optionally be joined to form an unsubstituted phenyl. In embodiments, $R^4$ and $R^{4A1}$ may optionally be joined to form an unsubstituted 5 to 6 membered heteroaryl.

In embodiments, $R^4$ and $R^{4A1}$ may optionally be joined to form a substituted or unsubstituted $C_3$-$C_8$ cycloalkenyl. In embodiments, $R^4$ and $R^{4A1}$ may optionally be joined to form a substituted or unsubstituted 3 to 6 membered heterocycloalkenyl. In embodiments, $R^4$ and $R^{4A1}$ may optionally be joined to form a substituted $C_3$-$C_8$ cycloalkenyl. In embodiments, $R^4$ and $R^{4A1}$ may optionally be joined to form a substituted 3 to 6 membered heterocycloalkenyl. In embodiments, $R^4$ and $R^{4A1}$ may optionally be joined to form an unsubstituted $C_3$-$C_8$ cycloalkenyl. In embodiments, $R^4$ and $R^{4A1}$ may optionally be joined to form an unsubstituted 3 to 6 membered heterocycloalkenyl. In embodiments, $R^4$ and $R^{4A1}$ may optionally be joined to form a substituted or unsubstituted $C_5$-$C_7$ cycloalkenyl. In embodiments, $R^4$ and $R^{4A1}$ may optionally be joined to form a substituted $C_5$-$C_7$ cycloalkenyl. In embodiments, $R^4$ and $R^{4A1}$ may optionally be joined to form an unsubstituted $C_5$-$C_7$ cycloalkenyl. In embodiments, $R^4$ and $R^{4A1}$ may optionally be joined to form a $R^{29}$-substituted $C_5$-$C_7$ cycloalkenyl.

In embodiments, $R^4$ and $R^{4A1}$ may optionally be joined to form a substituted or unsubstituted $C_5$ cycloalkyl. In embodiments, $R^4$ and $R^{4A1}$ may optionally be joined to form a substituted $C_5$ cycloalkyl. In embodiments, $R^4$ and $R^{4A1}$ may optionally be joined to form an unsubstituted $C_5$ cycloalkyl. In embodiments, $R^4$ and $R^{4A1}$ may optionally be joined to form a $R^{29}$-substituted $C_5$ cycloalkyl. In embodiments, $R^4$ and $R^{4A1}$ may optionally be joined to form a substituted or unsubstituted $C_5$ cycloalkenyl. In embodiments, $R^4$ and $R^{4A1}$ may optionally be joined to form a substituted $C_5$ cycloalkenyl. In embodiments, $R^4$ and $R^{4A1}$ may optionally be joined to form an unsubstituted $C_5$ cycloalkenyl. In embodiments, $R^4$ and $R^{4A1}$ may optionally be joined to form a $R^{29}$-substituted $C_5$ cycloalkenyl.

In embodiments, $R^4$ and $R^{4A1}$ may optionally be joined to form a substituted or unsubstituted $C_6$ cycloalkyl. In embodiments, $R^4$ and $R^{4A1}$ may optionally be joined to form a substituted $C_6$ cycloalkyl. In embodiments, $R^4$ and $R^{4A1}$ may optionally be joined to form an unsubstituted $C_6$ cycloalkyl. In embodiments, $R^4$ and $R^{4A1}$ may optionally be joined to form a $R^{29}$-substituted $C_6$ cycloalkyl. In embodiments, $R^4$ and $R^{4A1}$ may optionally be joined to form a substituted or unsubstituted $C_6$ cycloalkenyl. In embodiments, $R^4$ and $R^{4A1}$ may optionally be joined to form a substituted $C_6$ cycloalkenyl. In embodiments, $R^4$ and $R^{4A1}$ may optionally be joined to form an unsubstituted $C_6$ cycloalkenyl. In embodiments, $R^4$ and $R^{4A1}$ may optionally be joined to form a $R^{29}$-substituted $C_6$ cycloalkenyl.

In embodiments, $R^4$ and $R^{4A1}$ may optionally be joined to form a substituted or unsubstituted $C_7$ cycloalkyl. In embodiments, $R^4$ and $R^{4A1}$ may optionally be joined to form a substituted $C_7$ cycloalkyl. In embodiments, $R^4$ and $R^{4A1}$ may optionally be joined to form an unsubstituted $C_7$ cycloalkyl. In embodiments, $R^4$ and $R^{4A1}$ may optionally be joined to form a $R^{29}$-substituted $C_7$ cycloalkyl. In embodiments, $R^4$ and $R^{4A1}$ may optionally be joined to form a substituted or unsubstituted $C_7$ cycloalkenyl. In embodiments, $R^4$ and $R^{4A1}$ may optionally be joined to form a substituted $C_7$ cycloalkenyl. In embodiments, $R^4$ and $R^{4A1}$ may optionally be joined to form an unsubstituted $C_7$ cycloalkenyl. In embodiments, $R^4$ and $R^{4A1}$ may optionally be joined to form a $R^{29}$-substituted $C_7$ cycloalkenyl.

In embodiments, $R^4$ and $R^{4A1}$ may optionally be joined to form a substituted or unsubstituted 5 to 7 membered heterocycloalkenyl. In embodiments, $R^4$ and $R^{4A1}$ may optionally be joined to form a substituted 5 to 7 membered heterocycloalkenyl. In embodiments, $R^4$ and $R^{4A1}$ may optionally be joined to form an unsubstituted 5 to 7 membered heterocycloalkenyl. In embodiments, $R^4$ and $R^{4A1}$ may optionally be joined to form a $R^{29}$-substituted 5 to 7 membered heterocycloalkenyl.

In embodiments, $R^4$ and $R^{4A1}$ may optionally be joined to form a substituted or unsubstituted 5 membered heterocycloalkyl. In embodiments, $R^4$ and $R^{4A1}$ may optionally be joined to form a substituted 5 membered heterocycloalkyl. In embodiments, $R^4$ and $R^{4A1}$ may optionally be joined to form an unsubstituted 5 membered heterocycloalkyl. In embodiments, $R^4$ and $R^{4A1}$ may optionally be joined to form a $R^{29}$-substituted 5 membered heterocycloalkyl. In embodiments, $R^4$ and $R^{4A1}$ may optionally be joined to form a substituted or unsubstituted 5 membered heterocycloalkenyl. In embodiments, $R^4$ and $R^{4A1}$ may optionally be joined to form a substituted 5 membered heterocycloalkenyl. In embodiments, $R^4$ and $R^{4A1}$ may optionally be joined to form an unsubstituted 5 membered heterocycloalkenyl. In embodiments, $R^4$ and $R^{4A1}$ may optionally be joined to form a $R^{29}$-substituted 5 membered heterocycloalkenyl.

In embodiments, $R^4$ and $R^{4A1}$ may optionally be joined to form a substituted or unsubstituted 6 membered heterocycloalkyl. In embodiments, $R^4$ and $R^{4A1}$ may optionally be joined to form a substituted 6 membered heterocycloalkyl. In embodiments, $R^4$ and $R^{4A1}$ may optionally be joined to form an unsubstituted 6 membered heterocycloalkyl. In embodiments, $R^4$ and $R^{4A1}$ may optionally be joined to form a $R^{29}$-substituted 6 membered heterocycloalkyl. In embodiments, $R^4$ and $R^{4A1}$ may optionally be joined to form a substituted or unsubstituted 6 membered heterocycloalkenyl. In embodiments, $R^4$ and $R^{4A1}$ may optionally be joined to form a substituted 6 membered heterocycloalkenyl. In embodiments, $R^4$ and $R^{4A1}$ may optionally be joined to form an unsubstituted 6 membered heterocycloalkenyl. In embodiments, $R^4$ and $R^{4A1}$ may optionally be joined to form a $R^{29}$-substituted 6 membered heterocycloalkenyl.

In embodiments, $R^4$ and $R^{4A1}$ may optionally be joined to form a substituted or unsubstituted 7 membered heterocycloalkyl. In embodiments, $R^4$ and $R^{4A1}$ may optionally be joined to form a substituted 7 membered heterocycloalkyl. In embodiments, $R^4$ and $R^{4A1}$ may optionally be joined to form an unsubstituted 7 membered heterocycloalkyl. In embodiments, $R^4$ and $R^{4A1}$ may optionally be joined to form a $R^{29}$-substituted 7 membered heterocycloalkyl. In embodiments, $R^4$ and $R^{4A1}$ may optionally be joined to form a substituted or unsubstituted 7 membered heterocycloalkenyl. In embodiments, $R^4$ and $R^{4A1}$ may optionally be joined to form a substituted 7 membered heterocycloalkenyl. In embodiments, $R^4$ and $R^{4A1}$ may optionally be joined to form an unsubstituted 7 membered heterocycloalkenyl. In embodiments, $R^4$ and $R^{4A1}$ may optionally be joined to form a $R^{29}$-substituted 7 membered heterocycloalkenyl.

In embodiments, $R^4$ and $R^{4A1}$ may optionally be joined to form a substituted or unsubstituted piperidinyl. In embodiments, $R^4$ and $R^{4A1}$ may optionally be joined to form a substituted piperidinyl. In embodiments, $R^4$ and $R^{4A1}$ may optionally be joined to form an unsubstituted piperidinyl. In embodiments, $R^4$ and $R^{4A1}$ may optionally be joined to form a $R^{29}$-substituted piperidinyl. In embodiments, $R^4$ and $R^{4A1}$ may optionally be joined to form a substituted or unsubstituted phenyl. In embodiments, $R^4$ and $R^{4A1}$ may optionally be joined to form a substituted phenyl. In embodiments, $R^4$ and $R^{4A1}$ may optionally be joined to form an unsubstituted phenyl. In embodiments, $R^4$ and $R^{4A1}$ may optionally be joined to form a $R^{29}$-substituted phenyl.

In embodiments, $R^{4A}$ is independently hydrogen. In embodiments, $R^{4A}$ is independently $-CX^{4A}_3$. In embodiments, $R^{4A}$ is independently $-CHX^{4A}_2$. In embodiments, $R^{4A}$ is independently $-CH_2X^{4A}$. In embodiments, $R^{4A}$ is independently $-CN$. In embodiments, $R^{4A}$ is independently $-COOH$. In embodiments, $R^{4A}$ is independently $-CONH_2$. In embodiments, $R^{4A}$ is independently substituted or unsubstituted alkyl. In embodiments, $R^{4A}$ is independently substituted or unsubstituted heteroalkyl. In embodiments, $R^{4A}$ is independently substituted or unsubstituted cycloalkyl. In embodiments, $R^{4A}$ is independently, substituted or unsubstituted heterocycloalkyl. In embodiments, $R^{4A}$ is independently substituted or unsubstituted aryl. In embodiments, $R^{4A}$ is independently substituted or unsubstituted heteroaryl.

In embodiments, $R^{4A}$ is independently substituted alkyl. In embodiments, $R^{4A}$ is independently substituted heteroalkyl. In embodiments, $R^{4A}$ is independently substituted cycloalkyl. In embodiments, $R^{4A}$ is independently, substituted heterocycloalkyl. In embodiments, $R^{4A}$ is independently substituted aryl. In embodiments, $R^{4A}$ is independently substituted heteroaryl. In embodiments, $R^{4A}$ is independently unsubstituted alkyl. In embodiments, $R^{4A}$ is independently unsubstituted heteroalkyl. In embodiments, $R^{4A}$ is independently unsubstituted cycloalkyl. In embodiments, $R^{4A}$ is independently, unsubstituted heterocycloalkyl. In embodiments, $R^{4A}$ is independently unsubstituted aryl. In embodiments, $R^{4A}$ is independently unsubstituted heteroaryl.

In embodiments, $R^{4A}$ is independently substituted or unsubstituted $C_1$-$C_8$ alkyl. In embodiments, $R^{4A}$ is independently substituted or unsubstituted 2 to 8 membered heteroalkyl. In embodiments, $R^{4A}$ is independently substituted or unsubstituted $C_3$-$C_8$ cycloalkyl. In embodiments, $R^{4A}$ is independently, substituted or unsubstituted 3 to 8 membered heterocycloalkyl. In embodiments, $R^{4A}$ is independently substituted or unsubstituted $C_6$-$C_{10}$ aryl. In embodiments, $R^{4A}$ is independently substituted or unsubstituted 5 to 10 membered heteroaryl.

In embodiments, $R^{4A}$ is independently substituted $C_1$-$C_8$ alkyl. In embodiments, $R^{4A}$ is independently substituted 2 to 8 membered heteroalkyl. In embodiments, $R^{4A}$ is independently substituted $C_3$-$C_8$ cycloalkyl. In embodiments, $R^{4A}$ is independently, substituted 3 to 8 membered heterocycloalkyl. In embodiments, $R^{4A}$ is independently substituted $C_6$-$C_{10}$ aryl. In embodiments, $R^{4A}$ is independently substituted 5 to 10 membered heteroaryl. In embodiments, $R^{4A}$ is independently unsubstituted $C_1$-$C_8$ alkyl. In embodiments, $R^{4A}$ is independently unsubstituted 2 to 8 membered heteroalkyl. In embodiments, $R^{4A}$ is independently unsubstituted $C_3$-$C_8$ cycloalkyl. In embodiments, $R^{4A}$ is independently, unsubstituted 3 to 8 membered heterocycloalkyl. In embodiments, $R^{4A}$ is independently unsubstituted $C_6$-$C_{10}$ aryl. In embodiments, $R^{4A}$ is independently unsubstituted 5 to 10 membered heteroaryl.

In embodiments, $R^{4A}$ is independently substituted or unsubstituted $C_1$-$C_4$ alkyl. In embodiments, $R^{4A}$ is independently substituted or unsubstituted 2 to 4 membered heteroalkyl. In embodiments, $R^{4A}$ is independently substituted or unsubstituted $C_3$-$C_6$ cycloalkyl. In embodiments, $R^{4A}$ is independently, substituted or unsubstituted 3 to 6 membered heterocycloalkyl. In embodiments, $R^{4A}$ is independently substituted or unsubstituted phenyl. In embodiments, $R^{4A}$ is independently substituted or unsubstituted 5 to 6 membered heteroaryl.

In embodiments, $R^{4A}$ is independently substituted $C_1$-$C_4$ alkyl. In embodiments, $R^{4A}$ is independently substituted 2 to 4 membered heteroalkyl. In embodiments, $R^{4A}$ is independently substituted $C_3$-$C_6$ cycloalkyl. In embodiments, $R^{4A}$ is independently, substituted 3 to 6 membered heterocycloalkyl. In embodiments, $R^{4A}$ is independently substituted phenyl. In embodiments, $R^{4A}$ is independently substituted 5 to 6 membered heteroaryl. In embodiments, $R^{4A}$ is independently unsubstituted $C_1$-$C_4$ alkyl. In embodiments, $R^{4A}$ is independently unsubstituted 2 to 4 membered heteroalkyl. In embodiments, $R^{4A}$ is independently unsubstituted $C_3$-$C_6$ cycloalkyl. In embodiments, $R^{4A}$ is independently unsubstituted 3 to 6 membered heterocycloalkyl. In embodiments, $R^{4A}$ is independently unsubstituted phenyl. In embodiments, $R^{4A}$ is independently unsubstituted 5 to 6 membered heteroaryl. In embodiments, $R^{4A}$ is independently unsubstituted methyl. In embodiments, $R^{4A}$ is independently unsubstituted ethyl. In embodiments, $R^{4A}$ is independently unsubstituted propyl. In embodiments, $R^{4A}$ is independently unsubstituted isopropyl. In embodiments, $R^{4A}$ is independently unsubstituted tert-butyl.

In embodiments, $R^{4B}$ is independently hydrogen. In embodiments, $R^{4B}$ is independently $-CX^{4B}_3$. In embodiments, $R^{4B}$ is independently $-CHX^{4B}_2$. In embodiments, $R^{4B}$ is independently $-CH_2X^{4B}$. In embodiments, $R^{4B}$ is independently $-CN$. In embodiments, $R^{4B}$ is independently $-COOH$. In embodiments, $R^{4B}$ is independently $-CONH_2$. In embodiments, $R^{4B}$ is independently substituted or unsubstituted alkyl. In embodiments, $R^{4B}$ is independently substituted or unsubstituted heteroalkyl. In embodiments, $R^{4B}$ is independently substituted or unsubstituted cycloalkyl. In embodiments, $R^{4B}$ is independently, substituted or unsubstituted heterocycloalkyl. In embodiments, $R^{4B}$ is independently substituted or unsubstituted aryl. In embodiments, $R^{4B}$ is independently substituted or unsubstituted heteroaryl.

In embodiments, $R^{4B}$ is independently substituted alkyl. In embodiments, $R^{4B}$ is independently substituted heteroalkyl. In embodiments, $R^{4B}$ is independently substituted cycloalkyl. In embodiments, $R^{4B}$ is independently, substituted heterocycloalkyl. In embodiments, $R^{4B}$ is independently substituted aryl. In embodiments, $R^{4B}$ is independently substituted heteroaryl. In embodiments, $R^{4B}$ is independently unsubstituted alkyl. In embodiments, $R^{4B}$ is independently unsubstituted heteroalkyl. In embodiments, $R^{4B}$ is independently unsubstituted cycloalkyl. In embodiments, $R^{4B}$ is independently, unsubstituted heterocycloalkyl. In embodiments, $R^{4B}$ is independently unsubstituted aryl. In embodiments, $R^{4B}$ is independently unsubstituted heteroaryl.

In embodiments, $R^{4B}$ is independently substituted or unsubstituted $C_1$-$C_8$ alkyl. In embodiments, $R^{4B}$ is independently substituted or unsubstituted 2 to 8 membered heteroalkyl. In embodiments, $R^{4B}$ is independently substituted or unsubstituted $C_3$-$C_8$ cycloalkyl. In embodiments, $R^{4B}$ is independently, substituted or unsubstituted 3 to 8 membered heterocycloalkyl. In embodiments, $R^{4B}$ is independently substituted or unsubstituted $C_6$-$C_{10}$ aryl. In embodiments, $R^{4B}$ is independently substituted or unsubstituted 5 to 10 membered heteroaryl.

In embodiments, $R^{4B}$ is independently substituted $C_1$-$C_8$ alkyl. In embodiments, $R^{4B}$ is independently substituted 2 to 8 membered heteroalkyl. In embodiments, $R^{4B}$ is independently substituted $C_3$-$C_8$ cycloalkyl. In embodiments, $R^{4B}$ is independently, substituted 3 to 8 membered heterocycloalkyl. In embodiments, $R^{4B}$ is independently substituted $C_6$-$C_{10}$ aryl. In embodiments, $R^{4B}$ is independently substituted 5 to 10 membered heteroaryl. In embodiments, $R^{4B}$ is independently unsubstituted $C_1$-$C_8$ alkyl. In embodiments, $R^{4B}$ is independently unsubstituted 2 to 8 membered heteroalkyl. In embodiments, $R^{4B}$ is independently unsubstituted $C_3$-$C_8$ cycloalkyl. In embodiments, $R^{4B}$ is independently, unsubstituted 3 to 8 membered heterocycloalkyl. In embodiments, $R^{4B}$ is independently unsubstituted $C_6$-$C_{10}$ aryl. In embodiments, $R^{4B}$ is independently unsubstituted 5 to 10 membered heteroaryl.

In embodiments, $R^{4B}$ is independently substituted or unsubstituted $C_1$-$C_4$ alkyl. In embodiments, $R^{4B}$ is independently substituted or unsubstituted 2 to 4 membered heteroalkyl. In embodiments, $R^{4B}$ is independently substituted or unsubstituted $C_3$-$C_6$ cycloalkyl. In embodiments, $R^{4B}$ is independently, substituted or unsubstituted 3 to 6 membered heterocycloalkyl. In embodiments, $R^{4B}$ is independently substituted or unsubstituted phenyl. In embodiments, $R^{4B}$ is independently substituted or unsubstituted 5 to 6 membered heteroaryl.

In embodiments, $R^{4B}$ is independently substituted $C_1$-$C_4$ alkyl. In embodiments, $R^{4B}$ is independently substituted 2 to 4 membered heteroalkyl. In embodiments, $R^{4B}$ is independently substituted $C_3$-$C_6$ cycloalkyl. In embodiments, $R^{4B}$ is independently, substituted 3 to 6 membered heterocycloalkyl. In embodiments, $R^{4B}$ is independently substituted phenyl. In embodiments, $R^{4B}$ is independently substituted 5 to 6 membered heteroaryl. In embodiments, $R^{4B}$ is independently unsubstituted $C_1$-$C_4$ alkyl. In embodiments, $R^{4B}$ is independently unsubstituted 2 to 4 membered heteroalkyl. In embodiments, $R^{4B}$ is independently unsubstituted $C_3$-$C_6$ cycloalkyl. In embodiments, $R^{4B}$ is independently unsubstituted 3 to 6 membered heterocycloalkyl. In embodiments, $R^{4B}$ is independently unsubstituted phenyl. In embodiments, $R^{4B}$ is independently unsubstituted 5 to 6 membered heteroaryl. In embodiments, $R^{4B}$ is independently unsubstituted methyl. In embodiments, $R^{4B}$ is independently unsubstituted ethyl. In embodiments, $R^{4B}$ is independently unsubstituted propyl. In embodiments, $R^{4B}$ is independently unsubstituted isopropyl. In embodiments, $R^{4B}$ is independently unsubstituted tert-butyl.

In embodiments, $R^{4A}$ and $R^{4B}$ substituents bonded to the same nitrogen atom may be joined to form a substituted or unsubstituted heterocycloalkyl. In embodiments, $R^{4A}$ and $R^{4B}$ substituents bonded to the same nitrogen atom may be joined to form a substituted or unsubstituted heteroaryl. In embodiments, $R^{4A}$ and $R^{4B}$ substituents bonded to the same nitrogen atom may be joined to form a substituted heterocycloalkyl. In embodiments, $R^{4A}$ and $R^{4B}$ substituents bonded to the same nitrogen atom may be joined to form a substituted heteroaryl. In embodiments, $R^{4A}$ and $R^{4B}$ substituents bonded to the same nitrogen atom may be joined to form an unsubstituted heterocycloalkyl. In embodiments, $R^{4A}$ and $R^{4B}$ substituents bonded to the same nitrogen atom may be joined to form an unsubstituted heteroaryl.

In embodiments, $R^{4A}$ and $R^{4B}$ substituents bonded to the same nitrogen atom may be joined to form a substituted or unsubstituted 3 to 8 membered heterocycloalkyl. In embodiments, $R^{4A}$ and $R^{4B}$ substituents bonded to the same nitrogen atom may be joined to form a substituted or unsubstituted 5 to 10 membered heteroaryl. In embodiments, $R^{4A}$ and $R^{4B}$ substituents bonded to the same nitrogen atom may be joined to form a substituted 3 to 8 membered heterocycloalkyl. In embodiments, $R^{4A}$ and $R^{4B}$ substituents bonded to the same nitrogen atom may be joined to form a substituted 5 to 10 membered heteroaryl. In embodiments, $R^{4A}$ and $R^{4B}$ substituents bonded to the same nitrogen atom may be joined to form an unsubstituted 3 to 8 membered heterocycloalkyl. In embodiments, $R^{4A}$ and $R^{4B}$ substituents bonded to the same nitrogen atom may be joined to form an unsubstituted 5 to 10 membered heteroaryl.

In embodiments, $R^{4A}$ and $R^{4B}$ substituents bonded to the same nitrogen atom may be joined to form a substituted or unsubstituted 3 to 6 membered heterocycloalkyl. In embodiments, $R^{4A}$ and $R^{4B}$ substituents bonded to the same nitrogen atom may be joined to form a substituted or unsubstituted 5 to 6 membered heteroaryl. In embodiments, $R^{4A}$ and $R^{4B}$ substituents bonded to the same nitrogen atom may be joined to form a substituted 3 to 6 membered heterocycloalkyl. In embodiments, $R^{4A}$ and $R^{4B}$ substituents bonded to the same nitrogen atom may be joined to form a substituted 5 to 6 membered heteroaryl. In embodiments, $R^{4A}$ and $R^{4B}$ substituents bonded to the same nitrogen atom may be joined to form an unsubstituted 3 to 6 membered heterocycloalkyl. In embodiments, $R^{4A}$ and $R^{4B}$ substituents bonded to the same nitrogen atom may be joined to form an unsubstituted 5 to 6 membered heteroaryl.

In embodiments, $R^{4C}$ is independently hydrogen. In embodiments, $R^{4C}$ is independently —$CX^{4C}_3$. In embodiments, $R^{4C}$ is independently —$CHX^{4C}_2$. In embodiments, $R^{4C}$ is independently —$CH_2X^{4C}$. In embodiments, $R^{4C}$ is independently —CN. In embodiments, $R^{4C}$ is independently —COOH. In embodiments, $R^{4C}$ is independently —$CONH_2$. In embodiments, $R^{4C}$ is independently substituted or unsubstituted alkyl. In embodiments, $R^{4C}$ is independently substituted or unsubstituted heteroalkyl. In embodiments, $R^{4C}$ is independently substituted or unsubstituted cycloalkyl. In embodiments, $R^{4C}$ is independently, substituted or unsubstituted heterocycloalkyl. In embodiments, $R^{4C}$ is independently substituted or unsubstituted aryl. In embodiments, $R^{4C}$ is independently substituted or unsubstituted heteroaryl. In embodiments, $R^{4C}$ is independently substituted alkyl. In embodiments, $R^{4C}$ is independently substituted heteroalkyl. In embodiments, $R^{4C}$ is independently substituted cycloalkyl. In embodiments, $R^{4C}$ is independently, substituted heterocycloalkyl. In embodiments, $R^{4C}$ is independently substituted aryl. In embodiments, $R^{4C}$ is independently substituted heteroaryl. In embodiments, $R^{4C}$ is independently unsubstituted alkyl. In embodiments, $R^{4C}$ is independently unsubstituted heteroalkyl. In embodiments, $R^{4C}$ is independently unsubstituted cycloalkyl. In embodiments, $R^{4C}$ is independently, unsubstituted heterocycloalkyl. In embodiments, $R^{4C}$ is independently unsubstituted aryl. In embodiments, $R^{4C}$ is independently unsubstituted heteroaryl.

In embodiments, $R^{4C}$ is independently substituted or unsubstituted $C_1$-$C_8$ alkyl. In embodiments, $R^{4C}$ is independently substituted or unsubstituted 2 to 8 membered heteroalkyl. In embodiments, $R^{4C}$ is independently substituted or unsubstituted $C_3$-$C_8$ cycloalkyl. In embodiments, $R^{4C}$ is independently, substituted or unsubstituted 3 to 8 membered heterocycloalkyl. In embodiments, $R^{4C}$ is independently substituted or unsubstituted $C_6$-$C_{10}$ aryl. In embodiments, $R^{4C}$ is independently substituted or unsubstituted 5 to 10 membered heteroaryl.

In embodiments, $R^{4C}$ is independently substituted $C_1$-$C_8$ alkyl. In embodiments, $R^{4C}$ is independently substituted 2 to 8 membered heteroalkyl. In embodiments, $R^{4C}$ is independently substituted $C_3$-$C_8$ cycloalkyl. In embodiments, $R^{4C}$ is independently, substituted 3 to 8 membered heterocycloalkyl. In embodiments, $R^{4C}$ is independently substituted $C_6$-$C_{10}$ aryl. In embodiments, $R^{4C}$ is independently substituted 5 to 10 membered heteroaryl. In embodiments, $R^{4C}$ is independently unsubstituted $C_1$-$C_8$ alkyl. In embodiments, $R^{4C}$ is independently unsubstituted 2 to 8 membered heteroalkyl. In embodiments, $R^{4C}$ is independently unsubstituted $C_3$-$C_8$ cycloalkyl. In embodiments, $R^{4C}$ is independently, unsubstituted 3 to 8 membered heterocycloalkyl. In embodiments, $R^{4C}$ is independently unsubstituted $C_6$-$C_{10}$ aryl. In embodiments, $R^{4C}$ is independently unsubstituted 5 to 10 membered heteroaryl. In embodiments, $R^{4C}$ is independently substituted or unsubstituted $C_1$-$C_4$ alkyl. In embodiments, $R^{4C}$ is independently substituted or unsubstituted 2 to 4 membered heteroalkyl. In embodiments, $R^{4C}$ is independently substituted or unsubstituted $C_3$-$C_6$ cycloalkyl. In embodiments, $R^{4C}$ is independently, substituted or unsubstituted 3 to 6 membered heterocycloalkyl. In embodiments, $R^{4C}$ is independently substituted or unsubstituted phenyl. In embodiments, $R^{4C}$ is independently substituted or unsubstituted 5 to 6 membered heteroaryl.

In embodiments, $R^{4C}$ is independently substituted $C_1$-$C_4$ alkyl. In embodiments, $R^{4C}$ is independently substituted 2 to 4 membered heteroalkyl. In embodiments, $R^{4C}$ is independently substituted $C_3$-$C_6$ cycloalkyl. In embodiments, $R^{4C}$ is independently, substituted 3 to 6 membered heterocycloalkyl. In embodiments, $R^{4C}$ is independently substituted phenyl. In embodiments, $R^{4C}$ is independently substituted 5 to 6 membered heteroaryl. In embodiments, $R^{4C}$ is independently unsubstituted $C_1$-$C_4$ alkyl. In embodiments, $R^{4C}$ is independently unsubstituted 2 to 4 membered heteroalkyl. In embodiments, $R^{4C}$ is independently unsubstituted $C_3$-$C_6$ cycloalkyl. In embodiments, $R^{4C}$ is independently unsubstituted 3 to 6 membered heterocycloalkyl. In embodiments, $R^{4C}$ is independently unsubstituted phenyl. In embodiments, $R^{4C}$ is independently unsubstituted 5 to 6 membered heteroaryl. In embodiments, $R^{4C}$ is independently unsubstituted methyl. In embodiments, $R^{4C}$ is independently unsubstituted ethyl. In embodiments, $R^{4C}$ is independently unsubstituted propyl. In embodiments, $R^{4C}$ is independently unsubstituted isopropyl. In embodiments, $R^{4C}$ is independently unsubstituted tert-butyl.

In embodiments, $R^{4D}$ is independently hydrogen. In embodiments, $R^{4D}$ is independently —$CX^{4D}_3$. In embodiments, $R^{4D}$ is independently —$CHX^{4D}_2$. In embodiments, $R^{4D}$ is independently —$CH_2X^{4D}$. In embodiments, $R^{4D}$ is independently —CN. In embodiments, $R^{4D}$ is independently —COOH. In embodiments, $R^{4D}$ is independently —$CONH_2$. In embodiments, $R^{4D}$ is independently substituted or unsubstituted alkyl. In embodiments, $R^{4D}$ is independently substituted or unsubstituted heteroalkyl. In embodiments, $R^{4D}$ is independently substituted or unsubstituted cycloalkyl. In embodiments, $R^{4D}$ is independently, substituted or unsubstituted heterocycloalkyl. In embodiments, $R^{4D}$ is independently substituted or unsubstituted aryl. In embodiments, $R^{4D}$ is independently substituted or unsubstituted heteroaryl.

In embodiments, $R^{4D}$ is independently substituted alkyl. In embodiments, $R^{4D}$ is independently substituted heteroalkyl. In embodiments, $R^{4D}$ is independently substituted cycloalkyl. In embodiments, $R^{4D}$ is independently, substituted heterocycloalkyl. In embodiments, $R^{4D}$ is independently substituted aryl. In embodiments, $R^{4D}$ is independently substituted heteroaryl. In embodiments, $R^{4D}$ is independently unsubstituted alkyl. In embodiments, $R^{4D}$ is independently unsubstituted heteroalkyl. In embodiments, $R^{4D}$ is independently unsubstituted cycloalkyl. In embodiments, $R^{4D}$ is independently, unsubstituted heterocycloalkyl. In embodiments, $R^{4D}$ is independently unsubstituted aryl. In embodiments, $R^{4D}$ is independently unsubstituted heteroaryl.

In embodiments, $R^{4D}$ is independently substituted or unsubstituted $C_1$-$C_8$ alkyl. In embodiments, $R^{4D}$ is independently substituted or unsubstituted 2 to 8 membered heteroalkyl. In embodiments, $R^{4D}$ is independently substituted or unsubstituted $C_3$-$C_8$ cycloalkyl. In embodiments, $R^{4D}$ is independently, substituted or unsubstituted 3 to 8 membered heterocycloalkyl. In embodiments, $R^{4D}$ is independently substituted or unsubstituted $C_6$-$C_{10}$ aryl. In embodiments, $R^{4D}$ is independently substituted or unsubstituted 5 to 10 membered heteroaryl.

In embodiments, $R^{4D}$ is independently substituted $C_1$-$C_8$ alkyl. In embodiments, $R^{4D}$ is independently substituted 2 to 8 membered heteroalkyl. In embodiments, $R^{4D}$ is independently substituted $C_3$-$C_8$ cycloalkyl. In embodiments, $R^{4D}$ is independently, substituted 3 to 8 membered heterocycloalkyl. In embodiments, $R^{4D}$ is independently substituted $C_6$-$C_{10}$ aryl. In embodiments, $R^{4D}$ is independently substituted 5 to 10 membered heteroaryl. In embodiments, $R^{4D}$ is independently unsubstituted $C_1$-$C_8$ alkyl. In embodiments, $R^{4D}$ is independently unsubstituted 2 to 8 membered heteroalkyl. In embodiments, $R^{4D}$ is independently unsubstituted $C_3$-$C_8$ cycloalkyl. In embodiments, $R^{4D}$ is independently, unsubstituted 3 to 8 membered heterocycloalkyl. In embodiments, $R^{4D}$ is independently unsubstituted $C_6$-$C_{10}$ aryl. In embodiments, $R^{4D}$ is independently unsubstituted 5 to 10 membered heteroaryl.

In embodiments, $R^{4D}$ is independently substituted or unsubstituted $C_1$-$C_4$ alkyl. In embodiments, $R^{4D}$ is independently substituted or unsubstituted 2 to 4 membered heteroalkyl. In embodiments, $R^{4D}$ is independently substituted or unsubstituted $C_3$-$C_6$ cycloalkyl. In embodiments, $R^{4D}$ is independently, substituted or unsubstituted 3 to 6 membered heterocycloalkyl. In embodiments, $R^{4D}$ is independently substituted or unsubstituted phenyl. In embodiments, $R^{4D}$ is independently substituted or unsubstituted 5 to 6 membered heteroaryl.

In embodiments, $R^{4D}$ is independently substituted $C_1$-$C_4$ alkyl. In embodiments, $R^{4D}$ is independently substituted 2 to 4 membered heteroalkyl. In embodiments, $R^{4D}$ is independently substituted $C_3$-$C_6$ cycloalkyl. In embodiments, $R^{4D}$ is independently, substituted 3 to 6 membered heterocycloalkyl. In embodiments, $R^{4D}$ is independently substituted phenyl. In embodiments, $R^{4D}$ is independently substituted 5 to 6 membered heteroaryl. In embodiments, $R^{4D}$ is independently unsubstituted $C_1$-$C_4$ alkyl. In embodiments, $R^{4D}$ is independently unsubstituted 2 to 4 membered heteroalkyl. In embodiments, $R^{4D}$ is independently unsubstituted $C_3$-$C_6$ cycloalkyl. In embodiments, $R^{4D}$ is independently unsubstituted 3 to 6 membered heterocycloalkyl. In embodiments, $R^{4D}$ is independently unsubstituted phenyl. In embodiments, $R^{4D}$ is independently unsubstituted 5 to 6 membered heteroaryl. In embodiments, $R^{4D}$ is independently unsubstituted methyl. In embodiments, $R^{4D}$ is independently unsubstituted ethyl. In embodiments, $R^{4D}$ is independently unsubstituted propyl. In embodiments, $R^{4D}$ is independently unsubstituted isopropyl. In embodiments, $R^{4D}$ is independently unsubstituted tert-butyl.

In embodiments, $R^4$ is independently halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

In embodiments, $R^4$ is independently halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^4$ is independently halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$-substituted or unsubstituted $C_1$-$C_8$ alkyl, $R^{29}$-substituted or unsubstituted 2 to 8 membered heteroalkyl, $R^{29}$-substituted or unsubstituted $C_3$-$C_8$ cycloalkyl, $R^{29}$-substituted or unsubstituted 3 to 6 membered heterocycloalkyl, $R^{29}$-substituted or unsubstituted phenyl, or $R^{29}$-substituted or unsubstituted 5 to 6 membered heteroaryl. $X^4$ is $-F$, $-Cl$, $-Br$, or $-I$. In embodiments, $R^4$ is independently hydrogen. In embodiments, $R^4$ is independently methyl. In embodiments, $R^4$ is independently ethyl.

In embodiments, $R^{4A1}$ is independently hydrogen, halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^{4A1}$ is independently halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$-substituted or unsubstituted $C_1$-$C_8$ alkyl, $R^{29}$-substituted or unsubstituted 2 to 8 membered heteroalkyl, $R^{29}$-substituted or unsubstituted $C_3$-$C_8$ cycloalkyl, $R^{29}$-substituted or unsubstituted 3 to 6 membered heterocycloalkyl, $R^{29}$-substituted or unsubstituted phenyl, or $R^{29}$-substituted or unsubstituted 5 to 6 membered heteroaryl. In embodiments, $R^{4A1}$ is independently hydrogen. In embodiments, $R^{4A1}$ is independently methyl. In embodiments, $R^{4A1}$ is independently ethyl.

In embodiments, $R^{4B1}$ is independently hydrogen, halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^{4B1}$ is independently halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^4_3$, $-OCHX^4_2$, $R^{29}$—Substituted or unsubstituted $C_1$-$C_8$ alkyl, $R^{29}$-substituted or unsubstituted 2 to 8 membered heteroalkyl, $R^{29}$-substituted or unsubstituted $C_3$-$C_8$ cycloalkyl, $R^{29}$-substituted or unsubstituted 3 to 6 membered heterocycloalkyl, $R^{29}$-substituted or unsubstituted phenyl, or $R^{29}$-substituted or unsubstituted 5 to 6 membered heteroaryl. embodiments, $R^{4B}_1$ is independently hydrogen. In embodiments, $R^{4B1}$ is independently methyl. In embodiments, $R^{4B1}$ is independently ethyl.

In embodiments, $R^4$ and $R^{4A1}$ may optionally be joined to form a $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^4$ and $R^{4A1}$ may optionally be joined to form a $R^{29}$-substituted or unsubstituted $C_3$-$C_8$ cycloalkyl, $R^{29}$-substituted or unsubstituted 3 to 6 membered heterocycloalkyl, $R^{29}$-substituted or unsubstituted phenyl, or $R^{29}$-substituted or unsubstituted 5 to 6 membered heteroaryl.

$R^{29}$ is independently oxo, halogen, $-CX^{29}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{29}_3$, $-OCHX^{29}_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. In embodiments, $R^{29}$ is independently oxo, halogen, $-CX^{29}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{29}_3$, $-OCHX^{29}_2$, $R^{30}$-substituted or unsubstituted $C_1$-$C_8$ alkyl, $R^{30}$-substituted or unsubstituted 2 to 8 membered heteroalkyl, $R^{30}$-substituted or unsubstituted $C_3$-$C_8$ cycloalkyl, $R^{30}$-substituted or unsubstituted 3 to 6 membered heterocycloalkyl, $R^{30}$-substituted or unsubstituted phenyl, or $R^{30}$-substituted or unsubstituted 5 to 6 membered heteroaryl. $X^{29}$ is —F, —Cl, —Br, or —I.

In embodiments, $R^{29}$ is independently oxo. In embodiments, $R^{29}$ is independently halogen. In embodiments, $R^{29}$ is independently —$CH_3$. In embodiments, $R^{29}$ is independently —$CH_2CH_3$. In embodiments, $R^{29}$ is independently —$CH(CH_3)_2$. In embodiments, $R^{29}$ is independently —$OCH_3$. In embodiments, $R^{29}$ is independently —$OCH_2CH_3$. In embodiments, $R^{29}$ is independently —$OCH(CH_3)_2$. In embodiments, $R^{29}$ is independently $R^{30}$-substituted or unsubstituted $C_1$-$C_8$ alkyl. In embodiments, $R^{29}$ is independently $R^{30}$-substituted $C_1$-$C_8$ alkyl. In embodiments, $R^{29}$ is independently unsubstituted $C_1$-$C_8$ alkyl. In embodiments, $R^{29}$ is independently $R^{30}$-substituted or unsubstituted $C_1$-$C_4$ alkyl. In embodiments, $R^{29}$ is independently $R^{30}$-substituted $C_1$-$C_4$ alkyl. In embodiments, $R^{29}$ is independently unsubstituted $C_1$-$C_4$ alkyl.

In embodiments, $R^{29}$ is independently $R^{30}$-substituted or unsubstituted 2 to 8 membered heteroalkyl. In embodiments, $R^{29}$ is independently $R^{30}$-substituted 2 to 8 membered heteroalkyl. In embodiments, $R^{29}$ is independently unsubstituted 2 to 8 membered heteroalkyl. In embodiments, $R^{29}$ is independently $R^{30}$-substituted or unsubstituted 2 to 4 membered heteroalkyl. In embodiments, $R^{29}$ is independently $R^{30}$-substituted 2 to 4 membered heteroalkyl. In embodiments, $R^{29}$ is independently unsubstituted 2 to 4 membered heteroalkyl.

$R^{30}$ is independently oxo, halogen, —$CX^{30}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30}_3$, —$OCHX^{30}_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl. In embodiments, $R^{30}$ is independently oxo, halogen, —$CX^{30}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)$NH_2$, —NHC(O)OH, —NHOH, —$OCX^{30}_3$, —$OCHX^{30}_2$, $R^{31}$-substituted or unsubstituted $C_1$-$C_8$ alkyl, $R^{31}$-substituted or unsubstituted 2 to 8 membered heteroalkyl, $R^{31}$-substituted or unsubstituted $C_3$-$C_8$ cycloalkyl, $R^{31}$-substituted or unsubstituted 3 to 6 membered heterocycloalkyl, $R^{31}$-substituted or unsubstituted phenyl, or $R^{31}$-substituted or unsubstituted 5 to 6 membered heteroaryl. $X^{30}$ is —F, —Cl, —Br, or —I.

In embodiments, $R^{4A}$ is independently hydrogen, —$CX^{4A}_3$, —CN, —COOH, —$CONH_2$, —$CHX^{4A}_2$, —$CH_2X^{4A}$, $R^{29A}$-substituted or unsubstituted alkyl, $R^{29A}$-substituted or unsubstituted heteroalkyl, $R^{29A}$-substituted or unsubstituted cycloalkyl, $R^{29A}$-substituted or unsubstituted heterocycloalkyl, $R^{29A}$-substituted or unsubstituted aryl, or $R^{29A}$-substituted or unsubstituted heteroaryl. In embodiments, $R^{4A}$ is independently hydrogen, —$CX^{4A}_3$, —CN, —COOH, —$CONH_2$, —$CHX^{4A}_2$, —$CH_2X^{4A}$, $R^{29A}$-substituted or unsubstituted $C_1$-$C_8$ alkyl, $R^{29A}$-substituted or unsubstituted 2 to 8 membered heteroalkyl, $R^{29A}$-substituted or unsubstituted $C_3$-$C_8$ cycloalkyl, $R^{29A}$-substituted or unsubstituted 3 to 6 membered heterocycloalkyl, $R^{29A}$-substituted or unsubstituted phenyl, or $R^{29A}$-substituted or unsubstituted 5 to 6 membered heteroaryl. $X^{4A}$ is —F, —Cl, —Br, or —I. In embodiments, $R^{4A}$ is independently hydrogen. In embodiments, $R^{4A}$ is independently methyl. In embodiments, $R^{4A}$ is independently ethyl.

In embodiments, $R^{4A}$ and $R^{4B}$ substituents bonded to the same nitrogen atom may optionally be joined to form a $R^{29A}$-substituted or unsubstituted heterocycloalkyl or $R^{29A}$-substituted or unsubstituted heteroaryl. In embodiments, $R^{4A}$ and $R^{4B}$ substituents bonded to the same nitrogen atom may optionally be joined to form a $R^{29A}$-substituted or unsubstituted 3 to 6 membered heterocycloalkyl or $R^{29A}$-substituted or unsubstituted 5 to 6 membered heteroaryl.

$R^{29A}$ is independently oxo, halogen, —$CX^{29A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29A}_3$, —$OCHX^{29A}_2$, $R^{30A}$-substituted or unsubstituted alkyl, $R^{30A}$-substituted or unsubstituted heteroalkyl, $R^{30A}$-substituted or unsubstituted cycloalkyl, $R^{30A}$-substituted or unsubstituted heterocycloalkyl, $R^{30A}$-substituted or unsubstituted aryl, or $R^{30A}$-substituted or unsubstituted heteroaryl. In embodiments, $R^{29A}$ is independently oxo, halogen, —$CX^{29A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29A}_3$, —$OCHX^{29A}_2$, $R^{30A}$-substituted or unsubstituted $C_1$-$C_8$ alkyl, $R^{30A}$-substituted or unsubstituted 2 to 8 membered heteroalkyl, $R^{30A}$-substituted or unsubstituted $C_3$-$C_8$ cycloalkyl, $R^{30A}$-substituted or unsubstituted 3 to 6 membered heterocycloalkyl, $R^{30A}$-substituted or unsubstituted phenyl, or $R^{30A}$-substituted or unsubstituted 5 to 6 membered heteroaryl. $X^{29A}$ is —F, —Cl, —Br, or —I.

$R^{30A}$ is independently oxo, halogen, —$CX^{30A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30A}_3$, —$OCHX^{30A}_2$, $R^{31A}$-substituted or unsubstituted alkyl, $R^{31A}$-substituted or unsubstituted heteroalkyl, $R^{31A}$-substituted or unsubstituted cycloalkyl, $R^{31A}$-substituted or unsubstituted heterocycloalkyl, $R^{31A}$-substituted or unsubstituted aryl, or $R^{31A}$-substituted or unsubstituted heteroaryl. In embodiments, $R^{30A}$ is independently oxo, halogen, —$CX^{30A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{3A}_3$, —$OCHX^{3A}_2$, $R^{31A}$-substituted or unsubstituted $C_1$-$C_8$ alkyl, $R^{31A}$-substituted or unsubstituted 2 to 8 membered heteroalkyl, $R^{31A}$-substituted or unsubstituted $C_3$-$C_8$ cycloalkyl, $R^{31A}$-substituted or unsubstituted 3 to 6 membered heterocycloalkyl, $R^{31A}$-substituted or unsubstituted phenyl, or $R^{31A}$-substituted or unsubstituted 5 to 6 membered heteroaryl. $X^{30A}$ is —F, —Cl, —Br, or —I.

In embodiments, $R^{4B}$ is independently hydrogen, —$CX^{4B}_3$, —CN, —COOH, —$CONH_2$, —$CHX^{4B}_2$, —$CH_2X^{4B}$, $R^{29B}$-substituted or unsubstituted alkyl, $R^{29B}$-substituted or unsubstituted heteroalkyl, $R^{29B}$-substituted or unsubstituted cycloalkyl, $R^{29B}$-substituted or unsubstituted heterocycloalkyl, $R^{29B}$-substituted or unsubstituted aryl, or $R^{29B}$-substituted or unsubstituted heteroaryl. In embodiments, $R^{4B}$ is independently hydrogen, —$CX^{4B}_3$, —CN, —COOH, —$CONH_2$, —$CHX^{4B}_2$, —$CH_2X^{4B}$, $R^{29B}$-substituted or unsubstituted $C_1$-$C_8$ alkyl, $R^{29B}$-substituted or unsubstituted 2 to 8 membered heteroalkyl, $R^{29B}$-substituted or unsubstituted $C_3$-$C_8$ cycloalkyl, $R^{29B}$-substituted or unsubstituted 3 to 6 membered heterocycloalkyl, $R^{29B}$- substituted or unsubstituted phenyl, or $R^{29B}$-substituted or unsubstituted 5 to 6 membered heteroaryl. $X^{4B}$ is —F, —Cl, —Br, or —I. In embodiments, $R^{4B}$ is independently hydrogen. In embodiments, $R^{4B}$ is independently methyl. In embodiments, $R^{4B}$ is independently ethyl.

In embodiments, $R^{4A}$ and $R^{4B}$ substituents bonded to the same nitrogen atom may optionally be joined to form a $R^{29B}$-substituted or unsubstituted heterocycloalkyl or $R^{29B}$-substituted or unsubstituted heteroaryl. In embodiments, $R^{4A}$ and $R^{4B}$ substituents bonded to the same nitrogen atom may optionally be joined to form a $R^{29B}$-substituted or unsubstituted 3 to 6 membered heterocycloalkyl or $R^{29B}$-substituted or unsubstituted 5 to 6 membered heteroaryl.

$R^{29B}$ is independently oxo, halogen, —$CX^{29B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29B}_3$, —$OCHX^{29B}_2$, $R^{30B}$-substituted or unsubstituted alkyl, $R^{30B}$-substituted or unsubstituted heteroalkyl, $R^{30B}$-substituted or unsubstituted cycloalkyl, $R^{30B}$-substituted or unsubstituted heterocycloalkyl, $R^{30B}$-substituted or unsubstituted aryl, or $R^{30B}$-substituted or unsubstituted heteroaryl. In embodiments, $R^{29B}$ is independently oxo, halogen, —$CX^{29B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29B}_3$, —$OCHX^{29B}_2$, $R^{30B}$-substituted or unsubstituted $C_1$-$C_8$ alkyl, $R^{30B}$-substituted or unsubstituted 2 to 8 membered heteroalkyl, $R^{30B}$-substituted or unsubstituted $C_3$-$C_8$ cycloalkyl, $R^{30B}$-substituted or unsubstituted 3 to 6 membered heterocycloalkyl, $R^{30B}$-substituted or unsubstituted phenyl, or $R^{30B}$-substituted or unsubstituted 5 to 6 membered heteroaryl. $X^{29B}$ is —F, —Cl, —Br, or —I.

$R^{30B}$ is independently oxo, halogen, —$CX^{30B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30B}_3$, —$OCHX^{30B}_2$, $R^{31B}$-substituted or unsubstituted alkyl, $R^{31B}$-substituted or unsubstituted heteroalkyl, $R^{31B}$-substituted or unsubstituted cycloalkyl, $R^{31B}$-substituted or unsubstituted heterocycloalkyl, $R^{31B}$-substituted or unsubstituted aryl, or $R^{31B}$-substituted or unsubstituted heteroaryl. In embodiments, $R^{30B}$ is independently oxo, halogen, —$CX^{30B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30B}_3$, —$OCHX^{30B}_2$, $R^{31B}$-substituted or unsubstituted $C_1$-$C_8$ alkyl, $R^{31B}$-substituted or unsubstituted 2 to 8 membered heteroalkyl, $R^{31B}$-substituted or unsubstituted $C_3$-$C_8$ cycloalkyl, $R^{31B}$-substituted or unsubstituted 3 to 6 membered heterocycloalkyl, $R^{31B}$-substituted or unsubstituted phenyl, or $R^{31B}$-substituted or unsubstituted 5 to 6 membered heteroaryl. $X^{30B}$ is —F, —Cl, —Br, or —I.

In embodiments, $R^{4C}$ is independently hydrogen, —$CX^{4C}_3$, —CN, —COOH, —$CONH_2$, —$CHX^{4C}_2$, —$CH_2X^{4C}$, $R^{29C}$-substituted or unsubstituted alkyl, $R^{29C}$-substituted or unsubstituted heteroalkyl, $R^{29C}$-substituted or unsubstituted cycloalkyl, $R^{29C}$-substituted or unsubstituted heterocycloalkyl, $R^{29C}$-substituted or unsubstituted aryl, or $R^{29C}$-substituted or unsubstituted heteroaryl. In embodiments, $R^{4C}$ is independently hydrogen, —$CX^{4C}_3$, —CN, —COOH, —$CONH_2$, —$CHX^{4C}_2$, —$CH_2X^{4C}$, $R^{29C}$-substituted or unsubstituted $C_1$-$C_8$ alkyl, $R^{29C}$-substituted or unsubstituted 2 to 8 membered heteroalkyl, $R^{29C}$-substituted or unsubstituted $C_3$-$C_8$ cycloalkyl, $R^{29C}$-substituted or unsubstituted 3 to 6 membered heterocycloalkyl, $R^{29C}$-substituted or unsubstituted phenyl, or $R^{29C}$-substituted or unsubstituted 5 to 6 membered heteroaryl. $X^{4C}$ is —F, —Cl, —Br, or —I. In embodiments, $R^{4C}$ is independently hydrogen. In embodiments, $R^{4C}$ is independently methyl. In embodiments, $R^{4C}$ is independently ethyl.

$R^{29C}$ is independently oxo, halogen, —$CX^{29C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29C}_3$, —$OCHX^{29C}_2$, $R^{30C}$-substituted or unsubstituted alkyl, $R^{30C}$-substituted or unsubstituted heteroalkyl, $R^{30C}$-substituted or unsubstituted cycloalkyl, $R^{30C}$-substituted or unsubstituted heterocycloalkyl, $R^{30C}$-substituted or unsubstituted aryl, or $R^{30C}$-substituted or unsubstituted heteroaryl. In embodiments, $R^{29C}$ is independently oxo, halogen, —$CX^{29C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29C}_3$, —$OCHX^{29C}_2$, $R^{30C}$-substituted or unsubstituted $C_1$-$C_8$ alkyl, $R^{30C}$-substituted or unsubstituted 2 to 8 membered heteroalkyl, $R^{30C}$-substituted or unsubstituted $C_3$-$C_8$ cycloalkyl, $R^{30C}$-substituted or unsubstituted 3 to 6 membered heterocycloalkyl, $R^{30C}$-substituted or unsubstituted phenyl, or $R^{30C}$-substituted or unsubstituted 5 to 6 membered heteroaryl. $X^{29C}$ is —F, —Cl, —Br, or —I.

$R^{30C}$ is independently oxo, halogen, —$CX^{30C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30C}_3$, —$OCHX^{30C}_2$, $R^{31C}$-substituted or unsubstituted alkyl, $R^{31C}$-substituted or unsubstituted heteroalkyl, $R^{31C}$-substituted or unsubstituted cycloalkyl, $R^{31C}$-substituted or unsubstituted heterocycloalkyl, $R^{31C}$-substituted or unsubstituted aryl, or $R^{31C}$-substituted or unsubstituted heteroaryl. In embodiments, $R^{30C}$ is independently oxo, halogen, —$CX^{30C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30C}_3$, —$OCHX^{30C}_2$, $R^{31C}$-substituted or unsubstituted $C_1$-$C_8$ alkyl, $R^{31C}$-substituted or unsubstituted 2 to 8 membered heteroalkyl, $R^{31C}$-substituted or unsubstituted $C_3$-$C_8$ cycloalkyl, $R^{31C}$-substituted or unsubstituted 3 to 6 membered heterocycloalkyl, $R^{31C}$-substituted or unsubstituted phenyl, or $R^{31C}$-substituted or unsubstituted 5 to 6 membered heteroaryl. $X^{30C}$ is —F, —Cl, —Br, or —I.

In embodiments, $R^{4D}$ is independently hydrogen, —$CX^{4D}_3$, —CN, —COOH, —$CONH_2$, —$CHX^{4D}_2$, —$CH_2X^{4D}$, $R^{29D}$-substituted or unsubstituted alkyl, $R^{29D}$-substituted or unsubstituted heteroalkyl, $R^{29D}$-substituted or unsubstituted cycloalkyl, $R^{29D}$-substituted or unsubstituted heterocycloalkyl, $R^{29D}$-substituted or unsubstituted aryl, or $R^{29D}$-substituted or unsubstituted heteroaryl. In embodiments, $R^{4D}$ is independently hydrogen, —$CX^{4D}_3$, —CN, —COOH, —$CONH_2$, —$CHX^{4D}_2$, —$CH_2X^{4D}$, $R^{29D}$-substituted or unsubstituted $C_1$-$C_8$ alkyl, $R^{29D}$-substituted or unsubstituted 2 to 8 membered heteroalkyl, $R^{29D}$-substituted or unsubstituted $C_3$-$C_8$ cycloalkyl, $R^{29D}$-substituted or unsubstituted 3 to 6 membered heterocycloalkyl, $R^{29D}$-substituted or unsubstituted phenyl, or $R^{29D}$-substituted or unsubstituted 5 to 6 membered heteroaryl. $X^{4D}$ is —F, —Cl, —Br, or —I. In embodiments, $R^{4D}$ is independently hydrogen. In embodiments, $R^{4D}$ is independently methyl. In embodiments, $R^{4D}$ is independently ethyl.

$R^{29D}$ is independently oxo, halogen, —$CX^{29D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29D}_3$, —$OCHX^{29D}_2$, $R^{30D}$-substituted or unsubstituted alkyl, $R^{30D}$-substituted or unsubstituted heteroalkyl, $R^{30D}$-substituted or unsubstituted cycloalkyl, $R^{30D}$-substituted or unsubstituted heterocycloalkyl, $R^{30D}$-substituted or unsubstituted aryl, or $R^{30D}$-substituted or unsubstituted heteroaryl. In embodiments, $R^{29D}$ is independently oxo, halogen, —$CX^{29D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{29D}_3$, —$OCHX^{29D}_2$, $R^{30D}$-substituted or unsubstituted $C_1$-$C_8$ alkyl, $R^{30D}$-substituted or unsubstituted 2 to 8 membered heteroalkyl, $R^{30D}$-substituted or unsubstituted $C_3$-$C_8$ cycloalkyl, $R^{30D}$-substituted or unsubstituted 3 to 6 membered heterocycloalkyl, $R^{30D}$-substituted or unsubstituted phenyl, or $R^{30D}$-substituted or unsubstituted 5 to 6 membered heteroaryl. $X^{29D}$ is —F, —Cl, —Br, or —I.

$R^{30D}$ is independently oxo, halogen, —$CX^{30D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30D}_3$, —$OCHX^{30D}_2$, $R^{31D}$-substituted or unsubstituted alkyl, $R^{31D}$-substituted or unsubstituted heteroalkyl, $R^{31D}$-substituted or unsubstituted cycloalkyl, $R^{31D}$-substituted or unsubstituted heterocycloalkyl, $R^{31D}$-substituted or unsubstituted aryl, or $R^{31D}$-substituted or unsubstituted heteroaryl. In embodiments, $R^{30D}$ is independently oxo, halogen, —$CX^{30D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{30D}_3$, —$OCHX^{30D}_2$, $R^{31D}$-substituted or unsubstituted $C_1$-$C_8$ alkyl, $R^{31D}$-substituted or unsubstituted 2 to 8 membered heteroalkyl, $R^{31D}$-substituted or unsubstituted $C_3$-$C_8$ cycloalkyl, $R^{31D}$-substituted or unsubstituted 3 to 6 membered heterocycloalkyl, $R^{31D}$-substituted or unsubstituted phenyl, or $R^{31D}$-substituted or unsubstituted 5 to 6 membered heteroaryl. $X^{30D}$ is —F, —Cl, —Br, or —I.

$R^{31}$, $R^{31A}$, $R^{31B}$, $R^{31C}$, and $R^{31D}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{31}$, $R^{31A}$, $R^{31B}$, $R^{31C}$, and $R^{31D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{31}$, $R^{31A}$, $R^{31B}$, $R^{31C}$, and $R^{31D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $R^4$ is independently halogen. In embodiments, $R^4$ is independently hydrogen. In embodiments, $R^4$ is independently hydrogen or halogen. In embodiments, $R^4$ is independently methyl. In embodiments, $R^4$ is independently $C_1$-$C_4$ alkyl. In embodiments, $R^4$ is independently halogen or $C_1$-$C_4$ alkyl. In embodiments, $R^4$ is independently halogen or $C_1$-$C_3$ alkyl. In embodiments, $R^4$ is independently halogen or $C_1$-$C_2$ alkyl. In embodiments, $R^4$ is independently halogen or methyl. In embodiments, $R^4$ is independently substituted or unsubstituted methyl. In embodiments, $R^4$ is independently substituted or unsubstituted $C_1$-$C_4$ alkyl. In embodiments, $R^4$ is independently halogen or substituted or unsubstituted $C_1$-$C_4$ alkyl. In embodiments, $R^4$ is independently halogen or substituted or unsubstituted $C_1$-$C_3$ alkyl. In embodiments, $R^4$ is independently halogen or substituted or unsubstituted $C_1$-$C_2$ alkyl. In embodiments, $R^4$ is independently halogen or substituted or unsubstituted methyl. In embodiments, $R^4$ is independently substituted methyl. In embodiments, $R^4$ is independently substituted $C_1$-$C_4$ alkyl. In embodiments, $R^4$ is independently halogen or substituted $C_1$-$C_4$ alkyl. In embodiments, $R^4$ is independently halogen or substituted $C_1$-$C_3$ alkyl. In embodiments, $R^4$ is independently halogen or substituted $C_1$-$C_2$ alkyl. In embodiments, $R^4$ is independently halogen or substituted methyl. In embodiments, $R^4$ is independently unsubstituted methyl. In embodiments, $R^4$ is independently unsubstituted $C_1$-$C_4$ alkyl. In embodiments, $R^4$ is independently halogen or unsubstituted $C_1$-$C_4$ alkyl. In embodiments, $R^4$ is independently halogen or unsubstituted $C_1$-$C_3$ alkyl. In embodiments, $R^4$ is independently halogen or unsubstituted $C_1$-$C_2$ alkyl. In embodiments, $R^4$ is independently halogen or unsubstituted methyl.

In embodiments, $R^4$ is independently $C_1$-$C_4$ alkyl. In embodiments, $R^4$ is independently $C_1$-$C_3$ alkyl. In embodiments, $R^4$ is independently $C_1$-$C_2$ alkyl. In embodiments, $R^4$ is independently methyl. In embodiments, $R^4$ is independently ispropyl. In embodiments, $R^4$ is independently substituted or unsubstituted methyl or substituted or unsubstituted isopropyl.

In embodiments, $R^{4A1}$ is independently halogen. In embodiments, $R^{4A1}$ is independently hydrogen. In embodiments, $R^{4A1}$ is independently hydrogen or halogen. In embodiments, $R^{4A1}$ is independently methyl. In embodiments, $R^{4A1}$ is independently $C_1$-$C_4$ alkyl. In embodiments, $R^{4A1}$ is independently halogen or $C_1$-$C_4$ alkyl. In embodiments, $R^{4A1}$ is independently halogen or $C_1$-$C_3$ alkyl. In embodiments, $R^{4A1}$ is independently halogen or $C_1$-$C_2$ alkyl. In embodiments, $R^{4A1}$ is independently halogen or methyl. In embodiments, $R^{4A1}$ is independently substituted or unsubstituted methyl. In embodiments, $R^{4A1}$ is independently substituted or unsubstituted $C_1$-$C_4$ alkyl. In embodiments, $R^{4A1}$ is independently halogen or substituted or unsubstituted $C_1$-$C_4$ alkyl. In embodiments, $R^{4A1}$ is independently halogen or substituted or unsubstituted $C_1$-$C_3$ alkyl. In embodiments, $R^{4A1}$ is independently halogen or substituted or unsubstituted $C_1$-$C_2$ alkyl. In embodiments, $R^{4A1}$ is independently halogen or substituted or unsubstituted methyl. In embodiments, $R^{4A1}$ is independently substituted methyl. In embodiments, $R^{4A1}$ is independently substituted $C_1$-$C_4$ alkyl. In embodiments, $R^{4A1}$ is independently halogen or substituted $C_1$-$C_4$ alkyl. In embodiments, $R^{4A1}$ is independently halogen or substituted $C_1$-$C_3$ alkyl. In embodiments, $R^{4A1}$ is independently halogen or substituted $C_1$-$C_2$ alkyl. In embodiments, $R^{4A1}$ is independently halogen or substituted methyl. In embodiments, $R^{4A1}$ is independently unsubstituted methyl. In embodiments, $R^{4A1}$ is independently unsubstituted $C_1$-$C_4$ alkyl. In embodiments, $R^{4A1}$ is independently halogen or unsubstituted $C_1$-$C_4$ alkyl. In embodiments, $R^{4A1}$ is independently halogen or unsubstituted $C_1$-$C_3$ alkyl. In embodiments, $R^{4A1}$ is independently halogen or unsubstituted $C_1$-$C_2$ alkyl. In embodiments, $R^{4A1}$ is independently halogen or unsubstituted methyl.

In embodiments, $R^{4A1}$ is independently $C_1$-$C_4$ alkyl. In embodiments, $R^{4A1}$ is independently $C_1$-$C_3$ alkyl. In embodiments, $R^{4A1}$ is independently $C_1$-$C_2$ alkyl. In embodiments, $R^{4A1}$ is independently methyl. In embodiments, $R^{4A1}$ is independently ispropyl. In embodiments, $R^{4A1}$ is independently substituted or unsubstituted methyl or substituted or unsubstituted isopropyl.

In embodiments, $R^{4B1}$ is independently halogen. In embodiments, $R^{4B1}$ is independently hydrogen. In embodiments, $R^{4B1}$ is independently hydrogen or halogen. In embodiments, $R^{4B1}$ is independently methyl. In embodiments, $R^{4B1}$ is independently $C_1$-$C_4$ alkyl. In embodiments, $R^{4B1}$ is independently halogen or $C_1$-$C_4$ alkyl. In embodiments, $R^{4B1}$ is independently halogen or $C_1$-$C_3$ alkyl. In embodiments, $R^{4B1}$ is independently halogen or $C_1$-$C_2$ alkyl. In embodiments, $R^{4B1}$ is independently halogen or methyl. In embodiments, $R^{4B1}$ is independently substituted or unsubstituted methyl. In embodiments, $R^{4B1}$ is independently substituted or unsubstituted $C_1$-$C_4$ alkyl. In embodiments, $R^{4B1}$ is independently halogen or substituted or unsubstituted $C_1$-$C_4$ alkyl. In embodiments, $R^{4B1}$ is independently halogen or substituted or unsubstituted $C_1$-$C_3$ alkyl. In embodiments, $R^{4B1}$ is independently halogen or substituted or unsubstituted $C_1$-$C_2$ alkyl. In embodiments, $R^{4B1}$ is independently halogen or substituted or unsubstituted methyl. In embodiments, $R^{4B1}$ is independently substituted methyl. In embodiments, $R^{4B1}$ is independently substituted $C_1$-$C_4$ alkyl. In embodiments, $R^{4B1}$ is independently halogen or substituted $C_1$-$C_4$ alkyl. In embodiments, $R^{4B1}$ is independently halogen or substituted $C_1$-$C_3$ alkyl. In embodiments, $R^{4B1}$ is independently halogen or substituted $C_1$-$C_2$ alkyl. In embodiments, $R^{4B1}$ is independently halogen or substituted methyl. In embodiments, $R^{4B1}$ is independently unsubstituted methyl. In embodiments, $R^{4B1}$ is independently unsubstituted $C_1$-$C_4$ alkyl. In embodiments, $R^{4B1}$ is independently halogen or unsubstituted $C_1$-$C_4$ alkyl. In embodiments, $R^{4B1}$ is independently halogen or unsubstituted $C_1$-$C_3$ alkyl. In embodiments, $R^{4B1}$ is independently halogen or unsubstituted $C_1$-$C_2$ alkyl. In embodiments, $R^{4B1}$ is independently halogen or unsubstituted methyl.

In embodiments, $R^{4B1}$ is independently $C_1$-$C_4$ alkyl. In embodiments, $R^{4B1}$ is independently $C_1$-$C_3$ alkyl. In embodiments, $R^{4B1}$ is independently $C_1$-$C_2$ alkyl. In embodiments, $R^{4B1}$ is independently methyl. In embodiments, $R^{4B1}$ is independently ispropyl. In embodiments, $R^{4B1}$ is independently substituted or unsubstituted methyl or substituted or unsubstituted isopropyl.

In embodiments, X is —F. In embodiments, X is —Cl. In embodiments, X is —Br. In embodiments, X is —I. In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I. In embodiments, $X^4$ is —F. In embodiments, $X^4$ is —Cl. In embodiments, $X^4$ is —Br. In embodiments, $X^4$ is —I.

In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n4 is 0. In embodiments, n4 is 1. In embodiments, n4 is 2. In embodiments, n4 is 3. In embodiments, n4 is 4. In embodiments, m1 is 1. In embodiments, m1 is 2. In embodiments, m2 is 1. In embodiments, m2 is 2. In embodiments, m3 is 1. In embodiments, m3 is 2. In embodiments, m4 is 1. In embodiments, m4 is 2. In embodiments, v1 is 1. In embodiments, v1 is 2. In embodiments, v2 is 1. In embodiments, v2 is 2. In embodiments, v3 is 1. In embodiments, v3 is 2. In embodiments, v4 is 1. In embodiments, v4 is 2. In embodiments, z20 is 0. In embodiments, z20 is 1. In embodiments, z20 is 2. In embodiments, z20 is 3. In embodiments, z20 is 4. In embodiments, z20 is 5. In embodiments, z20 is 6. In embodiments, z20 is 7. In embodiments, z20 is 8. In embodiments, z20 is 9. In embodiments, z20 is 10. In embodiments, z20 is an integer from 0 to 2.

In embodiments, the compound is a compound described herein (e.g., in an aspect, embodiment, claim, figure, example, table, or scheme).

In embodiments, the compound is

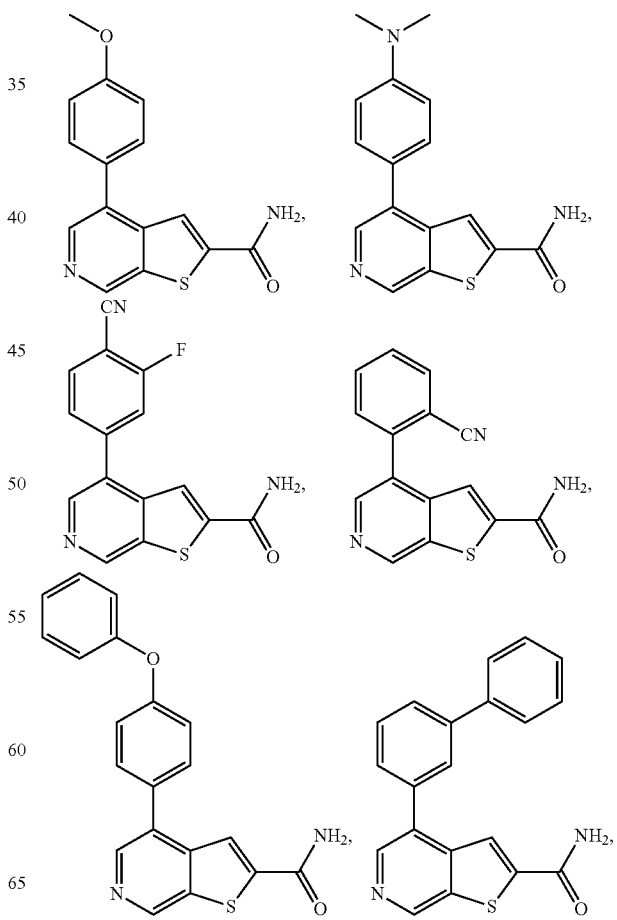

-continued

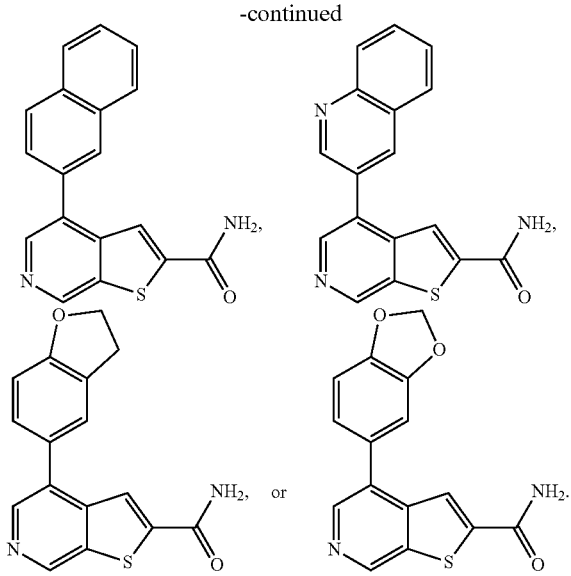

III. Pharmaceutical Compositions

In an aspect is provided a pharmaceutical composition including a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB) or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the second agent is an anti-inflammatory agent. In embodiments, the second agent is an anti-autoimmune disease agent. In embodiments, the second agent is an anti-infectious disease agent. In embodiments, the second agent is an anti-viral agent. In embodiments, the second agent is an anti-HIV agent. In embodiments, the anti-viral agent is an HIV reverse transcriptase inhibitor, HIV protease inhibitor, HIV integrase inhibitor, HIV fusion inhibitor, or HIV entry inhibitor. In embodiments, the second agent is abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat. In embodiments, the second agent is a combination of two or more anti-HIV agents (e.g., a combination of two or more of abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat). In embodiments, the pharmaceutical composition includes a second and third agent (e.g. therapeutic agents). In embodiments, the pharmaceutical composition includes a second, third, and fourth agent (e.g. therapeutic agents). In embodiments, the pharmaceutical composition includes a second, third, fourth, and fifth agent (e.g. therapeutic agents). In embodiments, the pharmaceutical composition includes a second, third, fourth, fifth, and sixth agent (e.g. therapeutic agents).

IV. Methods of Treatment

In an aspect is provided a method of treating HIV infection, the method including administering to a subject in need thereof an effective amount of a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method includes a decrease of the severity or frequency of the symptoms of an HIV infection, or elimination of the symptoms of an HIV infection.

In an aspect is provided a method of treating a disease associated with HIV Rev activity including administering to a subject in need thereof an effective amount of a compound (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB) described herein. In embodiments, the disease is associated with aberrant HIV Rev activity.

In embodiments, the method includes administering a second agent (e.g. therapeutic agent). In embodiments, the method includes administering a second agent (e.g. therapeutic agent) in a therapeutically effective amount. In embodiments, the second agent is an anti-inflammatory agent. In embodiments, the second agent is an anti-autoimmune disease agent. In embodiments, the second agent is an anti-infectious disease agent. In embodiments, the second agent is an anti-viral agent. In embodiments, the second agent is an anti-HIV agent. In embodiments, the anti-viral agent is an HIV reverse transcriptase inhibitor, HIV protease inhibitor, HIV integrase inhibitor, HIV fusion inhibitor, or HIV entry inhibitor. In embodiments, the second agent is abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat. In embodiments, the second agent is a combination of two or more anti-HIV agents (e.g., a combination of two or more of abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat). In embodiments, the method includes administering a second and third agent (e.g. therapeutic agents). In embodiments, the method includes administering a second, third, and fourth agent (e.g. therapeutic agents). In embodiments, the method includes administering a second, third, fourth, and fifth agent (e.g. therapeutic agents). In embodiments, the method includes administering a second, third, fourth, fifth, and sixth agent (e.g. therapeutic agents).

V. Methods of Inhibition

In an aspect is provided a method of inhibiting the level of Rev protein activity in a cell, the method including: contacting the Rev protein with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting HIV virion formation in an HIV infected cell, the method including: contacting the HIV infected cell with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method includes reducing the level of HIV Vpu protein relative to a control (e.g., absence of the compound).

In an aspect is provided a method of inhibiting HIV viral shedding from an HIV infected cell, the method including: contacting the HIV infected cell with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting HIV proliferation, the method including: contacting HIV with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting HIV proliferation, the method including: contacting an HIV infected cell with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting translation of HIV late proteins (e.g., from transcripts gag, pol, or env) the method including: contacting a Rev protein with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting Rev protein multimerization, the method including: contacting the Rev protein with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting Rev protein-RRE interaction, the method including: contacting the Rev protein with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting Rev protein-RRE interaction, the method including: contacting the RRE with a compound described herein (e.g., at stem loop 2).

In an aspect is provided a method of inhibiting Rev protein translocation between the nucleus and cytoplasm, the method including: contacting the Rev protein with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting Rev protein-CRM1 interaction, the method including: contacting the Rev protein with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting Rev protein-CRM1 interaction, the method including: contacting the CRM1 protein with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In an aspect is provided a method of inhibiting Rev protein-CRM1 interaction, the method including: contacting the Rev protein-CRM1 complex with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB).

In embodiments, the method of inhibiting includes preventing the formation of the Rev protein-CRM1 complex. In embodiments, the method of inhibiting includes reducing the activity of the Rev protein-CRM1 complex.

In an aspect is provided a method of inhibiting HIV virion release from a cell, the method including: contacting the cell with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method includes reducing the level of Rev activity in the cell. In embodiments, the method includes reducing the level of HIV Vpu activity in the cell. In embodiments, the method includes increasing the level of HIV env protein bound to CD4 protein in the cell.

In an aspect is provided a method of inhibiting the level of HIV Vpu activity in a cell, the method including: contacting the cell with a compound as described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method includes reducing the level of transcription of the HIV Vpu gene. In embodiments, the method includes induction of mutations in the HIV Vpu gene. In embodiments, the method includes deletion of at least a portion of the HIV Vpu gene from the HIV genome. In embodiments, the method includes inhibiting HIV virion release from a cell. In embodiments, the method includes easing the level of CD4 protein in an HIV infected cell.

In an aspect is provided a method of increasing the level of CD4 protein in an HIV infected cell, the method including: contacting the cell with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method includes reducing the level of HIV Vpu activity in the cell.

In embodiments, the method includes administering a second agent (e.g. therapeutic agent). In embodiments, the method includes administering a second agent (e.g. therapeutic agent) in a therapeutically effective amount. In embodiments, the second agent is an anti-inflammatory agent. In embodiments, the second agent is an anti-autoimmune disease agent. In embodiments, the second agent is an anti-infectious disease agent. In embodiments, the second agent is an anti-viral agent. In embodiments, the second agent is an anti-HIV agent. In embodiments, the anti-viral agent is an HIV reverse transcriptase inhibitor, HIV protease inhibitor, HIV integrase inhibitor, HIV fusion inhibitor, or HIV entry inhibitor. In embodiments, the second agent is abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat. In embodiments, the second agent is a combination of two or more anti-HIV agents (e.g., a combination of two or more of abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat). In embodiments, the method includes administering a second and third agent (e.g. therapeutic agents). In embodiments, the method includes administering a second, third, and fourth agent (e.g. therapeutic agents). In embodiments, the method includes administering a second, third, fourth, and fifth agent (e.g. therapeutic agents). In embodiments, the method includes administering a second, third, fourth, fifth, and sixth agent (e.g. therapeutic agents).

In an aspect is provided a method of modulating an human immunodeficiency virus (HIV) Vpu gene, the method including: contacting the human immunodeficiency virus with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method deletes the HIV Vpu gene. In embodiments, the method partially deletes the HIV Vpu gene. In embodiments, the method modulates the HIV Vpu gene.

In an aspect is provided a method of generating an attenuated human immunodeficiency virus, the method including: contacting the human immunodeficiency virus with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, an attenuated human immunodeficiency virus is Vpu deficient. In embodiments, the method induces a mutation of the HIV Vpu gene. In embodiments, the method induces a modulation of the transcription of the HIV Vpu gene relative to a control (e.g., transcription of the HIV Vpu gene in the absence of the method). In embodiments, the method reduces the transcription of the HIV Vpu gene relative to a control (e.g., transcription of the HIV Vpu gene in the absence of the method).

In an aspect is provided a method of generating a defective human immunodeficiency virus, the method including: contacting the human immunodeficiency virus with a compound described herein. In embodiments, the defective human immunodeficiency virus replicates to generate additional defective human immunodeficiency viruses.

In an aspect is provided a method of modulating an human immunodeficiency virus (HIV) Vpu gene, the method including: contacting a cell infected with a human immunodeficiency virus with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method induces a mutation of the HIV Vpu gene. In embodiments, the method induces a modulation of the transcription of the HIV Vpu gene relative to a control (e.g., transcription of the HIV Vpu gene in the absence of the method). In embodiments, the method reduces the transcription of the HIV Vpu gene relative to a control (e.g., transcription of the HIV Vpu gene in the absence of the method).

In an aspect is provided a method of generating an attenuated human immunodeficiency virus, the method including: contacting a cell infected with a human immunodeficiency virus with a compound described herein. In embodiments, the method includes transcribing the nucleic acids of the cell infected with a human immunodeficiency virus. In embodiments, the nucleic acids include the HIV Vpu gene. In embodiments, the nucleic acids include a mutated HIV Vpu gene. In embodiments, the nucleic acids do not include the HIV Vpu gene.

In an aspect is provided a method of generating a defective human immunodeficiency virus, the method including: contacting a cell infected with a human immunodeficiency virus with a compound described herein (e.g., a compound having the formula of Formula I, IIA, IIB, IC, IID, IIE, IIF, IIG, IIH, IIIA, IIIB, IIC, IIID, IIIE, IIIF, IIIG, IIIH, IVA, IVB, IC, IVD, IVE, IVF, IVG, IVH, VA, VB, IC, VD, VE, VF, VG, VH, VI, VIA, VIB, VII, VIIA, VIIB, VIII, VIIIA, VIIIB, IX, IXA, or IXB). In embodiments, the method includes transcribing the nucleic acids of the cell infected with a human immunodeficiency virus. In embodiments, the nucleic acids include the HIV Vpu gene. In embodiments, the nucleic acids include a mutated HIV Vpu gene. In embodiments, the nucleic acids do not include the HIV Vpu gene.

VI. Examples

Viral regulatory complexes perform critical functions and are important targets for therapeutic intervention. In HIV, the Tat and Rev proteins form regulatory complexes with multiple viral and cellular factors to direct transcription and export of the viral RNA. Rev is a 116 amino acid RNA binding protein that is expressed early in the life cycle of the virus. Rev binds the Rev Response Element (RRE), a highly structured 270 nt RNA element encoded within the env gene. Current models suggest that six Rev molecules bind the RNA in order to properly position two of the nuclear export sequences on Rev for binding to a dimer of the Crm1-RanGTP export complex. This complex is then exported through the nuclear pore and the complex disassembles allowing for translation of the late HIV proteins and packaging of the viral genome. Disrupting the Rev-RRE interaction prevents the expression of late viral proteins and the packaging of viral RNA, thus inhibiting virus replication.

The formation of the export complex is driven by several critical intermolecular interactions. Rev binds the RNA primarily through the arginine rich motif (ARM), an alpha helical domain that forms several important hydrogen bonds with RNA. Flanking the ARM of Rev are oligomerization domains that drive the formation of a stable Rev dimer. Rev dimers in turn form higher order structures through multimerization domains that are located opposite of the oligomerization domain. Identifying compounds which may provide interference with any of these interactions thus preventing the formation of a competent export complex is a challenge.

Because Viral regulatory complexes are difficult to recapitulate in vitro, the applicants developed a cell-based assay to optimize the assembly and presentation of viral complexes for drug screening. Using this method, a small molecule library was screened and multiple hits were identified that inhibit the activity of the viral complexes. A subsequent chemistry effort was focused on a thieno[2,3-b] pyridine scaffold, examples of which inhibited HIV replication and emergence from viral latency. Highlights of the SAR effort include migration to the regioisomeric thieno[2,3-c]pyridine ring system and the regioidentification of analogs with single-digit nM activity in both reporter and HIV infectivity assays, an improvement of ≥100-fold in potency over the original hits. These results validate the screening strategy employed and reveal a promising lead series for the development of a new class of HIV therapeutics.

The NMR structures of the Rev peptide complexed to RRE IIB or to an RNA aptamer (Baba, M. et al (1988) Proc Natl Acad Sci USA 85, 6132-6136; Battiste, J. L., et al. (1996) Science 273, 1547-1551; Ye, X., et al. (1996) Nat. Struct. Biol. 3, 1026-1033) show the α-helix bound in the widened IIB RNA major groove with arginine and asparagine side chains involved in base-specific recognition. A crystal structure of Rev-RRE shows a glutamine at position 51 in Rev that interacts with its counterpart to form the interface of the Rev dimer (Jayaraman, B., et al. (2014) Elife 3, e04120). We sought to develop a high-throughput assay to identify small molecule inhibitors of this interaction. We further hypothesized that small molecules containing a carboxamide moiety might compete for Rev-Rev dimerization or Rev binding to the RRE RNA.

The Tat-hybrid assay platform is used for characterizing RNA-protein or RNA-peptide interactions in mammalian cells (Tan, R., and Frankel, A. D. (1998) Proc. Natl. Acad. Sci. USA 95, 4247-4252; Landt, S. G., et al. (2000) Meth. Enzy. 318, 350-363). The system takes advantage of the function of the HIV transactivator Tat, which binds to the TAR RNA hairpin located at the 5' end of the viral transcripts (Rosen, C. A., et al. (1985) Cell 41, 813-823; Roy, S., et al. (1990) Genes Dev. 4, 1365-1373) and enhances processivity of RNA polymerase II transcription complexes initiated at the HIV LTR (Kao, S. Y., et al. (1987) Nature 330, 489-493; Feinberg, M. B., et al. (1991) Proc. Natl. Acad. Sci. USA 88, 4045-4049; Marciniak, R. A., and Sharp, P. A. (1991) EMBO J 10, 4189-4196). The Tat activation domain can be used to activate reporter expression via heterologous RNA-protein interactions (Southgate, et al. (1990) Nature 345, 640-642; Selby, M. J., and Peterlin, B. M. (1990) Cell 62, 769-776). Reporter activity is proportional to RNA-binding affinity and thus the assay has been used extensively to characterize RNA-protein interactions, including HIV Tat-TAR, bovine immunodeficiency virus (BIV) Tat-TAR, and HIV Rev-RRE among others (Tan, R., and Frankel, A. D. (1998) Proc. Natl. Acad. Sci. USA 95, 4247-4252; Calnan, B. J., et al. (1991) Science 252, 1167-1171; Chen, L., and Frankel, A. D. (1994) Biochemistry 33, 2708-2715; Chen, L., and Frankel, A. D. (1995). Proc. Natl. Acad. Sci. USA 92, 5077-5081; Tan, R., and Frankel, A. D. (1994). Biochemistry 33, 14579-14585; Smith, C. A., et al. (2000). Molec. Cell 6, 1067-1076; Peled-Zehavi, H., et al. (2001) Mol Cell Biol 21, 5232-5241; Nakamura, R. L., et al. (2012) PLoS One 7, e48194).

The applicants employed the Tat-hybrid platform to develop a Rev-RRE reporter assay and used this to screen ~4500 carboxamide-containing small molecules selected from a larger diversity library. Herein we describe the discovery and structure-activity studies of a thienopyridine inhibitor scaffold in which an unsubstituted carboxamide function was found to be important for activity. Optimized thienopyridine analogs exhibited low nM potencies in multiple reporter-based assays as well as in an HIV replication assay.

1. Assays

Small Molecule Screen. RNA reporter plasmids were constructed using the pHIV LTR vector (Landt, S. G., et al. (2000). Meth. Enzy. 318, 350-363). To express HIV Tat fusion proteins, a mammalian codon-optimized pcDNA-Tat vector with a fusion to HIV Rev (residues 3-70) was generated. A HeLa cell line expressing the pcDNA3 HIV-1 LTR-RREIIB-FFL reporter was generated to obtain a consistent background for library screens. The plasmid was tranfected into HeLa cells and stable integrants were selected using neomycin (G418) (800 µg/ml) for 10 days. Resistant cells were transfected with the pcDNA3 Tat-Rev3-70 plasmid harboring a hygromycin resistance marker. Individual clonal cell lines were assayed for luciferase signal and diaminoacridine, a nonspecific small molecule inhibitor of the reporter, was used to identify cell lines with high signal-to-noise. A Z' value of 0.95 was obtained for the cell line used for the small molecule screen.

A library of approximately 4500 carboxamide-containing compounds was assembled and tested in the reporter cell line at 30 µM. Reporter cells were plated in a white 96-well plate and compounds were added to the cells using a Biomek FX robotic liquid handler (Beckman Coulter). The cells were incubated with the compound for 48 hours then assayed for luciferase activity (Promega Bright Glo). The cytotoxicity of each compound was determined in parallel via MTT-based cell viability assays.

The test compounds that displayed activity were reconfirmed in duplicate or triplicate at multiple concentrations using the Tat-hybrid reporter cell lines or by transient transfection. Previously characterized thienopyridines and 3,6 diaminoacridine (DeJong et al, Biochemistry 42: 8035-8046 (2003)) were used as controls. Cells were counted and plated into white 384-well or 96-well cell-culture treated assay plates and compounds were added. After 48 hours, the cells were prepared for luminescence assays that were performed on a plate reader (Tecan Evolution or MD Analyst). The cytotoxicity of each compound was determined in parallel via MTT-based cell viability assays.

Tat hybrid reporter assay. The test compounds that displayed activity were tested in duplicate or triplicate at several doses using the Tat-hybrid reporter cell lines or by transient transfection. Previously characterized thienopyridines and diaminoacridine were used as controls. Cells were counted and plated into white 384-well cell-culture treated assay plates and compounds were added. After 48 hours, the cells were prepared for lumincescence assays that were performed on a plate reader (Tecan Evolution or MD Analyst). The cytotoxicity of each compound was determined in parallel via MTT-based cell viability assays.

Rev reporter assay. In the Rev reporter assay, 293T cells were transfected with an HIV RRE (Rev-dependent) reporter plus a pSV2 Rev expression plasmid (Hope, T. J., et al. (1990) Proc. Natl. Acad. Sci. USA 87, 7787-7791). Compounds were incubated with the cells for 48 hours and reporter activity was assessed by p24 ELISA. Leptomycin B, an inhibitor of the Crm1 pathway that inhibits Rev-dependent export, was included as a control. The cytotoxicity of each compound was determined in parallel via MTT-based cell viability assays.

U1 activation assay. U1 cells obtained from the AIDS Research and Reference Reagent Program were maintained under standard culture conditions in RPMI 1640 supplemented with 10% fetal bovine serum (heat inactivated), 2 mM L-glutamine, 100U/mL penicillin and 100 µg/mL streptomycin. U1 cells contain an integrated copy of a phorbol ester inducible HIV-1 provirus and addition of phytohemagglutinin (PHA) to the cell culture was used to induce virus production. On the day of the assay, the U1 cells were activated with PHA and 250,000 cells were plated in 96-well plates. Test compounds were diluted in media and applied to the cells at final concentrations from 1 to 10,000 nM. Cultures were incubated for 3 days and supernatants harvested. Cell-free virus production was measured by p24 ELISA on culture supernatant. Compound toxicity was determined by MTT cell-viability assay in parallel assays.

Virus spreading assay. Jurkat (E6-1) cells (NIH AIDS Reagent Program) were cultured in RPMI media supplemented with 25 mM HEPES pH 7.4, 10% heat-inactivated fetal calf serum (Hyclone, Waltham Mass.), and 1% penicillin/streptomycin. 2.5×105 Jurkat cells were inoculated with 250 pg p24 in 250 µl media in a 96-well flat bottom polystyrene cell culture microplate. Input virus was removed after 18 hours via washing cells phosphate-buffered saline (PBS). Cells were resuspended in 250 µl of media containing compounds at the described concentrations. Cells were incubated at 37° C., 5% CO2 and supernatant samples were removed every 48 hours and replaced with fresh media containing the compounds. Viral replication was quantified using ELISA to quantify p24 viral capsid protein in the culture supernatant. Mouse monoclonal and rabbit polyclonal α-p24 antibodies used in the ELISA were obtained from the NIH AIDS Reagent Program. Toxicity was monitored using the MTT cell viability assay (Mosmann, T. (1983). J Immunol Methods 65, 55-63).

HIV-1 replication assay in PBMCs. Virus isolates were obtained from the NIH AIDS Reagent Program. Human PBMCs, seronegative for HIV and hepatitis B virus (Astarte Biologics, LLC) were stimulated in R-3 medium (RPMI 1640 medium with 25 mM HEPES and L-glutamine, 20% heat-inactivated fetal bovine serum, 1% penicillin/streptomycin, 201U/mL IL-2) with 5 g/mL phytohemagglutinin (PHA-P) for 48 to 72 h. Stimulated PBMCs were resuspended and diluted in fresh R-3 medium and added to 96-well plates at 5×104 cells/well. The 50% tissue culture infective dose (TCID50) of each virus stock was measured by end-point dilution assay described by Reed and Muench (Reed, L. J., and Muench, H. (1938) American Journal of Hygiene 27, 493-497). Spinoculation (1,200×g, 2 hrs) was applied to improve the efficiency of infection.

Cells were infected with 40 TCID50s of virus stock under spinoculation in the presence of different concentrations of test compounds (biological quintuplicate wells/concentration) and incubated at 37° C., 5% CO2 for 7 days. On day 4, half of the supernatant was removed and replaced with fresh R-3 medium containing the appropriate concentration of test compounds. On day 7, cell-free supernatant samples were collected for analysis of p24 antigen expression measured by ELISA described above. Antiviral activity was assessed by the inhibition of p24 expression (Reed, L. J., and Muench, H. (1938) American Journal of Hygiene 27, 493-497.

2. Screening

Figure 15A:
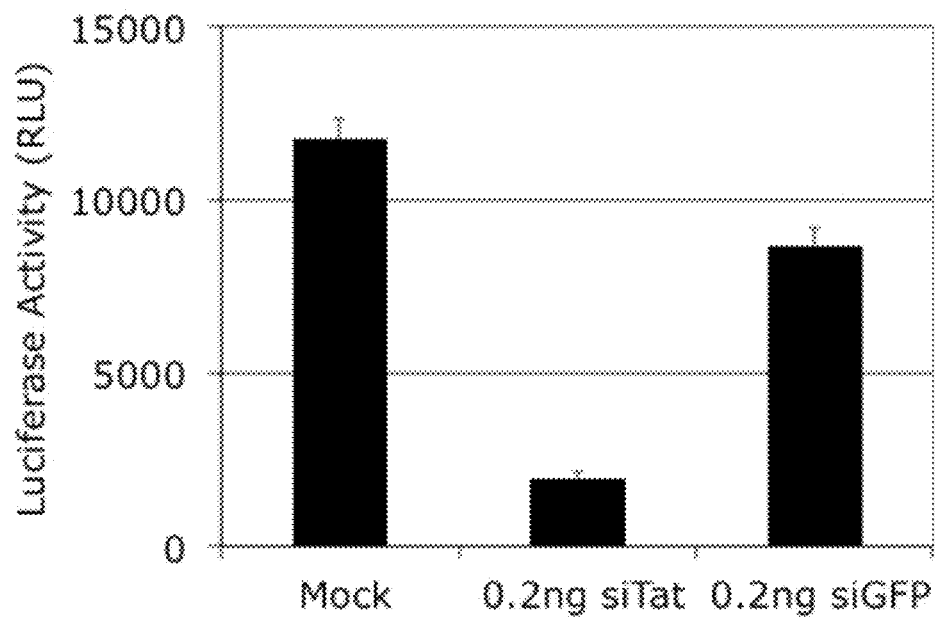
FIGS. 15A-15B. Evaluating the activity of the screening cell lines.
Figure 15B:
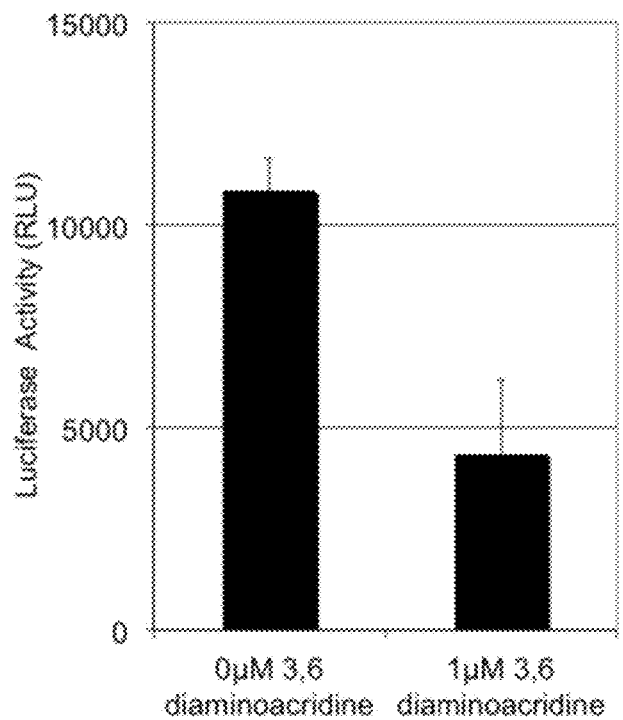

We developed a Tat-hybrid based screening approach to identify small molecules that target RNA-protein interactions. In brief, a plasmid encoding the HIV LTR, RRE RNA target, and a reporter gene is coexpressed with a plasmid encoding a fusion protein of the HIV Tat activation domain and a heterologous RNA-binding domain from the HIV Rev protein. A productive interaction between the RNA and RNA-binding protein confers activation of the reporter gene. To enable higher throughput, we engineered a Tat-hybrid reporter cell line encoding the RRE IIB RNA target and a Firefly Luciferase reporter. This reporter has a high signal-to-noise, and is compatible with multi-well plates, robotic liquid handling, and standard luminescence plate readers. The Tat-Rev expression plasmid was then integrated into the reporter cell line and clonal cell lines were selected that constitutively expressed the Luciferase reporter, suggesting presentation of the intact RNA-protein interaction. The assay was validated using siRNA knockdown of the Tat activation domain and with 3-diaminoacridine, a known small molecule inhibitor of the Rev-RRE interaction that served as a positive control, see FIGS. 15A-15B.

The RRE IIB-Rev screening cell line was plated in 384-well assay plates and compounds were added to the cells to a final concentration of 30 µM. Cells were prepared and assayed for luciferase activity. Compounds were screened in duplicate and the activity of each compound was highly consistent (typically <10% deviation in activity). In parallel, MTT cell viability assays were performed to assess the toxicity of compounds and minimize the level of false positives.

From the primary screen, we obtained 11 validated hits with confirmed dose-dependent activity and a lack of toxicity in the MTT assay. Of these 11 compounds, two were benzopyrans, one was a thiophene, and the remaining eight based on a thieno[2,3-b]pyridine ring system. To further validate the hits, we used an electrophoretic mobility shift assay (EMSA) to evaluate which of the three hit scaffolds were capable of disrupting the Rev-RRE IIB interaction in vitro. The thiophene scaffold disrupted the complex as determined by EMSA. This demonstrates that the Tat-hybrid screening method could identify bona fide inhibitors of RNA-protein interactions. We observed that compounds that disrupted the RNA-protein complex by EMSA, 3,6 diaminoacridine, neomycin B, and thiophenes were potentially toxic to cells under certain experimental conditions. These types of relatively non-specific intercalating agents (e.g., acridines) and RNA-binding compounds (e.g., aminoglycosides) can be readily picked up as binding inhibitors in EMSA assays by may be missing in cell-based assays because of their high toxicity. Conversely, the lack of EMSA inhibition by other types of compounds that scored well in the cell-based assay does not necessarily rule out Rev-RRE as their target since the in vitro EMSA lacks other proteins required for Rev function (e.g., Crm1 and Ran) and potential accessory factors (e.g., hnRNPs and chaperones) that may alter the nature of the RevRRE complexes for inhibitors to act upon. Additional experimental evidence supporting Rev-RRE as a plausible target of thienopyridines is provided herein.

Figure 2A:
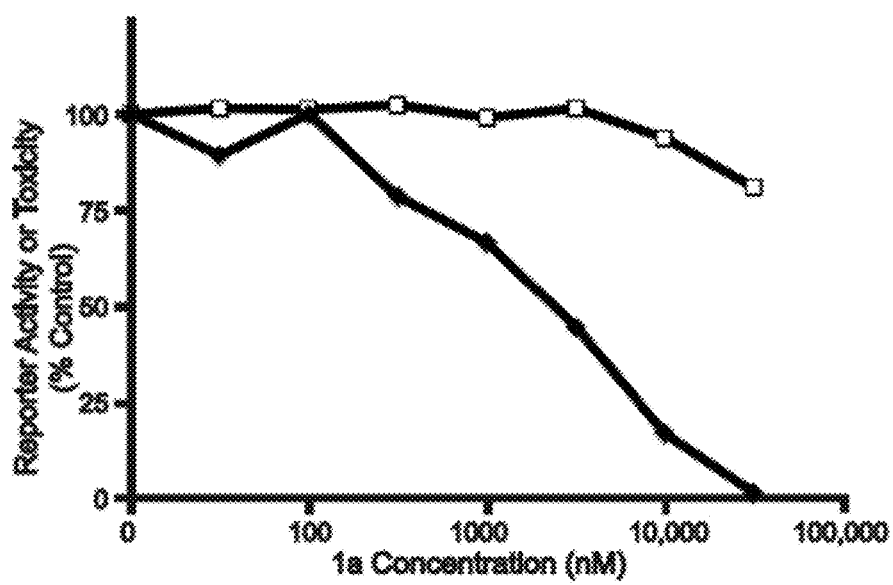
FIGS. 2A-2B. Dose response curves for the activity (filled) and toxicity (open) of thienopyridine analogs 1a and 1d.
Figure 2B:
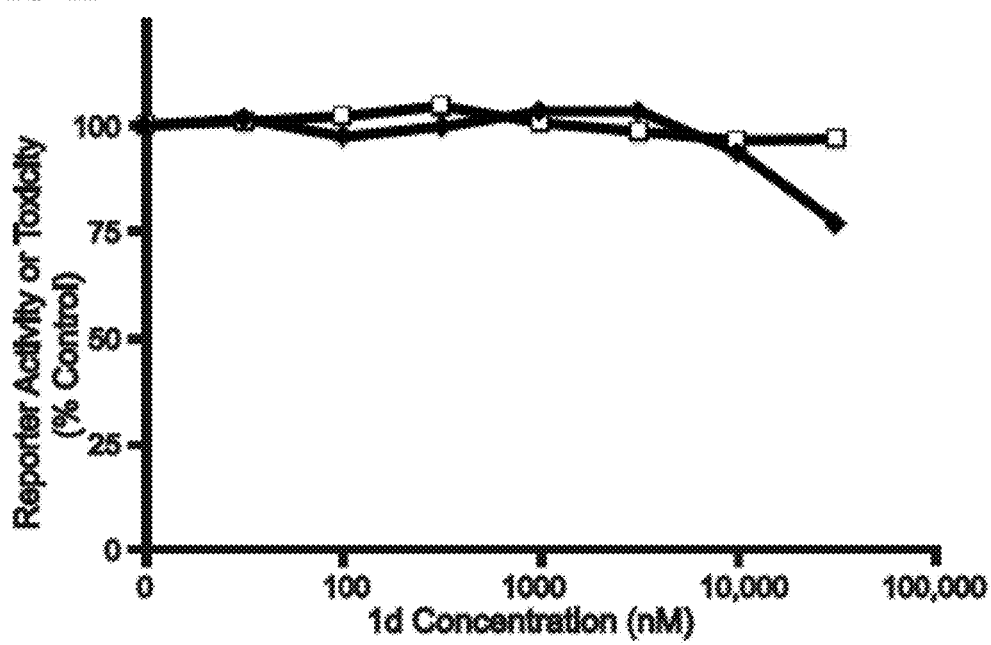

Compounds 1a-c (FIG. 1) are representative of the original thienopyridine hits, which varied in terms of substitution on the pyridine ring but universally possessed amino and carboxamide substitution on the thiophene ring. Commercially available analogs of 1a bearing a carboxylic acid (1d) or methyl ketone (1e) in place of the carboxamide were purchased and evaluated but were not significantly active in the Tat-hybrid assay, suggesting the importance of the carboxamide function for activity (FIGS. 1 and 2, Table 1).

TABLE 1

Activity of thienopyridine analogs 1 and 2 in reporter and antiviral assays.

| Compound | Tat-hybrid EC50 (nM) | U1 cell IC50 (nM) | Jurkat HIV-1 replication assay (nM) | LipE[a] |
|---|---|---|---|---|
| 1a (1284) | C | C | — | 4.7 |
| 1b (1270) | C | C | — | 5.2 |
| 1c (1655) | C | C | — | 4.5 |
| 1d (1286) | C | — | — | — |
| 1e (1287) | C | — | — | 2.4 |
| 1f (1560) | B | C | — | 6.2 |
| 2a (1556) | C | B | — | 5.8 |
| 2b (1558) | A | A | A | 5.9 |
| 2c (1617) | B | B | — | 6.5 |
| 2d (1557) | C | — | — | 6.2 |
| 2e (1559) | C | — | — | 5.3 |
| 2f (1570) | B | B | C | 5.2 |
| 2g (1651) | B | B | — | 5.75 |
| 2h (1649) | B | B | — | 5.0 |
| 2i (1604) | A | A | — | 5.3 |
| 2j (1661) | B | A | — | 4.6 |
| 2k (1662) | C | C | — | 4.8 |

A = <100 nM; B = 100-500 nM; C = >500 Nm.
[a]LipE = pKi − clogP; pKi estimated from Tat-hybrid EC50; clogP values were calculated in Vortex (Dotmatics) using the property XlogP.

Evaluation of additional commercial analogs suggested that modification of the 4 or 5 position of the thienopyridine ring was generally well tolerated and this afforded some confidence that improvements in potency could be realized with the synthesis of additional analogs.

3. Synthesis

Synthesis of thieno[2,3-c]pyridine analogs 2-4. Conditions: (a) 1-2 equiv. $R^1R^2NH$, $Et_3N$, DMF, 25-40° C., 12-24 hrs; (b) 2 equiv. 2-mercaptoacetamide, 10 wt % in MeOH/$NH_3$, 2 equiv. NaOMe, DMF, µW, 80° C., 10-60 min; (c) 1-2 equiv. Ar—$B(OH)_2$, 0.025 equiv $PCy_3$, 0.01 equiv. $Pd_2(dba)_3$, 1.7 equiv. $K_2CO_3$, dioxane, µW, 150° C., 30 min; (d) 0.75 equiv. 2-mercaptoacetamide, 10 wt % in MeOH/$NH_3$, 1.2 eq NaOMe, DMF, µW, 80° C., 10-60 min.

General Procedure A—Preparation of Thienopyridine Carboxamide Analogs 2.

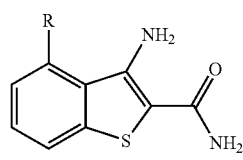

R = Aliphatic secondary amines

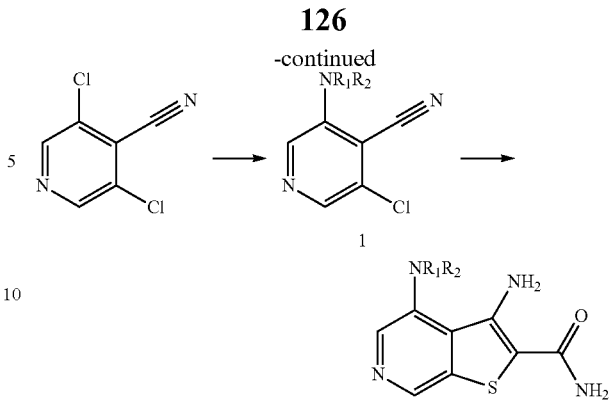

Step 1: To a solution of 3,5-dimethylpyridine-4-carbonitrile (1.2 M in DMF), triethylamine (2 equiv.) and the desired secondary amine (1-2 equiv.) is added and the solution is stirred overnight at 25-40° C. After cooling, volatiles are removed under reduced pressure and the residue redissolved in a minimum amount of methylene chloride and loaded directly onto a silica gel column. The desired aminopyridine intermediate (1) is eluted with either hexanes/ethyl acetate or methanol/methylene chloride.

Step 2: To a solution of the aminopyridine intermediate 1 (0.45 M in DMF), 2-mercaptoacetamide (2 equiv., 10% wt./vol in a methanolic ammonia solution) and sodium methoxide (2 equiv., 4.5 M solution in methanol) are added, and the reaction mixture is heated to 80° C. in a sealed vial in a CEM microwave reactor for 10-60 min. The volatiles are removed under reduced pressure and the residue is purified by silica chromatography using either hexanes/ethyl acetate or methanol/methylene chloride to afford the desired thienopyridine carboxamide analog 2. If required, further purification by preparative HPLC is performed using a gradient of methanol and water (0.05% TFA).

General Procedure B—Preparation of Thienopyridine Carboxamides 4.

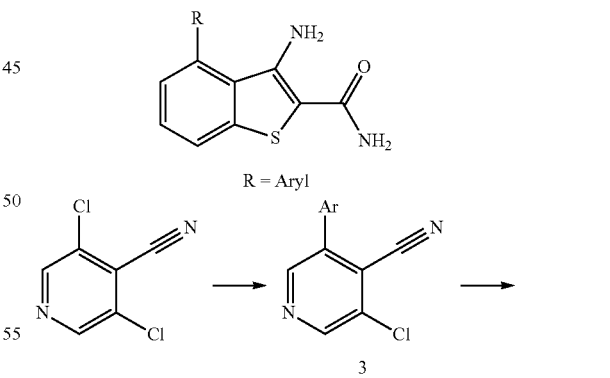

R = Aryl

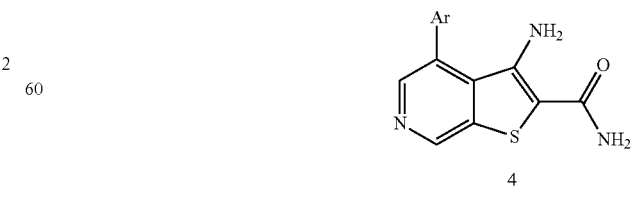

Step 1: To a solution of 3,5-dichloro-4-pyridinecarbonitrile in anhydrous dioxane (0.38 M) in a CEM microwave reaction vial, the desired arylboronic acid (1 equiv.), PCy₃ ligand (0.025 eq) and K₃PO₄ (1.27 M aqueous solution, 1.7 equiv.) are added. The reaction mixture is first rigorously degassed with argon and then Pd₂(dba)₃ (0.01 equiv.) is added and the reaction mixture is further degassed with argon and then heated at 150° C. for 30 min using a CEM microwave. After cooling, the crude reaction mixture is diluted with ethyl acetate and filtered through silica gel and the residue is concentrated under reduced pressure. The residue is applied to a silica gel column and the desired arylpyridine intermediate (3) is eluted with either hexanes/ethyl acetate or methanol/methylene chloride.

Step 2: To a solution of the arylpyridine intermediate 3 (0.45 M in DMF), 2-mercaptoacetamide (2 eq, 10% wt./vol in a methanolic ammonia solution) and sodium methoxide (2 eq, 4.5 M solution in methanol) are added, and the reaction mixture is heated to 80° C. in a CEM microwave reactor for 10-60 min. After cooling, the volatiles are removed under reduced pressure and the crude residue is purified by silica chromatography, eluting with either hexanes/ethyl acetate or methanol/methylene chloride. Relevant fractions are collected, concentrated and dried to afford the desired thienopyridine carboxamide 4. If required, further purification by preparative HPLC is performed using a gradient of methanol and water (0.05% TFA).

General Procedure C—Synthesis of Thienopyridine Carboxamides 6.

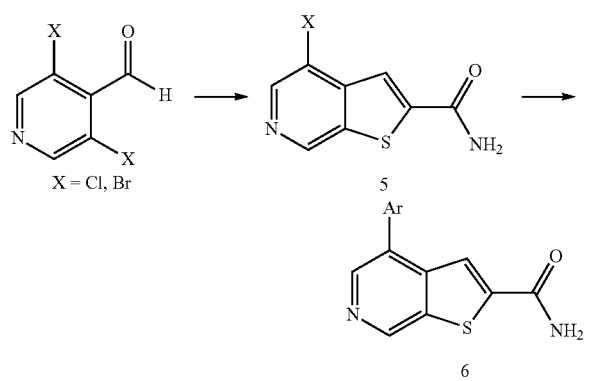

Step 1: To a solution of 3,5-dihalopyridinecarboxaldehyde 1 (0.67 M in DMF), 2-mercaptoacetamide (0.75 eq, 10% wt./vol in a methanolic ammonia solution) and sodium methoxide (1.2 eq, 4.5 M solution in methanol) are added, and the reaction mixture is heated to 80° C. in a CEM microwave reactor for 10-60 min. The volatiles are removed under reduced pressure and the residue is purified by silica chromatography using either hexanes/ethyl acetate or methanol/methylene to afford the desired thienopyridine intermediate (5, X=Cl or Br).

Step 2: To a solution of halopyridine 5 in anhydrous dioxane (0.38 M) in a CEM microwave reaction vial, the desired arylboronic acid (2 equiv.), PCy₃ ligand (0.025 equiv.) and K₃PO₄ (1.27 M aqueous solution, 1.7 equiv.) are added. The reaction mixture is first rigorously degassed with argon and then Pd₂(dba)₃ (0.01 equiv.) is added and the reaction mixture is further degassed with argon and then heated at 150° C. for 30 min using a CEM microwave. After cooling, the crude reaction mixture is diluted with ethyl acetate and filtered through silica gel and the residue is concentrated under reduced pressure. The crude residue is applied to a silica gel column and eluted with either hexanes/ethyl acetate or methanol/methylene chloride. Relevant fractions are collected, concentrated and dried to afford the desired thienopyridine carboxamide 6.

LCMS conditions: All samples were run using a C18 column using either a water/acetonitrile or water/methanol gradient starting at 95/5 and ramping to 5/95 over 2.5 minutes, holding at 5/95 for 1.5 minutes, then ramping down to 95/5 over 0.3 minutes and held at 95/5 for 0.2 minutes. Retention times are for UV detection (waters 2996 UV detector @ 254 nm). LCMS analysis (split flow) was performed on a Waters ZQ4000 quadrapole Mass Detector using an electrospray source.

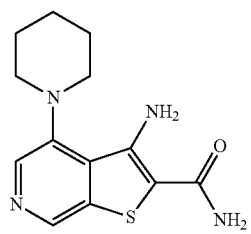 [SMILES: NC(=O)c1sc2cncc(N3CCCCC3)c2c1N]

3-amino-4-(piperidin-1-yl)thieno[2,3-c]pyridine-2-carboxamide 281589 (MAB-24-046C) 1H NMR (400 MHz, CDCl3) d 8.27 (s, 1H), 8.20 (s, 1H), 3.34 (m, 4H), 1.79 (m, 4H), 1.66 (m, 2H)

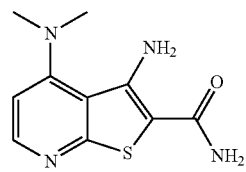 [SMILES: CN(C)c1ccnc2sc(C(N)=O)c(N)c12]

3-amino-4-(dimethylamino)thieno[2,3-b]pyridine-2-carboxamide 281591 (MAB-24-053B)) 1H NMR (400 MHz, CDCl3) d 8.40 (d, J=5.4 Hz, 1 H), 6.90 (br m, 1H), 6.86 (d, J=5.4 Hz, 1 H), 5.63 (br s, 1H), 3.45 (Br s, 1H), 2.86 (s, 6H)

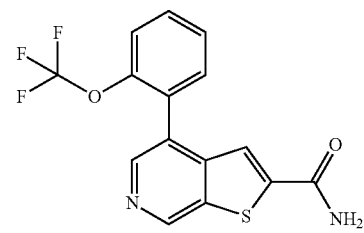 [SMILES: NC(=O)c1cc2c(-c3ccccc3OC(F)(F)F)cncc2s1]

4-[2-(trifluoromethoxy)phenyl]thieno[2,3-c]pyridine-2-carboxamide 701719 ret time 3.20 MH+ calc 339.0 obs 339.0

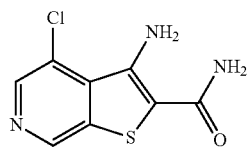 [SMILES: NC(=O)c1sc2cncc(Cl)c2c1N]

3-amino-4-chlorothieno[2,3-c]pyridine-2-carboxamide 530528 ret. Time 2.70 MH+ calc 228.0 MH+ obs. 228.3

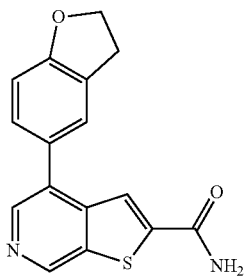 [SMILES: NC(=O)c1cc2c(-c3ccc4c(c3)CCO4)cncc2s1]

4-(2,3-dihydro-1-benzofuran-5-yl)thieno[2,3-c]pyridine-2-carboxamide 530559 ret. Time 2.68 MH+ calc. 297.1 obs. 297.5

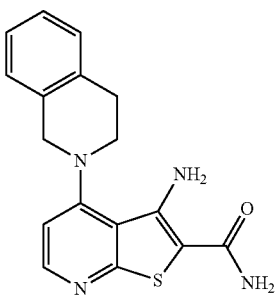 [SMILES: NC(=O)c1sc2nccc(N3CCc4ccccc4C3)c2c1N]

3-amino-4-(1,2,3,4-tetrahydroisoquinolin-2-yl)thieno[2,3-b]pyridine-2-carboxamide 304030 (MAB-24-120) 13C NMR (100 MHz, CDCl3) d 167.4, 148.6, 145.6, 141.8, 135.4, 134.4, 133.6, 133.3, 131.9, 129.0, 126.8, 126.4, 126.1, 99.9, 56.5, 51.0, 28.9

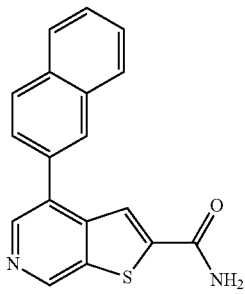 [SMILES: NC(=O)c1cc2c(-c3ccc4ccccc4c3)cncc2s1]

4-(naphthalen-2-yl)thieno[2,3-c]pyridine-2-carboxamide 701714 ret. Time 3.30 MH+ calc. 305.1 obs. 305.0

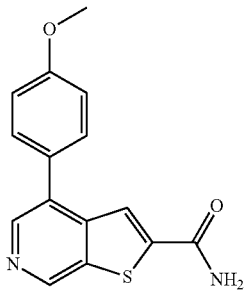 [SMILES: COc1ccc(-c2cncc3sc(C(N)=O)cc23)cc1]

4-(4-methoxyphenyl)thieno[2,3-c]pyridine-2-carboxamide 530555 (MAB-55-001) 13C NMR (100 MHz, CDCl3) d 159.8, 143.1, 143.0, 142.0, 137.5, 133.2, 130.1, 128.8, 124.2, 114.3, 55.3 ret time 2.80 MH+ calc 285.1 obs 285.4

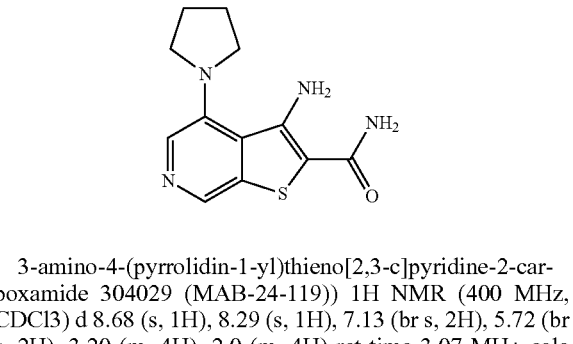

3-amino-4-(pyrrolidin-1-yl)thieno[2,3-c]pyridine-2-carboxamide 304029 (MAB-24-119)) 1H NMR (400 MHz, CDCl3) d 8.68 (s, 1H), 8.29 (s, 1H), 7.13 (br s, 2H), 5.72 (br s, 2H), 3.20 (m, 4H), 2.0 (m, 4H) ret time 3.07 MH+ calc 263.1 obs 262.9

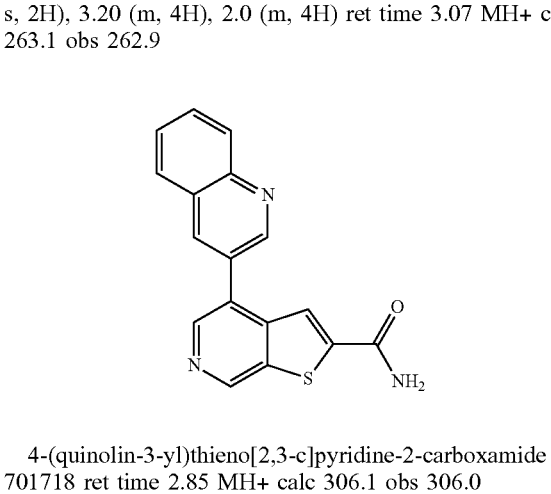

4-(quinolin-3-yl)thieno[2,3-c]pyridine-2-carboxamide 701718 ret time 2.85 MH+ calc 306.1 obs 306.0

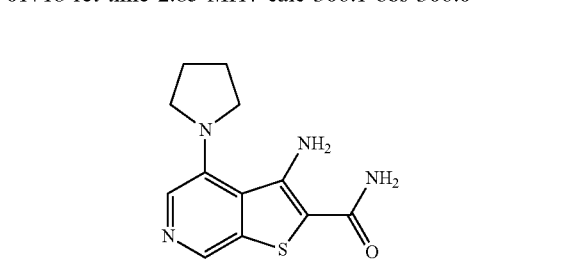

3-amino-4-(pyrrolidin-1-yl)thieno[2,3-c]pyridine-2-carboxamide 304029 ret time 3.07 MH+ calc 263.1 obs 262.9

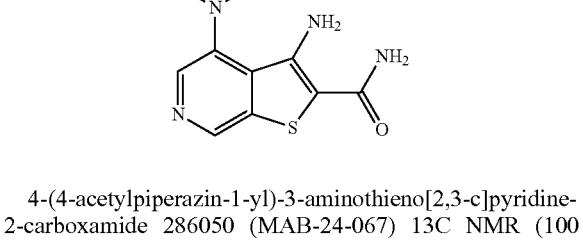

4-(4-acetylpiperazin-1-yl)-3-aminothieno[2,3-c]pyridine-2-carboxamide 286050 (MAB-24-067) 13C NMR (100

MHz, CDCl3) d 168.4, 166.7, 147.0, 144.8, 141.8, 134.8, 131.0, 101.4, 45.5, 40.7, 38.9, 21.2 ret time 1.98 MH+ calc 320.1 obs 320.0

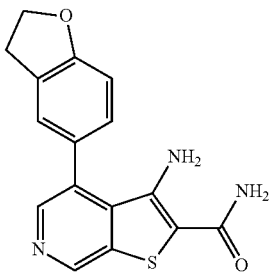 [SMILES: NC(=O)c1sc2cncc(-c3ccc4c(c3)CCO4)c2c1N]

3-amino-4-(2,3-dihydro-1-benzofuran-5-yl)thieno[2,3-c]pyridine-2-carboxamide 303964 (MAB-24-101B) 13C NMR (100 MHz, CDCl3) d 167.6, 161.1, 148.5, 144.8, 144.6, 134.0, 133.7, 129.7, 128.2, 127.5, 126.5, 109.7, 101.6, 71.9, 36.8, 29.8, 1H NMR (400 MHz, CDCl3) d 8.64 (s, 1H), 7.96 (s, 1H), 6.93 (m, 2H), 6.84 (m, 1H), 6.57 (m, 1H), 4.34 (t, J=8.7 Hz, 2 H), 2.97 (t, J=8.7 Hz, 2 H) ret time 2.25 MH+ calc 312.1 obs 312.0

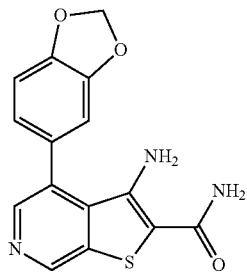 [SMILES: NC(=O)c1sc2cncc(-c3ccc4c(c3)OCO4)c2c1N]

3-amino-4-(2H-1,3-benzodioxol-5-yl)thieno[2,3-c]pyridine-2-carboxamide 304031 (MAB-24-101D) 1H NMR (400 MHz, CDCl3) d 8.90 (s, 1H), 8.20 (s, 1H), 7.25 (s, 1H), 6.90-6.82 (m, 2H), 6.25 (m, 2H) ret time 2.90 MH+ calc 314.1 obs 314.0

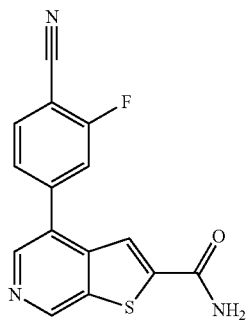 [SMILES: N#Cc1ccc(-c2cncc3sc(C(N)=O)cc23)cc1F]

4-(4-cyano-3-fluorophenyl)thieno[2,3-c]pyridine-2-carboxamide 701715 Ret time 2.93 MH+ calc 298.1 obs 298.6

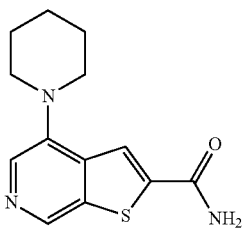 [SMILES: NC(=O)c1cc2c(N3CCCCC3)cncc2s1]

4-(piperidin-1-yl)thieno[2,3-c]pyridine-2-carboxamide 530584 ret time 2.30 MH+ calc 262.1 obs 262.0

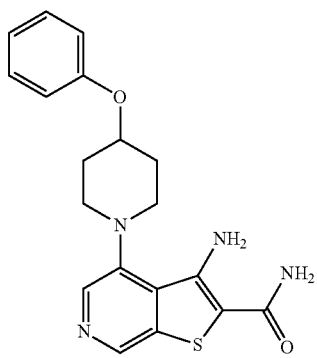 [SMILES: NC(=O)c1sc2cncc(N3CCC(Oc4ccccc4)CC3)c2c1N]

3-amino-4-(4-phenoxypiperidin-1-yl)thieno[2,3-c]pyridine-2-carboxamide 530525 ret time 3.30 MH+ calc 369.1 obs 369.6

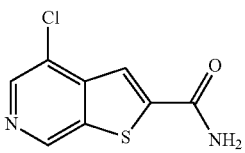

4-chlorothieno[2,3-c]pyridine-2-carboxamide 530529 ret time 2.68 MH+ calc 213.0 obs 213.3

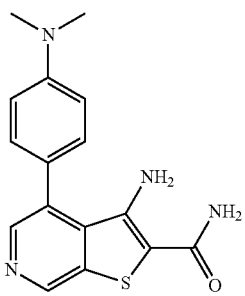 [SMILES: CN(C)c1ccc(-c2cncc3sc(C(N)=O)c(N)c23)cc1]

3-amino-4-[4-(dimethylamino)phenyl]thieno[2,3-c]pyridine-2-carboxamide 304243 ret time 2.96 MH+ calc 313.1 obs 313.6

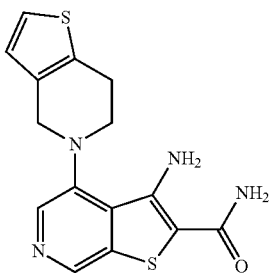 [SMILES: NC(=O)c1sc2cncc(N3CCc4sccc4C3)c2c1N]

3-amino-4-{4H,5H,6H,7H-thieno[3,2-c]pyridin-5-yl}thieno[2,3-c]pyridine-2-carboxamide 304384 ret time 3.10 MH+ calc 331.1 obs 331.5

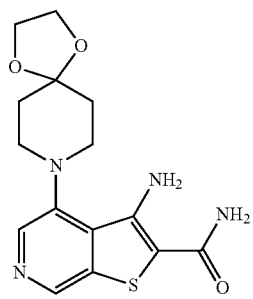 [SMILES: NC(=O)c1sc2cncc(N3CCC4(CC3)OCCO4)c2c1N]

3-amino-4-{1,4-dioxa-8-azaspiro[4.5]decan-8-yl}thieno[2,3-c]pyridine-2-carboxamide 304382 ret time 2.43 MH+ calc 335.1 obs 335.5

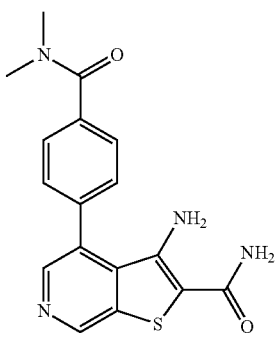 [SMILES: CN(C)C(=O)c1ccc(-c2cncc3sc(C(N)=O)c(N)c23)cc1]

3-amino-4-[4-(dimethylcarbamoyl)phenyl]thieno[2,3-c]pyridine-2-carboxamide 304246 ret time 2.52 MH+ calc 341.1 obs 341.6

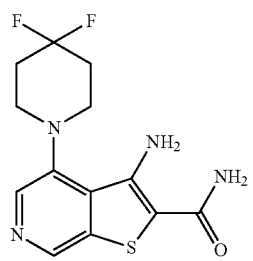 [SMILES: NC(=O)c1sc2cncc(N3CCC(F)(F)CC3)c2c1N]

3-amino-4-(4,4-difluoropiperidin-1-yl)thieno[2,3-c]pyridine-2-carboxamide 304380 ret time 2.73 MH+ calc 313.1 obs 313.5

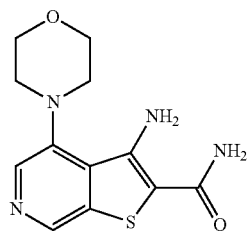 [SMILES: NC(=O)c1sc2cncc(N3CCOCC3)c2c1N]

3-amino-4-(morpholin-4-yl)thieno[2,3-c]pyridine-2-carboxamide 281588 (MAB-24-047C) 13C NMR (100 MHz, d6-DMSO) d 166.7, 147.0, 145.0, 141.7, 134.7, 134.1, 131.0, 101.4, 66.0, 53.3

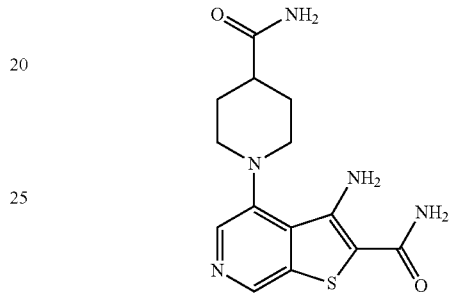

1-{3-amino-2-carbamoylthieno[2,3-c]pyridin-4-yl}piperidine-4-carboxamide 304245 ret time 1.95 MH+ calc 320.1 obs 320.5

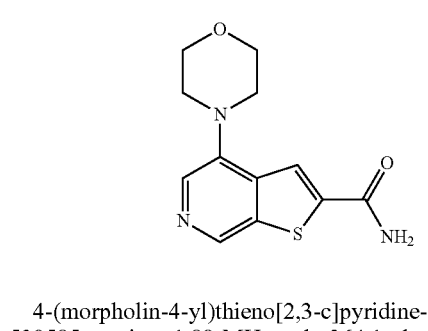

4-(morpholin-4-yl)thieno[2,3-c]pyridine-2-carboxamide 530585 ret time 1.88 MH+ calc 264.1 obs 264.0

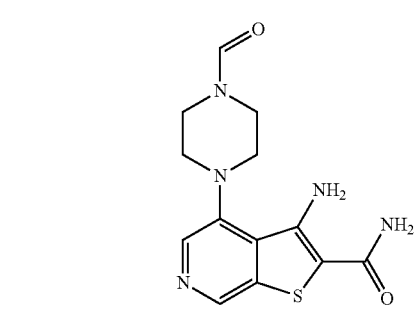 [SMILES: NC(=O)c1sc2cncc(N3CCN(C=O)CC3)c2c1N]

3-amino-4-(4-formylpiperazin-1-yl)thieno[2,3-c]pyridine-2-carboxamide 530522 (MAB-24-186A) 1H NMR (400 MHz, CDCl3) d 8.75 (s, 1H), 8.20 (s, 1H), 8.10 (s, 1H), 4.52 (m, 1H), 3.74 (m, 1H), 3.49 (m, 1H), 3.35 (m, 2H), 3.05-2.84 (m, 3H)

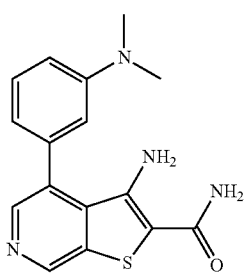 [SMILES: CN(C)c1cccc(-c2cncc3sc(C(N)=O)c(N)c23)c1]

3-amino-4-[3-(dimethylamino)phenyl]thieno[2,3-c]pyridine-2-carboxamide 304244 (MAB-24-163) 1H NMR (400 MHz, CDCl3) d 167.5, 150.2, 148.1, 144.4, 144.0, 136.1, 134.1, 134.0, 133.6, 129.4, 117.0, 112.9, 112.4, 101.2, 40.3 1H NMR (400 MHz, CDCl3) d 8.95 (m, 1H), 8.33 (m, 1H), 7.32 (m, 1H), 6.80 (m, 1H), 6.70 (m, 2H), 6.06 (m, 1H), 5.85 (br m, 1H), 2.97 (m, 6H) ret time 3.05 MH+ calc 313.1 obs 313.5

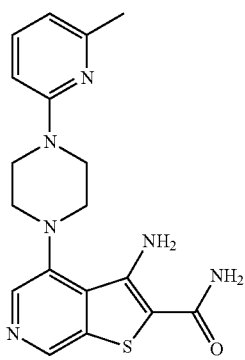 [SMILES: Cc1cccc(N2CCN(c3cncc4sc(C(N)=O)c(N)c34)CC2)n1]

3-amino-4-[4-(6-methylpyridin-2-yl)piperazin-1-yl]thieno[2,3-c]pyridine-2-carboxamide 286049 (MAB-24-066) 13C NMR (100 MHz, d6-DMSO) d 166.7, 158.5, 155.7, 147.1, 145.1, 141.7, 137.9, 134.6, 134.1, 131.0, 112.4, 104.0, 101.2, 52.9, 44.6) 1H NMR (400 MHz, d6-DMSO) d 8.33 (s, 1H), 8.26 (s, 1H), 7.4 (dd, J=8.5, 7.2 Hz, 1H), 7.26 (br s, 2H), 7.09 (m, 2H), 6.63 (d, J=8.5 Hz, 1H), 6.49 (m, 1H), 4.29 (m, 2H), 3.25 (m, 3H), 3.08 (m, 2H), 2.92 (m, 2H), 2.28 (s, 3H)

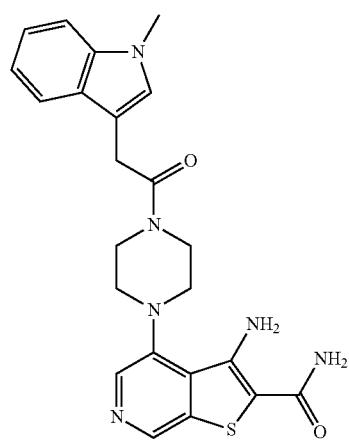 [SMILES: Cn1cc(CC(=O)N2CCN(c3cncc4sc(C(N)=O)c(N)c34)CC2)c2ccccc21]

3-amino-4-{4-[2-(1-methyl-1H-indol-3-yl)acetyl]piperazin-1-yl}thieno[2,3-c]pyridine-2-carboxamide 286057 (MAB-24-075-412) 1H NMR (400 MHz, CDCl3) d 8.68 (s, 1H), 8.06 (s, 1H), 7.57 (m, 1H), 7.24 (m, 3H), 7.09 (m, 1H), 6.95 (s, 1H), 5.66 (br s, 1H), 4.01 (d, J=13 Hz, 1H), 3.84 (m, 2H), 3.73 (s, 3H), 3.26 (m, 2H), 3.09 (d, J=11 Hz, 1H), 2.87, (m, 2H), 2.60 (m, 1H) ret 2.98 MH+ calc 449.2 obs 449.2

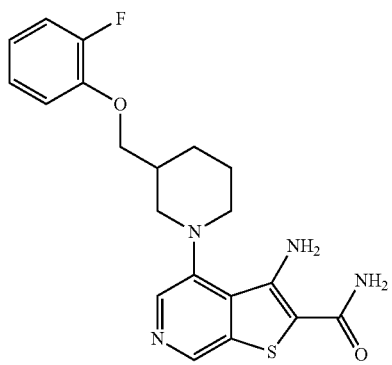 [SMILES: NC(=O)c1sc2cncc(N3CCCC(COc4ccccc4F)C3)c2c1N]

3-amino-4-[3-(2-fluorophenoxymethyl)piperidin-1-yl]thieno[2,3-c]pyridine-2-carboxamide 530523 ret time 3.38 MH+ calc 401.1 obs 401.5

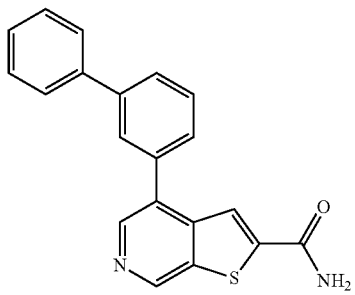 [SMILES: NC(=O)c1cc2c(-c3cccc(-c4ccccc4)c3)cncc2s1]

4-(3-phenylphenyl)thieno[2,3-c]pyridine-2-carboxamide 701020 ret time 3.48 MH+ calc 331.1 obs 331.0

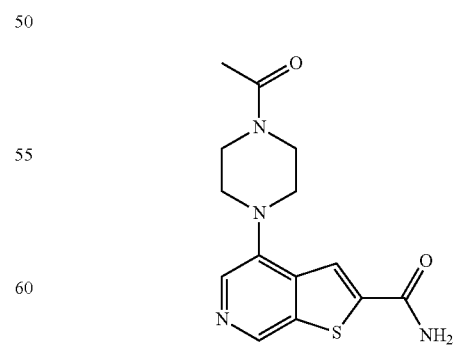

4-(4-acetylpiperazin-1-yl)thieno[2,3-c]pyridine-2-carboxamide 530586 ret time 1.87 MH+ calc 305.1 obs 305.0

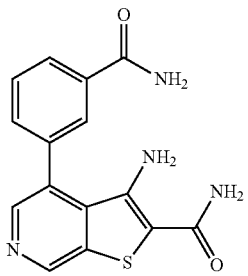 [SMILES: NC(=O)c1cccc(-c2cncc3sc(C(N)=O)c(N)c23)c1]

3-amino-4-(3-carbamoylphenyl)thieno[2,3-c]pyridine-2-carboxamide 304247 ret time 2.35 MH+ calc 313.1 obs 313.5

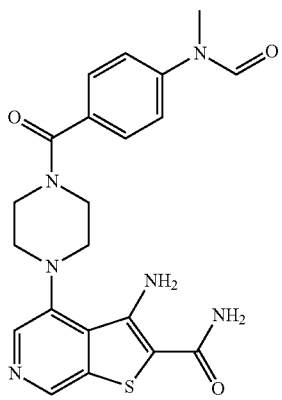 [SMILES: CN(C=O)c1ccc(C(=O)N2CCN(c3cncc4sc(C(N)=O)c(N)c34)CC2)cc1]

3-amino-4-{4-[4-(N-methylformamido)benzoyl]piperazin-1-yl}thieno[2,3-c]pyridine-2-carboxamide 286063 (MAB-24-075-457) NMR data not usable, ret time 2.62 MH+ calc 439.2 obs 439.1

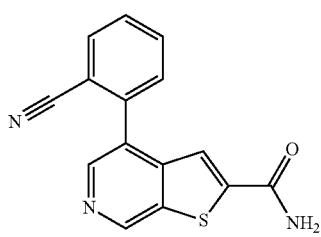 [SMILES: N#Cc1ccccc1-c1cncc2sc(C(N)=O)cc12]

4-(2-cyanophenyl)thieno[2,3-c]pyridine-2-carboxamide 701716 ret time 2.60 MH+ Calc 280.1 obs 280.0

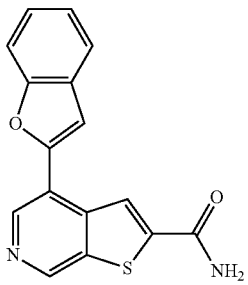 [SMILES: NC(=O)c1cc2c(-c3cc4ccccc4o3)cncc2s1]

4-(1-benzofuran-2-yl)thieno[2,3-c]pyridine-2-carboxamide 701717 ret time 3.37 MH+ calc 295.1 obs 294.9

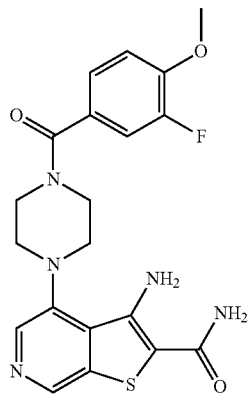 [SMILES: COc1ccc(C(=O)N2CCN(c3cncc4sc(C(N)=O)c(N)c34)CC2)cc1F]

3-amino-4-[4-(3-fluoro-4-methoxybenzoyl)piperazin-1-yl]thieno[2,3-c]pyridine-2-carboxamide 286059 (MAB-24-075-435) nmr data not usable, ret time 2.77 MH+ calc 430.1 obs 430.1

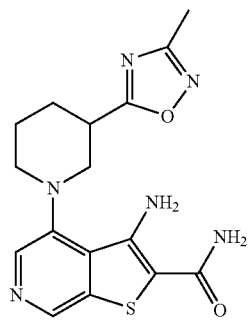 [SMILES: Cc1noc(C2CCCN(c3cncc4sc(C(N)=O)c(N)c34)C2)n1]

3-amino-4-[3-(3-methyl-1,2,4-oxadiazol-5-yl)piperidin-1-yl]thieno[2,3-c]pyridine-2-carboxamide 530526 ret time 2.63 MH+ calc 359.1 obs 359.5

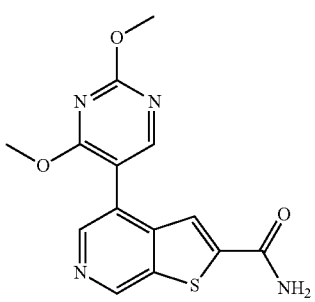 [SMILES: COc1ncc(-c2cncc3sc(C(N)=O)cc23)c(OC)n1]

4-(2,4-dimethoxypyrimidin-5-yl)thieno[2,3-c]pyridine-2-carboxamide 701721 ret time 2.60 MH+ calc 317.1 obs 317.0

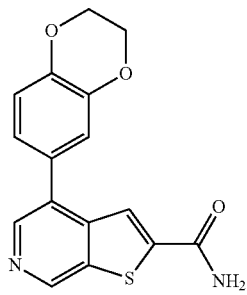 [SMILES: NC(=O)c1cc2c(-c3ccc4c(c3)OCCO4)cncc2s1]

4-(2,3-dihydro-1,4-benzodioxin-6-yl)thieno[2,3-c]pyridine-2-carboxamide 530560 ret time 2.78 MH+ calc 313.1 obs 313.5

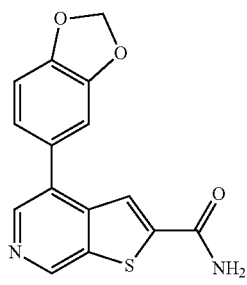 [SMILES: NC(=O)c1cc2c(-c3ccc4c(c3)OCO4)cncc2s1]

4-(2H-1,3-benzodioxol-5-yl)thieno[2,3-c]pyridine-2-carboxamide 530558 ret time 2.72 MH+ calc 299.1 obs 299.4

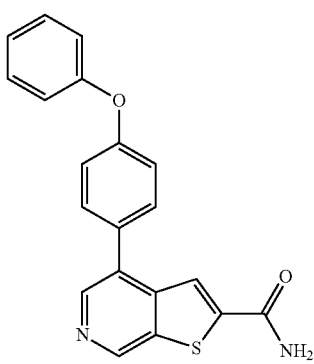 [SMILES: NC(=O)c1cc2c(-c3ccc(Oc4ccccc4)cc3)cncc2s1]

4-(4-phenoxyphenyl)thieno[2,3-c]pyridine-2-carboxamide

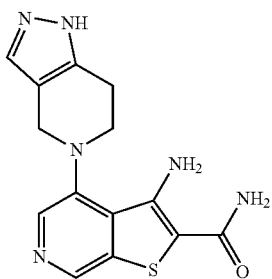 [SMILES: NC(=O)c1sc2cncc(N3CCc4[nH]ncc4C3)c2c1N]

3-amino-4-{1H,4H,5H,6H,7H-pyrazolo[4,3-c]pyridin-5-yl}thieno[2,3-c]pyridine-2-carboxamide 304383 ret time 2.13 MH+ calc 315.1 obs 315.5

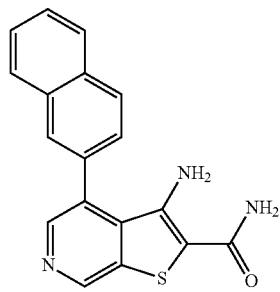 [SMILES: NC(=O)c1sc2cncc(-c3ccc4ccccc4c3)c2c1N]

3-amino-4-(naphthalen-2-yl)thieno[2,3-c]pyridine-2-carboxamide 304124 ret time 3.39 MH+ calc 320.1 obs 320.4

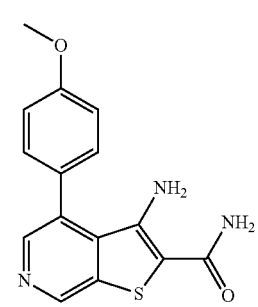 [SMILES: COc1ccc(-c2cncc3sc(C(N)=O)c(N)c23)cc1]

3-amino-4-(4-methoxyphenyl)thieno[2,3-c]pyridine-2-carboxamide 304122 ret time 2.83 MH+ calc 300.1 obs 300.4

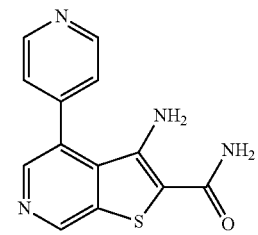 [SMILES: NC(=O)c1sc2cncc(-c3ccncc3)c2c1N]

3-amino-4-(pyridin-4-yl)thieno[2,3-c]pyridine-2-carboxamide 304119 ret time 1.93 MH+ calc 271.1 obs 270.9

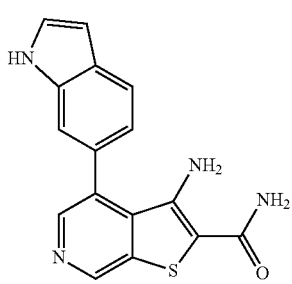 [SMILES: NC(=O)c1sc2cncc(-c3ccc4cc[nH]c4c3)c2c1N]

3-amino-4-(1H-indol-6-yl)thieno[2,3-c]pyridine-2-carboxamide 304118 ret time 2.75 MH+ calc 309.1 obs 309.0

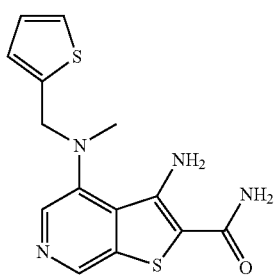 [SMILES: CN(Cc1cccs1)c1cncc2sc(C(N)=O)c(N)c12]

3-amino-4-[methyl(thiophen-2-ylmethyl)amino]thieno[2,3-c]pyridine-2-carboxamide

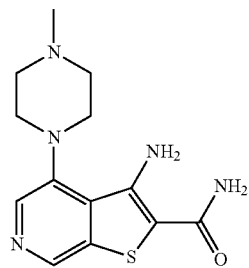 [SMILES: CN1CCN(c2cncc3sc(C(N)=O)c(N)c23)CC1]

3-amino-4-(4-methylpiperazin-1-yl)thieno[2,3-c]pyridine-2-carboxamide

4. Compound Characterization

With reasonable activity in the Tat-hybrid reporter assay, low toxicity in the MTT assay, and a nascent SAR profile, we embarked on structure-activity studies of the thienopyridine series. One of the first synthetic analogs examined was compound 2a derived from a thieno[2,3-c]pyridine ring system that is regioisomeric with the original hit compounds (FIG. 1). Gratifyingly, 2a analog exhibited sub-µM potency in both the Tat-hybrid assay and in a viral replication assay in U1 cells. The U1 cells contain an integrated and inducible HIV-1 provirus so this assay reports on inhibition of viral replication due to compound action occurring subsequent to retroviral genome integration (Table 1). The potency of analog 2a was similar to its directly analogous thieno[2,3-b]thionopyridine congener 1f in both assays (FIG. 1, Table 1). Subsequent SAR studies were focused on the thieno[2,3-c]thionopyridine ring system, which we found tractable synthetically even as it has been relatively underexplored as compared to thieno[2,3-b]thionopyridines.

Figure 3:
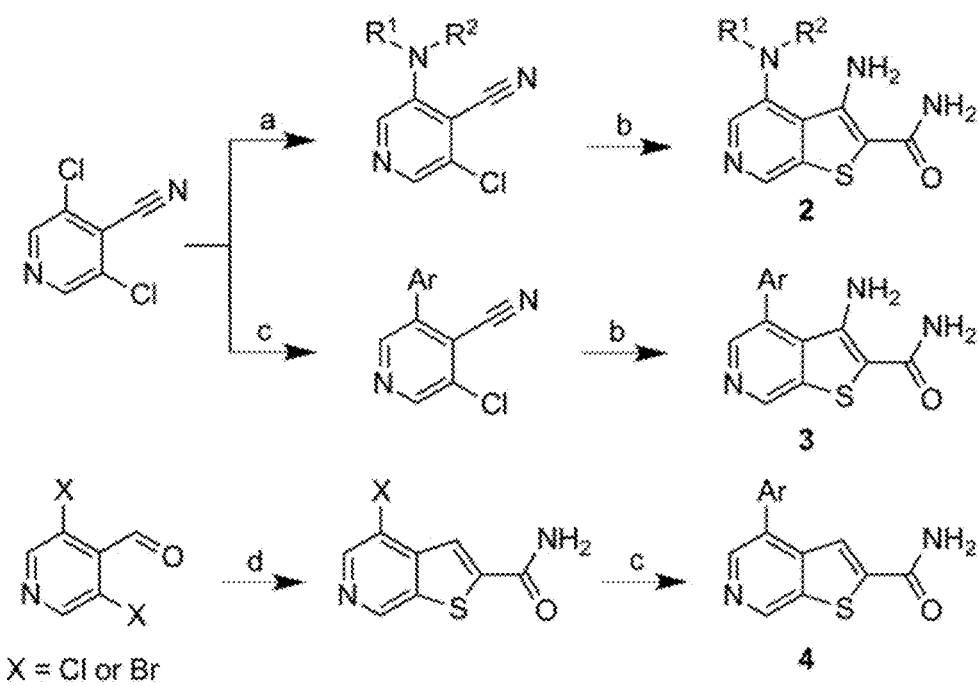
FIG. 3. Synthesis of thieno[2,3-c]pyridine analogs 2-4. Conditions: (a) 1-2 equiv. $R^1R^2NH$, $Et_3N$, DMF, 25-40° C., 12-24 hrs; (b) 2 equiv. 2-mercaptoacetamide, 10 wt % in MeOH/NH$_3$, 2 equiv. NaOMe, DMF, μW, 80° C., 10-60 min; (c) 1-2 equiv. Ar—B(OH)$_2$, 0.025 equiv PCy$_3$, 0.01 equiv. Pd$_2$(dba)$_3$, 1.7 equiv. K$_2$CO$_3$, dioxane, μW, 150° C., 30 min; (d) 0.75 equiv. 2-mercaptoacetamide, 10 wt % in MeOH/NH$_3$, 1.2 eq NaOMe, DMF, μW, 80° C., 10-60 min.

All thieno[2,3-c]pyridine analogs described herein were prepared by one of the three synthetic approaches described below (FIG. 3). Thus, the preparation of amine-bearing analogs 2 involved $S_NAr$ reaction of secondary amines with 3,5,-dichloro-4-pyridinecarbonitrile, followed by reaction with 2-mercaptoacetamide in the presence of sodium methoxide. Aryl and heteroaryl-substituted analogs 3 were prepared similarly, but beginning with Suzuki coupling reactions [Kudo, N.; Perseghini, M.; Fu, G. C. Angew. Chem., Int. Ed. 2006, 45, 1282-1284]. Finally, des-amino variants 4 were prepared from 3,5-dihalopyridinecarboxaldehyde via initial formation of the thieno[2,3-c]pyridine ring as before, followed by Suzuki coupling.

Figure 4:
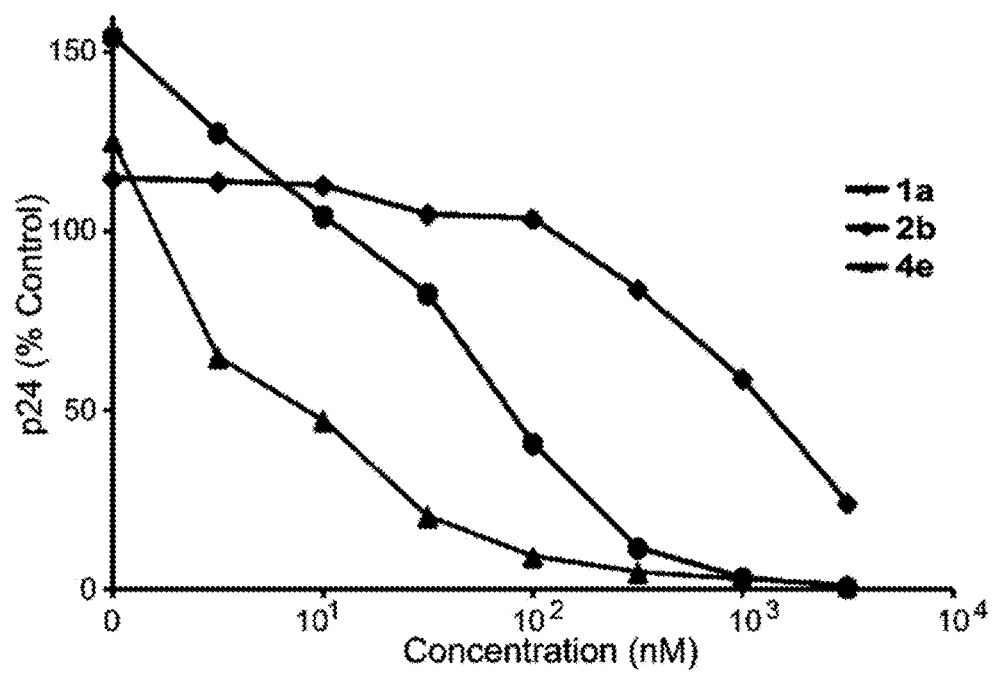
FIG. 4. Activity of Thienopyridine analogs 1a, 2b, and 4e in the U1 activation assay. U1 cells were plated in 96 well plates and activated by the addition of phytohemagglutinin. The test compounds were added to the cells at doses ranging from 1 nM to 3160 nM in triplicate and supernatants were collected 72 hours later. P24 values were determined by ELISA and average values for 1a (diamond), 2b (circle), and 4e (triangle) are shown.
Figure 5:
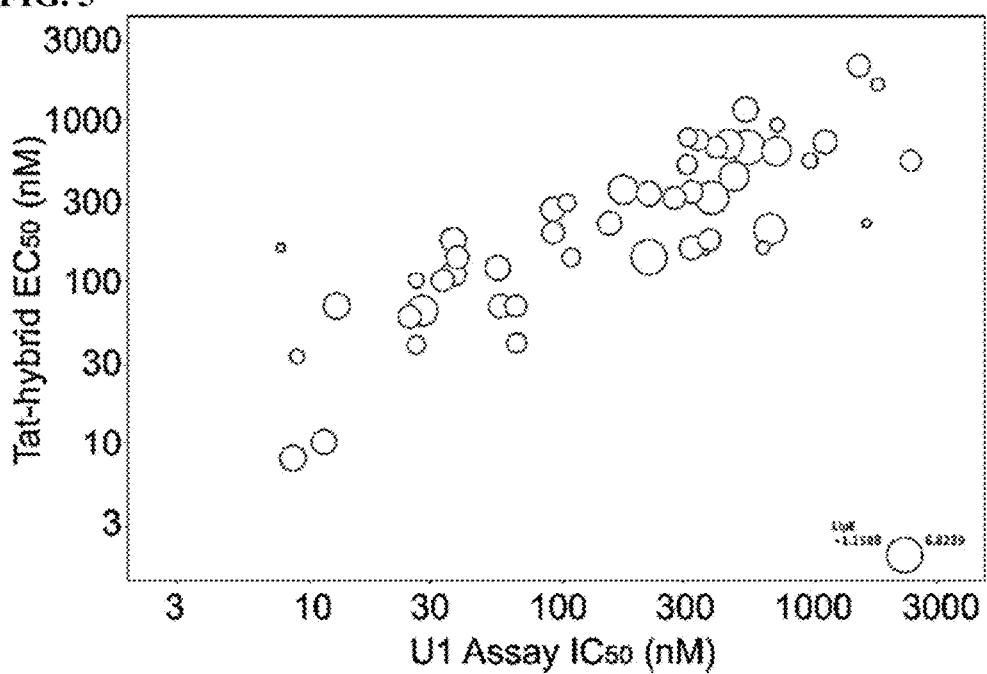
FIG. 5. Comparison of activities for thienopyridine analogs in the Tat-hybrid and U1 viral activation assays. Each data point is for one compound and the relative size indicates the LipE value for that compound.

New analogs were typically evaluated in both the Tat-hybrid assay, which reports on the Rev-RRE interaction, and in the viral activation assay in U1 cells (Table 1). Representative dose-response curves in the U1 assay are shown for analogs 2a, 2b, and 4e (FIG. 4). The U1 assay allowed us to assess antiviral activity of the new analogs in an assay that reports on the types of post-integration effects expected for a Rev-RRE inhibitors. In fact, the activities of ~50 synthetic thienopyridine analogs was well correlated in the two cell-based assays (FIG. 5), suggesting that compound activity remained "on-target" throughout the optimization of process.

Figure 6:
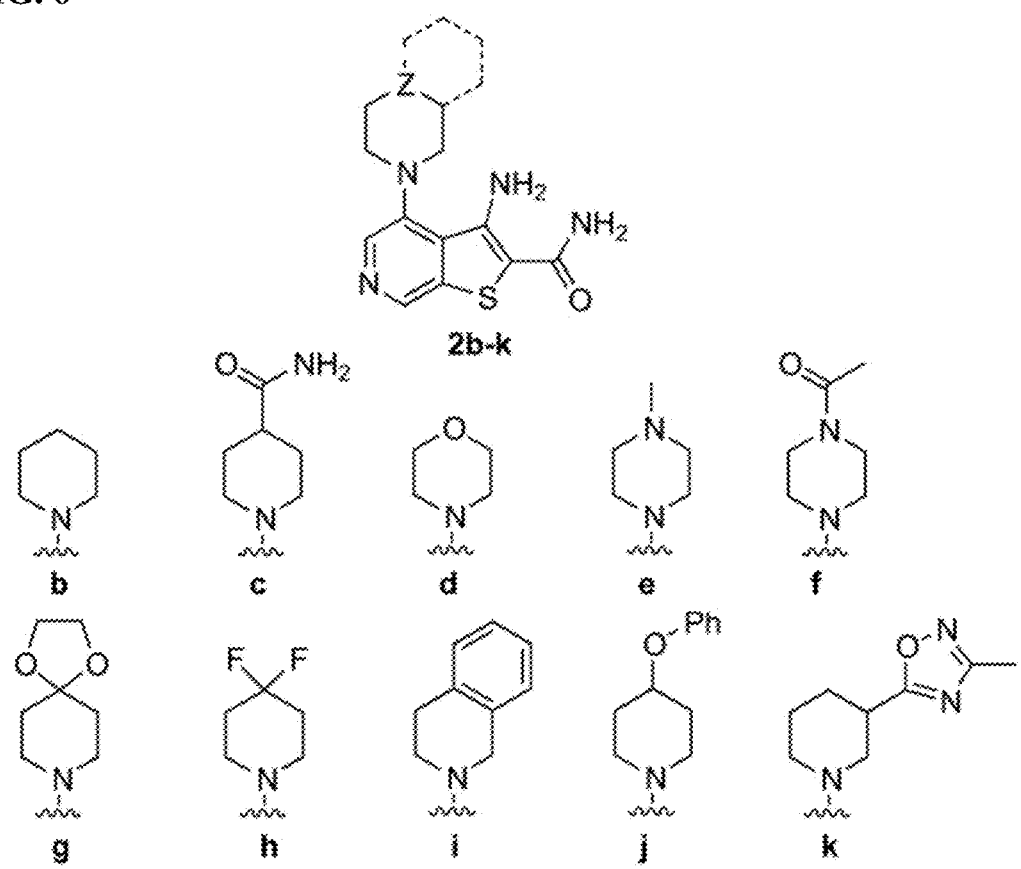
FIG. 6. Structures of thieno[2,3-c]pyridine analogs 2b-k

To further explore amine substitution as in analog 2a, additional analogs such as the piperidine 2b, morpholine 2d, and N-Me piperazine analog 2e were prepared and evaluated (FIG. 6 and Table 1). Piperidine analog 2b was nearly 10-fold more potent than dimethylamino analog 2a, an effect that appears to derive from the hydrophobicity of the ring since more hydrophilic piperidine rings (2c) as well as morpholine (2d) or piperazine (2e) rings at the same position led to less potent analogs. Spirocyclic (2g) and gem-diflouro (2h) substitutions at the 4-position proved inferior to the parent piperidine 2b. Tetrahydroquinoline (2i) and phenyl ether (2j) analogs were equipotent to 2b but with their additional mass and lipophilicity produced inferior LipE values. Finally, introduction of a heteroaryl ring at the 3-position of the piperidine ring as in 2k was poorly tolerated. Although N-acylpiperazine analog 2f was notably more potent than the basic N-methylpiperazine analog 2e, further exploration of piperazine acylation did not yield useful gains in potency.

Figure 7:
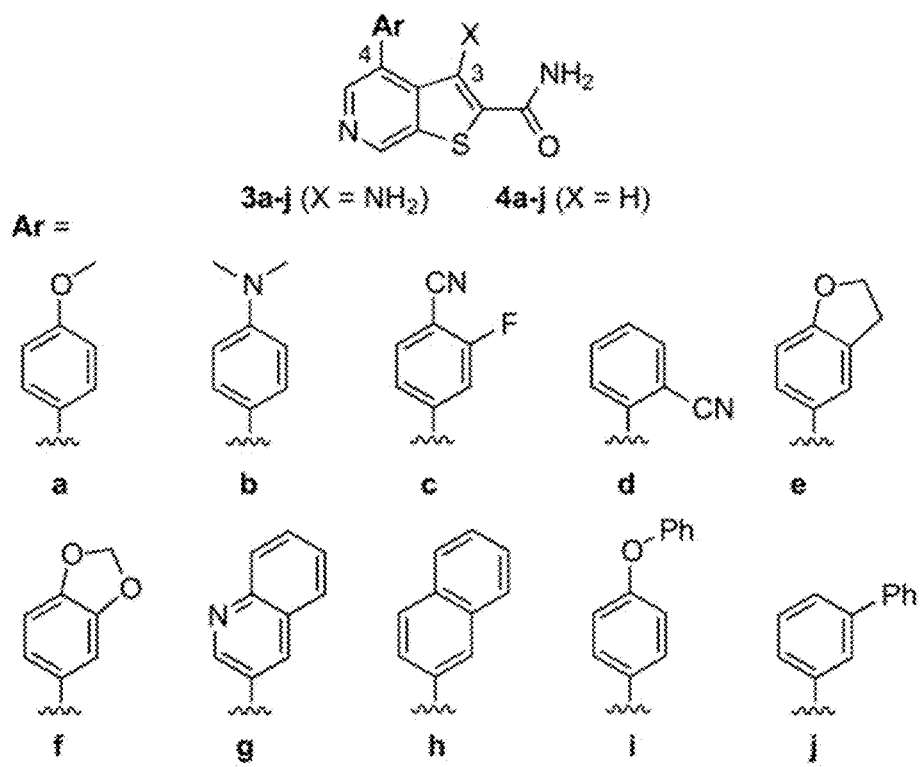
FIG. 7. Structures of thieno[2,3-c]pyridine analogs 3 and 4.

Having identified analogs like 2b and 2i that were up to ten-fold more potent than 2a, we next explored 4-aryl-substituted thienopyridine analogs either with (3a-j) or without (4a-j) a 3-amino group (FIG. 7 and Table 2).

TABLE 2

Activity of thienopyridine analogs 3 and 4 in reporter and antiviral assays.

| Compound | Tat-hybrid EC50 (nM) | U1 cell IC50 (nM) | Rev reporter EC50 (nM) | Jurkat HIV-1 replication assay (nM) | LipE[a] |
|---|---|---|---|---|---|
| 3a (1610) | A | A | — | — | 4.9 |
| 3b (1615) | B | A | — | — | 4.6 |
| 3e (1601) | B | A | — | — | 4.6 |
| 3f (1605) | B | B | — | — | 4.5 |
| 3j (1657) | C | — | — | — | 1.15 |
| 4a (1666) | A | A | B | A | 5.0 |
| 4c (1707) | B | B | — | — | 4.0 |
| 4d (1708) | C | C | — | — | 3.5 |
| 4e (1674) | A | A | B | A | 5.3 |
| 4f (1672) | A | A | — | — | 4.5 |
| 4g (1710) | A | A | — | A | 4.2 |
| 4h (1706) | A | A | — | A | 3.2 |
| 4i (1668) | B | A | — | — | 2.2 |
| 4j (1712) | B | B | — | — | 1.9 |

A = <100 nM; B = 100-500 nM; C = >500 nM.
[a]LipE = pKi – clogP; pKi estimated from Tat-hybrid EC50; clogP values were calculated in Vortex using the property XlogP.

In the case of substituted phenyl rings, we found substitution at the para and/or meta position(s) was favored over ortho substitution (compare 4c and 4d). Moderately electron-rich analogs like 3a/4a and 3e/4e were more potent than either electron-deficient congeners (4c) or more electron-rich analogs like 3f/4f. Consistent with substitution effects in the piperazine series (2k), bulky substitution at the 3-position (meta) as in 3j/4j was poorly tolerated. The clearest and most dramatic effect in this series was the favorable effect of removing the 3-amino group (as in analogs 4, X=H). Particularly potent were des-amino analogs bearing a moderately electron-rich aryl ring, as in the analogs 4a and 4e, which exhibited low-nM potency in both the Tat-hybrid and U1 assays and were the most potent analogs evaluated (Table 2).

Figure 8A:
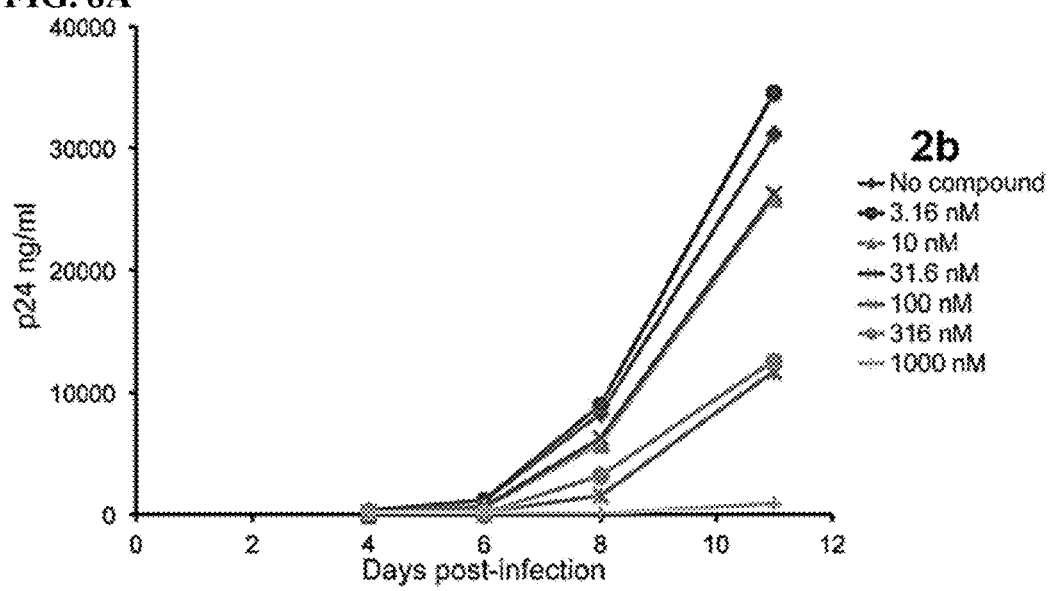
FIG. 8A-8C. Replication assays with HIV-1 isolate NL4-3 in Jurkat cells. Replication spreading assays were performed by infecting Jurkat cells with NL4-3 with compound at doses ranging from 3.16 nM to 1000 nM in triplicate. Supernatants were collected every 48-72 hours and p24 values were determined by ELISA.
Figure 8B:
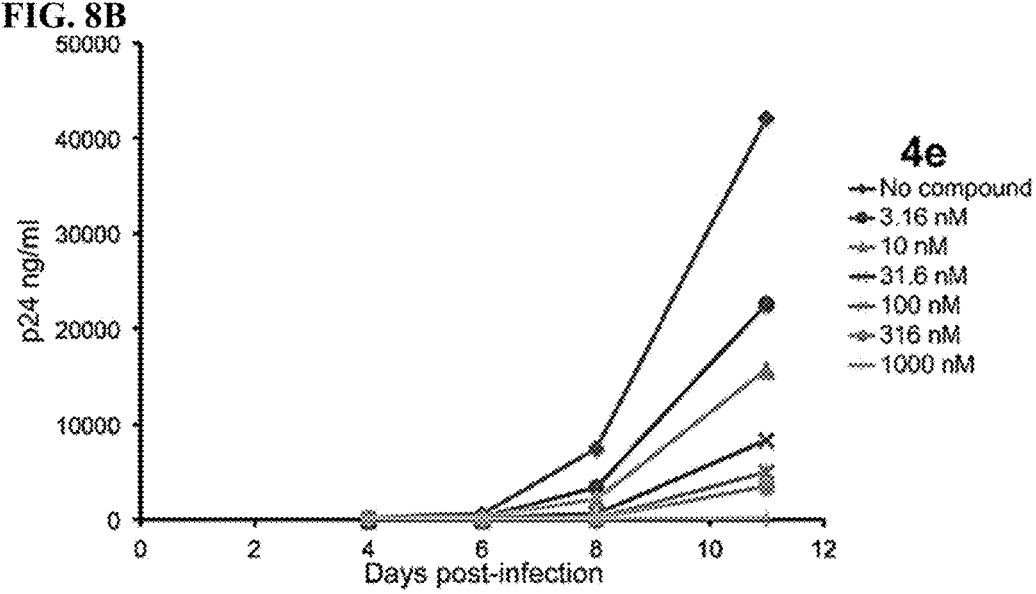
Figure 8C:
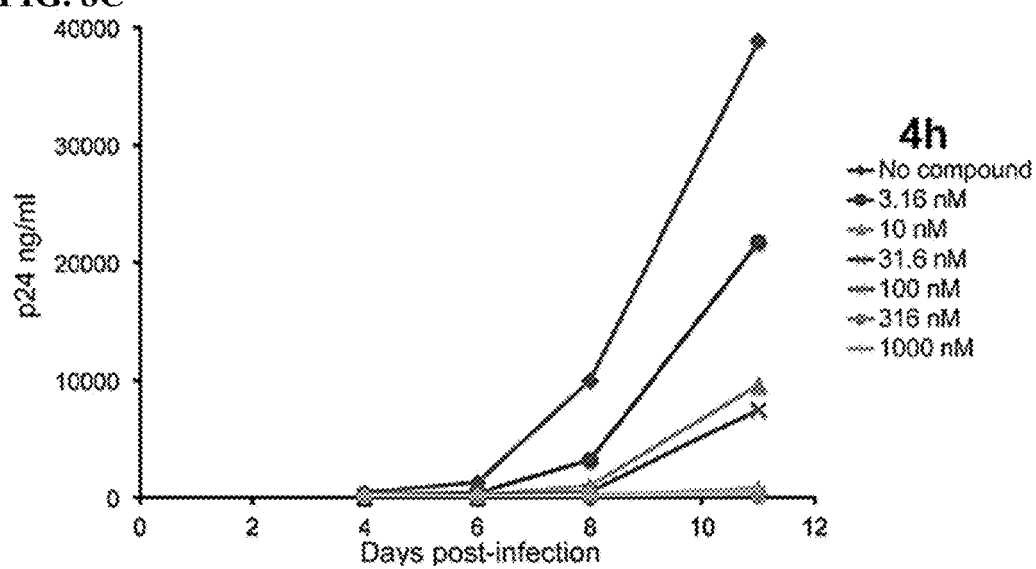

Analogs 4a and 4e combine exceptional potencies with reasonable calculated lipophilicities, thus affording very reasonable LipE ($pK_i$–clogP) values of 5.0 and 5.3, respectively. These analogs, along with the potent but more lipophilic analogs 4g and 4h were evaluated in an HIV-1 replication assay. Jurkat cells were infected with HIV-1 laboratory isolate NL4-3 in the presence of the test compounds and viral production was monitored by collecting viral supernatants and measuring p24 levels by ELISA assay. All four analogs displayed low-nM efficacy in this assay and moreover, their rank-order potencies in the infectivity assay were correlated with $IC_{50}$ values in the U1 activation assay (Table 2). Replication curves for two of the des-amino analogs 4e and 4h, are shown in FIG. 8 and toxicity was evaluated using the MTT cell viability method and the $TC_{50}$ was determined to be D (according to the scale D=<40,000 nM; E >40,000 nM). For comparison, AZT exhibited an $IC_{50}$ of A and $TC_{50}$ of E in these assays. The piperazine analog 2b was also evaluated in the infectivity assay and exhibited activities in the A range and a TC 50 of E (FIG. 8, analog 2b).

We next tested compound 4e in replication assays using primary cells and clinical isolates of HIV-1. Peripheral blood monocyte cells (PBMC) were stimulated with PHA and infected with several clinical isolates of HIV-1 in the presence of the compounds. Replication rates for the compounds determined again by collecting viral supernatants and measuring p24 levels by ELISA (Table 3).

TABLE 3

Activity of thienopyridine analog 4e in replication assays in PBMC.

| Viral Isolate | Coreceptor | IC50 (nM) |
|---|---|---|
| Ba-L | CCR5 | A |
| 93BR021 | CCR5 | A |
| 93BR028 | CCR5 | A |
| 92TH014 | CCR5 | A |
| 92UG005 | CXCR4 | A |
| 92HT599 | CXCR4 | A |
| LAI | CXCR4 | B |
| 92HT593 | CXCR4, CCR5 | A |

A = <100 nM; B = 100-500 nM; C = >500 nM.

Figure 9:
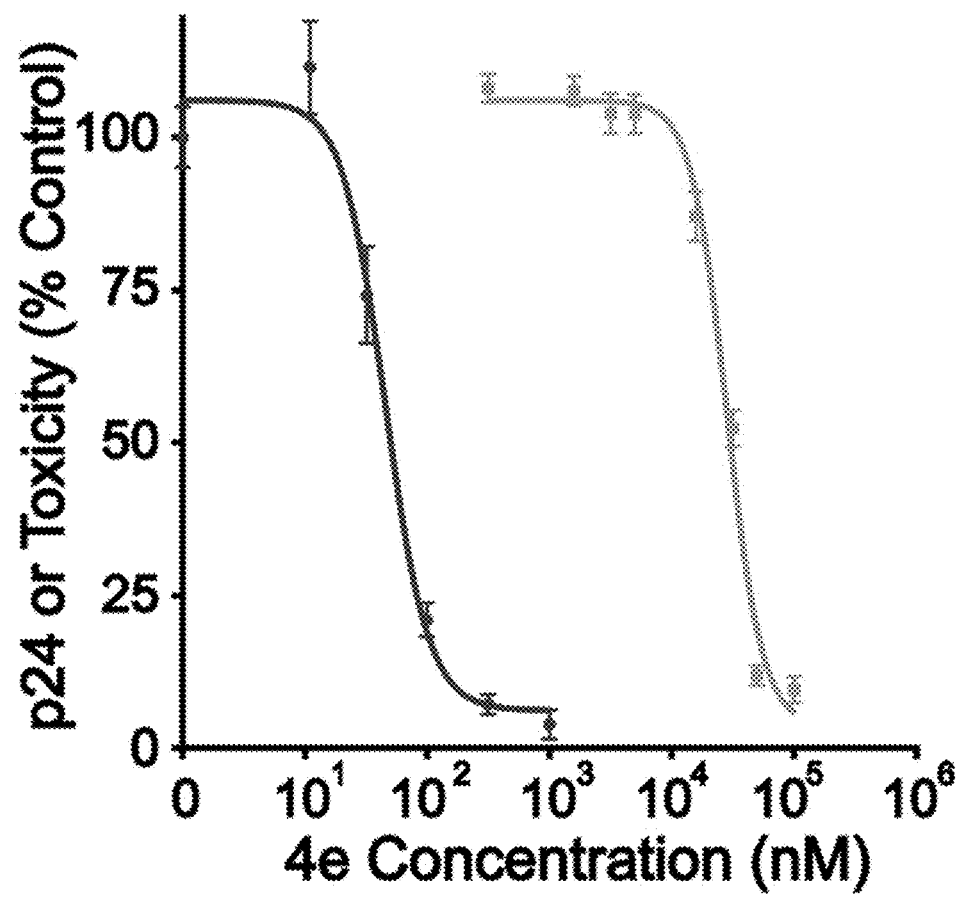
FIG. 9. Replication assay with HIV-1 primary isolate 93BR021 in PBMC. Replication assays were performed in PBMC by stimulating cells with phytohemagglutinin then infecting with clinical isolates of HIV. Compound 4e was added to PBMC at doses ranging from 1 nM to 1000 nM in triplicate or more, and supernatants were collected every 48-72 hours. p24 values were determined by ELISA and average replication curves are shown for 4e in circles (on the left) and toxicity is shown in squares (on the right).

Results of this experiment are shown in FIG. 9 where the replication and toxicity curves for isolate 93BR021 (CCR5-tropic, group M, subtype B) are shown. Here we observed an $IC_{50}$ value of A and therapeutic index of 533. AZT was again used as a positive control and exhibited an $IC_{50}$ of A and the $TC_{50}$ was determined to be D by MTT assay.

We next evaluated analogs 2b, 2f, 4a, and 4e in a panel of standard in vitro ADME assays to assess drug-like properties and the potential for efficacy in animals. All four analogs are "rule-of-five" compliant and exhibited moderate to high permeability across Caco-2 monolayers, a model of intestinal absorption (Table 4).

TABLE 4

In vitro ADME properties of selected thienopyridine analogs.

| Compound | Tat-hybrid EC 50 (nM) | Aqueous solubility pH 7.4 (μM) | Caco-2 $P_{app}$ (nm/sec) | HLM $T_{1/2}$ (min) |
|---|---|---|---|---|
| 2b | A | 34 | 505 | 28 |
| 2f | B | 258 | 97 | >60 |
| 4a | A | 0.44 | 594 | 8 |
| 4e | A | 0.28 | 666 | 18 |

A = <100 nM; B = 100-500 nM; C = >500 nM

Analogs 4a and 4e, with only two hydrogen bond donors, were more permeable but also notably less soluble than 2b and 2f. The more lipophilic analogs 4a and 4e also appear more prone to oxidative metabolism in the presence of human liver microsomes. This is perhaps unsurprising given the presence of methoxyphenyl (4a) and benzylic methylene (4e) functions, both potential sites of oxidative metabolism.

Here we used a screening approach based on the HIV LTR Tat-hybrid system to identify small molecules putatively targeting a protein-RNA interaction. A focused library of small molecule carboxamides was screened on the expectation that such molecules can interact with RNA bases and could potentially disrupt or alter Rev-RNA binding interactions. Of the various hits identified in the screen, a series of carboxamide-bearing thienopyridines emerged as the most promising hit scaffold. We then used an HIV reporter cell line and a U1 replication assay to validate the screening hits and to evaluate and additional ~100 commercial analogs. This analysis revealed that an unsubstituted carboxamide group at the 2-position of the thienopyridine ring was valuable for activity. Furthermore, substitution on the theinopyridine ring was well tolerated, particularly at the 4 and 5 positions. This initial survey of commercially available analogs provided a preliminary SAR profile that encouraged further synthetic efforts on the scaffold.

A variety of analogs were prepared based on a regioisomeric thieno[2,3-c]pyridine ring system. Substitution of 4 position with N-linked heteroaliphatic rings (2) or C-linked aryl and heteroaryl rings (3 and 4) was well tolerated, with the C-linked aryl analogs in general possessing superior potencies. Most significantly, we found that the 3-amino group is not essential for activity and in fact des-amino analogs in possess notably superior potencies in both the Tat-hybrid reporter assay and the U1 assay. The elimination of two hydrogen bond donors in such analogs likely improves intrinsic cell permeability. Of the des-amino analogs, compound 4e showed the best potencies and therapeutic indices in the reporter and U1 assays and the HIV replication assays, with an $EC_{50}$ of 8 nM in the reporter assay and $IC_{50}$ values of 9.0 nM and 4.0 nM in the U1 and HIV replication assays, respectively. By comparison, the most potent of the N-linked analogs, piperazine 2b, displayed an $EC_{50}$ of 65 nM in the reporter assay and $IC_{50}$ values of 28 nM and 76.8 nM in the U1 and HIV replication assays respectively. Overall, our structure activity studies improved potencies from the low μM to low nM regime. While further optimization of in vivo drug-like properties may be valuable, leads like 4e appear promising as a starting point for such efforts.

We tested selected compounds from our SAR studies (if, 2b, 4a and 4e) in a similar Rev-dependent reporter assay (Tables 1 and 2). Several additional experiments were described strongly suggesting that Rev is the target of the thienopyridines analogs, including additional reporter experiments that showed inhibition of a Rev-dependent, but not a CTE-dependent reporter, as well as experiments that showed that the protein composition of inhibitor-treated samples was consistent with an inhibitor of Rev function (Shuck-Lee D, et al Antimicrob Agents Chemother. 52:3169-3179; 2008).

Biochemical assays including EMSA did not show inhibition of the Rev-RRE interaction by the thienopyridine class in vitro. These assays generally capture a snapshot of Rev activity and lack critical interactions with cellular cofactors such as Crm1 and Ran. We have found that compounds that inhibit formation of RNA-protein complexes are often toxic, suggesting that EMSA or other in vitro assays may lack the sensitivity to reveal subtle effects of small molecule inhibitors. In some cases, such as with 3,6 diaminoacridine and neomycin B, inhibition of Rev-RRE formation is observed by EMSA, but both are toxic at therapeutic concentrations against HIV. Similarly, the thiophene class identified by the small molecule screen also inhibits the Rev-RRE interaction by EMSA, but several of the commercially available thiophene analogs showed substantial toxicity and thus were not pursued further. Interestingly, SAR analysis of the thiophenes and thienopyridines identified the thieonpyridine as a better scaffold that likely maintained similar binding characteristics.

Figure 17:
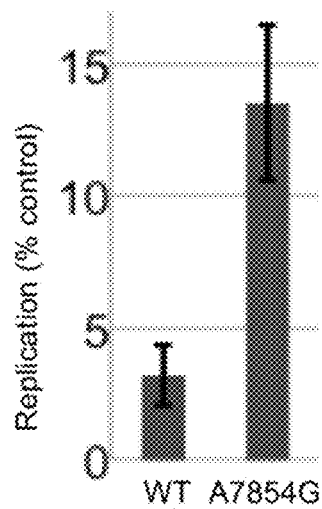
FIG. 17. The A7854G mutation in the RRE confers resistance to 62.5 nM 4e. Although we were initially concerned that the level of resistance conferred by the resistant-virus (IC50 5.1 nM) was nominal versus the NL4-3 control (IC50 6.2 nM), repeated analysis has shown that resistance is clear, especially at higher concentrations of compound. For example at 62.5 nM of compound 4e, viral replication occurs at a 4-fold higher rate than the control. Notably, the IC50 is significantly higher for the A7854G mutant (IC50 218.5 nM) versus the control (IC50 25.9 nM). This result suggests that the target of the thienopyridine compounds is the RRE.

Although our studies implicate Rev as the likely target of thienopyridine carboxamides, other targets may also be of interest. For example, our screen is dependent upon the activity of the HIV LTR, and thus an inhibitor of HIV transcription would also produce a positive response in the assay. However, this would appear unlikely because we showed that the thienopyridine compound 4a specifically targets the Rev-RRE reporter, but not the HIV Tat-TAR reporter, using the Tat-hybrid assay. The previous screen did not use the HIV LTR and these investigators further uncovered a thienopyridine resistance mutation in the RRE, consistent with the Rev-RRE interaction as the target of thienopyridines. We have also generated this RRE-defective virus and shown that it is resistant to compound 4e (FIG. 17). Though strongly supportive that Rev is the target of the compounds.

This work represents an early but important step toward the development of a new class of HIV therapeutics that could eventually find a place in future HIV combination therapies. While the weight of evidence suggests these compounds act by inhibition of the Rev-RRE interaction, further studies will be required to definitively establish their molecular pharmacology

TABLE 5

| 5. Compounds | |
|---|---|
| Compound | Assay Result: |
| AGS1674 | Tat hybrid EC50 (nM): A<br>Tat hybrid TC50 (nM): E<br>U1 IC50 (nM): A<br>U1 TC50 (nM): D<br>Jurkat replication IC50 (nM): A<br>Jurkat TC50 (nM): D |
| AGS1666 | Tat hybrid EC50 (nM): A<br>Tat hybrid TC50 (nM): D<br>U1 IC50 (nM): A<br>U1 TC50 (nM): D<br>Jurkat replication IC50 (nM): A<br>Jurkat TC50 (nM): D |
| AGS1706 | Tat hybrid EC50 (nM): A<br>Tat hybrid TC50 (nM): E<br>U1 IC50 (nM): A<br>U1 TC50 (nM): D<br>Jurkat replication IC50 (nM): A<br>Jurkat TC50 (nM): D |

TABLE 5-continued

5. Compounds

| Compound | Assay Result: |
|---|---|
| AGS1670 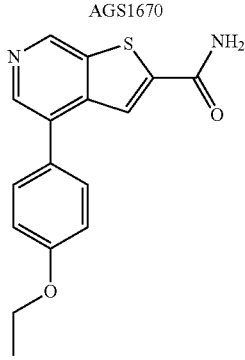 | Tat hybrid EC50 (nM): A<br>Tat hybrid TC50 (nM): D<br>U1 IC50 (nM): A<br>U1 TC50 (nM): D |
| AGS1710 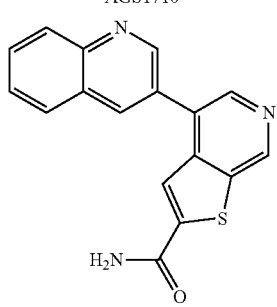 | Tat hybrid EC50 (nM): A<br>Tat hybrid TC50 (nM): E<br>U1 IC50 (nM): A<br>U1 TC50 (nM): E<br>Jurkat replication IC50 (nM): A<br>Jurkat TC50 (nM): E |
| AGS1676 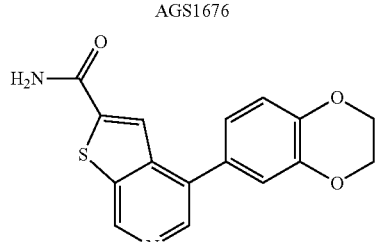 | Tat hybrid EC50 (nM): A<br>Tat hybrid TC50 (nM): D<br>U1 IC50 (nM): A<br>U1 TC50 (nM): D |
| AGS1558 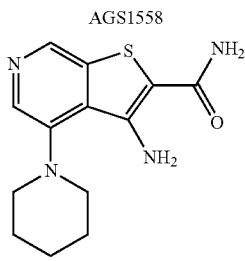 | Tat hybrid EC50 (nM): A<br>Tat hybrid TC50 (nM): E<br>U1 IC50 (nM): A<br>U1 TC50 (nM): D<br>Jurkat replication IC50 (nM): A<br>Jurkat TC50 (nM): E |
| AGS1604 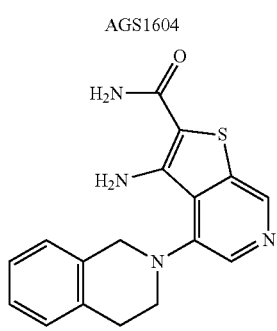 | Tat hybrid EC50 (nM): A<br>Tat hybrid TC50 (nM): D<br>U1 IC50 (nM): A<br>U1 TC50 (nM): D |

TABLE 5-continued
| 5. Compounds | |
|---|---|
| Compound | Assay Result: |
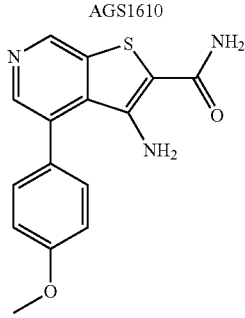 [SMILES: COc1ccc(-c2cncc3sc(C(N)=O)c(N)c23)cc1]
AGS1610
Tat hybrid EC50 (nM): A
Tat hybrid TC50 (nM): D
U1 IC50 (nM): A
U1 TC50 (nM): E
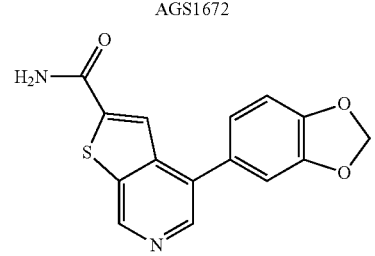 [SMILES: NC(=O)c1cc2c(-c3ccc4c(c3)OCO4)cncc2s1]
AGS1672
Tat hybrid EC50 (nM): A
Tat hybrid TC50 (nM): D
U1 IC50 (nM): A
U1 TC50 (nM): D
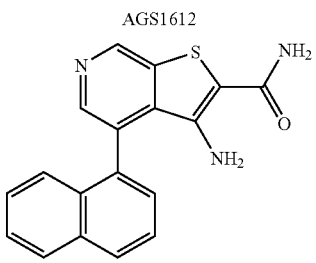 [SMILES: NC(=O)c1sc2cncc(-c3cccc4ccccc34)c2c1N]
AGS1612
Tat hybrid EC50 (nM): B
Tat hybrid TC50 (nM): E
U1 IC50 (nM): A
U1 TC50 (nM): D
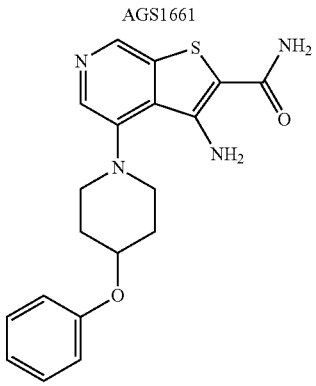 [SMILES: NC(=O)c1sc2cncc(N3CCC(Oc4ccccc4)CC3)c2c1N]
AGS1661
Tat hybrid EC50 (nM): B
Tat hybrid TC50 (nM): E
U1 IC50 (nM): A
U1 TC50 (nM): D 151 152
TABLE 5-continued
5. Compounds
| Compound | Assay Result: |
|---|---|
| AGS1654 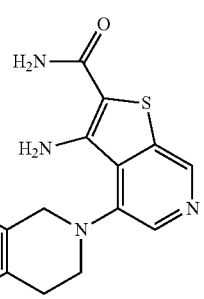 | Tat hybrid EC50 (nM): B<br>Tat hybrid TC50 (nM): D<br>U1 IC50 (nM): A<br>U1 TC50 (nM): D |
| AGS1653 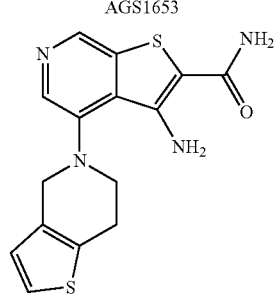 | Tat hybrid EC50 (nM): B<br>Tat hybrid TC50 (nM): E<br>U1 IC50 (nM): A<br>U1 TC50 (nM): D |
| AGS1615 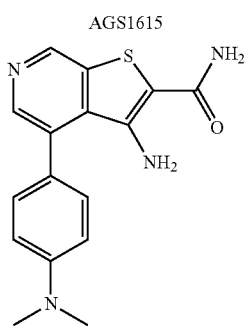 | Tat hybrid EC50 (nM): B<br>Tat hybrid TC50 (nM): D<br>U1 IC50 (nM): A<br>U1 TC50 (nM): E |
| AGS1707 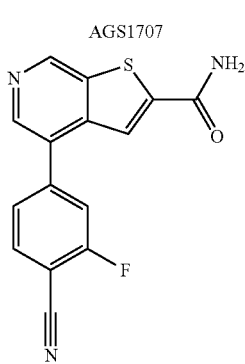 | Tat hybrid EC50 (nM): B<br>Tat hybrid TC50 (nM): E<br>U1 IC50 (nM): B |

TABLE 5-continued
| 5. Compounds | |
|---|---|
| Compound | Assay Result: |
| AGS1570 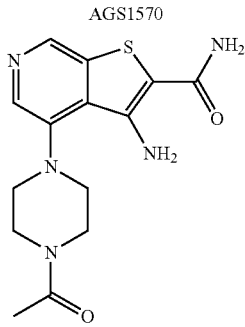 [SMILES: CC(=O)N1CCN(c2cncc3sc(C(N)=O)c(N)c23)CC1] | Tat hybrid EC50 (nM): B<br>Tat hybrid TC50 (nM): E<br>U1 IC50 (nM): B<br>U1 TC50 (nM): E<br>Jurkat replication IC50 (nM): C<br>Jurkat TC50 (nM): E |
| AGS1712 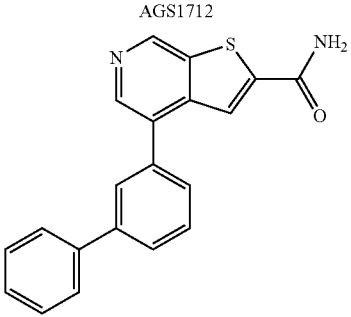 [SMILES: NC(=O)c1cc2c(-c3cccc(-c4ccccc4)c3)cncc2s1] | Tat hybrid EC50 (nM): B<br>Tat hybrid TC50 (nM): E<br>U1 IC50 (nM): B<br>U1 TC50 (nM): D |
| AGS1668 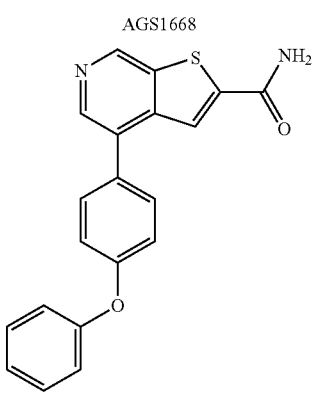 [SMILES: NC(=O)c1cc2c(-c3ccc(Oc4ccccc4)cc3)cncc2s1] | Tat hybrid EC50 (nM): B<br>Tat hybrid TC50 (nM): D<br>U1 IC50 (nM): B |
| AGS1703 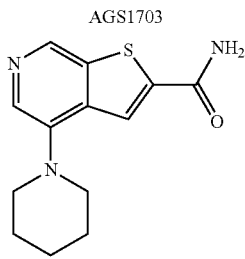 [SMILES: NC(=O)c1cc2c(N3CCCCC3)cncc2s1] | Tat hybrid EC50 (nM): B<br>Tat hybrid TC50 (nM): E<br>U1 IC50 (nM): B<br>U1 TC50 (nM): D |

TABLE 5-continued

| 5. Compounds | |
|---|---|
| Compound | Assay Result: |
| AGS1709 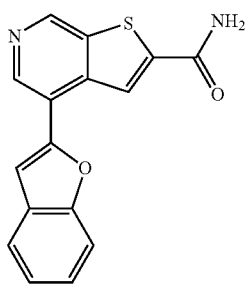 | Tat hybrid EC50 (nM): B<br>Tat hybrid TC50 (nM): E<br>U1 IC50 (nM): C<br>U1 TC50 (nM): D |
| AGS1656 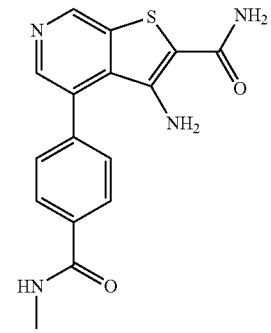 | Tat hybrid EC50 (nM): B<br>Tat hybrid TC50 (nM): D<br>U1 IC50 (nM): A<br>U1 TC50 (nM): E |
| AGS1618 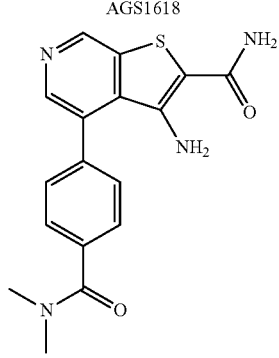 [SMILES: CN(C)C(=O)c1ccc(-c2cncc3sc(C(N)=O)c(N)c23)cc1] | Tat hybrid EC50 (nM): B<br>Tat hybrid TC50 (nM): D<br>U1 IC50 (nM): B<br>U1 TC50 (nM): E |
| AGS1601 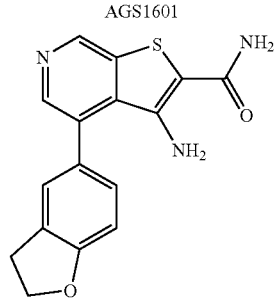 [SMILES: NC(=O)c1sc2cncc(-c3ccc4c(c3)CCO4)c2c1N] | Tat hybrid EC50 (nM): B<br>Tat hybrid TC50 (nM): D<br>U1 IC50 (nM): A<br>U1 TC50 (nM): E |
| AGS1560 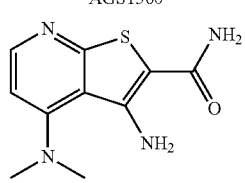 | Tat hybrid EC50 (nM): B<br>Tat hybrid TC50 (nM): E<br>U1 IC50 (nM): C<br>U1 TC50 (nM): E |

TABLE 5-continued

| 5. Compounds | |
|---|---|
| Compound | Assay Result: |
| AGS1613 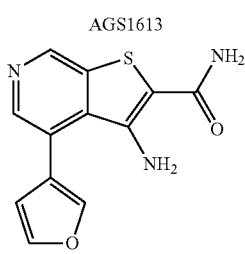 [SMILES: NC(=O)c1sc2cncc(-c3ccoc3)c2c1N] | Tat hybrid EC50 (nM): B<br>Tat hybrid TC50 (nM): E<br>U1 IC50 (nM): B<br>U1 TC50 (nM): D |
| AGS1711 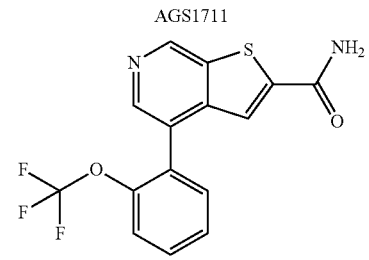 [SMILES: NC(=O)c1cc2c(-c3ccccc3OC(F)(F)F)cncc2s1] | Tat hybrid EC50 (nM): A<br>Tat hybrid TC50 (nM): E<br>U1 IC50 (nM): C<br>U1 TC50 (nM): D |
| AGS1665 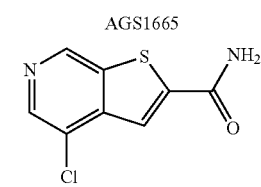 [SMILES: NC(=O)c1cc2c(Cl)cncc2s1] | Tat hybrid EC50 (nM): B<br>Tat hybrid TC50 (nM): D<br>U1 IC50 (nM): A<br>U1 TC50 (nM): D |
| AGS1606 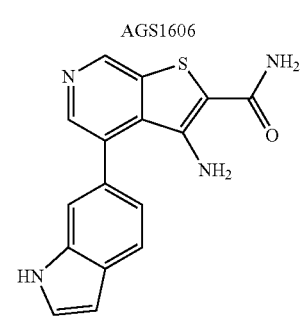 [SMILES: NC(=O)c1sc2cncc(-c3ccc4cc[nH]c4c3)c2c1N] | Tat hybrid EC50 (nM): B<br>Tat hybrid TC50 (nM): E<br>U1 IC50 (nM): B<br>U1 TC50 (nM): E |
| AGS1605 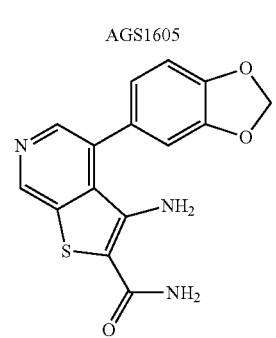 [SMILES: NC(=O)c1sc2cncc(-c3ccc4c(c3)OCO4)c2c1N] | Tat hybrid EC50 (nM): B<br>Tat hybrid TC50 (nM): D<br>U1 IC50 (nM): B<br>U1 TC50 (nM): E |

TABLE 5-continued
| 5. Compounds | |
|---|---|
| Compound | Assay Result: |
| AGS1617 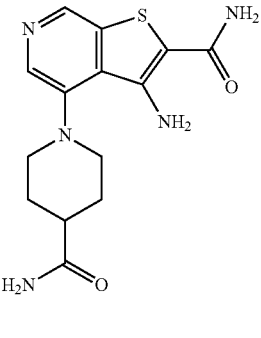 | Tat hybrid EC50 (nM): B<br>Tat hybrid TC50 (nM): D<br>U1 IC50 (nM): B<br>U1 TC50 (nM): E |
| AGS1649 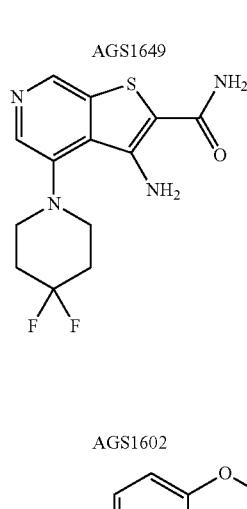 | Tat hybrid EC50 (nM): B<br>Tat hybrid TC50 (nM): D<br>U1 IC50 (nM): B<br>U1 TC50 (nM): E |
| AGS1602 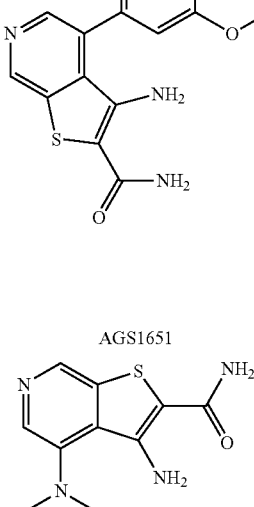 | Tat hybrid EC50 (nM): B<br>Tat hybrid TC50 (nM): D<br>U1 IC50 (nM): B<br>U1 TC50 (nM): E |
| AGS1651 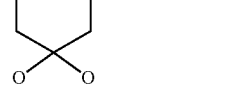 | Tat hybrid EC50 (nM): B<br>Tat hybrid TC50 (nM): D<br>U1 IC50 (nM): B<br>U1 TC50 (nM): E |

TABLE 5-continued

| 5. Compounds | |
|---|---|
| Compound | Assay Result: |
| AGS1704 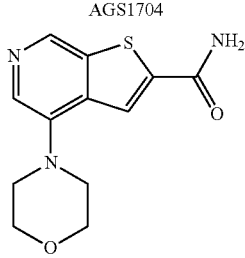 [SMILES: NC(=O)c1cc2c(N3CCOCC3)cncc2s1] | Tat hybrid EC50 (nM): B<br>Tat hybrid TC50 (nM): E<br>U1 IC50 (nM): B<br>U1 TC50 (nM): D |
| AGS1611 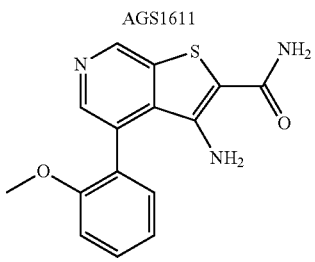 [SMILES: COc1ccccc1-c1cncc2sc(C(N)=O)c(N)c12] | Tat hybrid EC50 (nM): C<br>Tat hybrid TC50 (nM): E<br>U1 IC50 (nM): B<br>U1 TC50 (nM): E |
| AGS1708 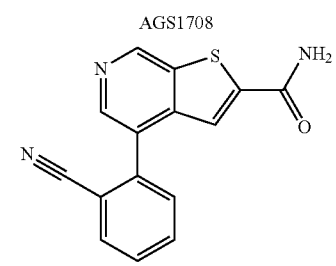 [SMILES: N#Cc1ccccc1-c1cncc2sc(C(N)=O)cc12] | Tat hybrid EC50 (nM): C<br>Tat hybrid TC50 (nM): E<br>U1 IC50 (nM): C<br>U1 TC50 (nM): E |
| AGS1713 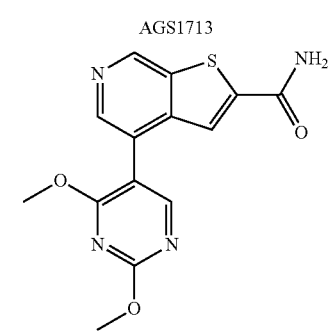 [SMILES: COc1ncc(-c2cncc3sc(C(N)=O)cc23)c(OC)n1] | Tat hybrid EC50 (nM): C<br>Tat hybrid TC50 (nM): E<br>U1 IC50 (nM): C<br>U1 TC50 (nM): E |
| AGS1614 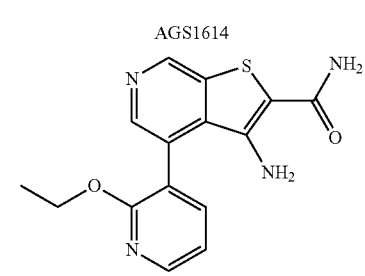 [SMILES: CCOc1ncccc1-c1cncc2sc(C(N)=O)c(N)c12] | Tat hybrid EC50 (nM): C<br>Tat hybrid TC50 (nM): E<br>U1 IC50 (nM): B<br>U1 TC50 (nM): E |

TABLE 5-continued

5. Compounds

| Compound | Assay Result: |
|---|---|
| AGS1658 | Tat hybrid EC50 (nM): C<br>Tat hybrid TC50 (nM): D<br>U1 IC50 (nM): C<br>U1 TC50 (nM): E |
| AGS1556 | Tat hybrid EC50 (nM): C<br>Tat hybrid TC50 (nM): D<br>U1 IC50 (nM): B<br>U1 TC50 (nM): E |
| AGS1662 | Tat hybrid EC50 (nM): C<br>Tat hybrid TC50 (nM): D<br>U1 IC50 (nM): C<br>U1 TC50 (nM): E |
| AGS1616 | Tat hybrid EC50 (nM): C<br>Tat hybrid TC50 (nM): D<br>U1 IC50 (nM): B<br>U1 TC50 (nM): E |
| AGS1659 | Tat hybrid EC50 (nM): C<br>Tat hybrid TC50 (nM): D<br>U1 IC50 (nM): C<br>U1 TC50 (nM): D |

TABLE 5-continued

| 5. Compounds | |
|---|---|
| Compound | Assay Result: |
| AGS1557 | Tat hybrid EC50 (nM): C<br>Tat hybrid TC50 (nM): D |
| AGS1619 | Tat hybrid EC50 (nM): C<br>Tat hybrid TC50 (nM): D |
| AGS1567 | Tat hybrid EC50 (nM): C<br>Tat hybrid TC50 (nM): D |
| AGS1569 | Tat hybrid EC50 (nM): C<br>Tat hybrid TC50 (nM): D |

TABLE 5-continued

5. Compounds

| Compound | Assay Result: |
|---|---|
| AGS1571 | Tat hybrid EC50 (nM): C<br>Tat hybrid TC50 (nM): D |
| AGS1568 | Tat hybrid EC50 (nM): C<br>Tat hybrid TC50 (nM): D |
| AGS1663 | Tat hybrid EC50 (nM): C<br>Tat hybrid TC50 (nM): D |
| AGS1660 | Tat hybrid EC50 (nM): C<br>Tat hybrid TC50 (nM): D |

TABLE 5-continued
5. Compounds
| Compound | Assay Result: |
|---|---|
| AGS1607 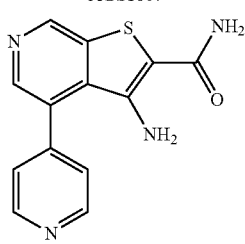 | Tat hybrid EC50 (nM): C<br>Tat hybrid TC50 (nM): E |
| AGS1577 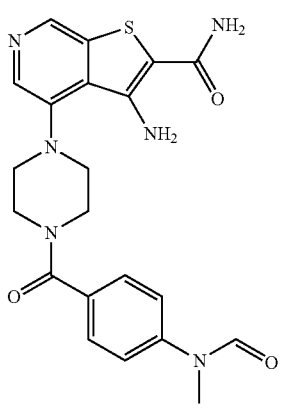 | Tat hybrid EC50 (nM): C<br>Tat hybrid TC50 (nM): D |
| AGS1572 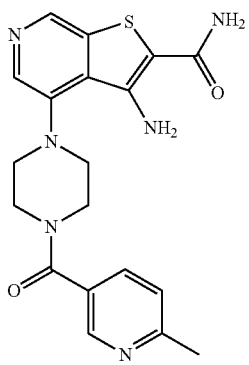 | Tat hybrid EC50 (nM): C<br>Tat hybrid TC50 (nM): D |
| AGS1573 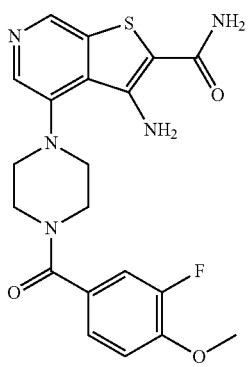 | Tat hybrid EC50 (nM): C<br>Tat hybrid TC50 (nM): D |

TABLE 5-continued
| 5. Compounds | |
|---|---|
| Compound | Assay Result: |
| AGS1608 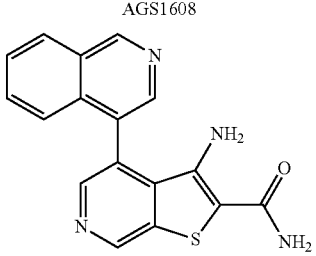 [SMILES: NC(=O)c1sc2cncc(-c3cncc4ccccc34)c2c1N] | Tat hybrid EC50 (nM): C<br>Tat hybrid TC50 (nM): E |
| AGS1657 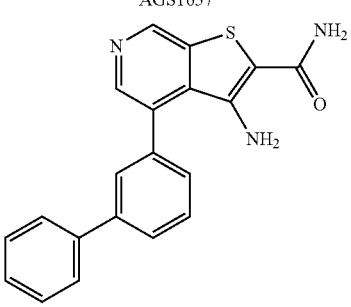 | Tat hybrid EC50 (nM): C<br>Tat hybrid TC50 (nM): D |
| AGS1705 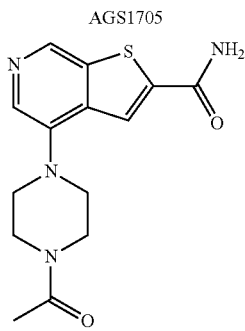 [SMILES: CC(=O)N1CCN(c2cncc3sc(C(N)=O)cc23)CC1] | Tat hybrid EC50 (nM): C<br>Tat hybrid TC50 (nM): E |
| AGS1559 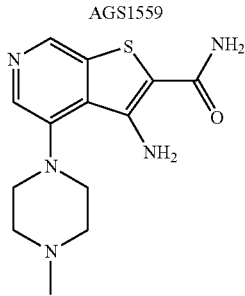 [SMILES: CN1CCN(c2cncc3sc(C(N)=O)c(N)c23)CC1] | Tat hybrid EC50 (nM): C<br>Tat hybrid TC50 (nM): D |

TABLE 5-continued
| 5. Compounds ||
|---|---|
| Compound | Assay Result: |
| AGS1574 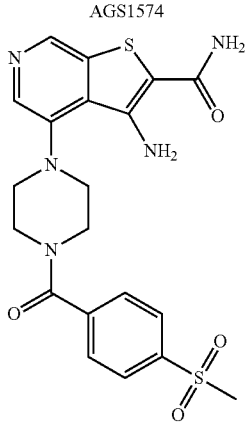 [SMILES: CS(=O)(=O)c1ccc(C(=O)N2CCN(c3cncc4sc(C(N)=O)c(N)c34)CC2)cc1] | Tat hybrid EC50 (nM): C<br>Tat hybrid TC50 (nM): D |
| AGS1575 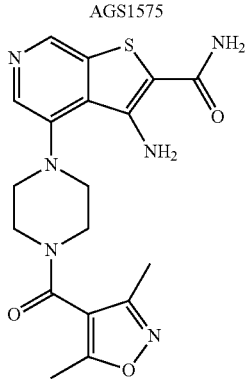 [SMILES: Cc1noc(C)c1C(=O)N1CCN(c2cncc3sc(C(N)=O)c(N)c23)CC1] | Tat hybrid EC50 (nM): C<br>Tat hybrid TC50 (nM): D |
| AGS1576 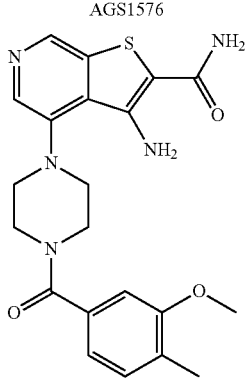 [SMILES: COc1cc(C(=O)N2CCN(c3cncc4sc(C(N)=O)c(N)c34)CC2)ccc1C] | Tat hybrid EC50 (nM): C<br>Tat hybrid TC50 (nM): D |
| AGS1609 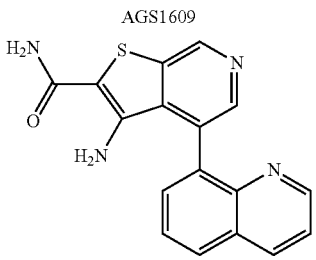 [SMILES: NC(=O)c1sc2cncc(-c3cccc4cccnc34)c2c1N] | Tat hybrid EC50 (nM): A<br>Tat hybrid TC50 (nM): E |

TABLE 5-continued

| 5. Compounds | |
|---|---|
| Compound | Assay Result: |
| AGS1664 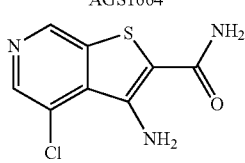 | Tat hybrid EC50 (nM): C<br>Tat hybrid TC50 (nM): D |
| AGS1603 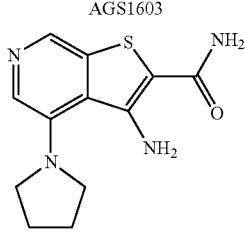 [SMILES: NC(=O)c1sc2cncc(N3CCCC3)c2c1N] | U1 IC50 (nM): B<br>U1 TC50 (nM): E |
| AGS1600 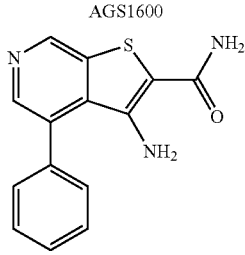 [SMILES: NC(=O)c1sc2cncc(-c3ccccc3)c2c1N] | U1 IC50 (nM): B<br>U1 TC50 (nM): E |

Table 5 key: A = <100 nM; B = 100-500 nM; C = >500 nM; D = <40,000 nM; E > 40,000 nM.

TABLE 6

| Additional compounds for treatment | |
|---|---|
| Compound | Assay Result |
| AGS1642 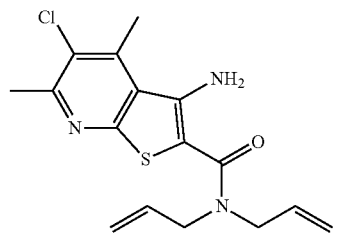 | Tat hybrid % inhibition at 5,000 nM: Z<br>Tat hybrid cell viability at 50,000 nM: X<br>U1% inhibition at 10,000 nm: Z |
| AGS1283 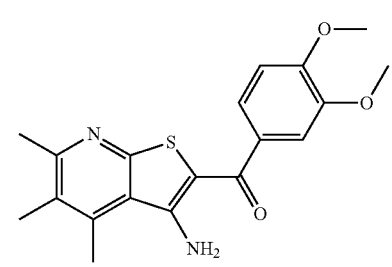 | Tat hybrid % inhibition at 5,000 nM: Z<br>Tat hybrid cell viability at 50,000 nM: X<br>U1% inhibition at 10,000 nM: Z |

TABLE 6-continued

Additional compounds for treatment

| Compound | Assay Result |
|---|---|
| AGS1630 | Tat hybrid % inhibition at 5,000 nM: Z<br>Tat hybrid cell viability at 50,000 nM: X<br>U1% inhibition at 10,000 nm: Z |
| AGS1539 | Tat hybrid % inhibition at 5,000 nM: Z<br>Tat hybrid cell viability at 50,000 nM: X<br>U1% inhibition at 10,000 nm: Z |
| AGS1528 | Tat hybrid % inhibition at 5,000 nM: Z<br>Tat hybrid cell viability at 50,000 nM: X<br>U1% inhibition at 10,000 nm: Z |
| AGS1631 | Tat hybrid % inhibition at 5,000 nM: Z<br>Tat hybrid cell viability at 50,000 nM: X<br>U1% inhibition at 10,000 nm: Z |
| AGS1537 | Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
|---|---|
| AGS1579 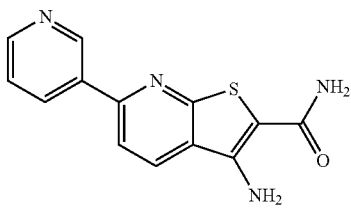 | Tat hydrid EC50 (nM): C<br>Tat hydrid EC50 (nM): D<br>Tat hybrid % inhibition at 5,000 nM: Z<br>Tat hydrid cell viability at 50,000 nM: X<br>U1% inhibition at 10,000 nm: Z |
| AGS1280 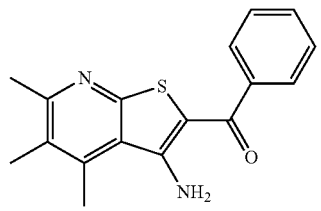 | Tat hybrid % inhibition at 5,000 nM: Z<br>Tat hybrid cell viability at 50,000 nM: X<br>U1% inhibition at 10,000 nm: Z |
| AGS1538 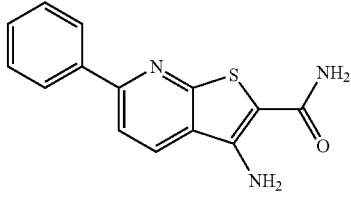 | Tat hybrid % inhibition at 5,000 nM: Z<br>Tat hybrid cell viability at 50,000 nM: X<br>U1% inhibition at 10,000 nm: Z |
| AGS1625 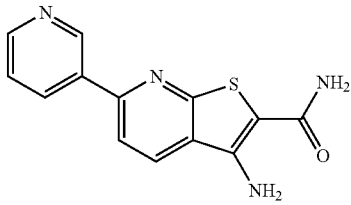 | Tat hybrid % inhibition at 5,000 nM: Z<br>Tat hybrid cell viability at 50,000 nM: X<br>U1% inhibition at 10,000 nm: Z |
| AGS1540 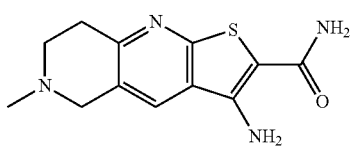 | Tat hybrid % inhibition at 5,000 nM: Z<br>Tat hybrid cell viability at 50,000 nM: X<br>U1% inhibition at 10,000 nm: Z |
| AGS1285 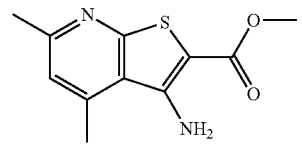 | Tat hybrid EC50 (nM): C<br>Tat hybrid EC50 (nM): E<br>Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
|---|---|
| AGS1282 | Tat hybrid % inhibition at 5,000 nM: Z<br>Tat hybrid cell viability at 50,000 nM: X<br>U1% inhibition at 10,000 nm: Z |
| AGS1295 | Tat hybrid % inhibition at 5,000 nM: Z<br>Tat hybrid cell viability at 50,000 nM: X<br>U1% inhibition at 10,000 nm: Z |
| AGS1531 | Tat hybrid % inhibition at 5,000 nM: Z<br>Tat hybrid cell viability at 50,000 nM: X<br>U1% inhibition at 10,000 nm: Z |
| AGS1281 | Tat hybrid % inhibition at 5,000 nM: Z<br>Tat hybrid cell viability at 50,000 nM: X<br>U1% inhibition at 10,000 nm: Z |
| AGS1275 | Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
|---|---|
| AGS1596 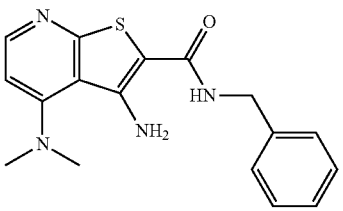 | Tat hybrid % inhibition at 5,000 nM: Z<br>Tat hybrid cell viability at 50,000 nM: Y<br>U1% inhibition at 10,000 nm: Z |
| AGS1622 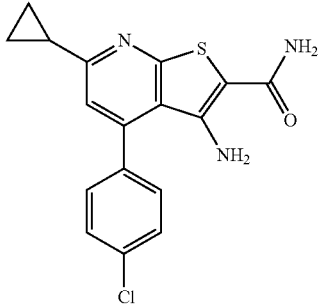 | Tat hybrid % inhibition at 5,000 nM: Z<br>Tat hybrid cell viability at 50,000 nM: Y<br>U1% inhibition at 10,000 nm: Z |
| AGS1519 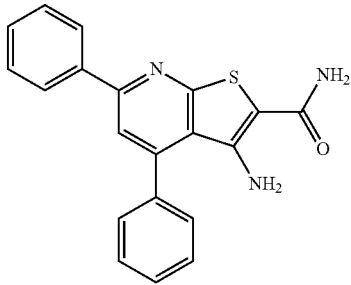 | Tat hybrid % inhibition at 5,000 nM: Z<br>Tat hybrid cell viability at 50,000 nM: Z<br>U1% inhibition at 10,000 nm: Z |
| AGS1525 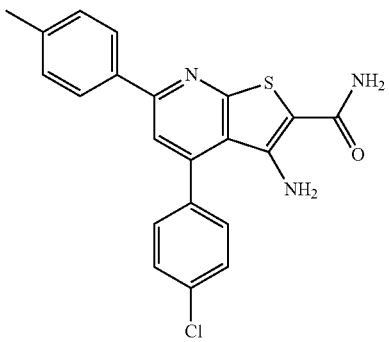 | Tat hybrid % inhibition at 5,000 nM: Z<br>Tat hybrid cell viability at 50,000 nM: Z<br>U1% inhibition at 10,000 nm: Z |

TABLE 6-continued

Additional compounds for treatment

| Compound | Assay Result |
|---|---|
| AGS1546 | Tat hybrid % inhibition at 5,000 nM: Z<br>Tat hybrid cell viability at 50,000 nM: X<br>U1% inhibition at 10,000 nm: Y |
| AGS1550 | Tat hybrid % inhibition at 5,000 nM: Z<br>Tat hybrid cell viability at 50,000 nM: X<br>U1% inhibition at 10,000 nm: Y |
| AGS1620 | Tat hybrid % inhibition at 5,000 nM: Z<br>Tat hybrid cell viability at 50,000 nM: X<br>U1% inhibition at 10,000 nm: Y |
| AGS1553 | Tat hybrid % inhibition at 5,000 nM: Z<br>Tat hybrid cell viability at 50,000 nM: Z<br>U1% inhibition at 10,000 nm: Y |
| AGS1647 | Tat hybrid % inhibition at 5,000 nM: Z<br>Tat hybrid cell viability at 50,000 nM: Y<br>U1% inhibition at 10,000 nm: Y |
| AGS1532 | Tat hybrid % inhibition at 5,000 nM: Z<br>Tat hybrid cell viability at 50,000 nM: X<br>U1% inhibition at 10,000 nm: Y |

TABLE 6-continued

Additional compounds for treatment

| Compound | Assay Result |
|---|---|
| AGS1533 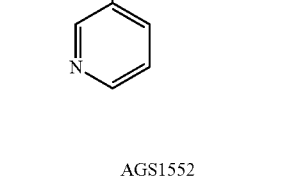 | Tat hybrid % inhibition at 5,000 nM: Z<br>Tat hybrid cell viability at 50,000 nM: Z<br>U1% inhibition at 10,000 nm: Y |
| AGS1552 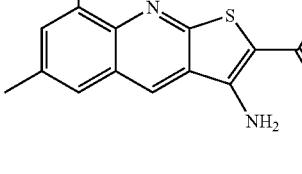 | Tat hybrid % inhibition at 5,000 nM: Z<br>Tat hybrid cell viability at 50,000 nM: X<br>U1% inhibition at 10,000 nm: Y |
| AGS1549 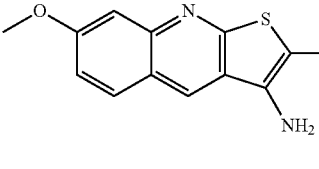 | Tat hybrid % inhibition at 5,000 nM: Z<br>Tat hybrid cell viability at 50,000 nM: Y<br>U1% inhibition at 10,000 nm: Y |
| AGS1548 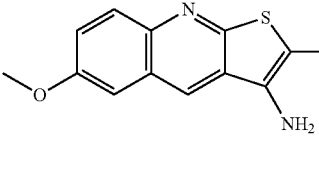 | Tat hybrid % inhibition at 5,000 nM: Z<br>Tat hybrid cell viability at 50,000 nM: X<br>U1% inhibition at 10,000 nm: Y |
| AGS1541 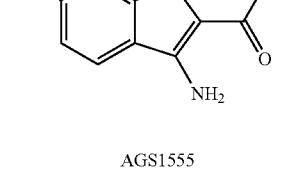 | Tat hybrid % inhibition at 5,000 nM: Z<br>Tat hybrid cell viability at 50,000 nM: X<br>U1% inhibition at 10,000 nm: Y |
| AGS1555 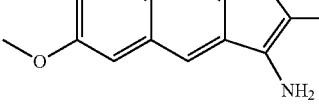 | Tat hybrid % inhibition at 5,000 nM: Z<br>Tat hybrid cell viability at 50,000 nM: X<br>U1% inhibition at 10,000 nm: Y |

TABLE 6-continued

| Additional compounds for treatment | |
|---|---|
| Compound | Assay Result |
| AGS1641 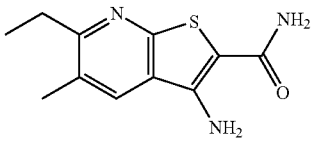 | Tat hybrid EC50 (nM): C<br>Tat hybrid % inhibition at 5,000 nM: Z<br>Tat hybrid cell viability at 50,000 nM: X<br>U1% inhibition at 10,000 nm: Y |
| AGS1627 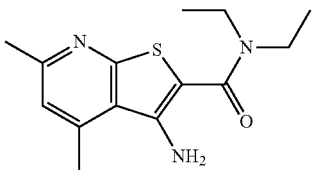 | Tat hybrid % inhibition at 5,000 M: Z<br>Tat hybrid cell viability at 50,000 nM: Y<br>U1% inhibition at 10,000 nm: Y |
| AGS1530 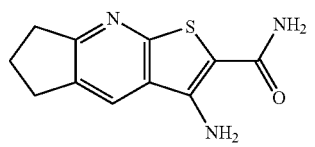 | Tat hybrid % inhibition at 5,000 nM: Z<br>Tat hybrid cell viability at 50,000 nM: X<br>U1% inhibition at 10,000 nM: Y |
| AGS1624 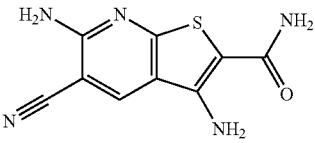 | Tat hybrid % inhibition at 5,000 nM: Z<br>Tat hybrid cell viability at 50,000 nM: Z<br>U1% inhibition at 10,000 nm: Y |
| AGS1544 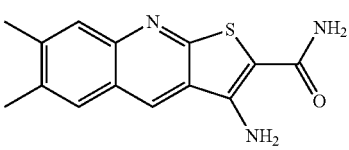 | Tat hybrid % inhibition at 5,000 nM: Z<br>Tat hybrid cell viability at 50,000 nM: X<br>U1% inhibition at 10,000 nm: Y |
| AGS1551 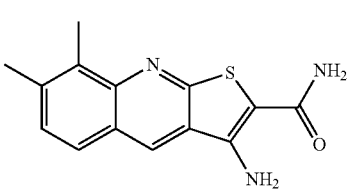 | Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
|---|---|
| AGS1646 | Tat hybrid % inhibition at 5,000 nM: Z<br>Tat hybrid cell viability at 50,000 nM: X<br>U1% inhibition at 10,000 nm: Z |
| AGS1599 | Tat hybrid % inhibition at 5,000 nM: Z<br>Tat hybrid cell viability at 50,000 nM: X<br>U1% inhibition at 10,000 nm: Z |
| AGS1547 | Tat hybrid % inhibition at 5,000 nM: Z<br>Tat hybrid cell viability at 50,000 nM: X<br>U1% inhibition at 10,000 nm: Z |
| AGS1279 | Tat hybrid % inhibition at 5,000 nM: Z<br>Tat hybrid cell viability at 50,000 nM: Y<br>U1% inhibition at 10,000 nm: Z |
| AGS1637 | Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
| --- | --- |
| AGS1271 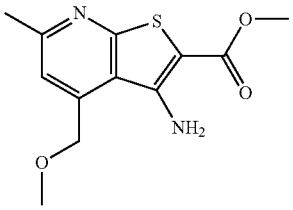 | Tat hybrid % inhibition at 5,000 nM: Z<br>Tat hybrid cell viability at 50,000 nM: X<br>U1% inhibition at 10,000 nm: Z |
| AGS1742 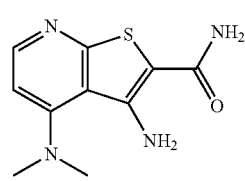 | Tat hybrid EC50 (nM): C<br>Tat hybrid EC50 (nM): E<br>U1 IC50 (nM): C<br>U1 TC50 (nM): E<br>Tat hybrid % inhibition at 5,000 nM: X<br>Tat hybrid cell viability at 50,000 nM: Y<br>U1% inhibition at 10,000 nm: X |
| AGS1278 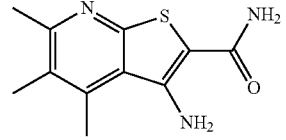 | Tat hybrid EC50 (nM): C<br>Tat hybrid EC50 (nM): E<br>Tat hybrid % inhibition at 5,000 nM: Y<br>Tat hybrid cell viability at 50,000 nM: X<br>U1% inhibition at 10,000 nm: X |
| AGS1644 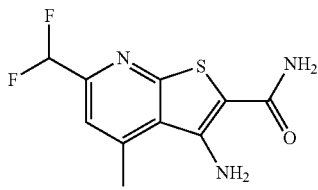 | Tat hybrid EC50 (nM): C<br>Tat hybrid EC50 (nM): E<br>Tat hybrid % inhibition at 5,000 nM: Y<br>Tat hybrid cell viability at 50,000 nM: X<br>U1% inhibition at 10,000 nm: X |
| AGS1648 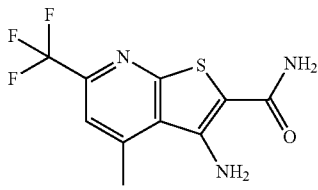 | Tat hybrid EC50 (nM): C<br>Tat hybrid EC50 (nM): E<br>Tat hybrid % inhibition at 5,000 nM: Y<br>Tat hybrid cell viability at 50,000 nM: Y<br>U1% inhibition at 10,000 nm: X |
| AGS1655 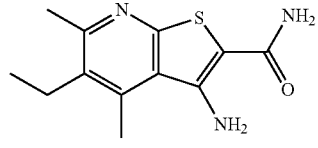 | Tat hybrid EC50 (nM): C<br>Tat hybrid EC50 (nM): E<br>U1 IC50 (nM): C<br>U1 TC50 (nM): E<br>Tat hybrid % inhibition at 5,000 nM: Y<br>Tat hybrid cell viability at 50,000 nM: Y<br>U1% inhibition at 10,000 nm: X |

TABLE 6-continued

Additional compounds for treatment

| Compound | Assay Result |
|---|---|
| AGS1741 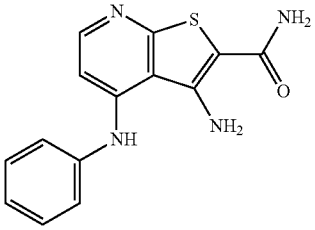 | Tat hybrid EC50 (nM): C<br>Tat hybrid EC50 (nM): E<br>U1 IC50 (nM): B<br>U1 TC50 (nM): E<br>Tat hybrid % inhibition at 5,000 nM: Y<br>Tat hybrid cell viability at 50,000 nM: Y<br>U1% inhibition at 10,000 nm: X |
| AGS1270 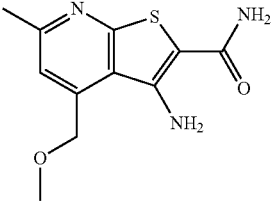 | Tat hybrid EC50 (nM): C<br>Tat hybrid EC50 (nM): E<br>U1 IC50 (nM): C<br>U1 TC50 (nM): E<br>Tat hybrid % inhibition at 5,000 nM: Y<br>Tat hybrid cell viability at 50,000 nM: X<br>U1 % inhibition at 10,000 nm: X |
| AGS1542 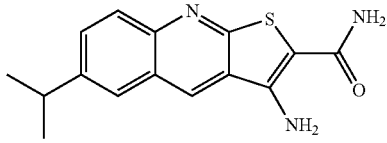 | Tat hybrid EC50 (nM): C<br>Tat hybrid EC50 (nM): D<br>Tat hybrid % inhibition at 5,000 nM: Y<br>Tat hybrid cell viability at 50,000 nM: X<br>U1% inhibition at 10,000 nm: X |
| AGS1534 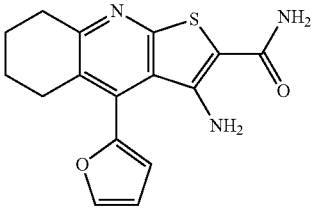 | Tat hybrid EC50 (nM): C<br>Tat hybrid EC50 (nM): E<br>U1 IC50 (nM): C<br>U1 TC50 (nM): D<br>Tat hybrid % inhibition at 5,000 nM: Y<br>Tat hybrid cell viability at 50,000 nM: X<br>U1% inhibition at 10,000 nm: X |
| AGS1284 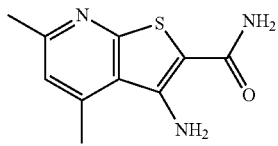 | Tat hybrid EC50 (nM): C<br>Tat hybrid EC50 (nM): E<br>U1 IC50 (nM): C<br>U1 TC50 (nM): E<br>Tat hybrid % inhibition at 5,000 nM: Y<br>Tat hybrid cell viability at 50,000 nM: Z<br>U1% inhibition at 10,000 nm: X |

TABLE 6-continued

| Additional compounds for treatment | |
|---|---|
| Compound | Assay Result |
| AGS1633 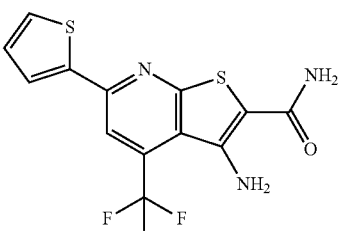 | Tat hybrid % inhibition at 5,000 nM: Y<br>Tat hybrid cell viability at 50,000 nM: Y<br>U1% inhibition at 10,000 nm: Z |
| AGS1639 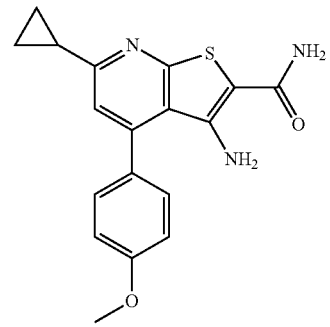 | Tat hybrid EC50 (nM): C<br>Tat hybrid EC50 (nM): E<br>Tat hybrid % inhibition at 5,000 nM: Y<br>Tat hybrid cell viability at 50,000 nM: X<br>U1% inhibition at 10,000 nm: Y |
| AGS1535 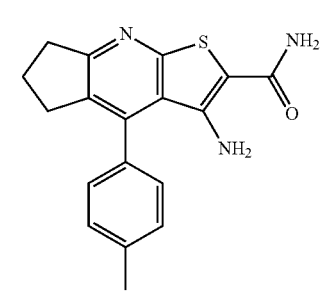 | U1 IC50 (nM): C<br>U1 TC50 (nM): D<br>Tat hybrid % inhibition at 5,000 nM: Y<br>Tat hybrid cell viability at 50,000 nM: X<br>U1% inhibition at 10,000 nm: X |
| AGS1628 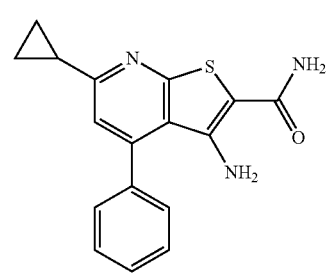 | Tat hybrid % inhibition at 5,000 nM: Y<br>Tat hybrid cell viability at 50,000 nM: X<br>U1% inhibition at 10,000 nm: Z |

TABLE 6-continued

| Additional compounds for treatment | |
|---|---|
| Compound | Assay Result |
| AGS1634 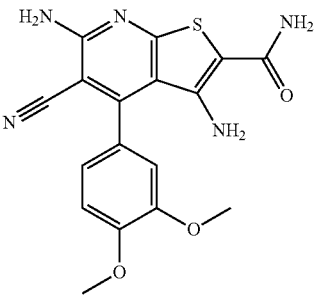 | Tat hybrid % inhibition at 5,000 nM: Y<br>Tat hybrid cell viability at 50,000 nM: Y<br>U1% inhibition at 10,000 nm: Z |
| AGS1626 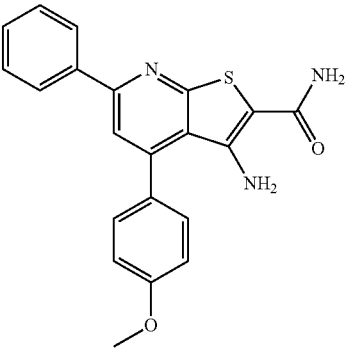 | Tat hybrid % inhibition at 5,000 nM: Z<br>Tat hybrid cell viability at 50,000 nM: X<br>U1% inhibition at 10,000 nm: Z |
| AGS1536 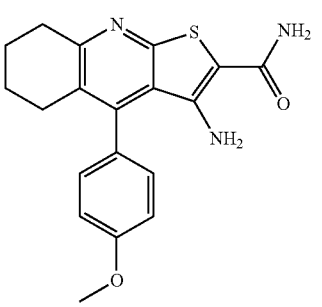 | Tat hybrid % inhibition at 5,000 nM: Z<br>Tat hybrid cell viability at 50,000 nM: X<br>U1% inhibition at 10,000 nm: X |
| AGS1288 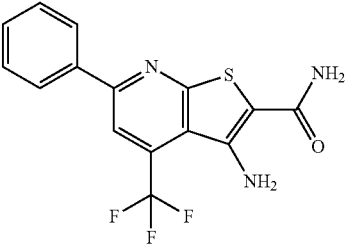 | Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
|---|---|
| AGS1638 | Tat hybrid % inhibition at 5,000 nM: Z<br>Tat hybrid cell viability at 50,000 nM: X<br>U1% inhibition at 10,000 nm: Z |
| AGS1580 | Tat hybrid EC50 (nM): C<br>Tat hybrid EC50 (nM): D<br>Tat hybrid % inhibition at 5,000 nM: Z<br>Tat hybrid cell viability at 50,000 nM: X<br>U1% inhibition at 10,000 nm: Y |
| AGS1632 | Tat hybrid % inhibition at 5,000 nM: Z<br>Tat hybrid cell viability at 50,000 nM: X<br>U1% inhibition at 10,000 nm: X |
| AGS1529 | Tat hybrid % ihibition at 5,000 nM: Z<br>Tat hybrid cell viability at 50,000 nM: X<br>U1% inhibition at 10,000 nm: Z |
| AGS1640 | Tat hybrid % inhibition at 5,000 nM: Z<br>Tat hybrid cell viability at 50,000 nM: Y<br>U1% inhibition at 10,000 nm: Z |

TABLE 6-continued

| Additional compounds for treatment | |
|---|---|
| Compound | Assay Result |
| AGS1598 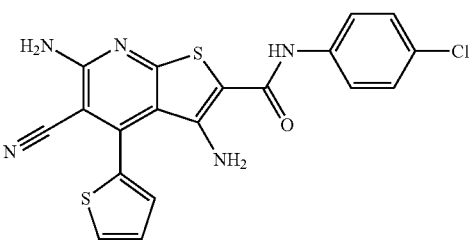 | Tat hybrid % inhibition at 5,000 nM: Z<br>Tat hybrid cell viability at 50,000 nM: X<br>U1% inhibition at 10,000 nm: Y |
| AGS1523 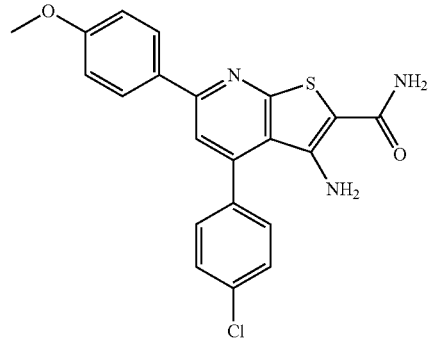 | Tat hybrid % inhibition at 5,000 nM: Z<br>Tat hybrid cell viability at 50,000 nM: X<br>U1% inhibition at 10,000 nm: Z |
| AGS1593 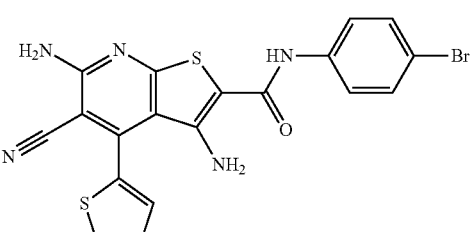 | Tat hybrid % inhibition at 5,000 nM: Z<br>Tat hybrid cell viability at 50,000 nM: X<br>U1% inhibition at 10,000 nm: Z |
| AGS1272 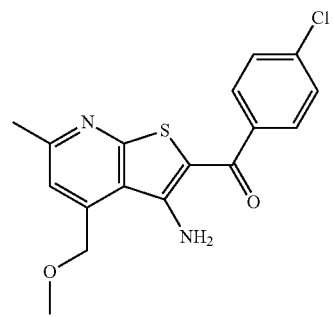 | Tat hybrid % inhibition at 5,000 nM: Z<br>Tat hybrid cell viability at 50,000 nM: X<br>U1% inhibition at 10,000 nm: Z |

TABLE 6-continued

| Additional compounds for treatment | |
|---|---|
| Compound | Assay Result |
| AGS1520 | Tat hybrid % inhibition at 5,000 nM: Z<br>Tat hybrid cell viability at 50,000 nM: Y<br>U1% inhibition at 10,000 nm: Z |
| AGS1276 | Tat hybrid % inhibition at 5,000 nM: Z<br>Tat hybrid cell viability at 50,000 nM: X<br>U1% inhibition at 10,000 nm: Z |
| AGS1645 | Tat hybrid % inhibition at 5,000 nM: Z<br>Tat hybrid cell viability at 50,000 nM: X<br>U1% inhibition at 10,000 nm: Z |
| AGS1273 | Tat hybrid % inhibition at 5,000 nM: Z<br>Tat hybrid cell viability at 50,000 nM: Y<br>U1% inhibition at 10,000 nm: Z |

TABLE 6-continued

Additional compounds for treatment

| Compound | Assay Result |
|---|---|
| AGS1286 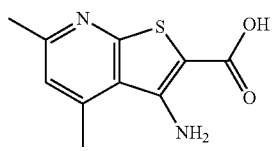 | Tat hybrid EC50 (nM): C<br>Tat hybrid EC50 (nM): E<br>Tat hybrid % inhibition at 5,000 nM: Z<br>Tat hybrid cell viability at 50,000 nM: X<br>U1% inhibition at 10,000 nm: Z |
| AGS1578 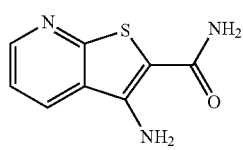 | Tat hybrid EC50 (nM): C<br>Tat hybrid EC50 (nM): E<br>Tat hybrid % inhibition at 5,000 nM: Z<br>Tat hybrid cell viability at 50,000 nM: Y<br>U1% inhibition at 10,000 nm: Z |
| AGS1524 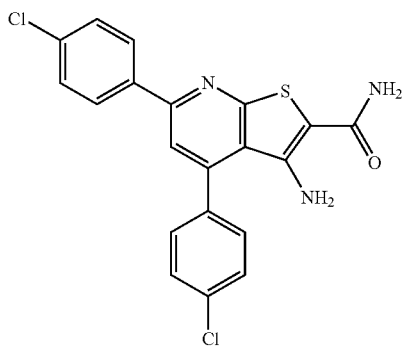 | Tat hybrid % inhibition at 5,000 nM: Z<br>Tat hybrid cell viability at 50,000 nM: X<br>U1% inhibition at 10,000 nm: Z |
| AGS1629 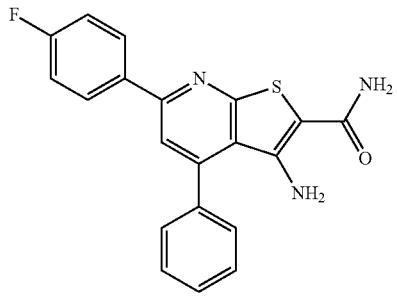 | Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
| --- | --- |
| AGS1274 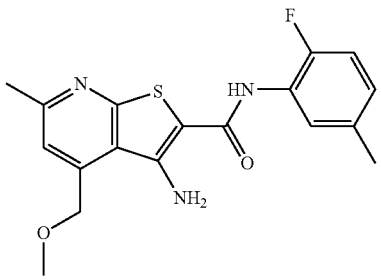 | Tat hybrid % inhibition at 5,000 nM: Z<br>Tat hybrid cell viability at 50,000 nM: X<br>U1% inhibition at 10,000 nm: Z |
| AGS1623 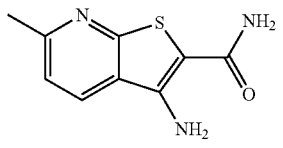 | Tat hybrid % inhibition at 5,000 nM: Z<br>Tat hybrid cell viability at 50,000 nM: X<br>U1% inhibition at 10,000 nm: Z |
| AGS1277 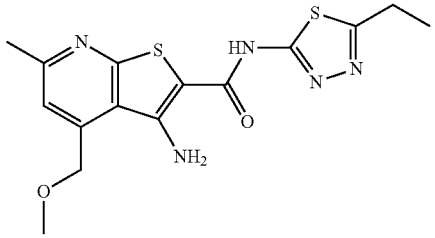 | Tat hybrid % inhibition at 5,000 nM: Z<br>Tat hybrid cell viability at 50,000 nM: X<br>U1% inhibition at 10,000 nm: Z |
| AGS1287 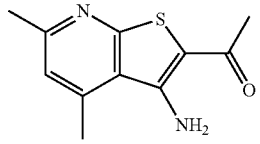 | Tat hybrid EC50 (nM): C<br>Tat hybrid EC50 (nM): E<br>Tat hybrid % inhibition at 5,000 nM: Z<br>Tat hybrid cell viability at 50,000 nM: Y<br>U1% inhibition at 10,000 nm: Y |
| AGS1581 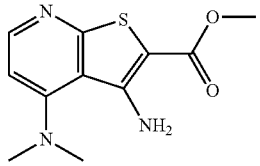 | Tat hybrid EC50 (nM): C<br>Tat hybrid EC50 (nM): D<br>Tat hybrid % inhibition at 5,000 nM: Z<br>Tat hybrid cell viability at 50,000 nM: X<br>U1% inhibition at 10,000 nm: Z |

TABLE 6-continued

Additional compounds for treatment

| Compound | Assay Result |
| --- | --- |
| AGS1643 | Tat hybrid % inhibition at 5,000 nM: Z<br>Tat hybrid cell viability at 50,000 nM: X<br>U1% inhibition at 10,000 nm: Z |
| AGS1597 | Tat hybrid % inhibition at 5,000 nM: Z<br>Tat hybrid cell viability at 50,000 nM: X<br>U1% inhibition at 10,000 nm: Z |
| AGS1636 | Tat hybrid % inhibition at 5,000 nM: Z<br>Tat hybrid cell viability at 50,000 nM: Y<br>U1% inhibition at 10,000 nm: Z |
| AGS1582 | Tat hybrid EC50 (nM): C<br>Tat hybrid EC50 (nM): D<br>Tat hybrid % inhibition at 5,000 nM: Z<br>Tat hybrid cell viability at 50,000 nM: X<br>U1% inhibition at 10,000 nm: Z |

Table 6 key: A = <100 nM; B = 100-500 nM; C = >500 nM; D = <40,000 nM; E >40,000 nM; X = >60%; Y = 30-60%; Z = <30%.

TABLE 7

Activity of thienopyridine analogs in the U1 latency assay, Tat-hybrid assay, and MTT toxicity.

| Compound | $R^4$ | $R^5$ | $R^6$ | U1 IC$_{50}$ (μM) | Tat-hybrid (% Inhibition) | MTT TC$_{50}$ (μM) |
| --- | --- | --- | --- | --- | --- | --- |
| 1. | Me | Et | Me | A | X | >38 |
| 2. | H | H | Me | B | Z | >75 |
| 3. | H | H | n-Bu | B | Z | 58.4 |
| 4. | NMe$_2$ | H | H | A | Y | >75 |
| 5. | CH$_2$OMe | H | Me | A | X | >75 |
| 6. | CF$_3$ | H | Me | A | X | >75 |

TABLE 7-continued

Activity of thienopyridine analogs in the U1 latency assay, Tat-hybrid assay, and MTT toxicity.

[Structure: thienopyridine core with R4, R5, R6 substituents, NH2, and C(O)NH2 groups]

| Compound | R⁴ | R⁵ | R⁶ | U1 IC₅₀ (μM) | Tat-hybrid (% Inhibition) | MTT TC₅₀ (μM) |
|---|---|---|---|---|---|---|
| 7. | H | Me | Me | B | Y | 37 |
| 8. | H | —CH₂CH₂CH₂— | | B | Z | >75 |
| 9. | H | —CH₂CH₂CH₂CH₂— | | B | Z | >75 |
| 10. | H | Me | 4-FPh | C | Z | >75 |
| 11. | Me | CH2COPh | Me | A | Y | >75 |
| 12. | —NHPh | H | H | A | Z | 53 |
| 13. | H | H | Pyridyl | C | Z | >75 |
| 14. | CF₃ | H | Bn | C | Z | >75 |
| 15. | 4-FPh | H | Thiophene | C | Y | 17.4 |
| 16. | tolyl | H | Ph | A | X | 22.6 |
| 17. | 4-MeOPh | H | 4-MeOPh | B | Y | 38.3 |
| 18. | 4-MeOPh | H | Ph | B | Y | 53.9 |
| 19. | —CH₂CH₂CH₂CH₂— | | Morpholine | C | Y | >75 |

A = <1 μM; B = 1-5 μM; C = >5 μM. X = >60%; Y = 30-60%; Z = <30%.

Testing the specificity of the thienopyridine compounds using the Tat-hybrid reporter system. We tested the activity of Compound 4a using the Tat-hybrid reporter assays using the HIV TAR reporter and HIV Tat protein that activates this reporter, and compared these results to the Rev-RRE reporter demonstrating good specificity for Rev-RRE, as described below.

Figure 16:
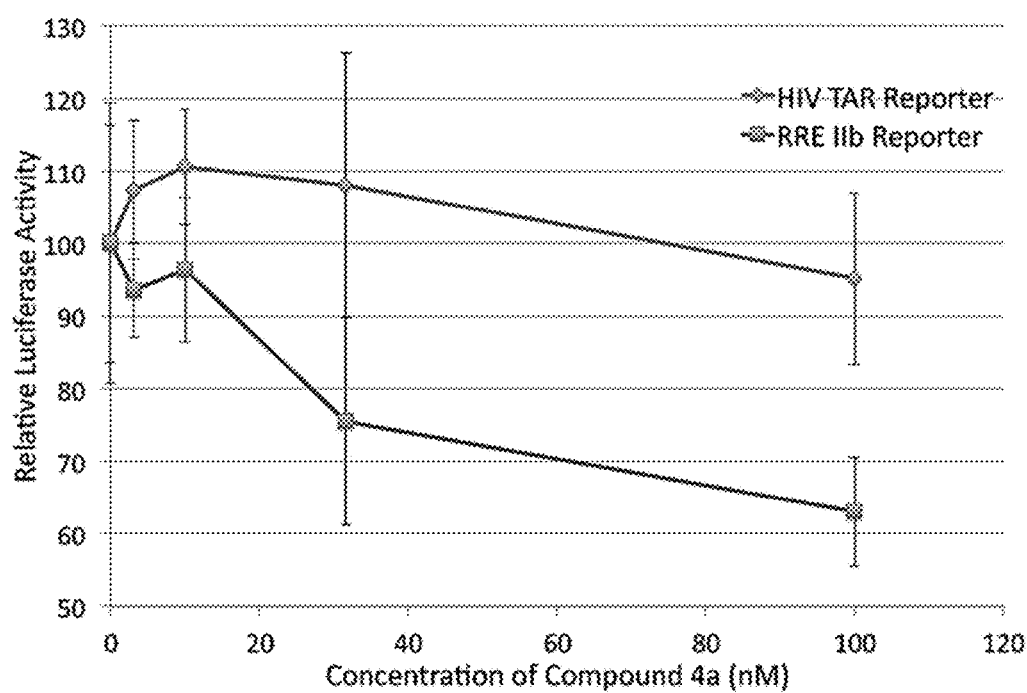
FIG. 16. Thienopyridine compound 4a specifically targets the Rev-RRE reporter. The expression of the HIV RRE IIb reporter was significantly inhibited in the presence of 100 nM Compound 4a while the expression of the HIV TAR reporter was not similarly inhibited.

A 96 well plate was seeded with 10,000 293T cells. We transfected each well with 10 ng of the HIV TAR Luciferase reporter and 5 ng of the HIV Tat 1-72 expression construct or 10 ng of the HIV RRE IIB Luciferase reporter and 5 ng of the HIV Tat (1-48)-Rev 3-70 expression construct, and with 2 ng of a CMV Renilla luciferase control. Compound 4a was added to a final concentration of 3.16, 10, 31.6, and 100 nM. Each condition was performed in quadruplet. Note, it was necessary to use transient transfection assays rather than stable cell lines in order to compare the two reporter systems, although the level of inhibition conferred by the compounds in the transient assays was lower than in the cell lines. The cells were incubated for 48 hours and dual luciferase assays were performed according to the manufacturers protocol (Promega). Reporter activity was normalized against the Renilla control. The results of this experiment are shown in FIG. 16.

7. Compound Effects on the Vpu Gene

Selection. The use of compounds described herein (e.g., thienopyridine compounds) results in a modulation (e.g., deletion or severe truncation of the Vpu gene). Viral protein U (Vpu) is a membrane-associated accessory protein, and while it is not essential for virus replication, it assists with functions that can maintain the integrity virus. Vpu is known to target the host restriction factor Tetherin which inhibits the release of the virus from infected cells. Vpu is also known to target the host CD4 receptor. Vpu does this by forming complexes with host factor, which confers its degradation through the proteasome.

In HIV, resistance selection is a commonly used method to identify the molecular target of drug. For example, long-term exposure to AZT will result resistance mutations in the HIV gene for Reverse Transcriptase. Major HIV drugs have documented resistance profiles that map to the molecular targets of the drug.

The compounds described herein (e.g., thienopyridine compounds) confer a very interesting and unique activity during resistance selection. Experiments with the compounds described herein, the thienopyridines confer a disruption or complete deletion of the HIV Vpu gene. This was a very striking and repeatable result. For example, in 5 independent selection experiments, disruptions or deletions of Vpu were identified.

TABLE 8

| Selection #1 | T6062C | Destroys ATG at AA#1 of Vpu |
| Selection #2 | Deletion of G6076-A6108 | 11AA deletion in Vpu |
| Selection #3 | G6126A | W42 to Stop, Trucates C-terminal 44 AAs |
| Selection #4 | C6064C | Creates Stop at AA#2 of Vpu |
| Selection #5 | G6063A | Destroys ATG at AA#1 of Vpu |

The fact that the selections resulted in deletions or gross mutations of Vpu does not necessarily imply that Vpu is the target of the compounds. Our current models suggest that Vpu may be a regulator of Rev, and deletion of Vpu may result in higher levels of Rev.

Figure 10:
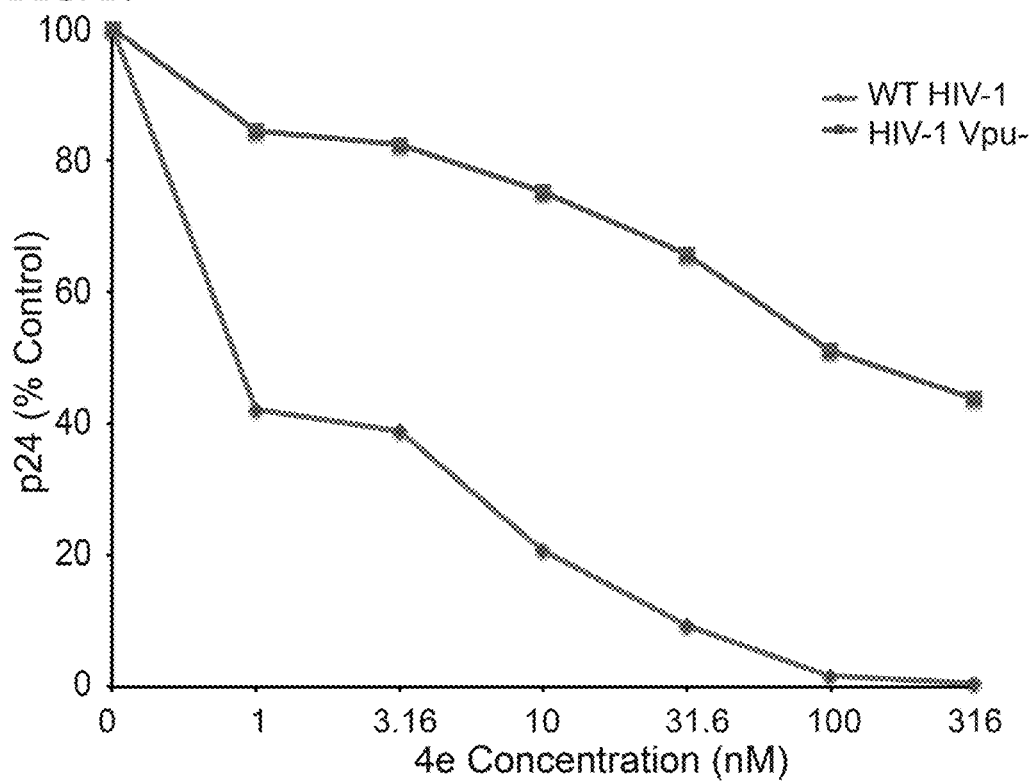
FIG. 10. In embodiments, HIV viruses are defective or deleted for Vpu are resistant to the compounds described herein. Replication assays with HIV-1 isolate NL4-3 or NL4-3 deleted for Vpu in Jurkat cells. Replication spreading assays were performed with compound at doses ranging from 1 nM to 316 nM in triplicate. Supernatants were collected every 48-72 hours and p24 values were determined by ELISA.

Effects on HIV Replication. HIV viruses that are defective or deleted for Vpu are resistant to thienopyridine compounds. In one replication experiment with compound AGS1674, the IC50 of the wild type virus was 5 nM, as depicted in FIG. 10. In contrast, the IC50 of the vpu defective virus was 150 nM. This result shows that the vpu-deficient virus is resistant to the compound AGS1674 (4e), as observed in FIG. 10.

The replication experiments show that the amount of Vpu present is proportional to the sensitivity of compound. Under normal circumstances with a virus that expresses the normal level of Vpu, the IC50 is 5 nM. In the absence of Vpu, the virus is resistant and displays an IC50 of approximately 30-fold higher (150 nM).

Figure 11A:
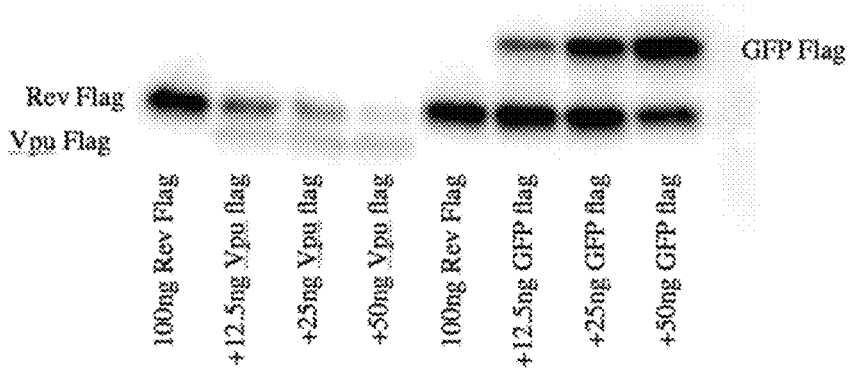
FIGS. 11A-11B. Rev was expressed in the presence or absence of Vpu and levels of both proteins were measured by western blot, shown in FIG. 11A. Co-transfection of Rev and Vpu resulted in a lower level Rev compared to the transfection of Rev alone or with Rev co-transfected with a GFP control, as observed in FIG. 11B.
Figure 11B:
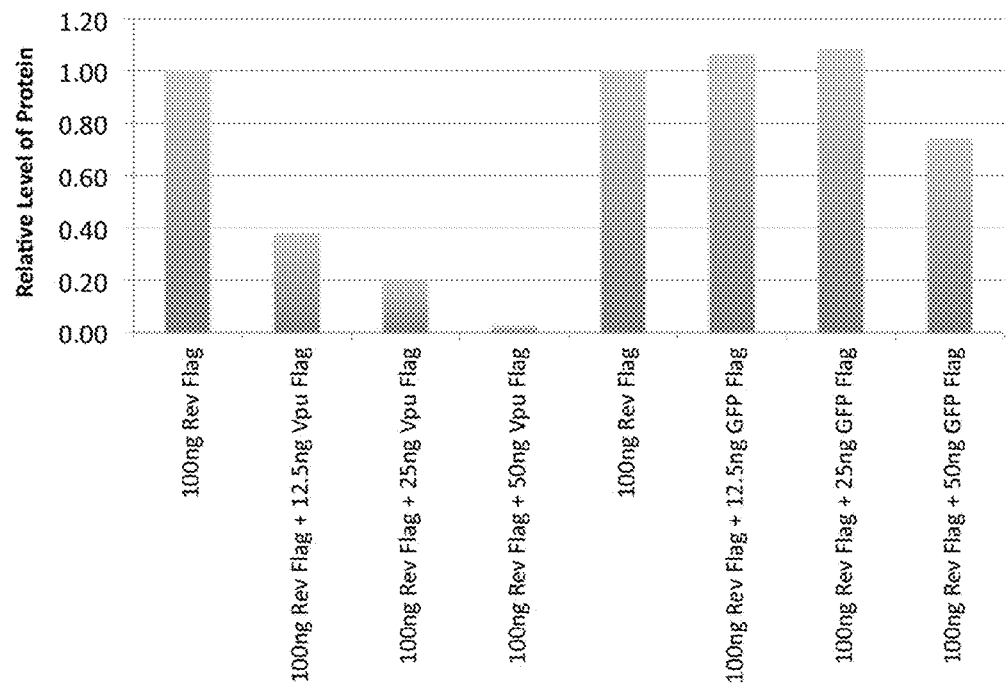

Vpu is a regulator of Rev. In this experiment, Rev was expressed in the presence or absence of Vpu and levels of both proteins were measured by western blot. Flag tagged Rev and either Flag tagged Vpu or Flag tagged GFP were transfected to 293T cells. Co-transfection of Rev and Vpu resulted in a lower level Rev compared to the transfection of Rev alone. In contrast, co-transfection of Rev and GFP did not result in a lower level of Rev, as seen in FIG. 11.

Figure 12:
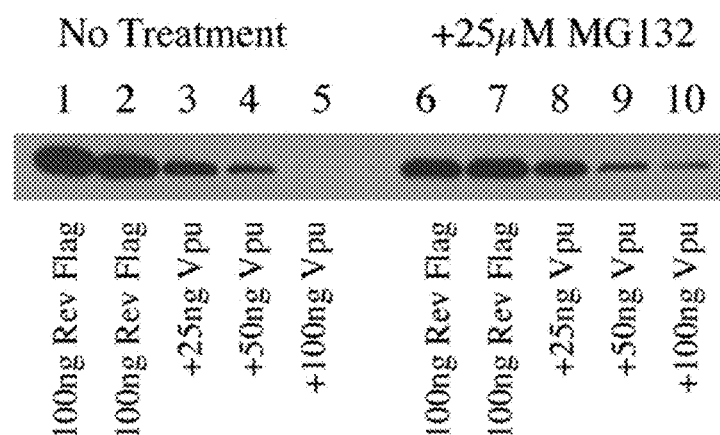
FIG. 12. Vpu-dependent degradation of Rev with the proteasome inhibitor MG132. As in the figure, expression of Rev is reduced when co-transfected with 100 ng of a Vpu expression plasmid (Lane 5). Treatment with MG132, an inhibitor of the proteasomal degradation, blocks Vpu-dependent degradation of Rev (Lane 10).

Next we tested the Vpu-dependent degradation of Rev with the proteasome inhibitor MG132. As shown in FIG. 12, expression of Rev is completely lost at when co-transfected with 100 ng of a Vpu expression plasmid (Lane 5). Treatment with MG132, an inhibitor of the proteasomal degradation, blocks Vpu-dependent degradation of Rev (Lane 10). This result is consistent with a model that Vpu confers degradation of Rev through the proteasome.

Figure 13:
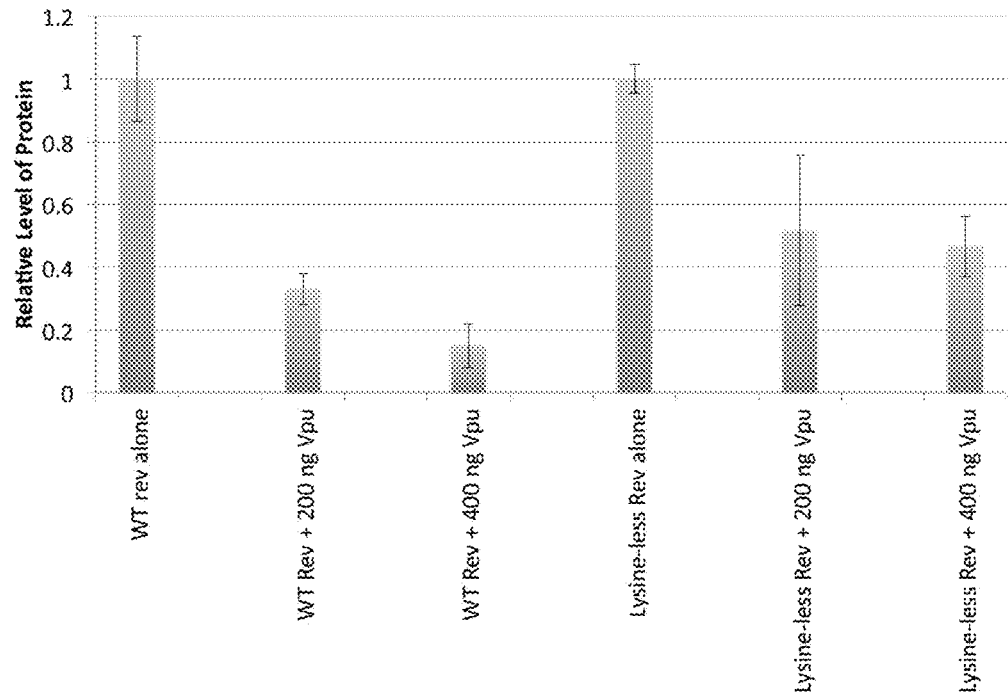
FIG. 13. Constructs encoding wild type Rev or Rev with both lysines mutated to arginines were created. The wild type and mutant Rev genes were fused to the Strep affinity tag lacking lysines. The wild type and lysine-less Rev constructs were co-transfected with Rev and protein levels were determined by western blot analysis, shown in FIG. 13.
Figure 14:
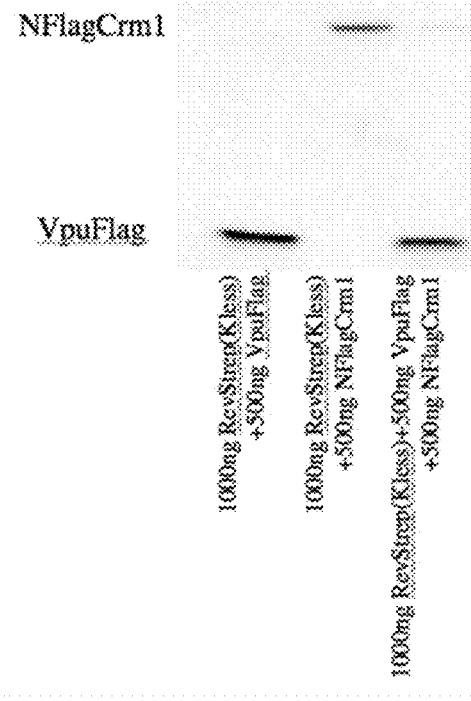
FIG. 14. An immunoprecipitation experiment. When affinity tagged Rev is cotransfected with Vpu, Rev and Vpu are detected in the same complex (Lane 1). Crm1 and Rev are also detected in complexes together. Crm1 is the host export factor that is known to bind Rev and facilitate export of RRE containing complexes from the nucleus to the cytoplasm (Lane 2).

Mutants of Rev lacking lysine residues are protected from degradation by Vpu. Rev encodes two lysine residues. Construct encoding wild type Rev or Rev with both lysines mutated to arginines were created. The wild type and mutant Rev genes were fused to the Strep affinity tag lacking lysines. The wild type and lysine-less Rev constructs were co-transfected with Rev and protein levels were determined by western blot analysis. The wild type Rev protein was more severely degraded compared to the lysine-less Rev protein, as shown in FIG. 13. This result is consistent with the hypothesis that Vpu-dependent degradation of Rev occurs through a ubiquitination step because lysines are a common substrate for ubiquitination.

Vpu and Rev interact with one another. In immunoprecipitation experiments, when affinity tagged Rev is cotransfected with Vpu, Rev and Vpu are detected in the same complex (Lane 1). Crm1 and Rev are also detected in complexes together. Crm1 is the host export factor that is known to bind Rev and facilitate export of RRE containing complexes from the nucleus to the cytoplasm (Lane 2). Expression of Vpu may compete with Crm1 for binding in Rev complexes or Vpu may displace Crm1 or reduce Crm1 binding in Rev complexes (Lane 3).

In embodiments, the compounds described herein (e.g., thienopyridine compounds) confer a loss of Vpu expression from an HIV infected cell. This has a significant potential for the treatment of HIV/AIDS. Vpu is especially important in cell types that highly express Tetherin (e.g., mature B cells, plasma cells, dendritic cells, and other cells that express Tetherin in response to interferon stimulation). Vpu deficient viruses may be more sensitive to Interferon treatment which stimulates the production of Tetherin in some cells.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Embodiments

Embodiment 1. A compound having the formula:

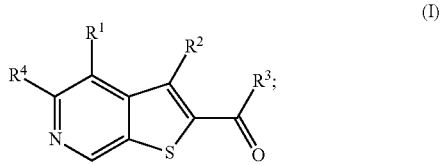

(I)

wherein, $R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)O R^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)O R^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)O R^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ is independently hydrogen, $-CX_3$, $-CN$, $-NH_2$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently $-F$, $-Cl$, $-Br$, or $-I$;

n1, n3, and n4 are independently an integer from 0 to 4; and m1, m3, m4, v1, v3, and v4 are independently an integer from 1 to 2.

Embodiment 2. The compound of embodiment 1 having the formula:

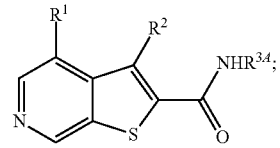

wherein $R^{3A}$ is hydrogen, $-CX^{3A}_3$, $-CHX^{3A}_2$, $-CH_2X^{3A}$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each $X^{3A}$ is independently $-F$, $-Cl$, $-Br$, or $-I$.

Embodiment 3. The compound of embodiment 2 wherein $R^{3A}$ is hydrogen.

Embodiment 4. The compound of one of embodiments 2 to 3 wherein $R^2$ is hydrogen.

Embodiment 5. The compound of one of embodiments 2 to 4 wherein $R^1$ is substituted or unsubstituted cycloalkyl, substituted or unsubstituted heterocycloalkyl, substituted or unsubstituted aryl, or substituted or unsubstituted heteroaryl.

Embodiment 6. The compound of one of embodiments 2 to 5, wherein $R^1$ is $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl;

$R^{20}$ is independently oxo, halogen, —$CX^{203}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20}_3$, —$OCHX^{20}_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; two $R^{20}$ substituents may optionally be joined to form a substituted or unsubstituted cycloalkyl, substituted or unsubstituted heterocycloalkyl, substituted or unsubstituted aryl, or substituted or unsubstituted heteroaryl and $X^{20}$ is —F, —Cl, —Br, or —I.

Embodiment 7. The compound of one of embodiments 2 to 6, having the formula:

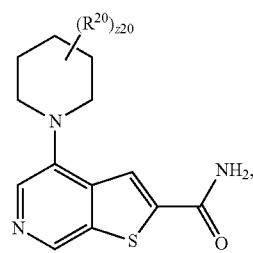

(IV)

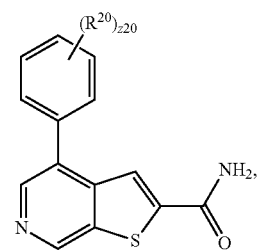

(V)

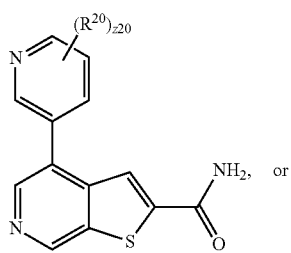

(VI)

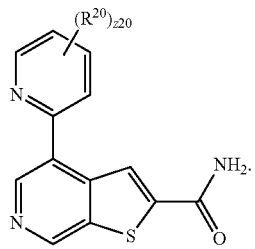

(VII)

Embodiment 8. The compound of one of embodiments 2 to 6, having the formula:

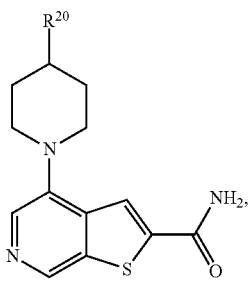

(IVA)

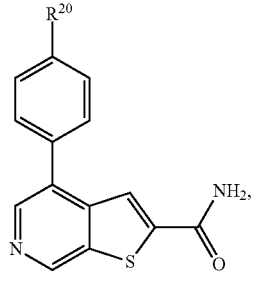

(VA)

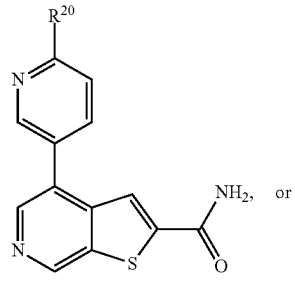

(VIA)

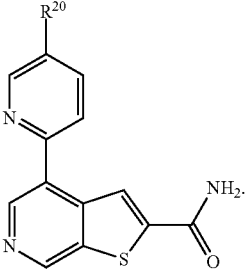

(VIIA)

Embodiment 9. The compound of one of embodiments 6 to 8, wherein $R^{20}$ is independently substituted or unsubstituted $C_1$-$C_8$ alkoxy, substituted or unsubstituted $C_3$-$C_8$ cycloalkoxy, substituted or unsubstituted 3 to 6 membered heterocycloalkoxy, substituted or unsubstituted phenoxy, or substituted or unsubstituted 5 to 6 membered heteroaryloxy.

Embodiment 10. The compound of one of embodiments 2 to 6, having the formula:

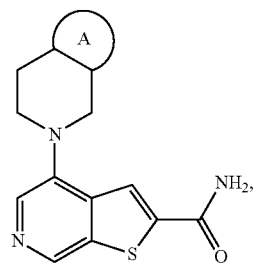

(IVB)

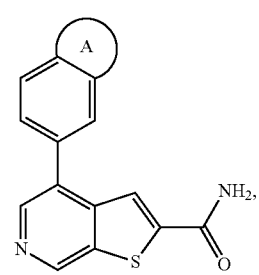

(VB)

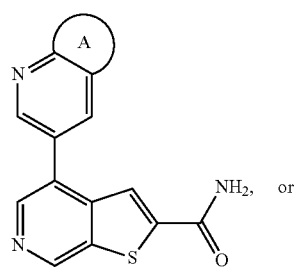

(VIB)

or

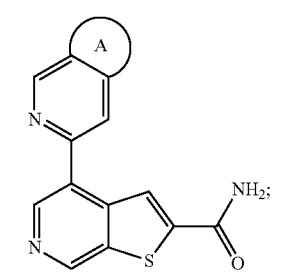

(VIIB)

wherein
Ring A is a substituted or unsubstituted cycloalkyl, substituted or unsubstituted heterocycloalkyl, substituted or unsubstituted aryl, or substituted or unsubstituted heteroaryl.

Embodiment 11. The compound of embodiment 10, wherein Ring A is a substituted or unsubstituted phenyl, substituted or unsubstituted pyridinyl, substituted or unsubstituted pyrazinyl, substituted or unsubstituted pyrimidinyl, substituted or unsubstituted pyridazinyl, substituted or unsubstituted pyrrolyl, substituted or unsubstituted furanyl, substituted or unsubstituted thienyl, substituted or unsubstituted imidazolyl, substituted or unsubstituted pyrazolyl, substituted or unsubstituted oxazolyl, substituted or unsubstituted isoxazolyl., substituted or unsubstituted thiazolyl, substituted or unsubstituted isothiazolyl, substituted or unsubstituted triazolyl, substituted or unsubstituted oxadi-azolyl, substituted or unsubstituted piperazinyl, substituted or unsubstituted piperidinyl, substituted or unsubstituted pyrrolidinyl, substituted or unsubstituted azetidinyl, substituted or unsubstituted aziridinyl, substituted or unsubstituted morpholinyl, substituted or unsubstituted dioxanyl, substituted or unsubstituted tetrahydropyranyl, substituted or unsubstituted tetrahydrofuranyl, substituted or unsubstituted oxetanyl, or substituted or unsubstituted oxiranyl.

Embodiment 12. The compound of embodiment 10, wherein Ring A is a substituted or unsubstituted phenyl, substituted or unsubstituted pyridinyl, substituted or unsubstituted pyrrolyl, substituted or unsubstituted furanyl, substituted or unsubstituted thienyl, substituted or unsubstituted piperidinyl, substituted or unsubstituted pyrrolidinyl, substituted or unsubstituted azetidinyl, substituted or unsubstituted aziridinyl, substituted or unsubstituted tetrahydropyranyl, substituted or unsubstituted tetrahydrofuranyl, substituted or unsubstituted oxetanyl, or substituted or unsubstituted oxiranyl.

Embodiment 13. The compound of embodiment 10, wherein Ring A is a substituted or unsubstituted pyrrolyl, substituted or unsubstituted furanyl, substituted or unsubstituted thienyl, substituted or unsubstituted pyrrolidinyl, or substituted or unsubstituted tetrahydrofuranyl.

Embodiment 14. A pharmaceutical composition comprising the compound of any one of embodiments 1 to 13 and a pharmaceutically acceptable excipient.

Embodiment 15. The pharmaceutical composition of embodiment 14, further comprising an anti-viral agent.

Embodiment 16. The pharmaceutical composition of embodiment 15, wherein the anti-viral agent is an HIV reverse transcriptase inhibitor, HIV protease inhibitor, HIV integrase inhibitor, HIV fusion inhibitor, or HIV entry inhibitor.

Embodiment 17. A method of inhibiting the level of Rev protein activity, the method comprising: contacting the Rev protein with a compound having the formula:

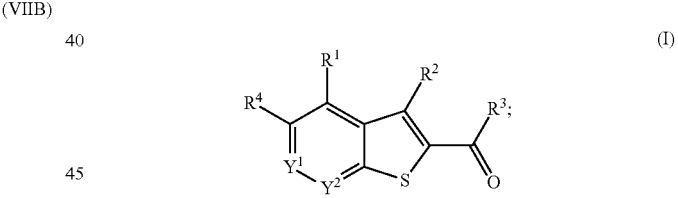

(I)

wherein,
$R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

221

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)O\ R^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^{4A1}$, and $R^{4B1}$ are independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^{4A1}$ may optionally be joined to form a substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ is independently hydrogen, —$CX_3$, —$NH_2$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently —F, —Cl, —Br, or —I;

n1, n3, and n4 are independently an integer from 0 to 4;

m1, m3, m4, v1, v3, and v4 are independently an integer from 1 to 2; and (i) $Y^1$ is $CR^{4A1}$ and $Y^2$ is N; or
(ii) $Y^1$ is N and $Y^2$ is $CR^{4B1}$.

Embodiment 18. A method of inhibiting HIV virion formation in an HIV infected cell, the method comprising: contacting the HIV infected cell with a compound having the formula:

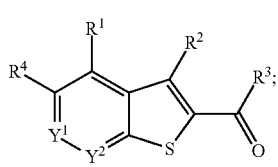

(I)

222 wherein, $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)O\ R^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)O\ R^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^{4A1}$, and $R^{4B1}$ are independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4c}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^{4A1}$ may optionally be joined to form a substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ is independently hydrogen, —$CX_3$, —CN, —$NH_2$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently —F, —Cl, —Br, or —I;

n1, n3, and n4 are independently an integer from 0 to 4;

m1, m3, m4, v1, v3, and v4 are independently an integer from 1 to 2; and (i) $Y^1$ is $CR^{4A1}$ and $Y^2$ is N; or (ii) $Y^1$ is N and $Y^2$ is $CR^{4B1}$.

Embodiment 19. A method of inhibiting HIV viral shedding from an HIV infected cell, the method comprising: contacting the HIV infected cell with a compound having the formula:

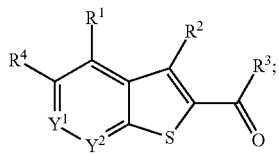

(I)

wherein, $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R''$, —$NR^{1A}C(O)O$ $R^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —N(O)$_{m3}$, —$NR^{3A}R^{3B}$, —C(O)$R^{3C}$, —C(O)—$OR^{3C}$, —C(O)$NR^{3A}R^{3B}$, —$OR^{3D}$, —$NR^{3A}SO_2R^{3D}$, —$NR^{3A}C(O)R^{3C}$, —$NR^{3A}C(O)O$ $R^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^{4A1}$, and $R^{4B1}$ are independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —N(O)$_{m4}$, —$NR^{4A}R^{4B}$, —C(O)$R^{4C}$, —C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^{4A1}$ may optionally be joined to form a substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$ and $R^{4D}$ is independently hydrogen, —$CX_3$, —CN, —$NH_2$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently —F, —Cl, —Br, or —I;

n1, n3, and n4 are independently an integer from 0 to 4;

m1, m3, m4, v1, v3, and v4 are independently an integer from 1 to 2; and (i) $Y^1$ is $CR^{4A1}$ and $Y^2$ is N; or (ii) $Y^1$ is N and $Y^2$ is $CR^{4B1}$.

Embodiment 20. A method of inhibiting HIV proliferation, the method comprising: contacting HIV with a compound having the formula:

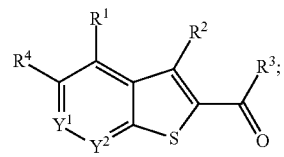

(I)

wherein, $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R''$, —$NR^{1A}C(O)O$ $R^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)O R$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$, R$^{4A1}$, and R$^{4B1}$ are independently hydrogen, halogen, —CX$^4{}_3$, —CHX$^4{}_2$, —CH$_2$X$^4$, —OCX$^4{}_3$, —OCH$_2$X$^4$, —OCHX$^4{}_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^4$ and R$^{4A1}$ may optionally be joined to form a substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$ and R$^{4D}$ is independently hydrogen, —CX$_3$, —CN, —COOH, —NH$_2$, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl;

each X, X$^1$, X$^2$, X$^3$, and X$^4$ is independently —F, —Cl, —Br, or —I;

n1, n3, and n4 are independently an integer from 0 to 4;

m1, m3, m4, v1, v3, and v4 are independently an integer from 1 to 2; and (i) Y$^1$ is CR$^{4A1}$ and Y$^2$ is N; or (ii) Y$^1$ is N and Y$^2$ is CR$^{4B1}$.

Embodiment 21. A method of treating HIV infection, the method comprising administering to a subject in need thereof an effective amount of a compound having the formula:

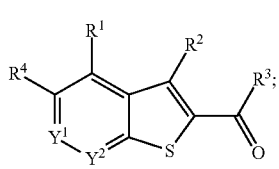

(I)

wherein,

R$^1$ is hydrogen, halogen, —CX$^1{}_3$, —CHX$^1{}_2$, —CH$_2$X$^1$, —OCX$^1{}_3$, —OCH$_2$X$^1$, —OCHX$^1{}_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)O R$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is hydrogen, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen, halogen, —CX$^3{}_3$, —CHX$^3{}_2$, —CH$_2$X$^3$, —OCX$^3{}_3$, —OCH$_2$X$^3$, —OCHX$^3{}_2$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)O R$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$, R$^{4A1}$, and R$^{4B1}$ are independently hydrogen, halogen, —CX$^4{}_3$, —CHX$^4{}_2$, —CH$_2$X$^4$, —OCX$^4{}_3$, —OCH$_2$X$^4$, —OCHX$^4{}_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^4$ and R$^{4A1}$ may optionally be joined to form a substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$ and R$^{4D}$ is independently hydrogen, —CX$_3$, —CN, —COOH, —NH$_2$, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl;

each X, X$^1$, X$^2$, X3, and X$^4$ is independently —F, —Cl, —Br, or —I;

n1, n3, and n4 are independently an integer from 0 to 4;

m1, m3, m4, v1, v3, and v4 are independently an integer from 1 to 2; and (iii) Y$^1$ is CR$^{4A1}$ and Y$^2$ is N; or (iv) Y$^1$ is N and Y$^2$ is CR$^{4B1}$.

---

---

What is claimed is:

1. A compound having the formula:

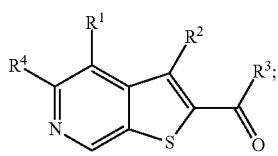

(I)

wherein,

R$^1$ is substituted or unsubstituted cycloalkyl, substituted or unsubstituted piperazinyl, substituted or unsubstituted piperidinyl, substituted or unsubstituted pyrrolidinyl, substituted or unsubstituted azetidinyl, substituted or unsubstituted aziridinyl, substituted or unsubstituted 4,5,6,7-tetrahydrothieno[3,2-b]pyridine, substituted or unsubstituted 1,2,3,4-tetrahydroisoquinolinyl, or substituted or unsubstituted 1,4,6,7-tetrahydro-5λ$^2$-pyrazolo[4,3-c]pyridinyl;

R$^2$ is hydrogen or —NR$^{2A}$R$^{2B}$;

R$^3$ is hydrogen, halogen, —CX$^3{}_3$, —CHX$^3{}_2$, —CH$_2$X$^3$, —OCX$^3{}_3$, —OCH$_2$X$^3$, —OCHX$^3{}_2$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is independently hydrogen, halogen, —CX$^4{}_3$, —CHX$^4{}_2$, —CH$_2$X$^4$, —OCX$^4{}_3$, —OCH$_2$X$^4$, —OCHX$^4{}_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, and R$^{4D}$ is independently hydrogen, —CX$_3$, —CN, —NH$_2$, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$, is independently —F, —Cl, —Br, or —I;

n1, n3, and n4 are independently an integer from 0 to 4; and m1, m3, m4, v1, v3, and v4 are independently an integer from 1 to 2.

2. The compound of claim 1 having the formula:

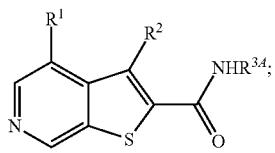

(IIIB)

wherein $R^{3A}$ is hydrogen, —$CX^{3A}_3$, —$CHX^{3A}_2$, —$CH_2X^{3A}$, —$C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each $X^{3A}$ is independently —F, —Cl, —Br, or —I.

3. The compound of claim 2 wherein $R^{3A}$ is hydrogen.

4. The compound of claim 2 wherein $R^2$ is hydrogen.

5. The compound of claim 2, wherein $R^1$ is $R^{20}$-substituted or unsubstituted piperazinyl, $R^{20}$-substituted or unsubstituted piperidinyl, $R^{20}$-substituted or unsubstituted pyrrolidinyl, $R^{20}$-substituted or unsubstituted 4,5,6,7-tetrahydrothieno[3,2-b]pyridine, or $R^{20}$-substituted or unsubstituted 1,2,3,4-tetrahydroisoquinolinyl, or $R^{20}$-substituted or unsubstituted 1,4,6,7-tetrahydro-5$\lambda^2$-pyrazolo[4,3-c]pyridinyl;

$R^{20}$ is independently oxo, halogen, —$CX^{20}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{20}_3$, —$OCHX^{20}_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; and $X^{20}$ is —F, —Cl, —Br, or —I.

6. The compound of claim 2, having the formula:

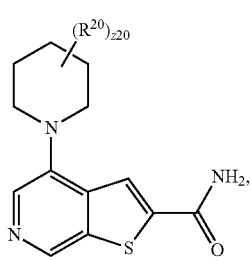

(IV)

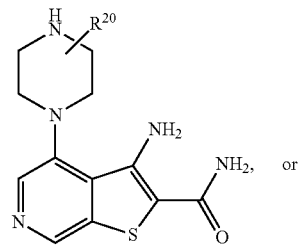

(VIII)

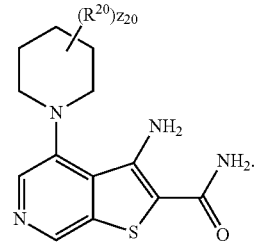

(IX)

7. The compound of claim 2, having the formula:

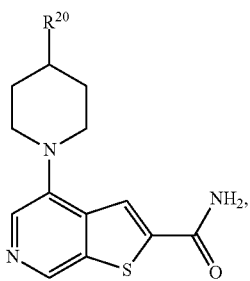

(IVA)

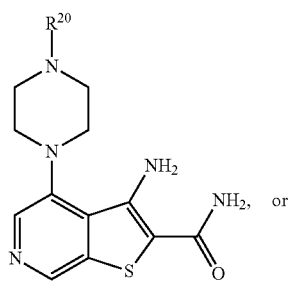

(VIIIA)

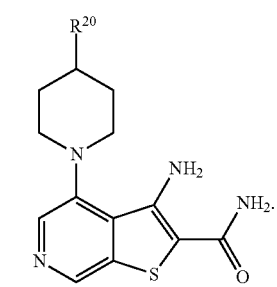

(IXA)

8. The compound of claim 5, wherein $R^{20}$ is independently halogen, —$CONH_2$, substituted or unsubstituted $C_1$-$C_8$ alkyl, substituted or unsubstituted $C_1$-$C_8$ alkoxy, substituted or unsubstituted $C_3$-$C_8$ cycloalkoxy, substituted or unsubstituted 3 to 6 membered heterocycloalkoxy, substituted or unsubstituted phenoxy, substituted or unsubstituted phenyl, substituted or unsubstituted 5 to 6 membered heteroaryl, or substituted or unsubstituted 5 to 6 membered heteroaryloxy.

9. A method of inhibiting the level of Rev protein activity, inhibiting human immunodeficiency virus (HIV) virion formation in an HIV infected cell, inhibiting HIV viral shedding from an HIV infected cell, inhibiting HIV proliferation, treating an HIV infection, inhibiting the level of HIV Vpu activity in a cell, or modulating an HIV Vpu gene, said method comprising administering to a subject in need thereof an effective amount of a compound having the formula:

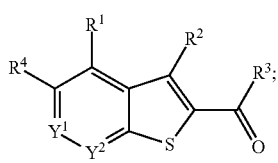

(I)

wherein, $R^1$ is hydrogen, halogen, $-CX^1{}_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, $-NR^{2A}R^{2B}$, $-C(O)-R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-CX^3{}_3$, $-CHX^3{}_2$, $-CH_2X^3$, $-OCX^3{}_3$, $-OCH_2X^3$, $-OCHX^3{}_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^{4A1}$, and $R^{4B1}$ are independently hydrogen, halogen, $-CX^4{}_3$, $-CHX^4{}_2$, $-CH_2X^4$, $-OCX^4{}_3$, $-OCH_2X^4$, $-OCHX^4{}_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^{4A1}$ may optionally be joined to form a substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, and $R^{4D}$ is independently hydrogen, $-CX_3$, $-NH_2$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^2A$ and $R^2B$ substituents bonded to the same nitrogen atom may optionally be joined to form a substituted or unsubstituted heterocycloalkyl or substituted or unsubstituted heteroaryl; $R^3A$ and $R^3B$ substituents bonded to the same nitrogen atom may optionally be joined to form a substituted or unsubstituted heterocycloalkyl or substituted or unsubstituted heteroaryl; $R^4A$ and $R^4B$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently $-F$, $-Cl$, $-Br$, or $-I$;

n1, n3, and n4 are independently an integer from 0 to 4; and m1, m3, m4, v1, v3, and v4 are independently an integer from 1 to 2; and $Y^1$ is N and $Y^2$ is $CR^{4B1}$.

10. The method of claim 9, wherein the compound has the formula:

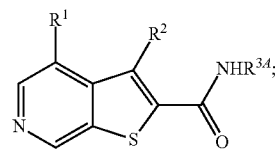

(IIIB)

wherein $R^{3A}$ is hydrogen, $-CX^{3A}{}_3$, $-CHX^{3A}{}_2$, $-CH_2X^{3A}$, $-C(O)NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each $X^{3A}$ is independently $-F$, $-Cl$, $-Br$, or $-I$.

11. The method of claim 9, wherein the compound has the formula:

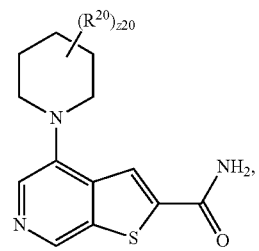

(IV)

(V)

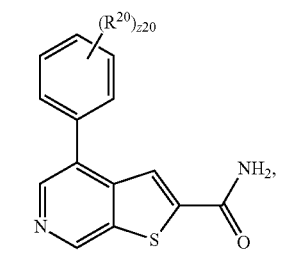

(VI)

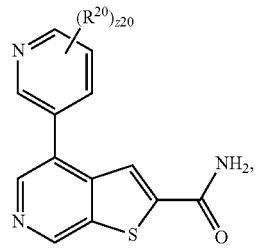

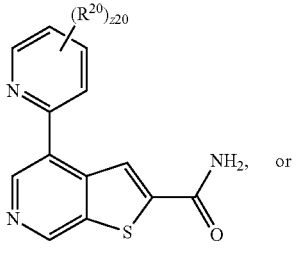

or

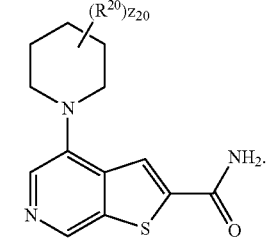

12. The method of claim 9, wherein the method is inhibiting the level of Rev protein activity, inhibiting HIV virion formation in an HIV infected cell, inhibiting HIV viral shedding from an HIV infected cell, inhibiting HIV proliferation, or treating an HIV infection.

13. The method of claim 9, wherein the method is inhibiting the level of HIV Vpu activity in a cell or modulating an HIV Vpu gene.

14. A compound having the following formula:

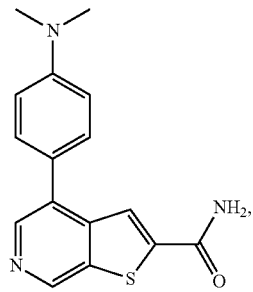

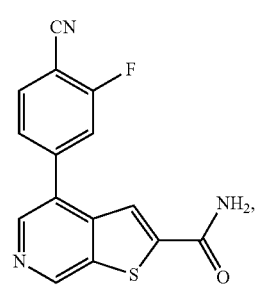

(VII)

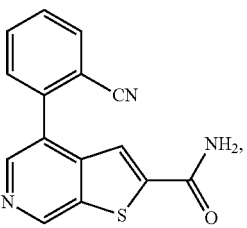

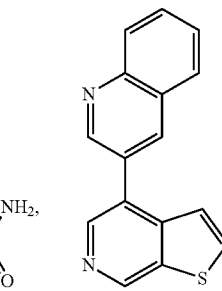

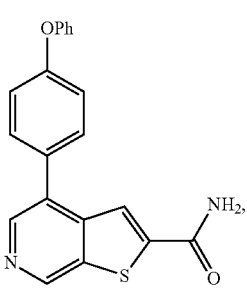

(VIII)

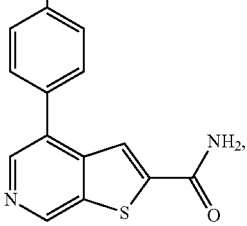

or

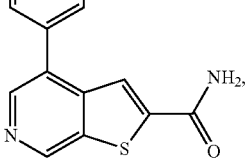

15. A compound of claim 2, having the formula:

-continued

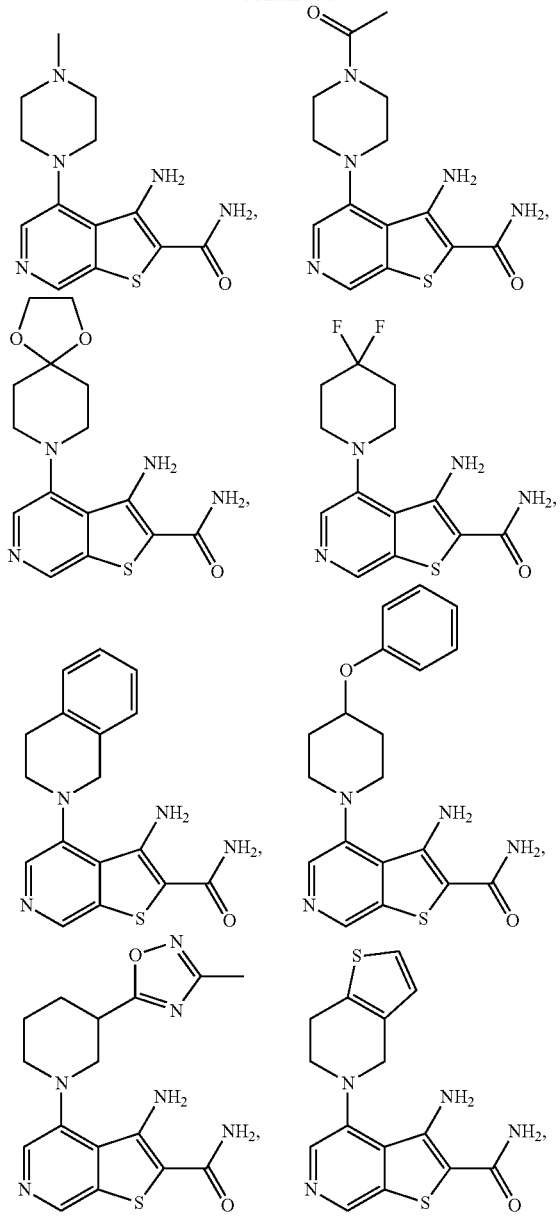

-continued

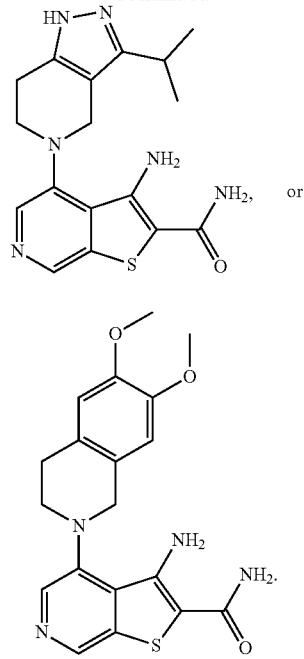

16. The method of claim 9, wherein the method is treating an HIV infection.

17. The method of claim 9 wherein $R^{3A}$ is hydrogen and $R^2$ is hydrogen.

18. A pharmaceutical composition comprising the compound of any one of claims 1 to 8, 14, or 15 and a pharmaceutically acceptable excipient.

19. The pharmaceutical composition of claim 18, further comprising an anti-viral agent.

20. The pharmaceutical composition of claim 19, wherein the anti-viral agent is an human immunodeficiency virus (HIV) reverse transcriptase inhibitor, human immunodeficiency virus (HIV) protease inhibitor, human immunodeficiency virus (HIV) integrase inhibitor, human immunodeficiency virus (HIV) fusion inhibitor, or human immunodeficiency virus (HIV) entry inhibitor.

* * * * *

SEQUENCE LISTING

```
<160> NUMBER OF SEQ ID NOS: 1

<210> SEQ ID NO 1
<211> LENGTH: 116
<212> TYPE: PRT
<213> ORGANISM: Homo sapiens

<400> SEQUENCE: 1

Met Ala Gly Arg Ser Gly Asp Ser Asp Glu Glu Leu Ile Arg Thr Val
1               5                   10                  15

Arg Leu Ile Lys Leu Leu Tyr Gln Ser Asn Pro Pro Pro Asn Pro Glu
            20                  25                  30

Gly Thr Arg Gln Ala Arg Arg Asn Arg Arg Arg Arg Trp Arg Glu Arg
        35                  40                  45

Gln Arg Gln Ile His Ser Ile Ser Glu Arg Ile Leu Ser Thr Tyr Leu
    50                  55                  60

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Val Leu Glu Ser
                100                 105                 110

Gly Thr Lys Glu
            115
```